United States Patent
Wu et al.

(10) Patent No.: US 11,466,047 B2
(45) Date of Patent: Oct. 11, 2022

(54) CYCLIC DI-NUCLEOTIDE COMPOUNDS AS STING AGONISTS

(71) Applicants: Merck Sharp & Dohme Corp., Rahway, NJ (US); Wen-Lian Wu, Green Brook, NJ (US); Jongwon Lim, Lexington, MA (US); Jared N. Cumming, Winchester, MA (US); Benjamin Wesley Trotter, Medfield, MA (US); Wonsuk Chang, Princeton, NJ (US)

(72) Inventors: Wen-Lian Wu, Green Brook, NJ (US); Jongwon Lim, Lexington, MA (US); Jared N. Cumming, Winchester, MA (US); Benjamin Wesley Trotter, Medfield, MA (US); Wonsuk Chang, Princeton, NJ (US)

(73) Assignee: Merck Sharp & Dohme LLC, Rahway, NJ (US)

( * ) Notice: Subject to any disclaimer, the term of this patent is extended or adjusted under 35 U.S.C. 154(b) by 503 days.

(21) Appl. No.: 16/611,624

(22) PCT Filed: May 7, 2018

(86) PCT No.: PCT/US2018/031380
§ 371 (c)(1),
(2) Date: Nov. 7, 2019

(87) PCT Pub. No.: WO2018/208667
PCT Pub. Date: Nov. 15, 2018

(65) Prior Publication Data
US 2020/0062798 A1    Feb. 27, 2020

Related U.S. Application Data

(60) Provisional application No. 62/505,194, filed on May 12, 2017.

(51) Int. Cl.
| | | |
|---|---|---|
| C07H 21/00 | (2006.01) | |
| C07H 21/04 | (2006.01) | |
| A61P 35/00 | (2006.01) | |
| A61P 37/02 | (2006.01) | |
| C07H 21/02 | (2006.01) | |

(52) U.S. Cl.
CPC .............. *C07H 21/00* (2013.01); *A61P 35/00* (2018.01); *A61P 37/02* (2018.01); *C07H 21/02* (2013.01); *C07H 21/04* (2013.01)

(58) Field of Classification Search
None
See application file for complete search history.

(56) References Cited

U.S. PATENT DOCUMENTS

| | | |
|---|---|---|
| 7,488,802 B2 | 2/2009 | Collins et al. |
| 7,521,051 B2 | 4/2009 | Collins et al. |

(Continued)

FOREIGN PATENT DOCUMENTS

| | | |
|---|---|---|
| EP | 3135290 A1 | 1/2018 |
| WO | 2001002369 A2 | 1/2001 |

(Continued)

OTHER PUBLICATIONS

Ablasser et al., Cell intrinsic immunity spreads to bystander cells via the intercellular transfer of cGAMP, Nature, Nov. 28, 2013, 530-546, 503.

Ablasser et al., cGAS produces a 2'-5'-linked cyclic dinucleotide second messenger that activates STING, Nature, Jun. 20, 2013, 380-385, 498.

Ausmees et al., Genetic Data Indicate that Proteins Containing the GGDEF Domain Possess Diguanylate Cyclase Activity, FEMS Microbiology, 2001, 163-167, Letters 204.

Berge, S.M., et al.,, "Pharmaceutical Salts", J. Pharm. Sci, 1977, pp. 1-19, vol. 66, No. 1.

(Continued)

*Primary Examiner* — Layla D Berry
(74) *Attorney, Agent, or Firm* — Julie M. Lake; Catherine D. Fitch

(57) ABSTRACT

A class of polycyclic compounds of general formula (I), wherein Base$^1$, Base$^2$, Y, Y$^a$, X$^a$, X$^{a1}$, X$^b$, X$^{b1}$, X$^c$, X$^{c1}$, X$^d$, X$^{d1}$, R$^1$, R$^{1a}$, R$^2$, R$^{2a}$, R$^3$, R$^4$, R$^{4a}$, R$^5$, R$^6$, R$^{6a}$, R$^7$, R$^{7a}$, R$^8$, R$^{8a}$, and R$^9$ are defined herein, that may be useful as inductors of type I interferon production, specifically as STING active agents, are provided. Also provided are processes for the synthesis and use of compounds.

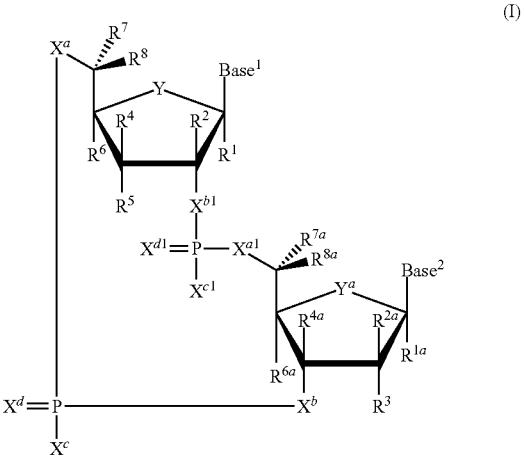

(I)

17 Claims, No Drawings
Specification includes a Sequence Listing.

(56) References Cited

U.S. PATENT DOCUMENTS

| | | | |
|---|---|---|---|
| 7,595,048 | B2 | 9/2009 | Honjo et al. |
| 8,008,449 | B2 | 8/2011 | Korman et al. |
| 8,168,757 | B2 | 5/2012 | Finnefroch et al. |
| 8,354,509 | B2 | 1/2013 | Carven et al. |
| 8,383,796 | B2 | 2/2013 | Korman et al. |
| 9,724,408 | B2 | 8/2017 | Dubensky, Jr. et al. |
| 2006/0040887 | A1 | 2/2006 | Karaolls |
| 2006/0167241 | A1 | 7/2006 | Hayakawa |
| 2008/0025979 | A1 | 1/2008 | Honjo et al. |
| 2008/0286296 | A1 | 11/2008 | Ebensen et al. |
| 2011/0271358 | A1 | 11/2011 | Freeman et al. |
| 2014/0206640 | A1 | 7/2014 | Girijavallabhan et al. |
| 2014/0329889 | A1 | 11/2014 | Vance et al. |
| 2014/0341976 | A1 | 11/2014 | Dubensky, Jr. et al. |
| 2015/0056224 | A1 | 2/2015 | Dubensky, Jr. et al. |
| 2015/0158886 | A1 | 6/2015 | Jones et al. |
| 2016/0074507 | A1 | 3/2016 | Manel et al. |
| 2016/0287698 | A1 | 10/2016 | Yan et al. |
| 2016/0362441 | A1 | 12/2016 | Vernejoul et al. |
| 2017/0050967 | A1 | 2/2017 | Burai et al. |
| 2017/0158724 | A1 | 6/2017 | Adams et al. |

FOREIGN PATENT DOCUMENTS

| | | | |
|---|---|---|---|
| WO | 2001002369 | A3 | 1/2001 |
| WO | 2002010192 | A2 | 2/2002 |
| WO | 2002057245 | | 7/2002 |
| WO | 2002068470 | A2 | 9/2002 |
| WO | 2004004771 | A1 | 2/2004 |
| WO | 2004056875 | A1 | 7/2004 |
| WO | 2004072286 | A1 | 8/2004 |
| WO | 2010027827 | A2 | 3/2010 |
| WO | 2010047774 | | 4/2010 |
| WO | 2010077634 | A1 | 7/2010 |
| WO | 2011066342 | A2 | 6/2011 |
| WO | 2013019906 | A1 | 2/2013 |
| WO | 2013185052 | A1 | 12/2013 |
| WO | 2014093936 | | 6/2014 |
| WO | 2014099824 | | 6/2014 |
| WO | 2014099941 | | 6/2014 |
| WO | 201479335 | A1 | 11/2014 |
| WO | 2014179760 | | 11/2014 |
| WO | 2014189805 | A1 | 11/2014 |
| WO | 2014189806 | | 11/2014 |
| WO | 2015017652 | | 2/2015 |
| WO | 2015074145 | A1 | 5/2015 |
| WO | 2015077354 | A1 | 5/2015 |
| WO | 2015148746 | A1 | 10/2015 |
| WO | 2015161137 | | 10/2015 |
| WO | 2015185565 | | 12/2015 |
| WO | 2015189117 | | 12/2015 |
| WO | 2016096174 | | 6/2016 |
| WO | 2016096577 | | 6/2016 |
| WO | 2016100261 | | 6/2016 |
| WO | 2016120305 | | 8/2016 |
| WO | 2016120605 | | 8/2016 |
| WO | 2016145102 | | 9/2016 |
| WO | 2017011522 | | 1/2017 |
| WO | 2017011622 | | 1/2017 |
| WO | 2017011920 | | 1/2017 |
| WO | 2017027645 | | 2/2017 |
| WO | 2017027646 | A1 | 2/2017 |
| WO | 2017075477 | A1 | 5/2017 |
| WO | 2017093933 | A1 | 6/2017 |
| WO | 2017100305 | | 6/2017 |
| WO | 2017123657 | | 7/2017 |
| WO | 2017123669 | | 7/2017 |
| WO | 2017161349 | A1 | 9/2017 |
| WO | 2017175147 | | 10/2017 |
| WO | 2017175156 | | 10/2017 |
| WO | 2017216726 | | 12/2017 |
| WO | 2018009466 | | 1/2018 |

OTHER PUBLICATIONS

Bhattacharya et al., Total Synthesis of 2'-deoxy-2'-arafluoro-tubericidin, -toyocamycin, -sangivamycin and certain related molecules, J. Chem. Soc., Perkin Trans. 1; Organic and Bio-Organic Chemistry, 1995, 1543-1550, 12.

Boehr et al., Establishing the Principles of Recognition in the Adenine-Binding Region of an Aminoglycoside Antibiotic Kinase [APH(3')-IIIa], Biochemistry, 2005, 12445-12453, 44(37).

Bookser et al., High-Throughput Five Minute Microwave Accelerated Glycosylation Approach to the Synthesis of Nucleoside Libraries, JOC Article, 2007, 173-179, 72.

Bruno et al., N-Substituted 2-aminobiphenylpalladium Methanesulfonate Precatalysts and Their Use in C-C and C-N Cross Couplings, The Journal of Organic Chamistry, 2014, 4161-4166, 79.

Dande et al., Improving RNA Interference in Mammalian Cells by 4'-Thio-Modified Small Interfering RNA (siRNA): Effect on siRNA Activity and Nuclease Stability When Used in Combination with 2'-O-Alkyl Modifications, Journal of Medicinal Chemistry, 2006, 1624-1634, 49(5).

Diner et al., The Innate Immune DNA Sensor cGAS Produces a Noncanonical Cyclic Dinucleotide that Activates Human STING, 3 Cell Reports, Cell Reports, 2013, 1355-1361, 3.

Downey et al., DMXAA Causes Tumor Site-Specific Vascular Disruption in Murine Non-Small Molecule Lung Cancer, and Like the Endogenous Non-Canonical Cyclic Dinucleotide STING Agonist, 2'3'-cGAMP, Induces M2 Macrophage Repolarization, PLOS One, 2014, 1-14, 9-6-e99988.

Ertem et al., Synthesis of RNA oligomers on heterogeneous templates, Nature, 1996, 238-240, 379-18.

Fagundes et al., Building unique bonds to fight misplaced DNA, Cell Research, 2013, 1065-1066, 2-9.

Fu, Juan, et al., STING agonist formulated cancer vaccines can cure established tumors resistant to PD-1 blockade, Science Translational Medicine, 2015, 1-13, 7.

Gadthula et al., Synthesis and Anti-HIV Activity of β-D-3'-Azido-2',3'-unsaturated Nucleosides and β-D-3'-Azido-3'deoxyribofuranosylnucleosides, Nucleoside, Nucleotides, Nucleic Acids, 2005, 1707-1727, 24.

Gaffney et al., One-Flask Syntheses of c-di-GMP and the [Rp,Rp] and [Rp,Sp] Thiophosphate Analogues, Organic Letters, 2010, 3269-3271, 12-14.

Gao et al., Cyclic [G(2',5')pA(3',5")p] Is the Metazoan Second Messenger Produced by DNA-Activated Cyclic GMP-AMP Synthase, Cell, 2013, 1094-1107, 153.

Gao et al., Structure-Function Ananlysis of STING Activation by c[G(2',5')pA(3',5')p] and Targeting by Antiviral DMXAA, Cell, 2013, 748-762, 154.

Goerlitzer, et al., 1,3-Dicarbonyl Compounds. XIV: 4-Oxo-4H-[1]benzofuro[3,2-b]pyrans, Archiv der Pharmazie, 1980, 385-398, vol. 313; Issue 5.

Gosselin et al., Systematic Synthesis and Biological Evaluation of α- and β-D-lyxofuranosyl Nucleosides of the Five Naturally Occurring Nucleic Acid Bases, J. Med. Chem, 1987, 982-991, 30.

Gould, Salt Selections for Basic Drugs, Intl. J. Pharmaceutics, 1986, pp. 201-217, vol. 33.

Guanghui Yi et al., Single Nucleotide Polymorphisms of Human STING Can Affect Innate Immune Response to Cyclic Dinucleotides, PLOS One, 2013, 1-16, 8-10-e77846.

Heping Shi, et al., Molecular basis for the specific recognition of the metazoan cyclic GMP-AMP by the innate immune adaptor protein STING, PNAS, 2015, 8947-8952, vol. 112/No. 29.

Ikeuchi et al., Practical synthesis of natural plant-growth regulator 2-azahypoxanthine, its derivatives, and biotin-labeled probes, Organic & Biomolecular Chemistry, 2014, 3813, 12(23).

Joshi et al., Selectivity of montmorillonite catalyzed prebiotic reactions of D, L-nucleotides, Orig Life Evol Biosph, 2007, 3-26, 37-3.

Kim et al., A Convenient and Versatile Syntheses of 2' (and 3') amino (and azido)-2'(and 3') deoxyadenosine as Diverse Synthetic Precursors of Cyclic Adenosine Diphosphate Ribose (cADPR), Bull. Korean Chem. Soc., 2004, 243, 25-2.

Kobayashi et al., Bacterial c-di-GMP Affects Hematopoietic Stem/Progenitors and their Niches through STING, Cell Reports, 2015, 71-84, 11.

Kranzusch et al., Structure-Guided Reporgramming of Human cGAS Dinucleotide Linkage Specificity, Cell Inc., Elsevier Inc., 2014, 1011-1021, 158.

Li et al., Cyclic GMP-AMP Synthase is Activated by Double-Stranded DNA-Induced Oligomerization, Immunity, 2013, 1019-1031, 39.

Li et al., Hydrolysis of 2'3'-cGAMP by ENPPI and Design of Nonhydrolyzable Analogs, 10 Nature Chemical Biology 1043 (Dec. 2014); Li et al., Hydrolysis of 2'3'-cGAMP by ENPPI and Design of Nonhydrolyzable Analogs: ERRATUM, Nature Chemical Biology, 2014, 1043, 10.

Li et al., Synthesis of 2'-Deoxy-2'-C—a-methylpurine Nucleosides, Synthesis, 2005, 2865-2870, 2005(17).

Liu et al., Activated STING in a Vascular and Pulmonary Syndrome, The New England Journal of Medicine, 2015, 507, 371-6.

Liu et al., Hepatitis B Virus Polymerase Disrupts K63-Linked Ubiquitination of STING to Block Inate Cytosolic DNA-Sensing Pathways, Journal of Virology, 2015, 2287, 89-4.

Lolicato et al., Cyclic Dinucleotides Bind the C-Linker of HCN4 to Control Channel cGAMP Responsiveness, 10 Nature Chemical Biology 457 (Jun. 2014); Lolicato et al., Cyclic Dinucleotides Bind the C-Linker of HCN4 to Control Channel cGAMP Responsiveness, Nature Chemical Biology, 2014, 457, 10.

Mikhailov et al., Conformational Peculiarities of 5'-C-methylnucleosides, Bioorganicheskaya Khimiya, 1989, 969-975, 15(7).

Minakawa et al., Nucleosides and nucleotides. 116. Convenient syntheses of 3-deazaadenosine, 3-deazaguanosine, and 3-deazainosine via ring closure of 5-ethynyl-1-B-D-ribofuranosylimidazole-4-carboxamide or -carbonitrile. Tetrahedron, 1993, 557-570, 49(3).

Minakawa et al., Nucleosides and Nucleotides. 143. Synthesis of 5-Amino-4-imidazolecarboxamide (AICA) Deoxyribosides from Deoxyinosines and Their Conversion into 3-Deazapurine Derivatives, Chemical & Pharmaceutical Bulletin, 1996, 288-295, 44(2).

O'Neill et al., Sensing the Dark Side of DNA, Sceince, 2013, 763, 339.

Ora et al., Hydrolytic reactions of cyclic bis(3'-5') diadenylic acid (c-di-AMP), J. Phys. Org. Chem, 2013, 218-225, 26.

Panne et al., Cytosolic DNA sensing unraveled, Nature Chemical Biology, 2013, 533, 9.

Patil et al., 4-aza-7,9-dideazaadenosine, a new cytotoxic synthetic C-nucleoside analogue of adenosine, Tetrahedron Letters, 1994, 5339-5342, 35(30).

Puech et al., Synthesis of 9-(3-deoxy- and 2,3-dideoxy-3-fluoro-β-D-xylofuranosyl)guanines as potential antiviral agents, Tetrahedron Letters, 1989, 3171-3174, 30-24.

Ramesh et al., A convenient synthesis of 1-(β-D-ribofuranosyl)imidazo[4,5-d]pyridazin-4(5H)-one (2-aza-3-deazainosine) and its 2'-deoxy counterpart by ring closure of imidazole nucleosides, Journal of the Chemical Society, Perkin Transaction 1, 1989, 1769-1774, 10.

Ren et al., Structural Basis for Molecular Discrimination by a 3',3'-cGAMP Sensing Riboswitch, Cell Reports, 2015, 1-12, 11.

Robins et al., Nucleic acid related compounds. 74. Synthesis and biological activity of 2'(and 3')-deoxy-2'(and 3')-methylenenucleoside analogs that function as mechanism-based inhibitors of S-adenosyl-L-homocysteine hydrolase and/or ribonucleotide reductase, Journal of Medicinal Chemistry, 1992, 2283-2293, 35(12).

Robins et al., Nucleic Acid-Related Compounds. 91. Biomimetic Reactions Are in Harmony with Loss of 2'-Substituents as Free Radicals (Not Anions) during Mechanism-Based Inactivation of Ribonucleotide Reductases. Differential Interactions of Azide, Halogen, and Alkylthio, J. Am. Chem. Soc., 1996, pp. 11341-11348, 118(46).

Roembke et al., A cyclic dinucleotide contianing 2-aminopurine is a general fluorescent sensor for c-di-GMP and 3'-3'-cGAMP, Molecular BioSystems, 2014, 1568-1575, 10.

Sawai et al., Preparation and Properties of Oligocytidylates with 2'-5' Internucleotide Linkage, Chem. Pharm. Bull. Jpn, 1985, 361-366, 58.

Sawai et al., Synthesis of 2'-5' Linked Oligouridylates in Awueous Medium using the Pd2+ Ion, Chem. Pharm. Bull, 1981, 2237-2245, 29(8).

Seela et al., Fluorinated Pyrrolo[2,3-d]pyrimidine Nucleosides: 7-Fluoro-7-deazapurine 2'-Deoxyribofuranosides and 2'-Deoxy-2'-fluoroarabinofuranosyl Derivatives, Synthesis, 2006, 2005-2012, (12).

Simm et al., Phenotypic Convergence Mediated by GGDEF-Domain-Containing Proteins, Journal of Bacteriology, 2005, 6816-6823, 187(19).

Stahl et al., Aminoquinazoline Compounds as A2A Antagonist, Handbook of Pharmaceutical Salts Properties, Selection, and Use, 2002, 330-331.

Sun et al., Cyclic GMP-AMP Synthase Is a Cytosolic DNA Sensor That Activates the Type I Interferon Pathway, Science, 2013, 786, 339.

Tezuka, T. et al, Synthesis of 2'-Modified Cyclic Bis(3'-5')diadenylic Acids (c-di-AMPs) and Their Promotion of Cell Division in a Freshwater Green Alga, Chem. Lett., 2012, 1723-1725, 41.

Tosolini et al., Human Monocyte Recognition of Adenosine-Based Cyclic Dinucleotides Unveils the A2a G∞s Protein-Coupled Receptor Tonic Inhibition of Mitochondrially Induced Cell Death, Molecular and Cellular Biology, 2015, 479-495, 35-2.

Urata et al., Regio- and Diastereo-Selectivity of Montmorillonite-Catalyzed Oligomerization of Racemic Adenosine 5'-Phosphorimidazolide, Nucleosides, Nucleotides and Nucleic Acids, Nucleosides, Nucleotides and Nucleic Acids, 2008, 421-430, 27.

Wang et al., Synthesis and Biological Activity of 5-Fluorotubercidin, Nucleosides, Nucleotides and Nucleic Acids, 2004, 161-170, 23(1).

Wu et al., Cyclic GMP-AMP Is an Endogenous Second Messenger in Innate Immune Signaling by Cytosolic DNA, Science 826, 2013, 826-830, 339.

Zeng et al., MAVS, cGAS, and Endogenous Retroviruses in T-Independent B Cell Responses, Science, 2014, 1486-1492, 346-6216.

Zhang et al., Cyclic GMP-AMP Containing Mixed Phosphodiester Linkages Is An Endogenous High-Affinity Ligand for STING, Molecular Cell, 2013, 226-235, 51.

Zhou et al., The ER-Associated Protein ZDHHC1 Is a Positive Regulator of DNA Virus-Triggered, MITA/STING-Dependent Innate Immune Signaling, Cell Host & Microbe, 2014, 450-461, 16.

CYCLIC DI-NUCLEOTIDE COMPOUNDS AS STING AGONISTS

CROSS-REFERENCE TO RELATED APPLICATIONS

This application is a National Stage application of International Patent Application No. PCT/US2018/031380, filed May 7, 2018, which claims priority to U.S. Provisional Patent Application No. 62/505,194, filed May 12, 2017.

FIELD OF THE INVENTION

The present disclosure relates to cyclic di-nucleotide compounds and derivatives thereof that may be useful as STING (Stimulator of Interferon Genes) agonists that activate the STING pathway. The present disclosure also relates to processes for the synthesis and to uses of such cyclic di-nucleotide compounds.

BACKGROUND OF THE INVENTION

The immune system has evolved to recognize and neutralize different types of threats in order to maintain the homeostasis of the host, and it is generally broken down into two arms: adaptive and innate. The adaptive immune system is specialized to recognize as foreign those antigens not naturally expressed in the host and to mount an anti-antigen response through the coordinated actions of many leukocyte subsets. The hallmark of adaptive immune responses is their ability to provide "memory" or long-lasting immunity against the encountered antigen. While this specific and long-lasting effect is critical to host health and survival, the adaptive immune response requires time to generate a full-blown response.

The innate immune system compensates for this time delay and is specialized to act quickly against different insults or danger signals. It provides the first line of defense against bacteria, viruses, parasites and other infectious threats, but it also responds strongly to certain danger signals associated with cellular or tissue damage. The innate immune system has no antigen specificity but does respond to a variety of effector mechanisms. Opsonization, phagocytosis, activation of the complement system, and production of soluble bioactive molecules such as cytokines or chemokines are all mechanisms by which the innate immune system mediates its response. By responding to these damage-associated molecular patterns (DAMPs) or pathogen-associated molecular patterns (PAMPs) described above, the innate immune system is able to provide broad protection against a wide range of threats to the host.

Free cytosolic DNA and RNA are among these PAMPs and DAMPs. It has recently been demonstrated that the main sensor for cytosolic DNA is cGAS (cyclic GMP-AMP synthase). Upon recognition of cytosolic DNA, cGAS catalyzes the generation of the cyclic-dinucleotide 2'3'-cGAMP, an atypical second messenger that strongly binds to the ER-transmembrane adaptor protein STING. A conformational change is undergone by cGAMP-bound STING, which translocates to a perinuclear compartment and induces the activation of critical transcription factors IRF-3 and NF-κB. This leads to a strong induction of type I interferons and production of pro-inflammatory cytokines such as IL-6, TNF-α and IFN-γ.

The importance of type I interferons and pro-inflammatory cytokines on various cells of the immune system has been very well established. In particular, these molecules strongly potentiate T-cell activation by enhancing the ability of dendritic cells and macrophages to uptake, process, present and cross-present antigens to T-cells. The T-cell stimulatory capacity of these antigen-presenting cells is augmented by the up-regulation of critical co-stimulatory molecules, such as CD80 or CD86. Finally, type I interferons can rapidly engage their cognate receptors and trigger the activation of interferon-responsive genes that can significantly contribute to adaptive immune cell activation.

From a therapeutic perspective, type I interferons are shown to have antiviral activities by directly inhibiting human hepatitis B virus and hepatitis C virus replication, and by stimulating immune responses to virally infected cells. Compounds that can induce type I interferon production are used in vaccines, where they act as adjuvants, enhancing specific immune responses to antigens and minimizing side effects by reducing dosage and broadening the immune response.

In addition, interferons, and compounds that can induce interferon production, have potential use in the treatment of human cancers. Such molecules are potentially useful as anti-cancer agents with multiple pathways of activity. Interferons can inhibit human tumor cell proliferation directly and may be synergistic with various approved chemotherapeutic agents. Type I interferons can significantly enhance anti-tumor immune responses by inducing activation of both the adaptive and innate immune cells. Finally, tumor invasiveness may be inhibited by interferons by modulating enzyme expression related to tissue remodeling.

In view of the potential of type I interferons and type I interferon-inducing compounds as anti-viral and anti-cancer agents, there remains a need for new agents that can induce potent type I interferon production. With the growing body of data demonstrating that the cGAS-STING cytosolic DNA sensory pathway has a significant capacity to induce type I interferons, the development of STING activating agents is rapidly taking an important place in today's anti-tumor therapy landscape.

SUMMARY OF THE INVENTION

The present disclosure relates to novel compounds of general formula (I). In particular, the present disclosure relates to compounds having the general structural formula (I):

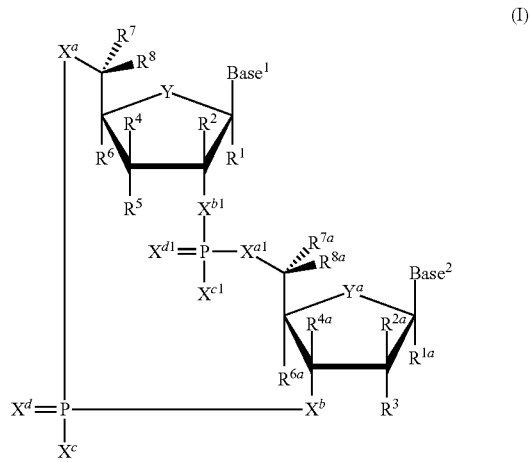

or pharmaceutically acceptable salts, hydrates, solvates, or prodrugs thereof, as described herein. Embodiments of the disclosure include compounds of general formula (I), and pharmaceutically acceptable salts, hydrates, solvates, or prodrugs thereof, as well as synthesis and isolation of compounds of general formula (I), and pharmaceutically acceptable salts, hydrates, solvates, or prodrugs thereof. The compounds of general formula (I), and their pharmaceutically acceptable salts, hydrates, solvates, and/or prodrugs, may be useful as agents to induce immune responses, to induce STING-dependent type I interferon production, and/or to treat a cell proliferation disorders, such as cancers, in a subject. The compounds of general formula (I) could further be used in combination with other therapeutically effective agents, including but not limited to, other drugs useful for the treatment of cell proliferation disorders, such as cancers. The invention further relates to processes for preparing compounds of general formula (I), and pharmaceutical compositions that comprise compounds of general formula (I) and pharmaceutically acceptable salts thereof.

Other embodiments, aspects and features of the present disclosure are either further described in or will be apparent from the ensuing description, examples and appended claims.

DETAILED DESCRIPTION OF THE INVENTION

The present disclosure includes compounds of general formula (I), and pharmaceutically acceptable salts, hydrates, solvates, or prodrugs thereof. These compounds and their pharmaceutically acceptable salts, hydrates, solvates, and/or prodrugs may be useful as agents to induce immune responses, to induce STING-dependent type I interferon production, and/or to treat a cell proliferation disorder.

Embodiments disclosed herein relate to compounds of general formula (I):

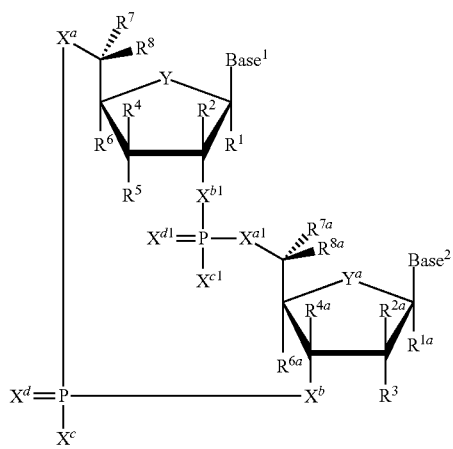

(I)

or a pharmaceutically acceptable salts, hydrates, solvates, or prodrugs thereof, wherein Base$^1$ and Base$^2$ are each independently selected from the group consisting of

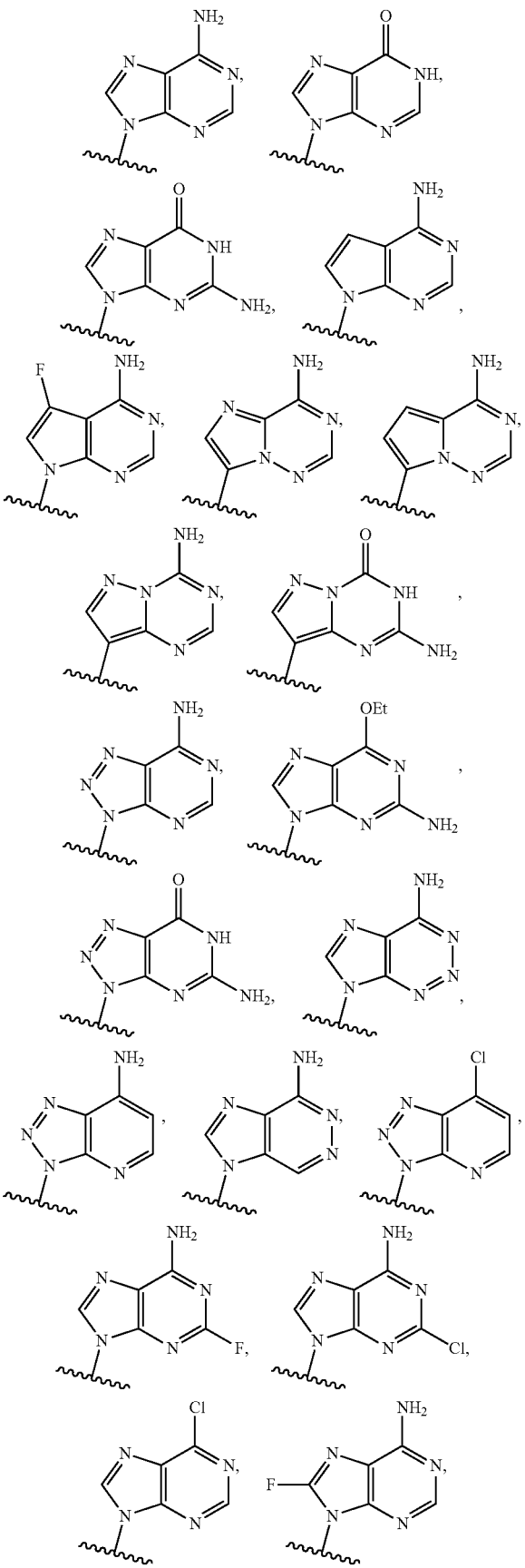

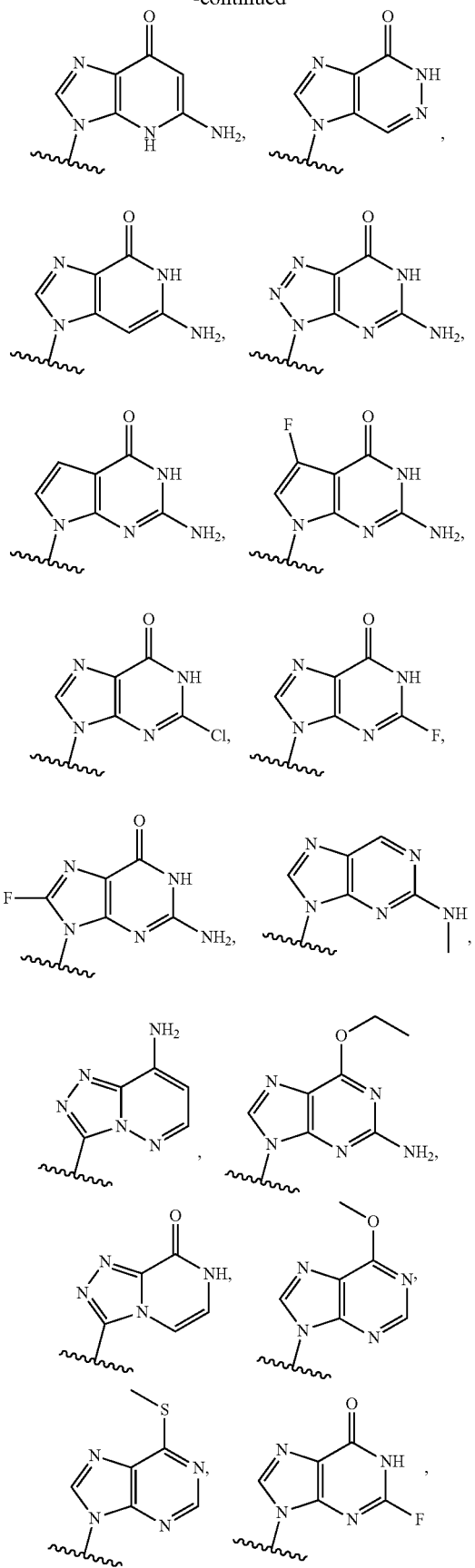
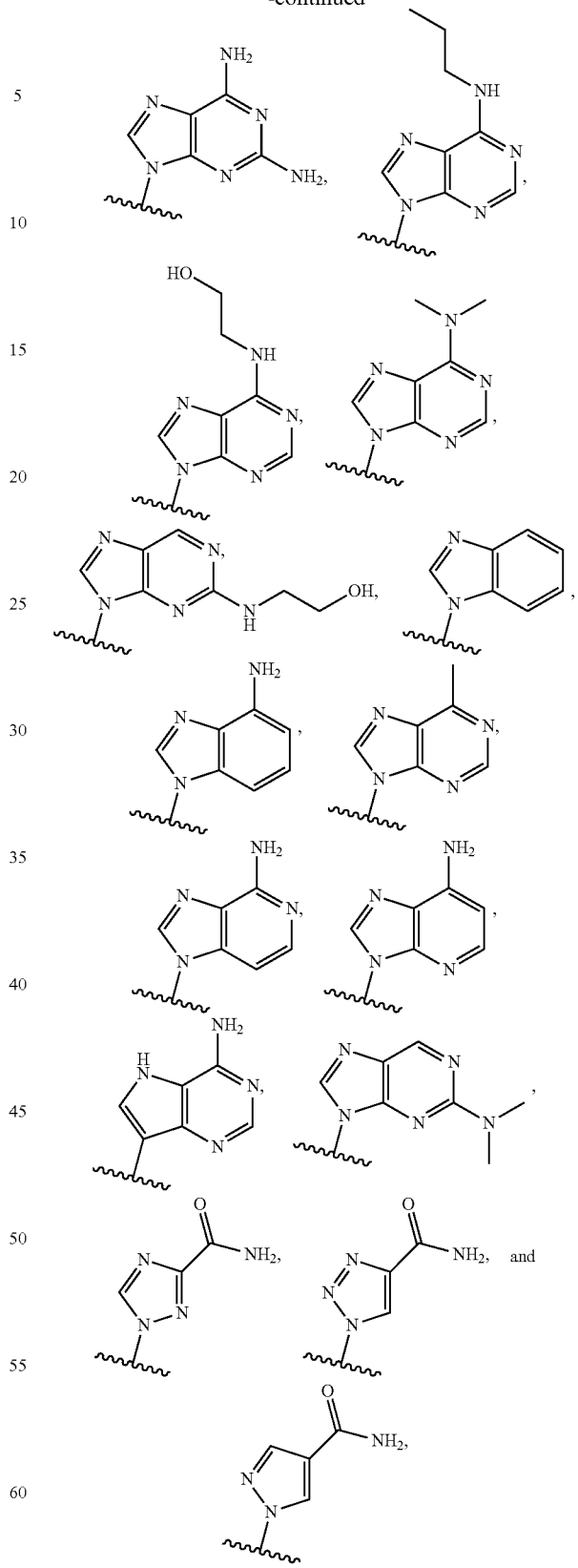
where Base[1] and Base[2] each may be independently substituted by 0-3 substituents $R^{10}$, where each $R^{10}$ is independently selected from the group consisting of F, Cl, I, Br, OH, SH, $NH_2$, $C_{1-3}$ alkyl, $C_{3-6}$ cycloalkyl, $O(C_{1-3}$ alkyl), $O(C_{3-6}$ cycloalkyl), S(C$_{1-3}$ alkyl), S(C$_{3-6}$ cycloalkyl), NH(C$_{1-3}$ alkyl), NH(C$_{3-6}$ cycloalkyl), N(C$_{1-3}$ alkyl)$_2$, and N(C$_{3-6}$ cycloalkyl)$_2$; Y and Y$^a$ are each independently selected from the group consisting of —O—, —S—, —SO$_2$—, —CH$_2$—, and —CF$_2$—; X$^a$ and X$^{a1}$ are each independently selected from the group consisting of —O—, —S—, and —CH$_2$—; X$^b$ and X$^{b1}$ are each independently selected from the group consisting of —O—, —S—, and —CH$_2$—; X$^c$ and X$^{c1}$ are each independently selected from the group consisting of SR$^9$, OR$^9$, and NR$^9$R$^9$; X$^d$ and X$^{d1}$ are each independently selected from the group consisting of O and S; R$^1$ and R$^{1a}$ are each independently selected from the group consisting of H, F, Cl, Br, I, OH, CN, N$_3$, C$_1$-C$_6$ alkyl, C$_2$-C$_6$ alkenyl, C$_2$-C$_6$ alkynyl, C$_1$-C$_6$ haloalkyl, C$_2$-C$_6$ haloalkenyl, C$_2$-C$_6$ haloalkynyl, —O—C$_1$-C$_6$ alkyl, —O—C$_2$-C$_6$ alkenyl, and —O—C$_2$-C$_6$ alkynyl, where said R$^1$ and R$^{1a}$ C$_1$-C$_6$ alkyl, C$_2$-C$_6$ alkenyl, C$_2$-C$_6$ alkynyl, C$_1$-C$_6$ haloalkyl, C$_2$-C$_6$ haloalkenyl, C$_2$-C$_6$ haloalkynyl, —O—C$_1$-C$_6$ alkyl, —O—C$_2$-C$_6$ alkenyl, and —O—C$_2$-C$_6$ alkynyl are substituted by 0 to 3 substituents selected from the group consisting of F, Cl, Br, I, OH, CN, and N$_3$; R$^2$ and R$^{2a}$ are each independently selected from the group consisting of H, F, Cl, Br, I, OH, CN, N$_3$, C$_1$-C$_6$ alkyl, C$_2$-C$_6$ alkenyl, C$_2$-C$_6$ alkynyl, C$_1$-C$_6$ haloalkyl, C$_2$-C$_6$ haloalkenyl, C$_2$-C$_6$ haloalkynyl, —O—C$_1$-C$_6$ alkyl, —O—C$_2$-C$_6$ alkenyl, and —O—C$_2$-C$_6$ alkynyl, where said R$^2$ and R$^{2a}$ C$_1$-C$_6$ alkyl, C$_2$-C$_6$ alkenyl, C$_2$-C$_6$ alkynyl, C$_1$-C$_6$ haloalkyl, C$_2$-C$_6$ haloalkenyl, C$_2$-C$_6$ haloalkynyl, —O—C$_1$-C$_6$ alkyl, —O—C$_2$-C$_6$ alkenyl, and —O—C$_2$-C$_6$ alkynyl are substituted by 0 to 3 substituents selected from the group consisting of F, Cl, Br, I, OH, CN, and N$_3$; R$^3$ is selected from the group consisting of H, F, Cl, Br, I, OH, CN, N$_3$, C$_1$-C$_6$ alkyl, C$_2$-C$_6$ alkenyl, C$_2$-C$_6$ alkynyl, C$_1$-C$_6$ haloalkyl, C$_2$-C$_6$ haloalkenyl, C$_2$-C$_6$ haloalkynyl, —O—C$_1$-C$_6$ alkyl, —O—C$_2$-C$_6$ alkenyl, and —O—C$_2$-C$_6$ alkynyl, where said R$^3$ C$_1$-C$_6$ alkyl, C$_2$-C$_6$ alkenyl, C$_2$-C$_6$ alkynyl, C$_1$-C$_6$ haloalkyl, C$_2$-C$_6$ haloalkenyl, C$_2$-C$_6$ haloalkynyl, —O—C$_1$-C$_6$ alkyl, —O—C$_2$-C$_6$ alkenyl, and —O—C$_2$-C$_6$ alkynyl are substituted by 0 to 3 substituents selected from the group consisting of F, Cl, Br, I, OH, CN, and N$_3$; R$^4$ and R$^{4a}$ are each independently selected from the group consisting of H, F, Cl, Br, I, OH, CN, N$_3$, C$_1$-C$_6$ alkyl, C$_2$-C$_6$ alkenyl, C$_2$-C$_6$ alkynyl, C$_1$-C$_6$ haloalkyl, C$_2$-C$_6$ haloalkenyl, C$_2$-C$_6$ haloalkynyl, —O—C$_1$-C$_6$ alkyl, —O—C$_2$-C$_6$ alkenyl, and —O—C$_2$-C$_6$ alkynyl, where said R$^4$ and R$^{4a}$ C$_1$-C$_6$ alkyl, C$_2$-C$_6$ alkenyl, C$_2$-C$_6$ alkynyl, C$_1$-C$_6$ haloalkyl, C$_2$-C$_6$ haloalkenyl, C$_2$-C$_6$ haloalkynyl, —O—C$_1$-C$_6$ alkyl, —O—C$_2$-C$_6$ alkenyl, and —O—C$_2$-C$_6$ alkynyl are substituted by 0 to 3 substituents selected from the group consisting of F, Cl, Br, I, OH, CN, and N$_3$; R$^5$ is selected from the group consisting of H, F, Cl, Br, I, OH, CN, N$_3$, C$_1$-C$_6$ alkyl, C$_2$-C$_6$ alkenyl, C$_2$-C$_6$ alkynyl, C$_1$-C$_6$ haloalkyl, C$_2$-C$_6$ haloalkenyl, C$_2$-C$_6$ haloalkynyl, —O—C$_1$-C$_6$ alkyl, —O—C$_2$-C$_6$ alkenyl, and —O—C$_2$-C$_6$ alkynyl, where said R$^5$ C$_1$-C$_6$ alkyl, C$_2$-C$_6$ alkenyl, C$_2$-C$_6$ alkynyl, C$_1$-C$_6$ haloalkyl, C$_2$-C$_6$ haloalkenyl, C$_2$-C$_6$ haloalkynyl, —O—C$_1$-C$_6$ alkyl, —O—C$_2$-C$_6$ alkenyl, and —O—C$_2$-C$_6$ alkynyl are substituted by 0 to 3 substituents selected from the group consisting of F, Cl, Br, I, OH, CN, and N$_3$; R$^6$ and R$^{6a}$ are each independently selected from the group consisting of H, F, Cl, Br, I, OH, CN, N$_3$, C$_1$-C$_6$ alkyl, C$_2$-C$_6$ alkenyl, C$_2$-C$_6$ alkynyl, C$_1$-C$_6$ haloalkyl, C$_2$-C$_6$ haloalkenyl, C$_2$-C$_6$ haloalkynyl, —O—C$_1$-C$_6$ alkyl, —O—C$_2$-C$_6$ alkenyl, and —O—C$_2$-C$_6$ alkynyl, where said R$^6$ and R$^{6a}$ C$_1$-C$_6$ alkyl, C$_2$-C$_6$ alkenyl, C$_2$-C$_6$ alkynyl, C$_1$-C$_6$ haloalkyl, C$_2$-C$_6$ haloalkenyl, C$_2$-C$_6$ haloalkynyl, —O—C$_1$-C$_6$ alkyl, —O—C$_2$-C$_6$ alkenyl, and —O—C$_2$-C$_6$ alkynyl are substituted by 0 to 3 substituents selected from the group consisting of F, Cl, Br, I, OH, CN, and N$_3$; R$^7$ and R$^{7a}$ are each independently selected from the group consisting of H, F, Cl, Br, I, OH, CN, N$_3$, C$_1$-C$_6$ alkyl, C$_2$-C$_6$ alkenyl, C$_2$-C$_6$ alkynyl, C$_1$-C$_6$ haloalkyl, C$_2$-C$_6$ haloalkenyl, C$_2$-C$_6$ haloalkynyl, —O—C$_1$-C$_6$ alkyl, —O—C$_2$-C$_6$ alkenyl, and —O—C$_2$-C$_6$ alkynyl, where said R$^7$ and R$^{7a}$ C$_1$-C$_6$ alkyl, C$_2$-C$_6$ alkenyl, C$_2$-C$_6$ alkynyl, C$_1$-C$_6$ haloalkyl, C$_2$-C$_6$ haloalkenyl, C$_2$-C$_6$ haloalkynyl, —O—C$_1$-C$_6$ alkyl, —O—C$_2$-C$_6$ alkenyl, and —O—C$_2$-C$_6$ alkynyl are substituted by 0 to 3 substituents selected from the group consisting of F, Cl, Br, I, OH, CN, and N$_3$; R$^8$ and R$^{8a}$ are each independently selected from the group consisting of H, F, Cl, Br, I, OH, CN, N$_3$, C$_1$-C$_6$ alkyl, C$_2$-C$_6$ alkenyl, C$_2$-C$_6$ alkynyl, C$_1$-C$_6$ haloalkyl, C$_2$-C$_6$ haloalkenyl, C$_2$-C$_6$ haloalkynyl, —O—C$_1$-C$_6$ alkyl, —O—C$_2$-C$_6$ alkenyl, and —O—C$_2$-C$_6$ alkynyl, where said R$^8$ and R$^{8a}$ C$_1$-C$_6$ alkyl, C$_2$-C$_6$ alkenyl, C$_2$-C$_6$ alkynyl, C$_1$-C$_6$ haloalkyl, C$_2$-C$_6$ haloalkenyl, C$_2$-C$_6$ haloalkynyl, —O—C$_1$-C$_6$ alkyl, —O—C$_2$-C$_6$ alkenyl, and —O—C$_2$-C$_6$ alkynyl are substituted by 0 to 3 substituents selected from the group consisting of F, Cl, Br, I, OH, CN, and N$_3$; each R$^9$ is independently selected from the group consisting of H, C$_1$-C$_{20}$ alkyl,

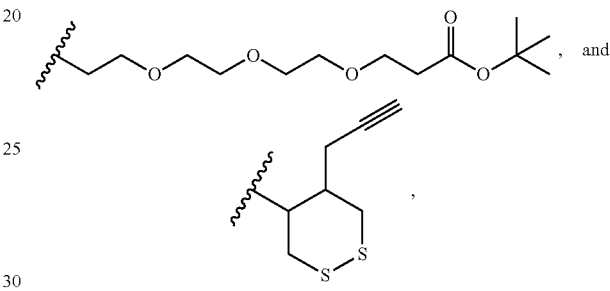, and where each R$^9$ C$_1$-C$_{20}$ alkyl is optionally substituted by 0 to 3 substituents independently selected from the group consisting of OH, —O—C$_1$-C$_{20}$ alkyl, —S—C(O)C$_1$-C$_6$ alkyl, and C(O)OC$_1$-C$_6$ alkyl; optionally R$^{1a}$ and R$^3$ are connected to form C$_1$-C$_6$ alkylene, C$_2$-C$_6$ alkenylene, —O—C$_1$-C$_6$ alkylene, or —O—C$_2$-C$_6$ alkenylene, such that where R$^{1a}$ and R$^3$ are connected to form —O—C$_1$-C$_6$ alkylene, or —O—C$_2$-C$_6$ alkenylene, said O is bound at the R$^3$ position; optionally R$^{2a}$ and R$^3$ are connected to form C$_1$-C$_6$ alkylene, C$_2$-C$_6$ alkenylene, —O—C$_1$-C$_6$ alkylene, or —O—C$_2$-C$_6$ alkenylene, such that where R$^{2a}$ and R$^3$ are connected to form —O—C$_1$-C$_6$ alkylene, or —O—C$_2$-C$_6$ alkenylene, said O is bound at the R$^3$ position; optionally R$^3$ and R$^{6a}$ are connected to form C$_1$-C$_6$ alkylene, C$_2$-C$_6$ alkenylene, —O—C$_1$-C$_6$ alkylene, or —O—C$_2$-C$_6$ alkenylene, such that where R$^3$ and R$^{6a}$ are connected to form —O—C$_1$-C$_6$ alkylene, or —O—C$_2$-C$_6$ alkenylene, said O is bound at the R$^3$ position; optionally R$^4$ and R$^5$ are connected to form C$_1$-C$_6$ alkylene, C$_2$-C$_6$ alkenylene, —O—C$_1$-C$_6$ alkylene, or —O—C$_2$-C$_6$ alkenylene, such that where R$^4$ and R$^5$ are connected to form —O—C$_1$-C$_6$ alkylene, or —O—C$_2$-C$_6$ alkenylene, said O is bound at the R$^5$ position; optionally R$^5$ and R$^6$ are connected to form —O—C$_1$-C$_6$ alkylene, —O—C$_2$-C$_6$ alkenylene, or —O—C$_2$-C$_6$ alkynylene, such that where R$^5$ and R$^6$ are connected to form —O—C$_1$-C$_6$ alkylene, —O—C$_2$-C$_6$ alkenylene, or —O—C$_2$-C$_6$ alkynylene, said O is bound at the R$^5$ position; optionally R$^7$ and R$^8$ are connected to form C$_1$-C$_6$ alkylene or C$_2$-C$_6$ alkenylene; and optionally R$^{7a}$ and R$^{8a}$ are connected to form C$_1$-C$_6$ alkylene or C$_2$-C$_6$ alkenylene; and provided that at least one of

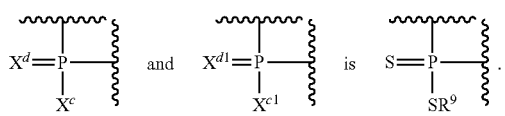

In embodiments, the disclosure relates to compounds of general structural formula (I), or pharmaceutically acceptable salts, hydrates, or solvates thereof. In specific embodiments, the disclosure relates to compounds of general structural formula (I), or pharmaceutically acceptable salts thereof.

In a first embodiment, Base[1] and Base[2] are each independently selected from the group consisting of

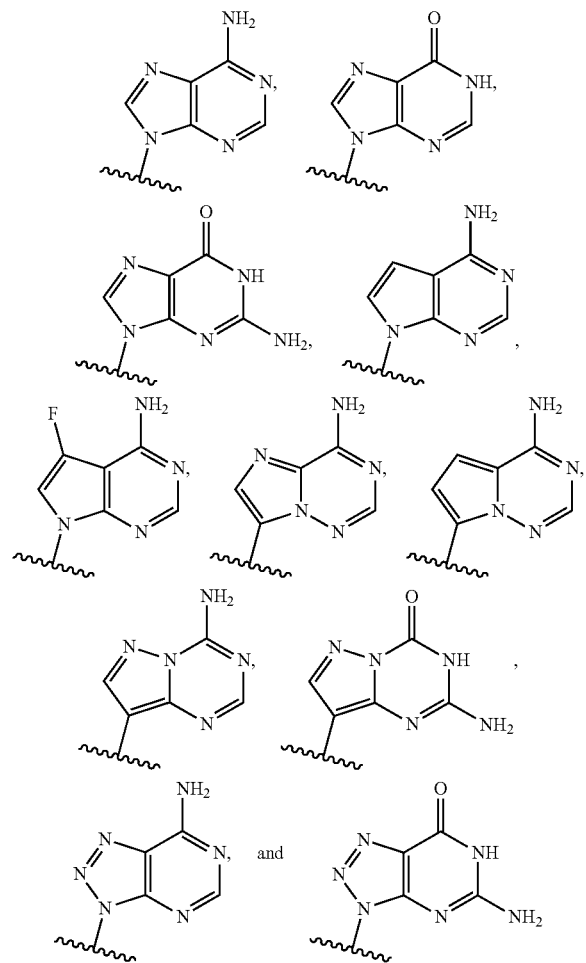

where Base[1] and Base[2] each may be independently substituted by 0-3 substituents $R^{10}$, where each $R^{10}$ is independently selected from the group consisting of F, Cl, I, Br, OH, SH, $NH_2$, $C_{1-3}$ alkyl, $C_{3-6}$ cycloalkyl, $O(C_{1-3}$ alkyl), $O(C_{3-6}$ cycloalkyl), $S(C_{1-3}$ alkyl), $S(C_{3-6}$ cycloalkyl), $NH(C_{1-3}$ alkyl), $NH(C_{3-6}$ cycloalkyl), $N(C_{1-3}$ alkyl)$_2$, and $N(C_{3-6}$ cycloalkyl)$_2$. In particular aspects, Base[1] and Base[2] are each independently selected from the group consisting of

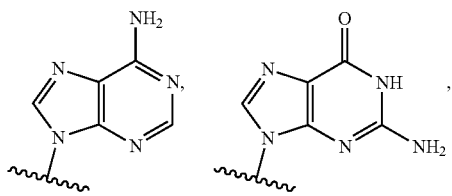

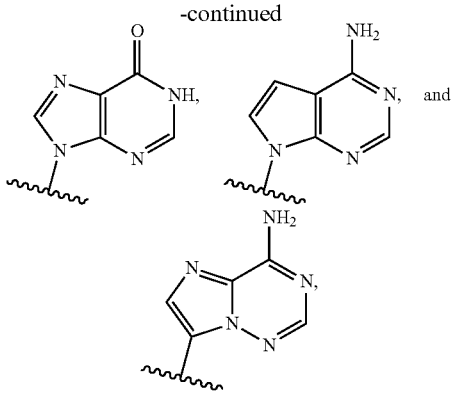

where Base[1] and Base[2] each may be independently substituted by 0-3 substituents $R^{10}$, where each $R^{10}$ is independently selected from the group consisting of F, Cl, I, Br, OH, SH, $NH_2$, $C_{1-3}$ alkyl, $C_{3-6}$ cycloalkyl, $O(C_{1-3}$ alkyl), $O(C_{3-6}$ cycloalkyl), $S(C_{1-3}$ alkyl), $S(C_{3-6}$ cycloalkyl), $NH(C_{1-3}$ alkyl), $NH(C_{3-6}$ cycloalkyl), $N(C_{1-3}$ alkyl)$_2$, and $N(C_{3-6}$ cycloalkyl)$_2$. In all aspects of this embodiment, all other groups are as provided in the general formula (I) above.

In a second embodiment, Y and $Y^a$ are each independently selected from the group consisting of —O— and —S—. In aspects of this embodiment, Y is —O—, and $Y^a$ is —O—. In additional aspects of this embodiment, Y is —O—, and $Y^a$ is —S—. In further aspects of this embodiment, Y is —S—, and $Y^a$ is —O—. In still further aspects of this embodiment, Y is —S—, and $Y^a$ is —S—. In this embodiment, all other groups are as provided in the general formula (I) above or in the first embodiment described above.

In a third embodiment, $X^a$ and $X^{a1}$ are each independently selected from the group consisting of —O—, —S—, and —CH$_2$—. In aspects of this embodiment, $X^a$ and $X^{a1}$ are each independendently selected from the group consisting of —O— and —S—. In this embodiment, all other groups are as provided in the general formula (I) above or in the first through second embodiments described above.

In a fourth embodiment, $X^b$ and $X^{b1}$ are each independently selected from the group consisting of —O—, —S—, and —CH$_2$—. In aspects of this embodiment, $X^b$ and $X^{b1}$ are each independendently selected from the group consisting of —O— and —S—. In this embodiment, all other groups are as provided in the general formula (I) above or in the first through third embodiments described above.

In a fifth embodiment, $X^c$ and $X^{c1}$ are each independently selected from the group consisting of —$OR^9$, —$SR^9$, and —$NR^9R^9$, where each $R^9$ is independently selected from the group consisting of H, $C_1$-$C_{20}$ alkyl,

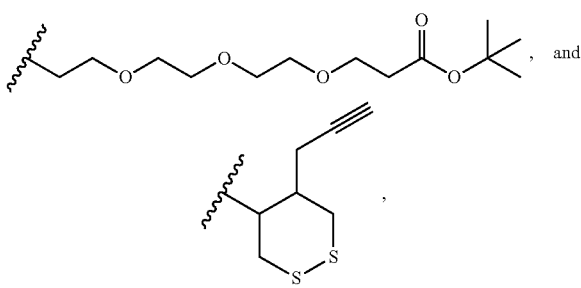

where each $R^9$ $C_1$-$C_{20}$ alkyl is optionally substituted by 0 to 3 substituents independently selected from the group consisting of OH, —O—$C_1$-$C_{20}$ alkyl, —S—C(O)$C_1$-$C_6$ alkyl, and C(O)O$C_1$-$C_6$ alkyl. In particular aspects, $X^c$ and $X^{c1}$ are each independently selected from the group consisting of —OH, —SH, In a sixth embodiment, $X^d$ and $X^{d1}$ are each independently selected from the group consisting of O and S. In this embodiment, all other groups are as provided in the general formula (I) above or in the first through fifth embodiments described above.

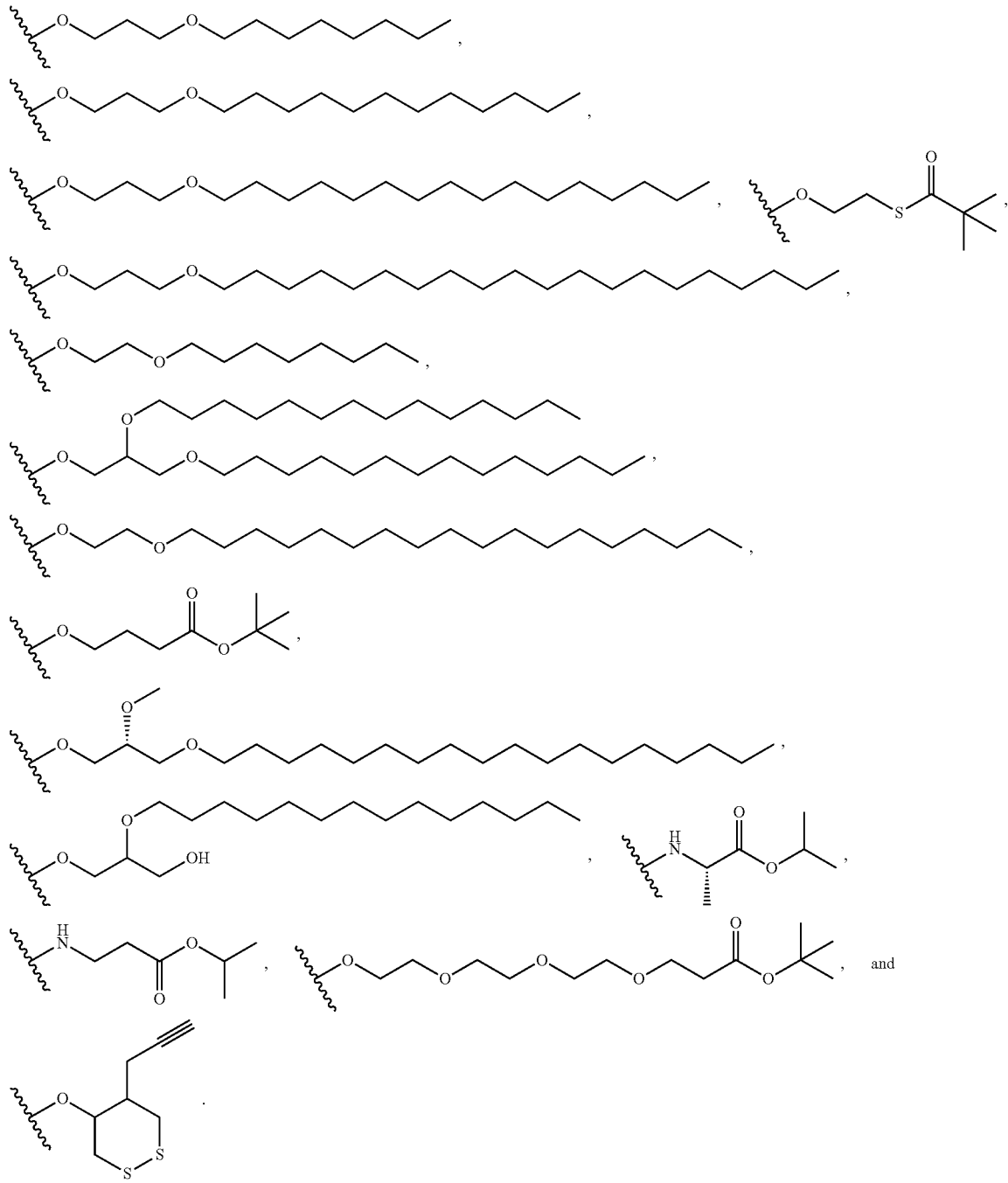

In more particular aspects, $X^c$ and $X^{c1}$ are each independently selected from the group consisting of —OH and —SH. In all aspects of this embodiment, all other groups are as provided in the general formula (I) above or in the first through fourth embodiment described above.

In a seventh embodiment, $R^1$ and $R^{1a}$ are each H. In this embodiment, all other groups are as provided in the general formula (I) above or in the first through sixth embodiments described above.

In an eighth embodiment, $R^2$ and $R^{2a}$ are each independently selected from the group consisting of H, F, Cl, I, Br, OH, CN, $N_3$, $C_1$-$C_6$ alkyl, and $C_1$-$C_6$ haloalkyl, where said $R^2$ and $R^{2a}$ $C_1$-$C_6$ alkyl or $C_1$-$C_6$ haloalkyl are substituted by 0 to 3 substituents selected from the group consisting of OH, CN, and $N_3$. In particular aspects, $R^2$ and $R^{2a}$ are each independently selected from the group consisting of H, F, Cl, I, Br, OH, CN, $N_3$, $CF_3$, $CH_3$, $CH_2OH$, and $CH_2CH_3$. In more particular aspects, $R^2$ and $R^{2a}$ are each independently selected from the group consisting of H, F, Cl, OH, CN, $N_3$, and $CH_3$. In even more particular aspects, $R^2$ and $R^{2a}$ are each independently selected from the group consisting of H, F, and OH. In even still more particular aspects, $R^2$ is H. In all aspects of this embodiment, all other groups are as provided in the general formula (I) above or in the first through seventh embodiments described above.

In a ninth embodiment, $R^3$ is selected from the group consisting H, F, Cl, I, Br, OH, CN, $N_3$, $C_1$-$C_6$ alkyl, and $C_1$-$C_6$ haloalkyl, where said $R^3$ $C_1$-$C_6$ alkyl or $C_1$-$C_6$ haloalkyl are substituted by 0 to 3 substituents selected from the group consisting of OH, CN, and $N_3$. In particular aspects, $R^3$ is selected from the group consisting of H, F, Cl, I, Br, OH, CN, $N_3$, $CF_3$, $CH_3$, $CH_2OH$, and $CH_2CH_3$. In more particular aspects, $R^3$ is selected from the group consisting of H, F, Cl, OH, CN, $N_3$, and $CH_3$. In even more particular aspects, $R^3$ is selected from the group consisting of H, F, and OH. In even still more particular aspects, $R^3$ is H. In all aspects of this embodiment, all other groups are as provided in the general formula (I) above or in the first through eighth embodiments described above.

In a tenth embodiment, $R^4$ and $R^{4a}$ are each independently selected from the group consisting of H, F, Cl, I, Br, CN, OH, $N_3$, $C_1$-$C_6$ alkyl, and $C_1$-$C_6$ haloalkyl, where said $R^4$ and $R^{4a}$, $C_1$-$C_6$ alkyl or $C_1$-$C_6$ haloalkyl are substituted by 0 to 3 substituents selected from the group consisting of OH, CN, and $N_3$. In particular aspects, $R^4$ and $R^{4a}$ are each independently selected from the group consisting of H, F, Cl, I, Br, OH, CN, $N_3$, $CF_3$, $CH_3$, $CH_2OH$, and $CH_2CH_3$. In more particular aspects, $R^4$ and $R^{4a}$ are each independently selected from the group consisting of H, F, Cl, OH, CN, $N_3$, and $CH_3$. In even more particular aspects, $R^4$ and $R^{4a}$ are each independently selected from the group consisting of H, F, and OH. In all aspects of this embodiment, all other groups are as provided in the general formula (I) above or in the first through ninth embodiments described above.

In an eleventh embodiment, $R^5$ is selected from the group consisting of H, F, I, Br, OH, CN, $N_3$, $C_1$-$C_6$ alkyl, and $C_1$-$C_6$ haloalkyl, where said $R^5$ $C_1$-$C_6$ alkyl or $C_1$-$C_6$ haloalkyl are substituted by 0 to 3 substituents selected from the group consisting of OH, CN, and $N_3$. In particular aspects, $R^5$ is selected from the group consisting of H, F, Cl, I, Br, OH, CN, $N_3$, $CF_3$, $CH_3$, $CH_2OH$, and $CH_2CH_3$. In more particular aspects, $R^5$ is selected from the group consisting of H, F, Cl, OH, CN, $N_3$, and $CH_3$. In even more particular aspects, $R^5$ is selected from the group consisting of H, F, and OH. In all aspects of this embodiment, all other groups are as provided in the general formula (I) above or in the first through tenth embodiments described above.

In a twelfth embodiment, $R^6$ and $R^{6a}$ are each independently selected from the group consisting of H, F, Cl, I, Br, OH, CN, $N_3$, $C_1$-$C_6$ alkyl, $C_2$-$C_6$ alkenyl, and $C_2$-$C_6$ alkynyl, where said $R^6$ and $R^{6a}$ $C_1$-$C_6$ alkyl, $C_2$-$C_6$ alkenyl, and $C_2$-$C_6$ alkynyl are substituted by 0 to 3 substituents selected from the group consisting of F, Cl, Br, I, OH, CN, and $N_3$. In particular aspects, $R^6$ and $R^{6a}$ are each independently selected from the group consisting of H, F, Cl, I, Br, OH, CN, $N_3$, $CF_3$, $CH_3$, $CH_2OH$, $CH_2CH_3$, —CH=$CH_2$, —C≡CH, and —C≡C—CH. In more particular aspects, $R^6$ and $R^{6a}$ are each independently selected from the group consisting of H, F, CN, $N_3$, $CH_3$, —CH=$CH_2$, and —C≡CH. In even more particular aspects, $R^6$ and $R^{6a}$ are each H. In all aspects of this embodiment, all other groups are as provided in the general formula (I) above or in the first through eleventh embodiments described above.

In a thirteenth embodiment, $R^7$ and $R^{7a}$ are each independently selected from the group consisting of H, $C_1$-$C_6$ alkyl, and $C_1$-$C_6$ haloalkyl, where said $R^7$ and $R^{7a}$ $C_1$-$C_6$ alkyl or $C_1$-$C_6$ haloalkyl are substituted by 0 to 3 substituents selected from the group consisting of OH, CN, and $N_3$. In particular aspects, $R^7$ and $R^{7a}$ are each independently selected from the group consisting of H, $CF_3$, $CH_3$, and $CH_2CH_3$. In more particular aspects, $R^7$ and $R^{7a}$ are each H. In all aspects of this embodiment, all other groups are as provided in the general formula (I) above or in the first through twelfth embodiments described above.

In a fourteenth embodiment, $R^8$ and $R^{8a}$ are each independently selected from the group consisting of H, $C_1$-$C_6$ alkyl, and $C_1$-$C_6$ haloalkyl, where said $R^8$ and $R^{8a}$ $C_1$-$C_6$ alkyl or $C_1$-$C_6$ haloalkyl are substituted by 0 to 3 substituents selected from the group consisting of OH, CN, and $N_3$. In particular aspects, $R^8$ and $R^{8a}$ are each independently selected from the group consisting of H, $CF_3$, $CH_3$, and $CH_2CH_3$. In more particular aspects, $R^8$ and $R^{8a}$ are each H. In all aspects of this embodiment, all other groups are as provided in the general formula (I) above or in the first through thirteenth embodiments described above.

In a fifteenth embodiment, $R^{1a}$ and $R^3$ are connected to form $C_1$-$C_6$ alkylene, $C_2$-$C_6$ alkenylene, —O—$C_1$-$C_6$ alkylene, or —O—$C_2$-$C_6$ alkenylene, such that where $R^{1a}$ and $R^3$ are connected to form —O—$C_1$-$C_6$ alkylene or —O—$C_2$-$C_6$ alkenylene, said O is bound at the $R^3$ position. In this embodiment, all other groups are as provided in the general formula (I) above or in the first through fourteenth embodiments described above.

In a sixteenth embodiment, $R^{2a}$ and $R^3$ are connected to form $C_1$-$C_6$ alkylene, $C_2$-$C_6$ alkenylene, —O—$C_1$-$C_6$ alkylene, or —O—$C_2$-$C_6$ alkenylene, such that where $R^{2a}$ and $R^3$ are connected to form —O—$C_1$-$C_6$ alkylene or —O—$C_2$-$C_6$ alkenylene, said O is bound at the $R^3$ position. In this embodiment, all other groups are as provided in the general formula (I) above or in the first through fourteenth embodiments described above.

In a seventeenth embodiment, $R^3$ and $R^{6a}$ are connected to form $C_2$-$C_6$ alkylene, $C_2$-$C_6$ alkenylene, —O—$C_1$-$C_6$ alkylene, or —O—$C_2$-$C_6$ alkenylene such that where $R^3$ and $R^{6a}$ are connected to form —O—$C_1$-$C_6$ alkylene or —O—$C_2$-$C_6$ alkenylene, said O is bound at the $R^3$ position. In this embodiment, all other groups are as provided in the general formula (I) above or in the first through fourteenth embodiments described above.

In an eighteenth embodiment, $R^4$ and $R^5$ are connected to form $C_1$-$C_6$ alkylene, $C_2$-$C_6$ alkenylene, —O—$C_1$-$C_6$ alkylene, or —O—$C_2$-$C_6$ alkenylene, such that where $R^4$ and $R^5$ are connected to form —O—$C_1$-$C_6$ alkylene or —O—$C_2$-$C_6$ alkenylene, said O is bound at the $R^5$ position. In this embodiment, all other groups are as provided in the general formula (I) above or in the first through fourteenth embodiments described above.

In a nineteenth embodiment, $R^5$ and $R^6$ are connected to form $C_1$-$C_6$ alkylene, $C_2$-$C_6$ alkenylene, —O—$C_1$-$C_6$ alkylene, or —O—$C_2$-$C_6$ alkenylene, such that where $R^5$ and $R^6$ are connected to form —O—$C_1$-$C_6$ alkylene or —O—$C_2$-$C_6$ alkenylene, said O is bound at the $R^5$ position. In this embodiment, all other groups are as provided in the general formula (I) above or in the first through fourteenth embodiments described above.

In a twentieth embodiment, $R^7$ and $R^8$ are connected to form $C_1$-$C_6$ alkylene or $C_2$-$C_6$ alkenylene. In this embodiment, all other groups are as provided in the general formula (I) above or in the first through fourteenth embodiments described above.

In a twenty-first embodiment, $R^{7a}$ and $R^{8a}$ are connected to form $C_1$-$C_6$ alkylene or $C_2$-$C_6$ alkenylene. In this embodiment, all other groups are as provided in the general formula (I) above or in the first through fourteenth embodiments described above.

In a twenty-second embodiment, Base$^1$ and Base$^2$ are each independently selected from the group consisting of

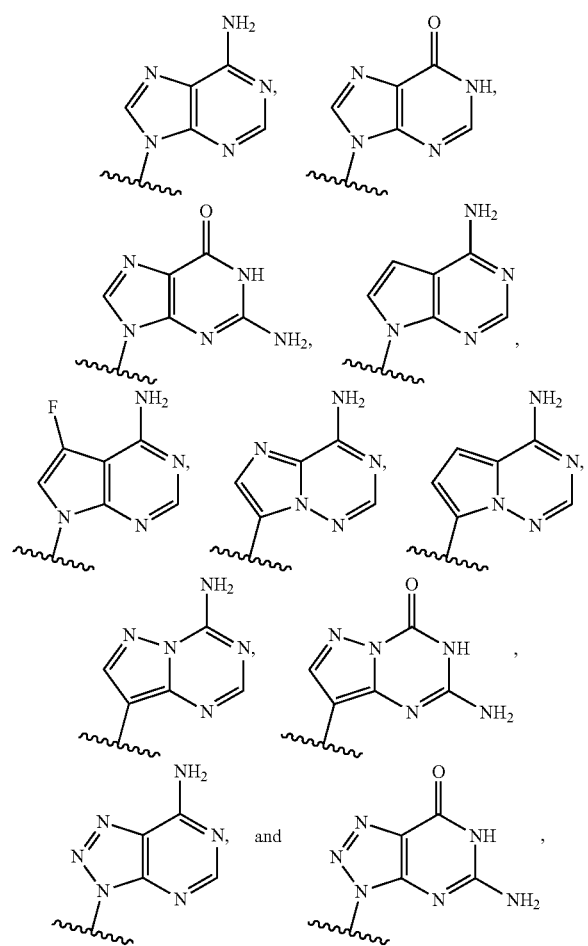

where Base$^1$ and Base$^2$ each may be independently substituted by 0-3 substituents $R^{10}$, where each $R^{10}$ is independently selected from the group consisting of F, Cl, I, Br, OH, SH, $NH_2$, $C_{1-3}$ alkyl, $C_{3-6}$ cycloalkyl, $O(C_{1-3}$ alkyl), $O(C_{3-6}$ cycloalkyl), $S(C_{1-3}$ alkyl), $S(C_{3-6}$ cycloalkyl), $NH(C_{1-3}$ alkyl), $NH(C_{3-6}$ cycloalkyl), $N(C_{1-3}$ alkyl)$_2$, and $N(C_{3-6}$ cycloalkyl)$_2$; Y and Y$^a$ are each independently selected from the group consisting of —O— and —S—; X$^a$ and X$^{a1}$ are each independently selected from the group consisting of O and S; X$^b$ and X$^{b1}$ are each independently selected from the group consisting of O and S; X$^c$ and X$^{c1}$ are each independently selected from the group consisting of SR$^9$, OR$^9$, and NR$^9$R$^9$; X$^d$ and X$^{d1}$ are each independently selected from the group consisting of O and S; R$^1$ and R$^{1a}$ are each H; R$^2$ and R$^{2a}$ are each independently selected from the group consisting of H, F, Cl, Br, I, OH, CN, N$_3$, $C_1$-$C_6$ alkyl, and $C_1$-$C_6$ haloalkyl, where said R$^2$ and R$^{2a}$ $C_1$-$C_6$ alkyl or $C_1$-$C_6$ haloalkyl are substituted by 0 to 3 substituents selected from the group consisting of OH, CN, and N$_3$; R$^3$ is selected from the group consisting of H, F, Cl, Br, I, OH, CN, N$_3$, $C_1$-$C_6$ alkyl, and $C_1$-$C_6$ haloalkyl, where said R$^3$ $C_1$-$C_6$ alkyl or $C_1$-$C_6$ haloalkyl are substituted by 0 to 3 substituents selected from the group consisting of OH, CN, and N$_3$; R$^4$ and R$^{4a}$ are each independently selected from the group consisting of H, F, Cl, I, Br, CN, OH, N$_3$, $C_1$-$C_6$ alkyl, and $C_1$-$C_6$ haloalkyl, where said R$^4$ and R$^{4a}$ $C_1$-$C_6$ alkyl or $C_1$-$C_6$ haloalkyl are substituted by 0 to 3 substituents selected from the group consisting of OH, CN, and N$_3$; R$^5$ is selected from the group consisting of H, F, Cl, Br, I, OH, N$_3$, $C_1$-$C_6$ alkyl, and $C_1$-$C_6$ haloalkyl, where said R$^5$ $C_1$-$C_6$ alkyl or $C_1$-$C_6$ haloalkyl are substituted by 0 to 3 substituents selected from the group consisting of F, Cl, Br, I, OH, CN, and N$_3$; R$^6$ and R$^{6a}$ are each independently selected from the group consisting of H, F, Cl, I, Br, OH, CN, N$_3$, $C_1$-$C_6$ alkyl, $C_2$-$C_6$ alkenyl, and $C_2$-$C_6$ alkynyl, where said R$^6$ and R$^{6a}$ $C_1$-$C_6$ alkyl, $C_2$-$C_6$ alkenyl, and $C_2$-$C_6$ alkynyl are substituted by 0 to 3 substituents selected from the group consisting of F, Cl, Br, I, OH, CN, and N$_3$; R$^7$ and R$^{7a}$ are each independently selected from the group consisting of H, $C_1$-$C_6$ alkyl, and $C_1$-$C_6$ haloalkyl, where said R$^7$ and R$^{7a}$ $C_1$-$C_6$ alkyl or $C_1$-$C_6$ haloalkyl are substituted by 0 to 3 substituents selected from the group consisting of OH, CN, and N$_3$; R$^8$ and R$^{8a}$ are each independently selected from the group consisting of H, $C_1$-$C_6$ alkyl, and $C_1$-$C_6$ haloalkyl, where said R$^8$ and R$^{8a}$ $C_1$-$C_6$ alkyl or $C_1$-$C_6$ haloalkyl are substituted by 0 to 3 substituents selected from the group consisting of OH, CN, and N$_3$; each R$^9$ is independently selected from the group consisting of H, $C_1$-$C_6$ alkyl,

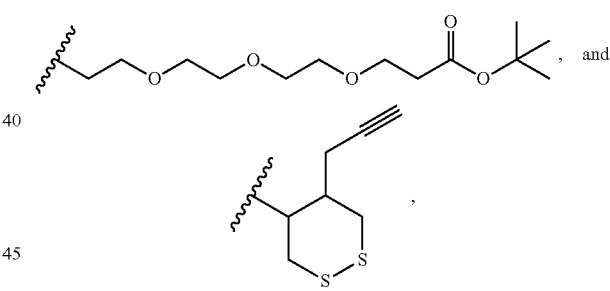

where each R$^9$ $C_1$-$C_6$ alkyl is optionally substituted by 1 to 2 substituents independently selected from the group consisting of OH, —O—$C_1$-$C_{20}$ alkyl, —S—C(O)$C_1$-$C_6$ alkyl, and —C(O)O$C_1$-$C_6$ alkyl; optionally R$^3$ and R$^{6a}$ are connected to form $C_2$-$C_6$ alkylene, $C_2$-$C_6$ alkenylene, —O—$C_1$-$C_6$ alkylene, or —O—$C_2$-$C_6$ alkenylene, such that where R$^3$ and R$^{6a}$ are connected to form —O—$C_1$-$C_6$ alkylene or —O—$C_2$-$C_6$ alkenylene, said O is bound at the R$^3$ position; and optionally R$^5$ and R$^6$ are connected to form $C_1$-$C_6$ alkylene, $C_2$-$C_6$ alkenylene, —O—$C_1$-$C_6$ alkylene, or —O—$C_2$-$C_6$ alkenylene, such that where R$^5$ and R$^6$ are connected to form —O—$C_1$-$C_6$ alkylene or —O—$C_2$-$C_6$ alkenylene, said O is bound at the R$^5$ position. In this embodiment, all other groups are as provided in the general formula (I) above or in the first through fourteenth embodiments described above.

In a twenty-third embodiment, Base' and Base$^2$ are each independently selected from the group consisting of

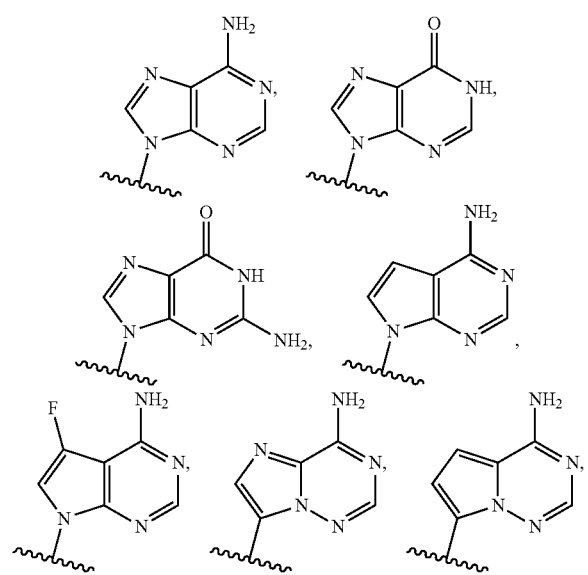
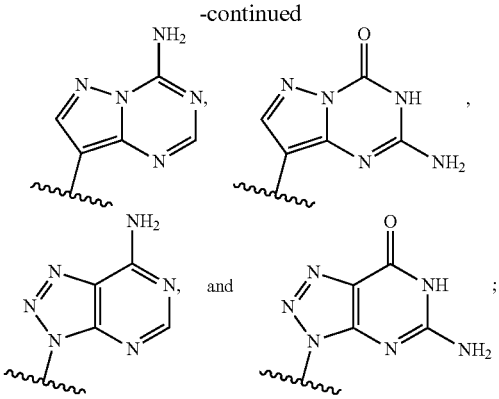
and $Y^a$ are each independently selected from the group consisting of —O— and —S—; $X^a$ and $X^{a1}$ are each independently selected from the group consisting of O and S; $X^b$ and $X^{b1}$ are each independently selected from the group consisting of O and S; $X^c$ and $X^{c1}$ are each independently selected from the group consisting of —OH, —SH,
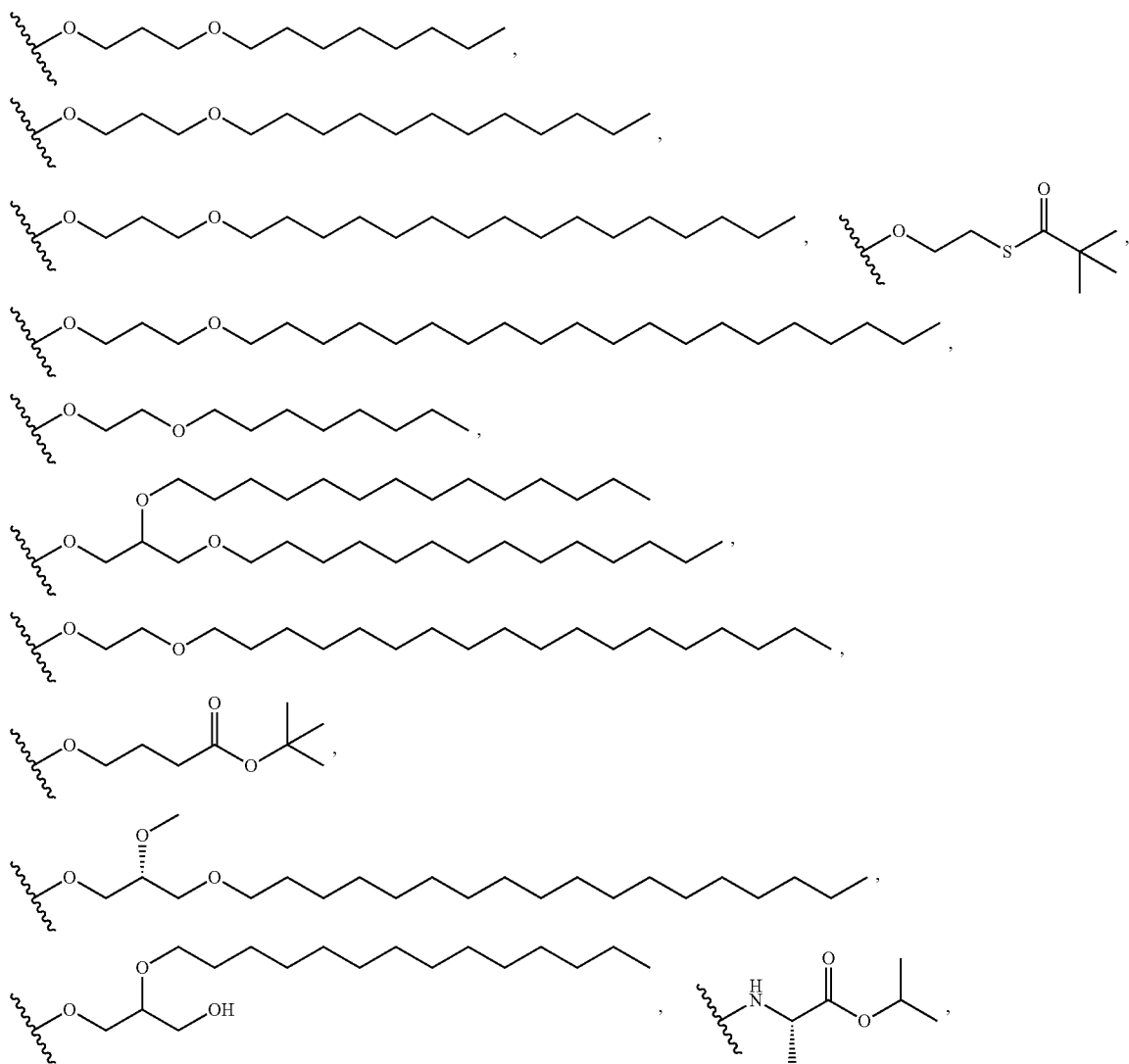

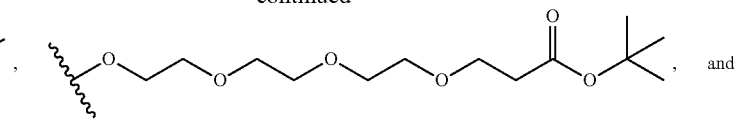

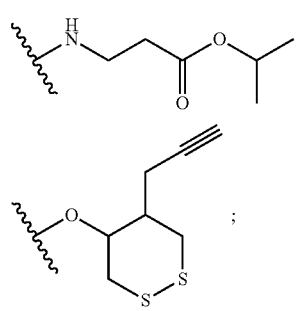

$X^d$ and $X^{d1}$ are each independently selected from the group consisting of O and S; $R^1$ and $R^{1a}$ are each H; $R^2$ and $R^{2a}$ are each independently selected from the group consisting of H, F, Cl, I, Br, OH, CN, $N_3$, $CF_3$, $CH_3$, $CH_2OH$, and $CH_2CH_3$; $R^3$ is selected from the group consisting of H, F, Cl, I, Br, OH, CN, $N_3$, $CF_3$, $CH_3$, $CH_2OH$, and $CH_2CH_3$; $R^4$ and $R^{4a}$ are each independently selected from the group consisting of H, F, Cl, I, Br, OH, CN, $N_3$, $CF_3$, $CH_3$, $CH_2OH$, and $CH_2CH_3$; $R^5$ is selected from the group consisting of H, F, Cl, I, Br, OH, CN, $N_3$, $CF_3$, $CH_3$, $CH_2OH$, and $CH_2CH_3$; $R^6$ and $R^{6a}$ are each independently selected from the group consisting of H, F, Cl, I, Br, OH, CN, $N_3$, $CF_3$, $CH_3$, $CH_2OH$, $CH_2CH_3$, —CH=$CH_2$, —C≡CH, and —C≡C—CH; $R^7$ and $R^{7a}$ are each independently selected from the group consisting of H, $CF_3$, $CH_3$, and $CH_2CH_3$; $R^8$ and $R^{8a}$ are each independently selected from the group consisting of H, $CF_3$, $CH_3$, and $CH_2CH_3$; optionally $R^3$ and $R^{6a}$ are connected to $C_2$-$C_6$ alkylene, $C_2$-$C_6$ alkenylene, —O—$C_1$-$C_6$ alkylene, or —O—$C_2$-$C_6$ alkenylene, such that where $R^3$ and $R^{6a}$ are connected to form —O—$C_1$-$C_6$ alkylene or —O—$C_2$-$C_6$ alkenylene, said O is bound at the $R^3$ position; and optionally $R^5$ and $R^6$ are connected to form $C_1$-$C_6$ alkylene, $C_2$-$C_6$ alkenylene, —O—$C_1$-$C_6$ alkylene, or —O—$C_2$-$C_6$ alkenylene, such that where $R^5$ and $R^6$ are connected to form —O—$C_1$-$C_6$ alkylene or —O—$C_2$-$C_6$ alkenylene, said O is bound at the $R^5$ position. In this embodiment, all other groups are as provided in the general formula (I) above or in the first through fourteenth embodiments described above.

In a twenty-fourth embodiment, Base$^1$ and Base$^2$ are each independently selected from the group consisting of

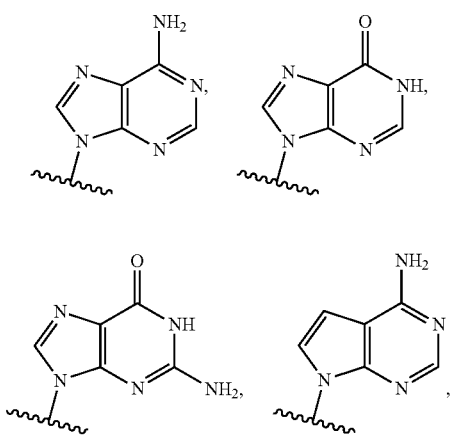

Y and $Y^a$ are each independently selected from the group consisting of —O— and —S—; $X^a$ and $X^{a1}$ are each O; $X^b$ and $X^{b1}$ are each 0; $X^c$ and $X^{c1}$ are each independently selected from the group consisting of —OH, and —SH; $X^d$ and $X^{d1}$ are each independently selected from the group consisting of O and S; $R^1$ and $R^{1a}$ are each H; $R^2$ and $R^{2a}$ are each independently selected from the group consisting of H, F, Cl, OH, CN, $N_3$, and $CH_3$; $R^3$ is selected from the group consisting of H, F, Cl, OH, CN, $N_3$, and $CH_3$; $R^4$ and $R^{4a}$ are each independently selected from the group consisting of H, F, Cl, OH, CN, $N_3$, and $CH_3$; $R^5$ is selected from the group consisting of H, F, Cl, OH, CN, $N_3$, and $CH_3$; $R^6$ and $R^{6a}$ are each independently selected from the group consisting of H, F, CN, $N_3$, $CH_3$, —CH=$CH_2$, and —C≡CH; $R^7$ and $R^{7a}$ are each H; $R^8$ and $R^{8a}$ are each H; optionally $R^3$ and $R^{6a}$ are connected to form —O—$C_1$-$C_6$ alkylene or —O—$C_2$-$C_6$ alkenylene, such that O is bound at the $R^3$ position; and optionally $R^5$ and $R^6$ are connected to form $C_1$-$C_6$ alkylene, $C_2$-$C_6$ alkenylene, —O—$C_1$-$C_6$ alkylene, or —O—$C_2$-$C_6$ alkenylene, such that where $R^5$ and $R^6$ are connected to form —O—$C_1$-$C_6$ alkylene or —O—$C_2$-$C_6$ alkenylene, said O is bound at the $R^5$ position. In this embodiment, all other groups are as provided in the general formula (I) above or in the first through fourteenth embodiments described above.

In a twenty-fifth embodiment, Base$^1$ and Base$^2$ are each independently selected from the group consisting of

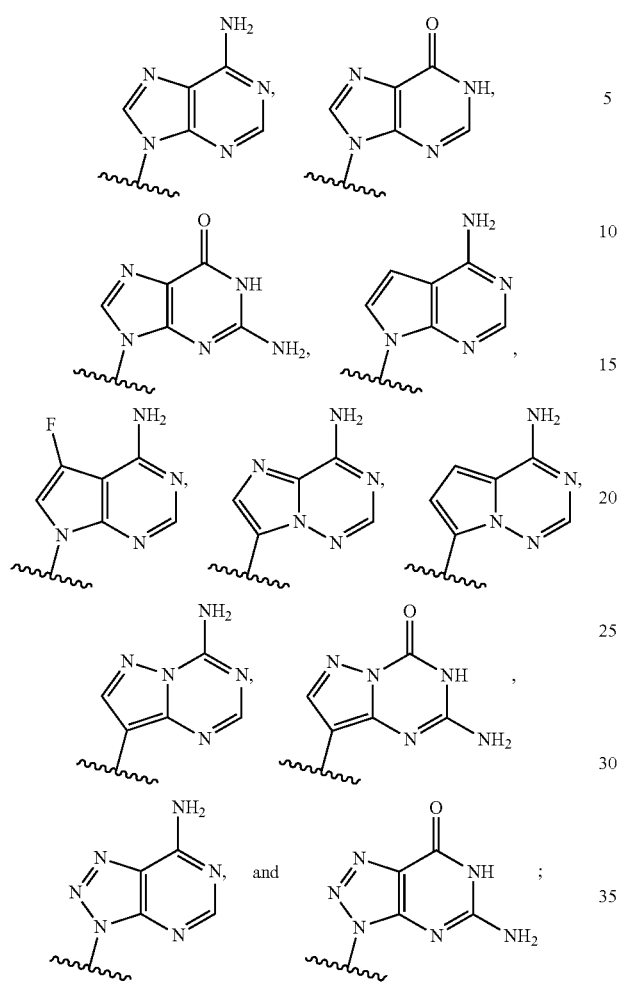

Y and $Y^a$ are each independently selected from the group consisting of —O— and —S—; $X^a$ and $X^{a1}$ are each 0; $X^b$ and $X^{b1}$ are each 0; $X^c$ and $X^{c1}$ are each independently selected from the group consisting of —OH and —SH; $X^d$ and $X^{d1}$ are each independently selected from the group consisting of O and S; $R^1$ and $R^{1a}$ are each H; $R^2$ and $R^{2a}$ are each independently selected from the group consisting of H, F, Cl, OH, CN, $N_3$, and $CH_3$; $R^3$ is selected from the group consisting of H, F, Cl, OH, CN, $N_3$, and $CH_3$; $R^4$ and $R^{4a}$ are each independently selected from the group consisting of H, F, Cl, OH, CN, $N_3$, and $CH_3$; $R^5$ is selected from the group consisting of H, F, Cl, OH, CN, $N_3$, and $CH_3$; $R^6$ and $R^{6a}$ are each independently selected from the group consisting of H, F, CN, $N_3$, $CH_3$, —CH=$CH_2$, and —C≡CH; $R^7$ and $R^{7a}$ are each H; $R^8$ and $R^{8a}$ are each H; optionally $R^3$ and $R^{6a}$ are connected to form —O—$C_1$-$C_6$ alkylene or —O—$C_2$-$C_6$ alkenylene, such that where $R^3$ and $R^{6a}$ are connected to form —O—$C_1$-$C_6$ alkylene or —O—$C_2$-$C_6$ alkenylene, said 0 is bound at the $R^3$ position; and optionally $R^5$ and $R^6$ are connected to form $C_1$-$C_6$ alkylene, $C_2$-$C_6$ alkenylene, —O—$C_1$-$C_6$ alkylene, or —O—$C_2$-$C_6$ alkenylene, such that where $R^5$ and $R^6$ are connected to form —O—$C_1$-$C_6$ alkylene or —O—$C_2$-$C_6$ alkenylene, said O is bound at the $R^5$ position. In this embodiment, all other groups are as provided in the general formula (I) above or in the first through fourteenth embodiments described above.

In a twenty-sixth embodiment, Base¹ and Base² are each independently selected from the group consisting of

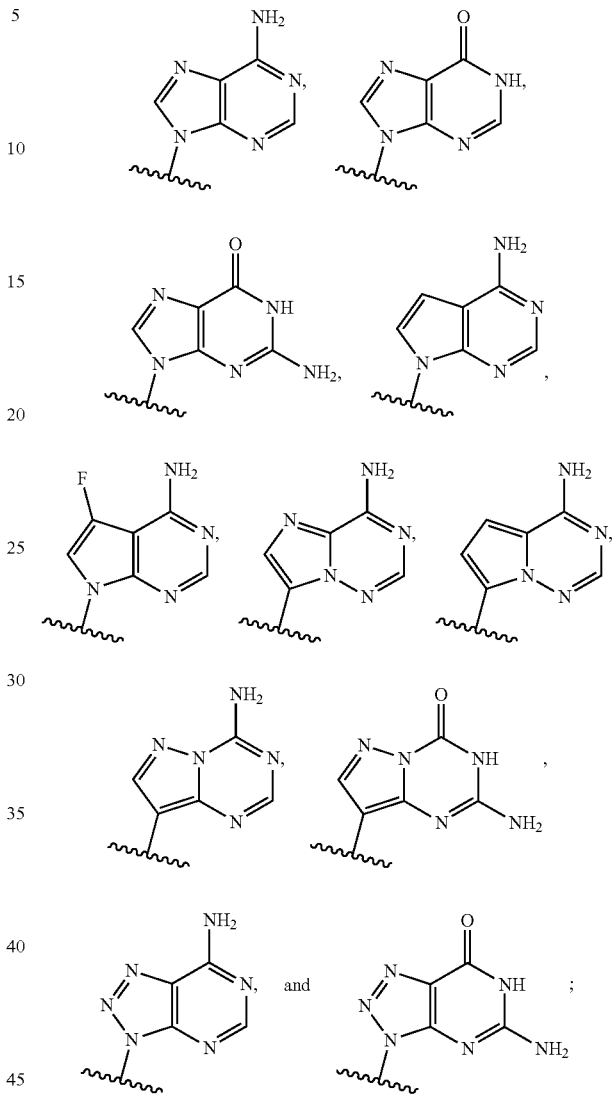

Y and $Y^a$ are each independently selected from the group consisting of —O— and —S—; $X^a$ and $X^{a1}$ are each 0; $X^b$ and $X^{b1}$ are each 0; $X^c$ and $X^{c1}$ are each independently selected from the group consisting of SH and OH; $X^d$ and $X^{d1}$ are each independently selected from the group consisting of O and S; $R^1$ and $R^{1a}$ are each H; $R^2$ and $R^{2a}$ are each independently selected from the group consisting of H, F, and OH; $R^3$ is selected from the group consisting of H, F, and OH; $R^4$ and $R^{4a}$ are each independently selected from the group consisting of H, F, and OH; $R^5$ is selected from the group consisting of H, F, and OH; $R^6$ and $R^{6a}$ are each H; $R^7$ and $R^{7a}$ are each H; $R^8$ and $R^{8a}$ are each H; and optionally $R^3$ and $R^{6a}$ are connected to form —O—$C_1$-$C_6$ alkylene or —O—$C_2$-$C_6$ alkenylene, such that where $R^3$ and $R^{6a}$ are connected to form —O—C alkylene or —O—$C_2$-$C_6$ alkenylene, said O is bound at the $R^3$ position. In this embodiment, all other groups are as provided in the general formula (I) above or in the first through fourteenth embodiments described above.

In a twenty-seventh embodiment, Base$^1$ and Base$^2$ are each independently selected from the group consisting of

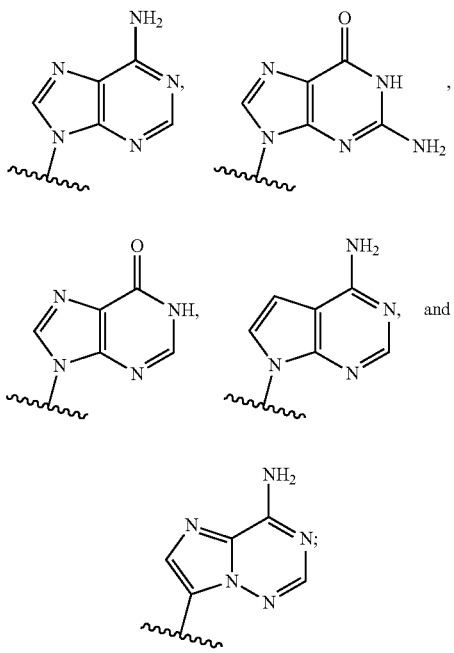

Y and Y$^a$ are each independently selected from the group consisting of —O— and —S—; X$^a$ and X$^{a1}$ are each independently O; X$^b$ and X$^{b1}$ are each independently O; X$^c$ and X$^{c1}$ are each independently selected from the group consisting of —SH and —OH; X$^d$ and X$^{d1}$ are each independently selected from the group consisting of O and S; R$^2$ and R$^{2a}$ are each H; R$^2$ is H; R$^{2a}$ is selected from the group consisting of H, F, and OH; R$^3$ is selected from the group consisting of H, F, and OH; R$^4$ is selected from the group consisting of H, F, and OH; R$^{4a}$ is H; R$^5$ is selected from the group consisting of H, F, and OH; R$^6$ and R$^{6a}$ are each H; R$^7$ and R$^{7a}$ are each H; and R$^8$ and R$^{8a}$ are each H. In this embodiment, all other groups are as provided in the general formula (I) above or in the first through fourteenth embodiments described above.

In a twenty-eighth embodiment, Base$^1$ and Base$^2$ are each independently selected from the group consisting of

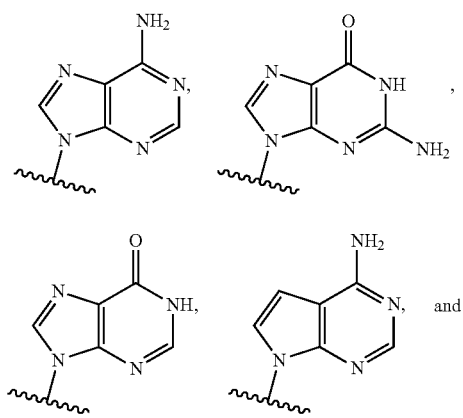

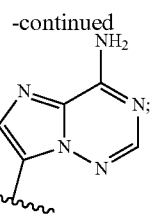

Y and Y$^a$ are each independently selected from the group consisting of —O— and —S—; X$^a$ and X$^{a1}$ are each independently O; X$^b$ and X$^{b1}$ are each independently O; X$^c$ and X$^{c1}$ are each independently selected from the group consisting of —SH and —OH; X$^d$ and X$^{d1}$ are each independently selected from the group consisting of O and S; R$^1$ and R$^{1a}$ are each H; R$^2$ is H; R$^{2a}$ is selected from the group consisting of H, F, and OH; R$^3$ is selected from the group consisting of H, F, and OH; R$^4$ is selected from the group consisting of H, F, and OH; R$^{4a}$ is H; R$^5$ is selected from the group consisting of H, F, and OH; R$^6$ and R$^{6a}$ are each H; R$^7$ and R$^{7a}$ are each H; and R$^8$ and R$^{8a}$ are each H; and R$^3$ and R$^{6a}$ are connected to form —O—C$_1$-C$_6$ alkylene or —O—C$_2$-C$_6$ alkenylene, such that where R$^3$ and R$^{6a}$ are connected to form —O—C$_1$-C$_6$ alkylene or —O—C$_2$-C$_6$ alkenylene, said O is bound at the R$^3$ position. In this embodiment, all other groups are as provided in the general formula (I) above or in the first through fourteenth embodiments described above.

A twenty-ninth embodiment relates to a pharmaceutical composition, said pharmaceutical composition comprising (a) a compound according to any one of general formula (I) above or the first through twenty-eighth embodiments described above or a pharmaceutically acceptable salt thereof; and (b) a pharmaceutically acceptable carrier.

A thirtieth embodiment relates to methods of inducing an immune response in a subject, comprising administering a therapeutically effective amount of a compound according to any one of general formula (I) above or the first through twenty-eighth embodiments described above or a pharmaceutically acceptable salt thereof to the subject.

A thirty-first embodiment relates to methods of inducing an immune response in a subject, comprising administering a therapeutically effective amount of a composition according to the twenty-ninth embodiment described above to the subject.

A thirty-second embodiment relates to methods of inducing a STING-dependent type I interferon production in a subject, comprising administering a therapeutically effective amount of a compound according to any one of general formula (I) above or the first through twenty-eighth embodiments described above or a pharmaceutically acceptable salt thereof to the subject.

A thirty-third embodiment relates to methods of inducing STING-dependent type I interferon production in a subject, comprising administering a therapeutically effective amount of a composition according to the twenty-ninth embodiment described above to the subject.

A thirty-fourth embodiment relates to methods of inducing STING-dependent cytokine production in a subject, comprising administering a therapeutically effective amount of a compound according to any one of general formula (I) above or the first through twenty-eighth embodiments described above or a pharmaceutically acceptable salt thereof to the subject.

A thirty-fifth embodiment relates to methods of inducing a STING-dependent cytokine production in a subject, comprising administering a therapeutically effective amount of a composition according to the twenty-ninth embodiment described above to the subject.

In each embodiment described herein, variables $Base^1$, $Base^2$, Y, $Y^a$, $X^a$, $X^{a1}$, $X^b$, $X^{b1}$, $X^c$, $X^{c1}$, $X^d$, $X^{d1}$, $R^1$, $R^{1a}$, $R^2$, $R^{2a}$, $R^3$, $R^4$, $R^{4a}$, $R^5$, $R^6$, $R^{6a}$, $R^7$, $R^{7a}$, $R^8$, $R^{8a}$, and $R^9$ of general formula (I), and the various aspects thereof, are each selected independently from each other.

A thirty-sixth embodiment relates to a compound selected from the group consisting of

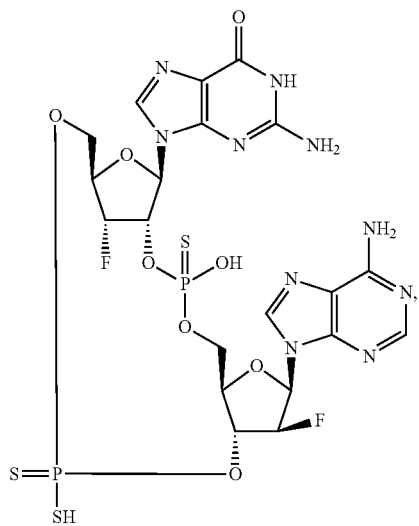

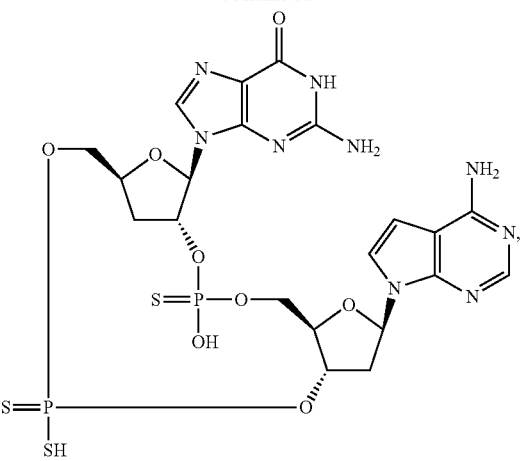

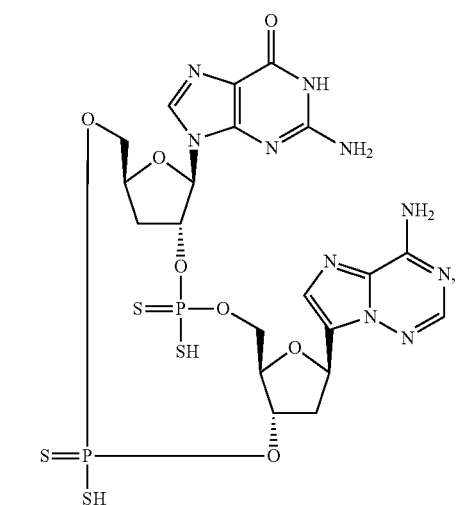

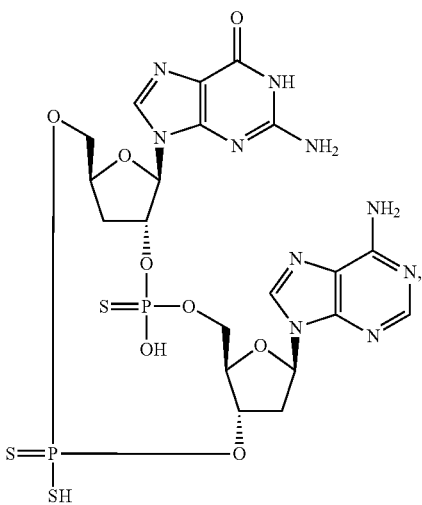

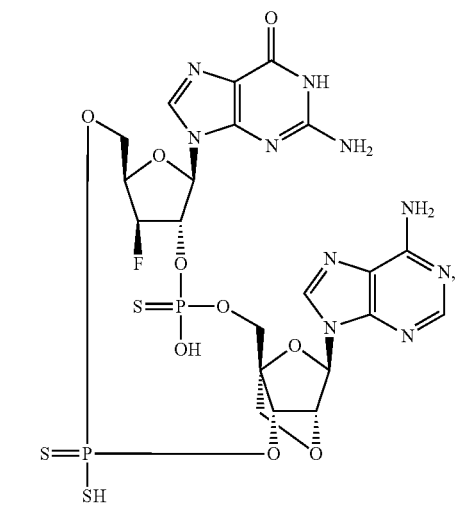

27
-continued
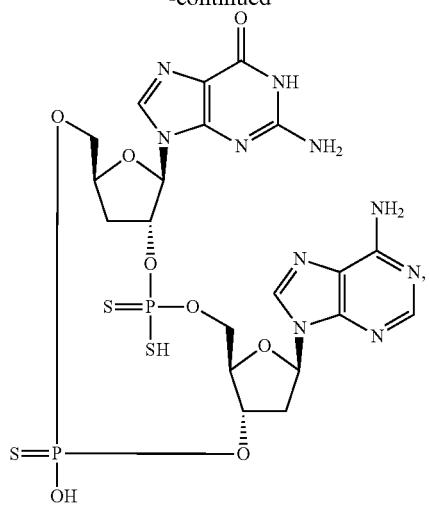
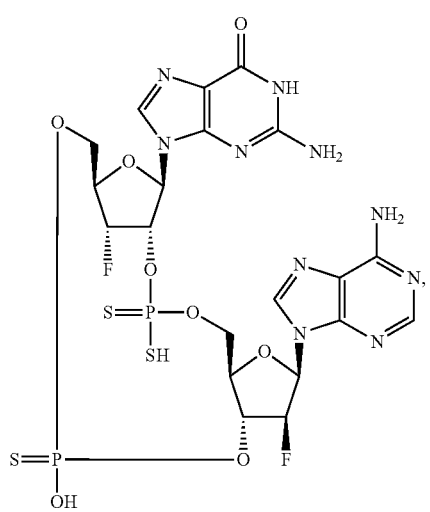
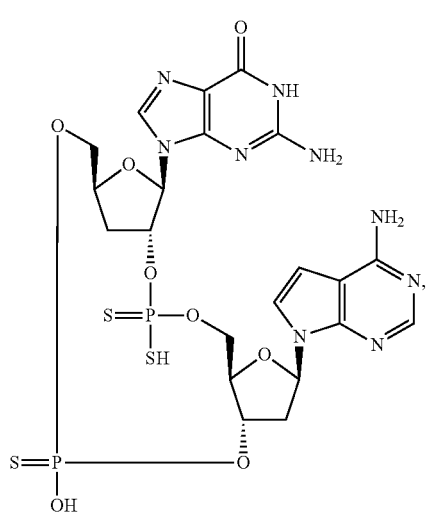
28
-continued
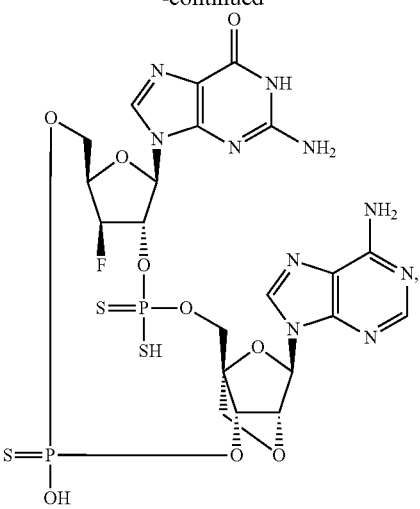
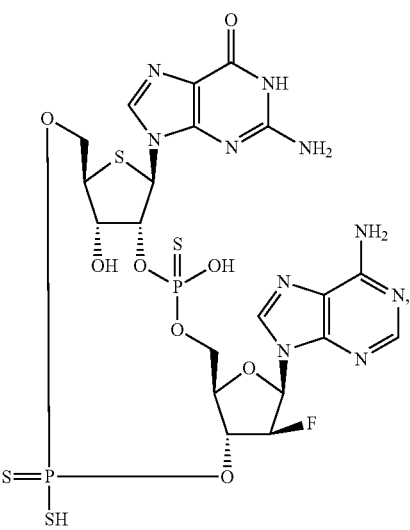
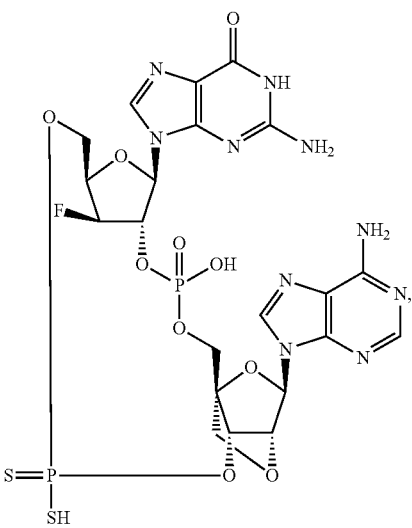

-continued
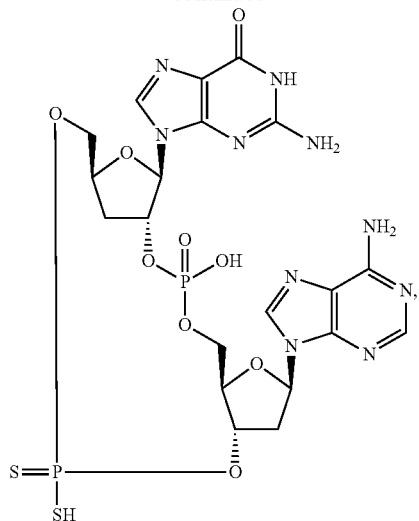
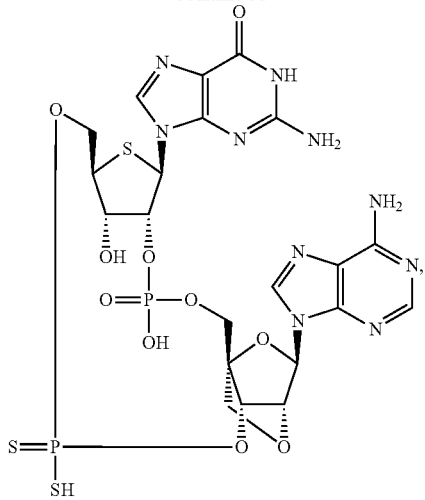
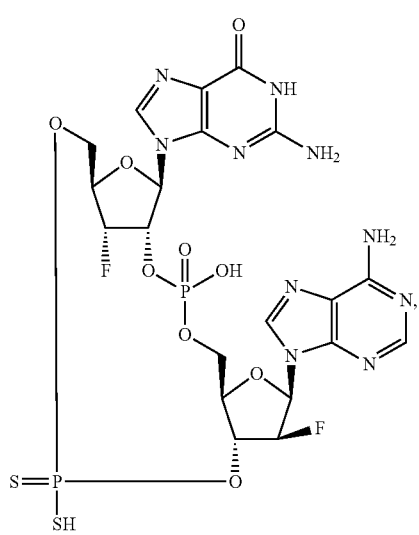
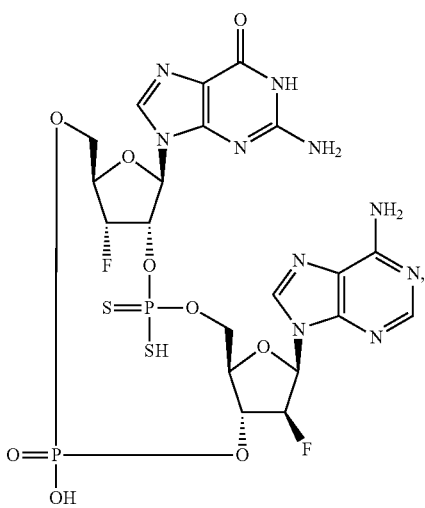
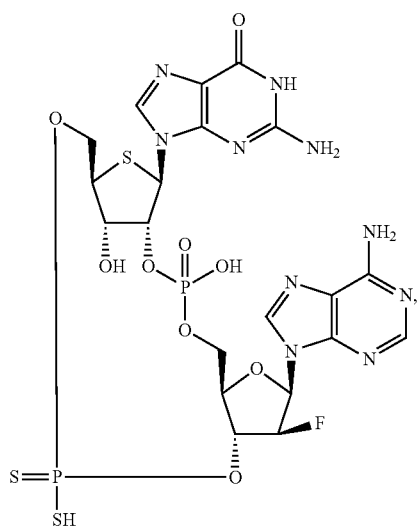
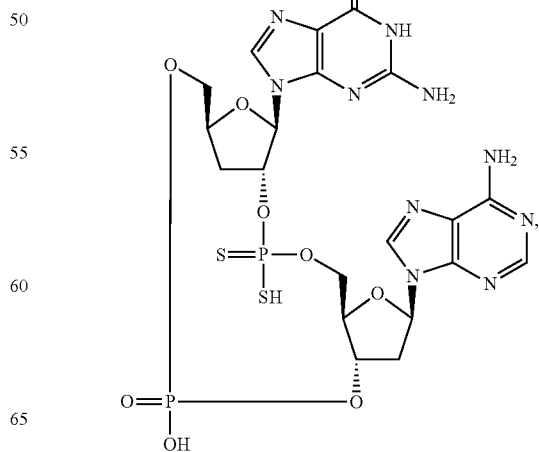

-continued

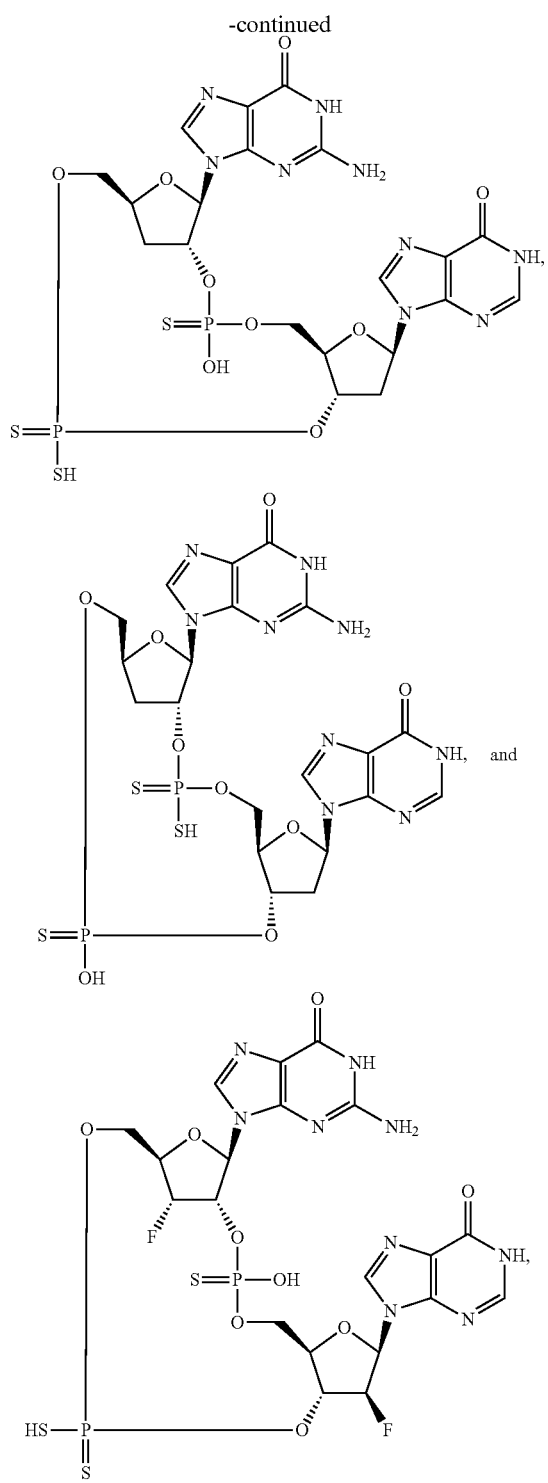

and pharmaceutically acceptable salts, hydrates, solvates, and prodrugs thereof. In aspects, the disclosure relates to the compounds set forth above, or pharmaceutically acceptable salts, hydrates, or solvates thereof. In specific embodiments, the disclosure relates to the compounds set forth above or pharmaceutically acceptable salts thereof.

A thirty-seventh embodiment relates to a pharmaceutical composition, said pharmaceutical composition comprising (a) a compound according to the thirty-sixth embodiment above or a pharmaceutically acceptable salt thereof; and (b) a pharmaceutically acceptable carrier.

A thirty-eight embodiment relates to methods of inducing an immune response in a subject, comprising administering a therapeutically effective amount of a compound according to the thirty-sixth embodiment above or a pharmaceutically acceptable salt thereof to the subject.

A thirty-ninth embodiment relates to methods of inducing an immune response in a subject, comprising administering a therapeutically effective amount of a composition according to the thirty-seventh embodiment above to the subject.

A fortieth embodiment relates to methods of inducing STING-dependent type I interferon production in a subject, comprising administering a therapeutically effective amount of a compound according to the thirty-sixth embodiment above or a pharmaceutically acceptable salt thereof to the subject.

A forty-first embodiment relates to methods of inducing STING-dependent type I interferon production in a subject, comprising administering a therapeutically effective amount of a composition according to the thirty-seventh embodiment above to the subject.

A forty-second embodiment relates to methods of inducing STING-dependent cytokine production in a subject, comprising administering a therapeutically effective amount of a compound according to the thirty-sixth embodiment above or a pharmaceutically acceptable salt thereof to the subject.

A forty-third embodiment relates to methods of inducing a STING-dependent cytokine production in a subject, comprising administering a therapeutically effective amount of a composition according to the thirty-seventh embodiment above to the subject.

A forty-fourth embodiment relates to methods of treating a cell proliferation disorder in a patient in need of therapy, comprising administering a therapeutically effective amount of a compound of general formula (I), or a pharmaceutically acceptable salt thereof to the patient. In aspects of this embodiment, the cell proliferation disorder is cancer.

A forty-fifth embodiment relates to methods of treating a cell proliferation disorder in a patient in need of therapy, said method comprising administering a therapeutically effective amount of a composition according to the thirty-seventh embodiment described above to the patient. In aspects of this embodiment, the cell proliferation disorder is cancer.

A forty-sixth embodiment relates to a compound selected from the exemplary species depicted in Examples 1 through 27 shown below.

A forty-seventh embodiment relates to a a pharmaceutical composition, said pharmaceutical composition comprising (a) a compound according to the forty-sixth embodiment above or a pharmaceutically acceptable salt thereof; and (b) a pharmaceutically acceptable carrier.

A forty-eighth embodiment relates to methods of inducing an immune response in a subject, comprising administering a therapeutically effective amount of a compound according to the forty-sixth embodiment above or a pharmaceutically acceptable salt thereof to the subject.

A forty-ninth embodiment relates to methods of inducing an immune response in a subject, comprising administering a therapeutically effective amount of a composition according to the forty-seventh embodiment above to the subject.

A fiftieth embodiment relates to methods of inducing STING-dependent type I interferon production in a subject, comprising administering a therapeutically effective amount of a compound according to the forty-sixth embodiment above or a pharmaceutically acceptable salt thereof to the subject.

A fifty-first embodiment relates to methods of inducing STING-dependent type I interferon production in a subject, comprising administering a therapeutically effective amount of a composition according to the forty-seventh embodiment above to the subject.

A fifty-second embodiment relates to methods of inducing STING-dependent cytokine production in a subject, comprising administering a therapeutically effective amount of a compound according to the forty-sixth embodiment above or a pharmaceutically acceptable salt thereof to the subject.

A fifty-third embodiment relates to methods of inducing STING-dependent cytokine production in a subject, comprising administering a therapeutically effective amount of a composition according to the forty-seventh embodiment above to the subject.

A fifty-fourth embodiment relates to methods of treating a cell proliferation disorder in a patient in need of therapy, comprising administering a therapeutically effective amount of according to the forty-sixth embodiment above or a pharmaceutically acceptable salt thereof to the patient. In aspects of this embodiment, the cell proliferation disorder is cancer.

A fifty-fifth embodiment relates to methods of treating a cell proliferation disorder in a patient in need of therapy, said method comprising administering a therapeutically effective amount of a composition according to the fifty-seventh embodiment described above to the patient. In aspects of this embodiment, the cell proliferation disorder is cancer.

Other embodiments of the present disclosure include the following:

(a) A pharmaceutical composition comprising an effective amount of a compound of general formula (I), or a pharmaceutically acceptable salt thereof, and a pharmaceutically acceptable carrier.

(b) The pharmaceutical composition of (a), further comprising an active agent selected from the group consisting of STING agonist compounds, anti-viral compounds, antigens, adjuvants, CTLA-4 and PD-1 pathway antagonists and other immunomodulatory agents, lipids, liposomes, peptides, anti-cancer and chemotherapeutic agents.

(c) A pharmaceutical combination that is (i) a compound of general formula (I), or a pharmaceutically acceptable salt thereof, and (ii) an active agent selected from the group consisting of STING agonist compounds, anti-viral compounds, antigens, adjuvants, CTLA-4 and PD-1 pathway antagonists and other immunomodulatory agents, lipids, liposomes, peptides, anti-cancer and chemotherapeutic agents; wherein the compound of general formula (I), or pharmaceutically acceptable salt thereof, and the active agent are each employed in an amount that renders the combination effective for inducing an immune response in a patient.

(d) A method of inducing an immune response in a patient, which comprises administering to the subject a therapeutically effective amount of a compound of general formula (I), or a pharmaceutically acceptable salt thereof.

(e) A method of inducing an immune response in a patient, which comprises administering to the subject a therapeutically effective amount of a composition of (a), a composition of (b), or a combination of (c).

(f) A method of inducing STING-dependent type I interferon production in a patient, which comprises administering to the subject a therapeutically effective amount of a compound of general formula (I), or a pharmaceutically acceptable salt thereof.

(g) A method of inducing STING-dependent type I interferon production in a patient, which comprises administering to the subject a therapeutically effective amount of a composition of (a), a composition of (b), or a combination of (c).

(h) A method of inducing STING-dependent cytokine production in a patient, which comprises administering to the subject a therapeutically effective amount of a compound of general formula (I), or a pharmaceutically acceptable salt thereof.

(i) A method of inducing STING-dependent cytokine production in a patient, which comprises administering to the subject a therapeutically effective amount of a composition of (a), a composition of (b), or a combination of (c).

(j) A method of treating a cell proliferation disorder in a subject, said method comprising administering a therapeutically effective amount of a compound of general formula (I), or a pharmaceutically acceptable salt thereof to the subject;

(k) The method of (j), wherein the cell proliferation disorder is cancer.

(l) A method of treating a cell proliferation disorder in a subject, said method comprising administering a therapeutically effective amount of a composition of (a), a composition of (b), or a combination of (c) to the subject.

(m) The method of (1), wherein the cell proliferation disorder is cancer.

The present disclosure also includes a compound of the present disclosure for use (i) in, (ii) as a medicament for, or (iii) in the preparation of a medicament for: (a) inducing an immune response in a patient, or (b) inducing STING-dependent cytokine production in a patient. In these uses, the compounds of the present disclosure can optionally be employed in combination with one or more active agents selected from STING agonist compounds, anti-viral compounds, antigens, adjuvants, CTLA-4 and PD-1 pathway antagonists and other immunomodulatory agents, lipids, liposomes, peptides, anti-cancer agents, and chemotherapeutic agents.

Additional embodiments of the disclosure include the pharmaceutical compositions, combinations and methods set forth in (a) through (m) above and the uses set forth in the preceding paragraph, wherein the compound of the present disclosure employed therein is a compound of one of the embodiments, aspects, instances, occurrences, or features of the compounds described above. In all of these embodiments, the compound may optionally be used in the form of a pharmaceutically acceptable salt, as appropriate.

In the embodiments of the compound provided above, it is to be understood that each embodiment may be combined with one or more other embodiments, to the extent that such a combination provides a stable compound and is consistent with the description of the embodiments. It is further to be understood that the embodiments of compositions and methods provided as (a) through (m) above are understood to include all embodiments of the compounds, including such embodiments as result from combinations of embodiments.

The term "subject" (alternatively "patient") as used herein refers to a mammal that has been the object of treatment, observation, or experiment. The mammal may be male or female. The mammal may be one or more selected from the group consisting of humans, bovine (e.g., cows), porcine (e.g., pigs), ovine (e.g., sheep), capra (e.g., goats), equine (e.g., horses), canine (e.g., domestic dogs), feline (e.g., house cats), Lagomorpha (rabbits), rodents (e.g., rats or mice), *Procyon lotor* (e.g., raccoons). In particular embodiments, the subject is human.

As used herein, the term "immune response" relates to any one or more of the following: specific immune response, non-specific immune response, both specific and non-specific response, innate response, primary immune response, adaptive immunity, secondary immune response, memory immune response, immune cell activation, immune cell proliferation, immune cell differentiation, and cytokine expression. In certain embodiments, a compound of general formula (I), or a pharmaceutically acceptable salt of the foregoing, is administered in conjunction with one or more additional therapeutic agents including anti-viral compounds, vaccines intended to stimulate an immune response to one or more predetermined antigens, adjuvants, CTLA-4 and PD-1 pathway antagonists and other immunomodulatory agents, lipids, liposomes, peptides, anti-cancer agents, and chemotherapeutic agents, etc. In certain embodiments, a compound of general formula (I), or a pharmaceutically acceptable salt of the foregoing, is administered in conjunction with one or more additional compositions including anti-viral compounds, vaccines intended to stimulate an immune response to one or more predetermined antigens, adjuvants, CTLA-4 and PD-1 pathway antagonists and other immunomodulatory agents, lipids, liposomes, peptides, anti-cancer agents, and chemotherapeutic agents, etc.

Compounds

The term "alkyl" refers to a monovalent straight or branched chain, saturated aliphatic hydrocarbon radical having a number of carbon atoms in the specified range. Thus, for example, "$C_{1-6}$ alkyl" (or "$C_1$-$C_6$ alkyl") refers to any of the hexyl alkyl and pentyl alkyl isomers as well as n-, iso-, sec- and tert-butyl, n- and iso-propyl, ethyl, and methyl. As another example, "$C_{1-4}$ alkyl" refers to n-, iso-, sec- and tert-butyl, n- and isopropyl, ethyl, and methyl.

As used herein, the term "alkylene" refers to a bivalent straight chain, saturated aliphatic hydrocarbon radical having a number of carbon atoms in the specified range.

As used herein, the term "alkenyl" refers to a monovalent straight or branched chain, unsaturated aliphatic hydrocarbon radical having a number of carbon atoms in the specified range and including one or more double bond.

As used herein, the term "alkenylene" refers to a bivalent straight chain, unsaturated aliphatic hydrocarbon radical having a number of carbon atoms in the specified range and including one or more double bond.

As used herein, the term "alkynyl" refers to a monovalent straight or branched chain, unsaturated aliphatic hydrocarbon radical having a number of carbon atoms in the specified range and including one or more triple bond.

As used herein, the term "alkynylene" refers to a bivalent straight chain, unsaturated aliphatic hydrocarbon radical having a number of carbon atoms in the specified range and including one or more triple bond.

The term "halogen" (or "halo") refers to fluorine, chlorine, bromine, and iodine (alternatively referred to as fluoro, chloro, bromo, and iodo or F, Cl, Br, and I).

The term "haloalkyl" refers to an alkyl group as defined above in which one or more of the hydrogen atoms have been replaced with a halogen. Thus, for example, "$C_{1-6}$ haloalkyl" (or "$C_1$-$C_6$ haloalkyl") refers to a $C_1$ to $C_6$ linear or branched alkyl group as defined above with one or more halogen substituents. The term "fluoroalkyl" has an analogous meaning except the halogen substituents are restricted to fluoro. Suitable fluoroalkyls include the series $(CH_2)_{0-4}CF_3$ (i.e., trifluoromethyl, 2,2,2-trifluoroethyl, 3,3,3-trifluoro-n-propyl, etc.). As used herein, the term "haloalkenyl" refers to an alkenyl group as defined above in which one or more of the hydrogen atoms have been replaced with a halogen.

As used herein, the term "haloalkynyl" refers to an alkynyl group as defined above in which one or more of the hydrogen atoms have been replaced with a halogen.

As used herein, the term "alkoxy" as used herein, alone or in combination, includes an alkyl group connected to the oxy connecting atom. The term "alkoxy" also includes alkyl ether groups, where the term "alkyl" is defined above, and "ether" means two alkyl groups with an oxygen atom between them. Examples of suitable alkoxy groups include methoxy, ethoxy, n-propoxy, i-propoxy, n-butoxy, s-butoxy, t-butoxy, methoxymethane (also referred to as "dimethyl ether"), and methoxyethane (also referred to as "ethyl methyl ether").

As used herein, the term "cycloalkyl" refers to a saturated hydrocarbon containing one ring having a specified number of carbon atoms. Examples of cycloalkyl include cyclopropyl, cyclobutyl, cyclopentyl, and cyclohexyl.

As used herein, the term "heterocycle", "heterocyclyl", or "heterocyclic", as used herein, represents a stable 3- to 6-membered monocyclic that is either saturated or unsaturated, and that consists of carbon atoms and from one to two heteroatoms selected from the group consisting of N, O, and S. The heterocyclic ring may be attached at any heteroatom or carbon atom which results in the creation of a stable structure. The term includes heteroaryl moieties. Examples of such heterocyclic elements include, but are not limited to, azepinyl, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothiopyranyl sulfone, 1,3-dioxolanyl, furyl, imidazolidinyl, imidazolinyl, imidazolyl, indolinyl, indolyl, isochromanyl, isoindolinyl, isoquinolinyl, isothiazolidinyl, isothiazolyl, isothiazolidinyl, morpholinyl, naphthyridinyl, oxadiazolyl, 2-oxoazepinyl, oxazolyl, 2-oxopiperazinyl, 2-oxopiperdinyl, 2-oxopyrrolidinyl, piperidyl, piperazinyl, pyridyl, pyrazinyl, pyrazolidinyl, pyrazolyl, pyridazinyl, pyrimidinyl, pyrrolidinyl, pyrrolyl, quinazolinyl, quinolinyl, quinoxalinyl, tetrahydrofuryl, tetrahydroisoquinolinyl, tetrahydroquinolinyl, thiamorpholinyl, thiamorpholinyl sulfoxide, thiazolyl, thiazolinyl, thienofuryl, thienothienyl, triazolyl and thienyl.

As used herein, the term "spirocycle" or "spirocyclic ring" refers to a pendant cyclic group formed by substituents on a single atom.

The term "compound" refers to the compound and, in certain embodiments, to the extent they are stable, any hydrate or solvate thereof. A hydrate is the compound complexed with water, and a solvate is the compound complexed with a solvent, which may be an organic solvent or an inorganic solvent.

A "stable" compound is a compound that can be prepared and isolated and whose structure and properties remain or can be caused to remain essentially unchanged for a period of time sufficient to allow use of the compound for the purposes described herein (e.g., therapeutic administration to a subject). The compounds of the present invention are limited to stable compounds embraced by general formula (I), or pharmaceutically acceptable salts thereof.

Unless expressly stated to the contrary, all ranges cited herein are inclusive; i.e., the range includes the values for the upper and lower limits of the range as well as all values in between. As an example, temperature ranges, percentages, ranges of equivalents, and the like described herein include the upper and lower limits of the range and any value in the continuum there between. Numerical values provided herein, and the use of the term "about", may include variations of ±1%, ±2%, ±3%, ±4%, ±5%, ±10%, ±15%, and ±20% and their numerical equivalents.

As used herein, the term "one or more" item includes a single item selected from the list as well as mixtures of two or more items selected from the list.

In the compounds of general formula (I), and pharmaceutically acceptable salts of the foregoing, the atoms may exhibit their natural isotopic abundances, or one or more of the atoms may be artificially enriched in a particular isotope having the same atomic number, but an atomic mass or mass number different from the atomic mass or mass number predominantly found in nature. The present disclosure is meant to include all suitable isotopic variations of the compounds of general formula (I), and pharmaceutically acceptable salts of the foregoing. For example, different isotopic forms of hydrogen (H) include protium ($^{1}$H), deuterium ($^{2}$H), and tritium ($^{3}$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within general formula (I), and the pharmaceutically acceptable salts of the foregoing, can be prepared without undue experimentation by conventional techniques well known to those skilled in the art or by processes analogous to those described in the Schemes and Examples herein using appropriate isotopically-enriched reagents and/or intermediates.

In particular embodiments of the compounds of general formula (I), and/or pharmaceutically acceptable salts of the foregoing, the compounds are isotopically enriched with deuterium. In aspects of these embodiments, one or more of Base$^{1}$, Base$^{2}$, Y, Y$^{a}$, X$^{a}$, X$^{a1}$, X$^{b}$, X$^{b1}$, X$^{c}$, X$^{c1}$, X$^{d}$, X$^{d1}$, R$^{1}$, R$^{1a}$, R$^{2}$, R$^{2a}$, R$^{3}$, R$^{4}$, R$^{4a}$, R$^{5}$, R$^{6}$, R$^{6a}$, R$^{7}$, R$^{7a}$, R$^{8}$, R$^{8a}$, and R$^{9}$ may include deuterium.

As shown in the general structural formulas and the structures of specific compounds as provided herein, a straight line at a chiral center includes both (R) and (S) stereoisomers and mixtures thereof. Also, unless otherwise specified (e.g., 100% purified compound), reference to a particular stereochemistry at a position provides a compound having the indicated stereochemistry but does not exclude the presence of stereoisomers having different stereochemistry at the indicated position.

Recitation or depiction of a specific compound in the claims (i.e., a species) without a specific stereoconfiguration designation, or with such a designation for less than all chiral centers, is intended to encompass, for such undesignated chiral centers, the racemate, racemic mixtures, each individual enantiomer, a diastereoisomeric mixture and each individual diastereomer of the compound where such forms are possible due to the presence of one or more asymmetric centers.

The invention includes all possible enantiomers and diastereomers and mixtures of two or more stereoisomers, for example mixtures of enantiomers and/or diastereomers, in all ratios. Thus, enantiomers are a subject of the invention in enantiomerically pure form, both as levorotatory and as dextrorotatory antipodes, in the form of racemates and in the form of mixtures of the two enantiomers in all ratios. In the case of a cis/trans isomerism, the invention includes both the cis form and the trans form, as well as mixtures of these forms in all ratios. The preparation of individual stereoisomers can be carried out, if desired, by separation of a mixture by customary methods, for example by chromatography or crystallization, by the use of stereochemically uniform starting materials for the synthesis or by stereoselective synthesis.

Optionally a derivatization can be carried out before a separation of stereoisomers. The separation of a mixture of stereoisomers can be carried out at an intermediate step during the synthesis of a compound of general formula (I), or a pharmaceutically acceptable salt of the foregoing, or it can be done on a final racemic product. Absolute stereochemistry may be determined by X-ray crystallography of crystalline products or crystalline intermediates that are derivatized, if necessary, with a reagent containing a stereogenic center of known configuration. Unless a particular isomer, salt, solvate (including hydrates) or solvated salt of such racemate, enantiomer, or diastereomer is indicated, the present invention includes all such isomers, as well as salts, solvates (including hydrates), and solvated salts of such racemates, enantiomers, diastereomers, and mixtures thereof.

Those skilled in the art will recognize that chiral compounds, and in particular sugars, can be drawn in a number of different ways that are equivalent. Those skilled in the art will further recognize that the identity and regiochemical position of the substituents on ribose can vary widely and that the same principles of stereochemical equivalence apply regardless of substituent. Non-limiting examples of such equivalence include those exemplified below.

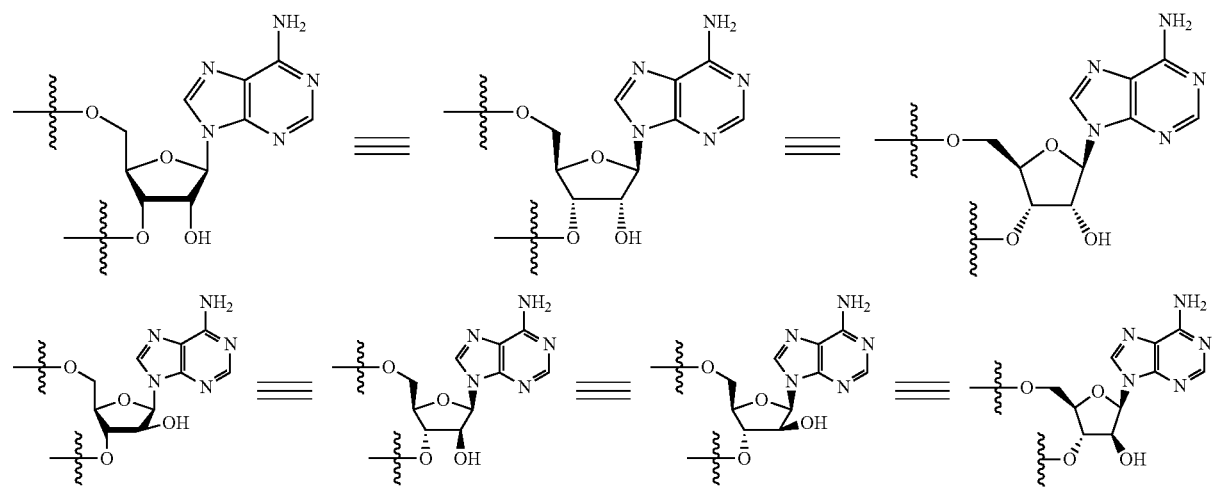

Salts

As indicated above, the compounds of the present invention can be employed in the form of pharmaceutically acceptable salts. Those skilled in the art will recognize those instances in which the compounds of the invention may form salts. Examples of such compounds are described herein by reference to possible salts. Such reference is for illustration only. Pharmaceutically acceptable salts can be used with compounds for treating patients. Non-pharmaceutical salts may, however, be useful in the preparation of intermediate compounds.

The term "pharmaceutically acceptable salt" refers to a salt (including an inner salt such as a zwitterion) that possesses effectiveness similar to the parent compound and that is not biologically or otherwise undesirable (e.g., is neither toxic nor otherwise deleterious to the recipient thereof). Thus, an embodiment of the invention provides pharmaceutically acceptable salts of the compounds of the invention. The term "salt(s)", as employed herein, denotes any of the following: acidic salts formed with inorganic and/or organic acids, as well as basic salts formed with inorganic and/or organic bases. Salts of compounds of the invention may be formed by methods known to those of ordinary skill in the art, for example, by reacting a compound of the invention with an amount of acid or base, such as an equivalent amount, in a medium such as one in which the salt precipitates or in aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates ("mesylates"), naphthalenesulfonates, nitrates, oxalates, phosphates, propionates, salicylates, succinates, sulfates, tartarates, thiocyanates, toluenesulfonates (also known as tosylates) and the like. Suitable salts include acid addition salts that may, for example, be formed by mixing a solution of a compound with a solution of a pharmaceutically acceptable acid such as hydrochloric acid, sulfuric acid, acetic acid, trifluoroacetic acid, or benzoic acid. Additionally, acids that are generally considered suitable for the formation of pharmaceutically useful salts from basic pharmaceutical compounds are discussed, for example, by P. Stahl et al, Camille G. (eds.), *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamine, t-butyl amine, choline, and salts with amino acids such as arginine, lysine and the like. Basic nitrogen-containing groups may be quarternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), aralkyl halides (e.g., benzyl and phenethyl bromides), and others. Compounds carrying an acidic moiety can be mixed with suitable pharmaceutically acceptable salts to provide, for example, alkali metal salts (e.g., sodium or potassium salts), alkaline earth metal salts (e.g., calcium or magnesium salts), and salts formed with suitable organic ligands such as quaternary ammonium salts. Also, in the case of an acid (such as —COOH) or alcohol group being present, pharmaceutically acceptable esters can be employed to modify the solubility or hydrolysis characteristics of the compound.

All such acid salts and base salts are intended to be pharmaceutically acceptable salts within the scope of the invention and all acid and base salts are considered equivalent to the free forms of the corresponding compounds for purposes of the invention.

In addition, when a compound of the invention contains both a basic moiety, such as, but not limited to an aliphatic primary, secondary, tertiary or cyclic amine, an aromatic or heteroaryl amine, pyridine or imidazole, and an acidic moiety, such as, but not limited to tetrazole or carboxylic acid, zwitterions ("inner salts") may be formed and are included within the terms "salt(s)" as used herein. It is understood that certain compounds of the invention may exist in zwitterionic form, having both anionic and cationic centers within the same compound and a net neutral charge. Such zwitterions are included within the invention.

Methods of Preparing Compounds

Several methods for preparing the compounds of general formula (I), and pharmaceutically acceptable salts of the foregoing, are described in the following Schemes and Examples. Starting materials and intermediates are purchased from commercial sources, made from known procedures, or are otherwise illustrated. In some cases the order of carrying out the steps of the reaction schemes may be varied to facilitate the reaction or to avoid unwanted reaction products.

In the following Methods and Schemes, PG1 or PG2 represents a protecting group, selected from the options described below. All other variables have the same meaning as provided above.

Method 1

One method for the preparation of examples of the instant invention is detailed in Scheme 1. This procedure was adequately modified from the previously reported procedure (Zhao, Jianwei et al., *Thiophosphate analogs of c-di-GMP: Impact on polymorphism, Nucleosides, Nucleotides and Nucleic Acids*, 2009, 28, 352-378). The sequence starts with modified ribo-nucleoside with a nucleobase of which amino group was appropriately protected with an alkyl or phenyl carbonyl group, and DMTr ether at 5'-O position. It was treated with diphenyl phosphorochloridate and subsequently lithium sulfide to convert the 2'-OH to a hydrogen phosphonothioate. Then, DMTr ether was removed under acidic condition. The resulting 5'-hydroxyl group was reacted with 2'-O-phosphoramidites of fully protected second modified ribo-nucleoside to give a coupled compound. It was immediately either thioated or oxidized with elemental sulfur or t-butyl hydroperoxide. Then, the 5'-hydroxyl group of the second ribo-nucleoside was deprotected with dichloroacetic acid. Using diphenyl phosphorochloridate as a coupling reagent, the hydrogen phosphonothioate at 3'-O of the first ribo-nucleoside was reacted with 5'-OH of the second ribo-nucleoside to give a cyclic product. It was immediately thioated with 3H-benzo[c][1,2]dithiol-3-one or elemental sulfur. Treatment with methylamine plus fluoride anion in case of silyl protection was used provided the desired cyclic dinucleotide IIa or IIb.

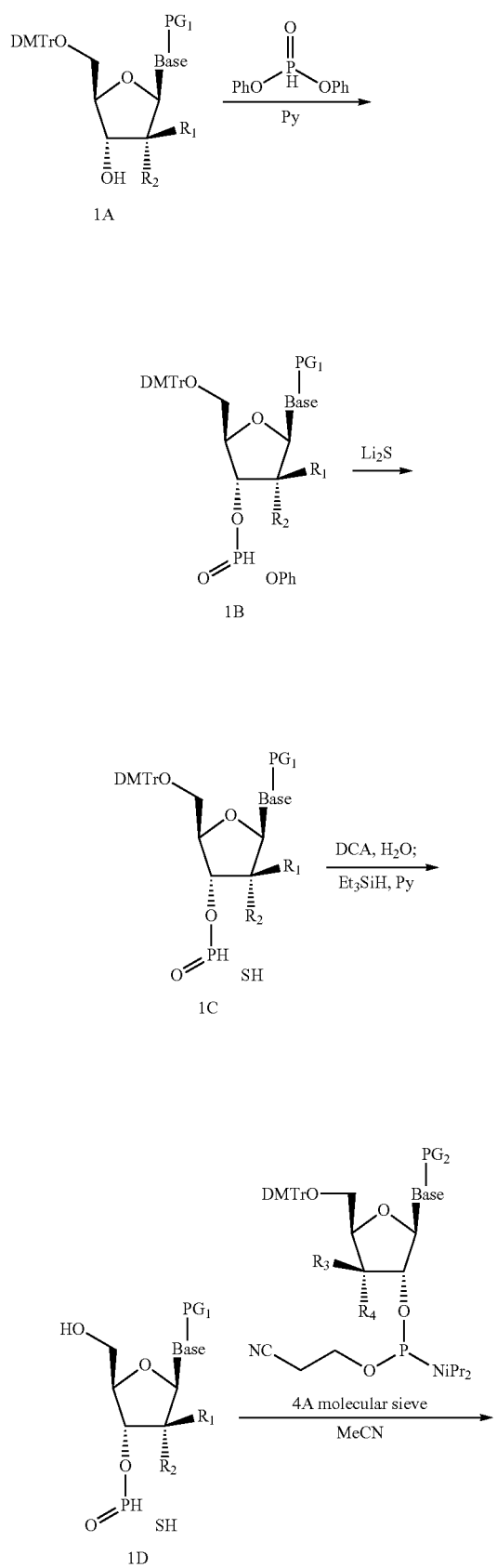
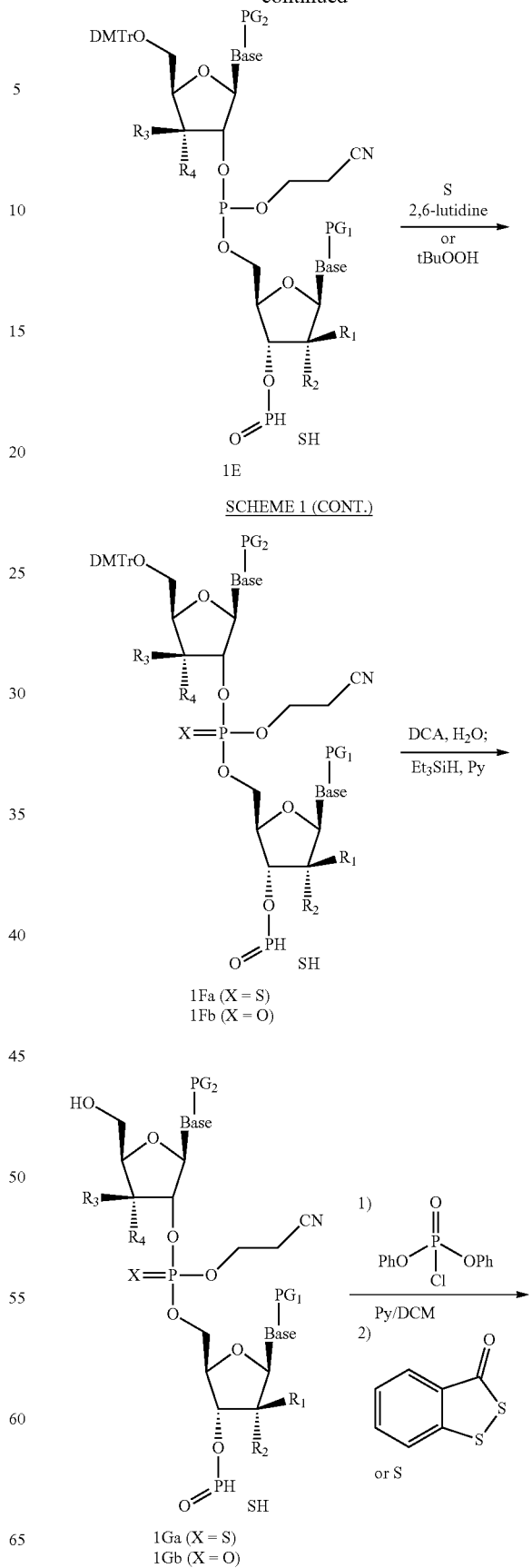

SCHEME 2

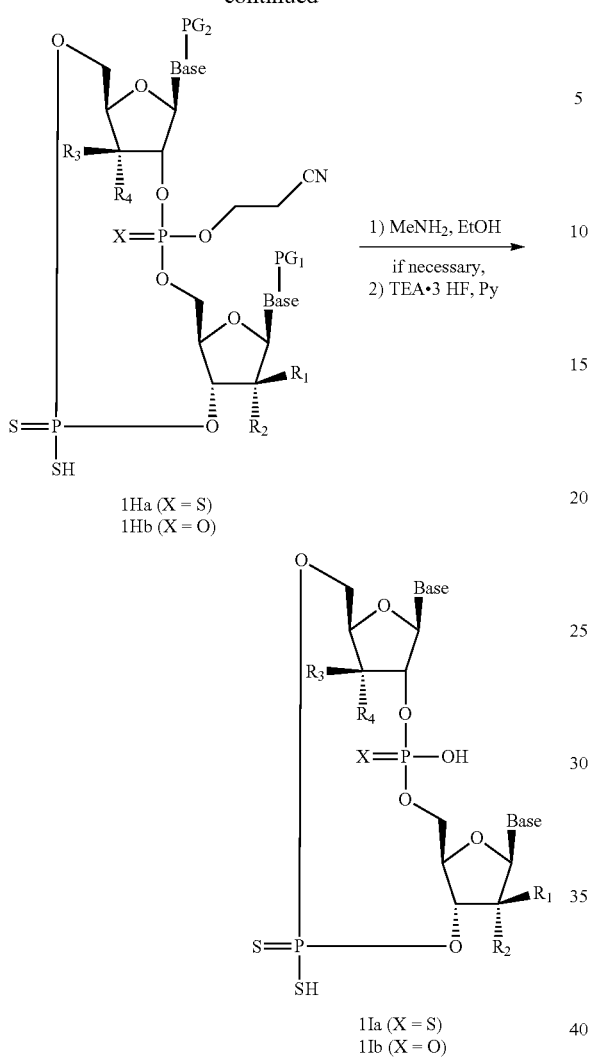

1Ha (X = S)
1Hb (X = O)

1Ia (X = S)
1Ib (X = O)

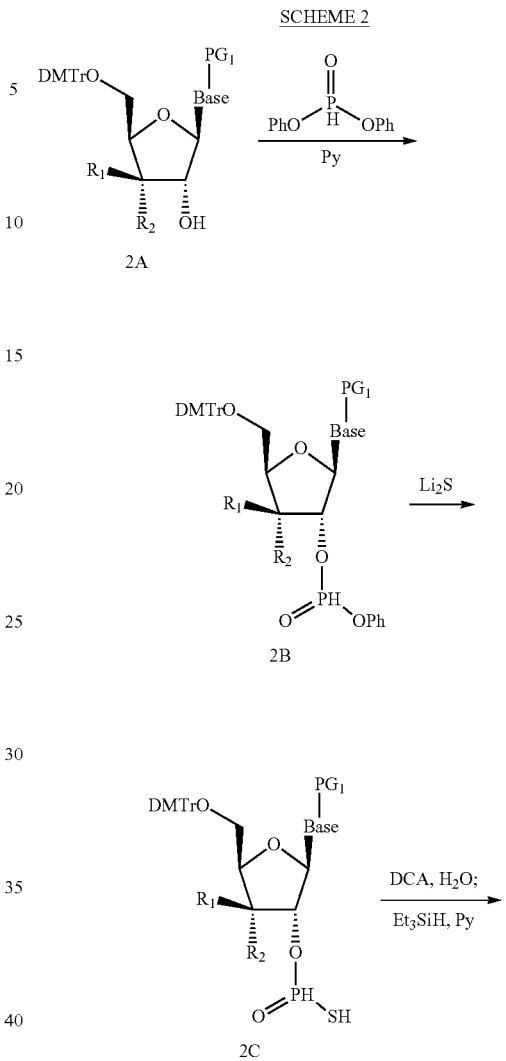

Method 2

Another method for the preparation of examples of the instant invention is detailed in Scheme 2. This procedure was modified from Scheme 1. The sequence starts with modified ribo-nucleoside with a nucleobase of which amino group was appropriately protected with an alkyl or phenyl carbonyl group, and DMTr ether at 5'-O position. It was treated with diphenyl phosphorochloridate and subsequently lithium sulfide ($Li_2S$) to convert the 2'-OH to a hydrogen phosphonothioate. Then, DMTr ether was removed under acidic conditions. The resulting 5'-hydroxyl group was reacted with 3'-phosphoramidites of fully protected second modified ribo-nucleoside to give a coupled compound. It was immediately thioated with elemental sulfur. Then, the 5'-hydroxyl group of the second ribo-nucleoside was deprotected with dichloroacetic acid. Using diphenyl phosphorochloridate as a coupling reagent, the hydrogen phosphonothioate at 2'-O of the first ribo-nucleoside was reacted with 5'-OH of the second ribo-nucleoside to give a cyclic product. It was immediately thioated with 3H-benzo[c][1,2]dithiol-3-one or elemental sulfur. Treatment with methylamine plus fluoride anion in case of silyl protection was used provided the desired cyclic dinucleotide 21.

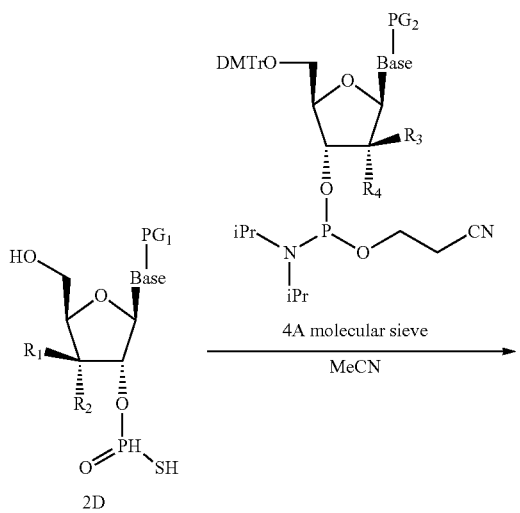

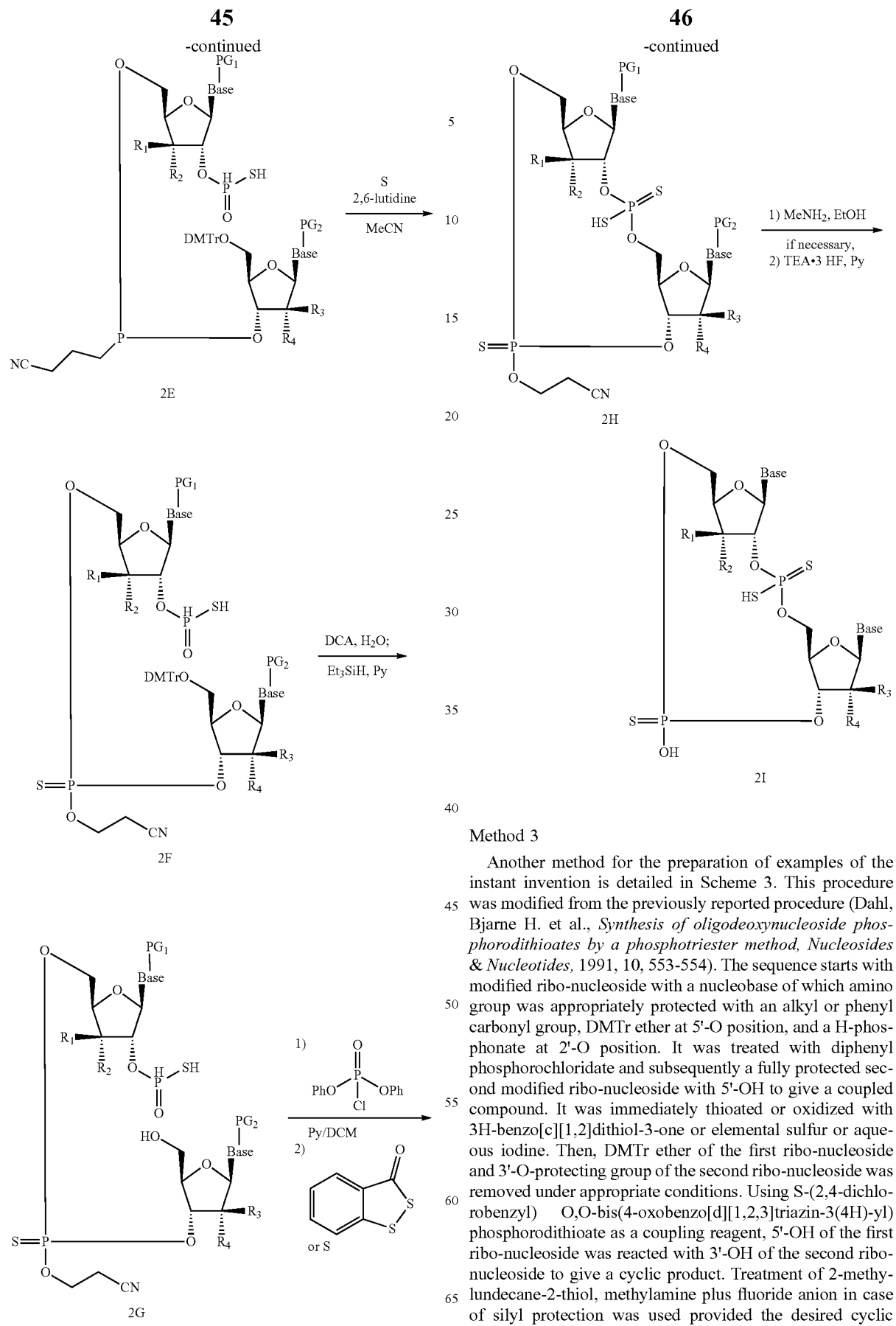

Method 3

Another method for the preparation of examples of the instant invention is detailed in Scheme 3. This procedure was modified from the previously reported procedure (Dahl, Bjarne H. et al., *Synthesis of oligodeoxynucleoside phosphorodithioates by a phosphotriester method, Nucleosides & Nucleotides,* 1991, 10, 553-554). The sequence starts with modified ribo-nucleoside with a nucleobase of which amino group was appropriately protected with an alkyl or phenyl carbonyl group, DMTr ether at 5'-O position, and a H-phosphonate at 2'-O position. It was treated with diphenyl phosphorochloridate and subsequently a fully protected second modified ribo-nucleoside with 5'-OH to give a coupled compound. It was immediately thioated or oxidized with 3H-benzo[c][1,2]dithiol-3-one or elemental sulfur or aqueous iodine. Then, DMTr ether of the first ribo-nucleoside and 3'-O-protecting group of the second ribo-nucleoside was removed under appropriate conditions. Using S-(2,4-dichlorobenzyl) O,O-bis(4-oxobenzo[d][1,2,3]triazin-3(4H)-yl) phosphorodithioate as a coupling reagent, 5'-OH of the first ribo-nucleoside was reacted with 3'-OH of the second ribo-nucleoside to give a cyclic product. Treatment of 2-methylundecane-2-thiol, methylamine plus fluoride anion in case of silyl protection was used provided the desired cyclic dinucleotide 3Ga or 3Gb.

SCHEME 3
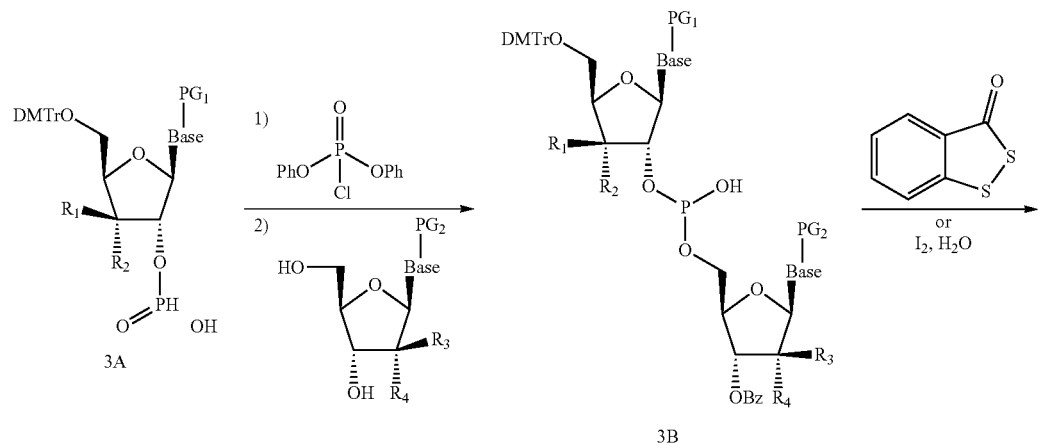
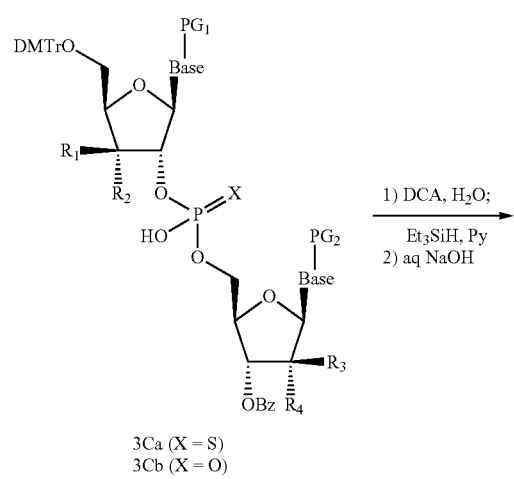
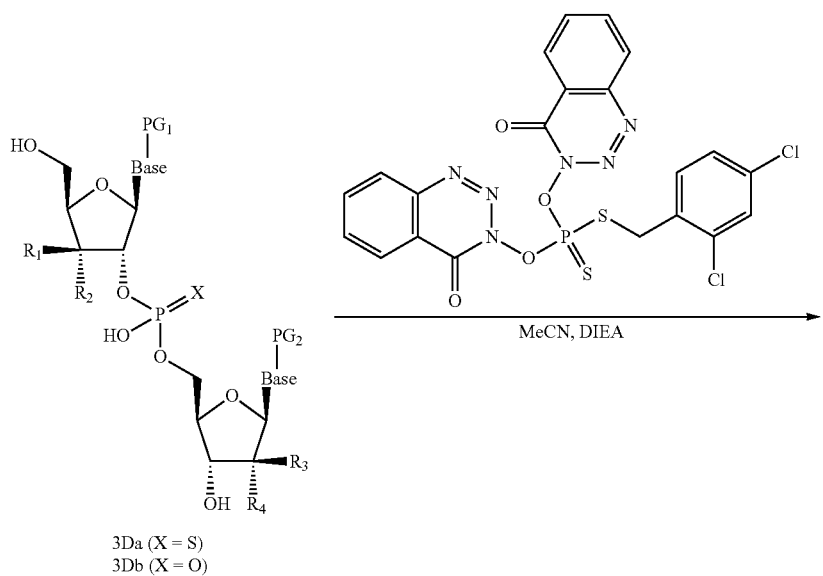

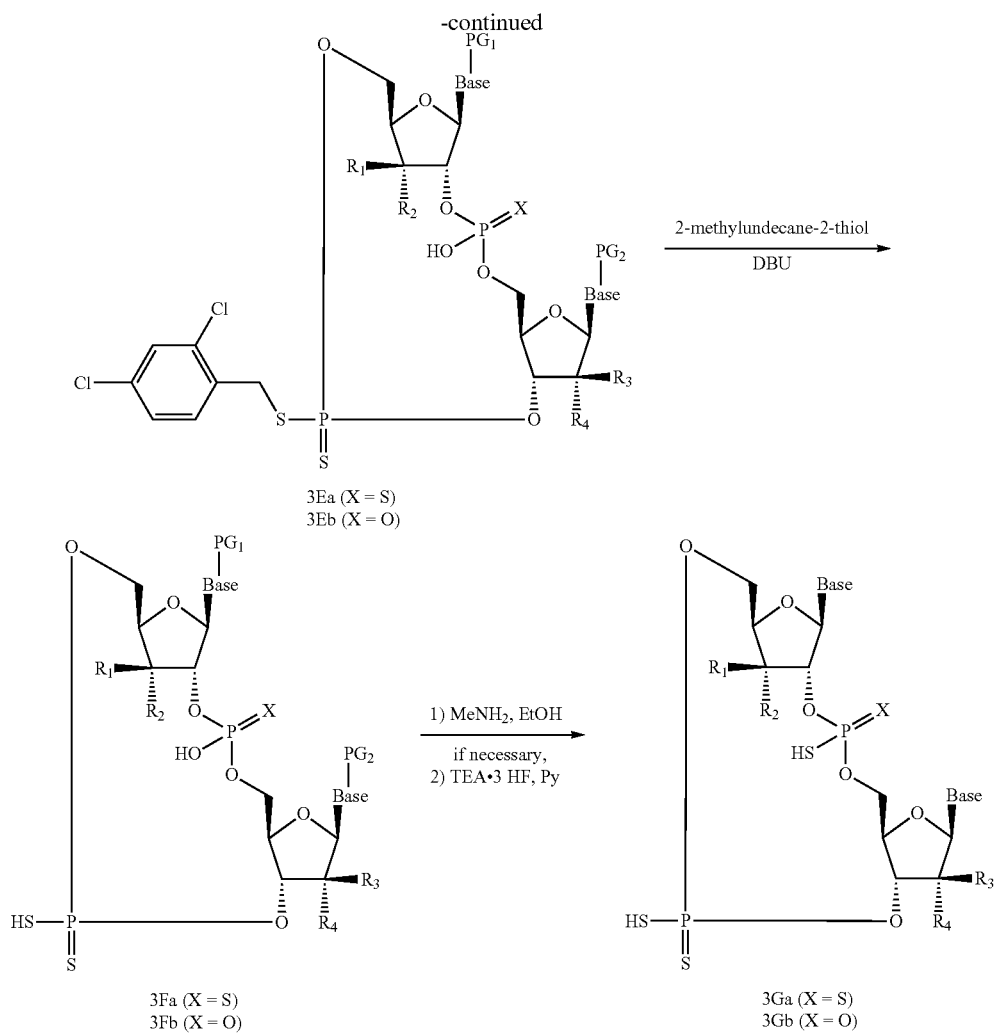

3Ea (X = S)
3Eb (X = O)

3Fa (X = S)
3Fb (X = O)

3Ga (X = S)
3Gb (X = O)

Method 4

Another method for the preparation of examples of the instant invention is detailed in Scheme 4. This procedure was modified from Scheme 3. The sequence starts with modified ribo-nucleoside with a nucleobase of which amino group was appropriately protected with an alkyl or phenyl carbonyl group, DMTr ether at 5'-O position, and a H-phosphonate at 2'-O position. It was treated with 2,4-dichlorobenzyl phosphorodichloridodithioate, 3-hydroxybenzo[d][1,2,3]triazin-4(3H)-one, and subsequently a protected second modified ribo-nucleoside with 3'- and 5'-OH to give a coupled compound. Then, DMTr ether of the first ribo-nucleoside was removed under an acidic conditions. Using 3-(bis(diisopropylamino) phosphanyl)oxy)propanenitrile as a coupling reagent, 5'-OH of the first ribo-nucleoside was reacted with 3'-OH of the second ribo-nucleoside to give a cyclic product. Treatment of 2-methylundecane-2-thiol, methylamine plus fluoride anion in case of silyl protection was used provided the desired cyclic dinucleotide 4E.

SCHEME 4

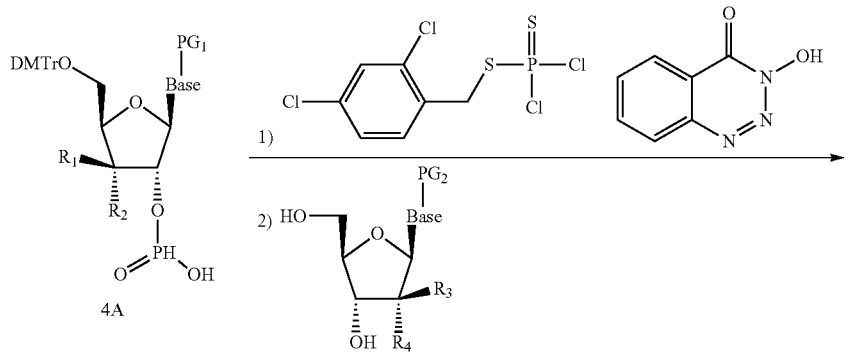

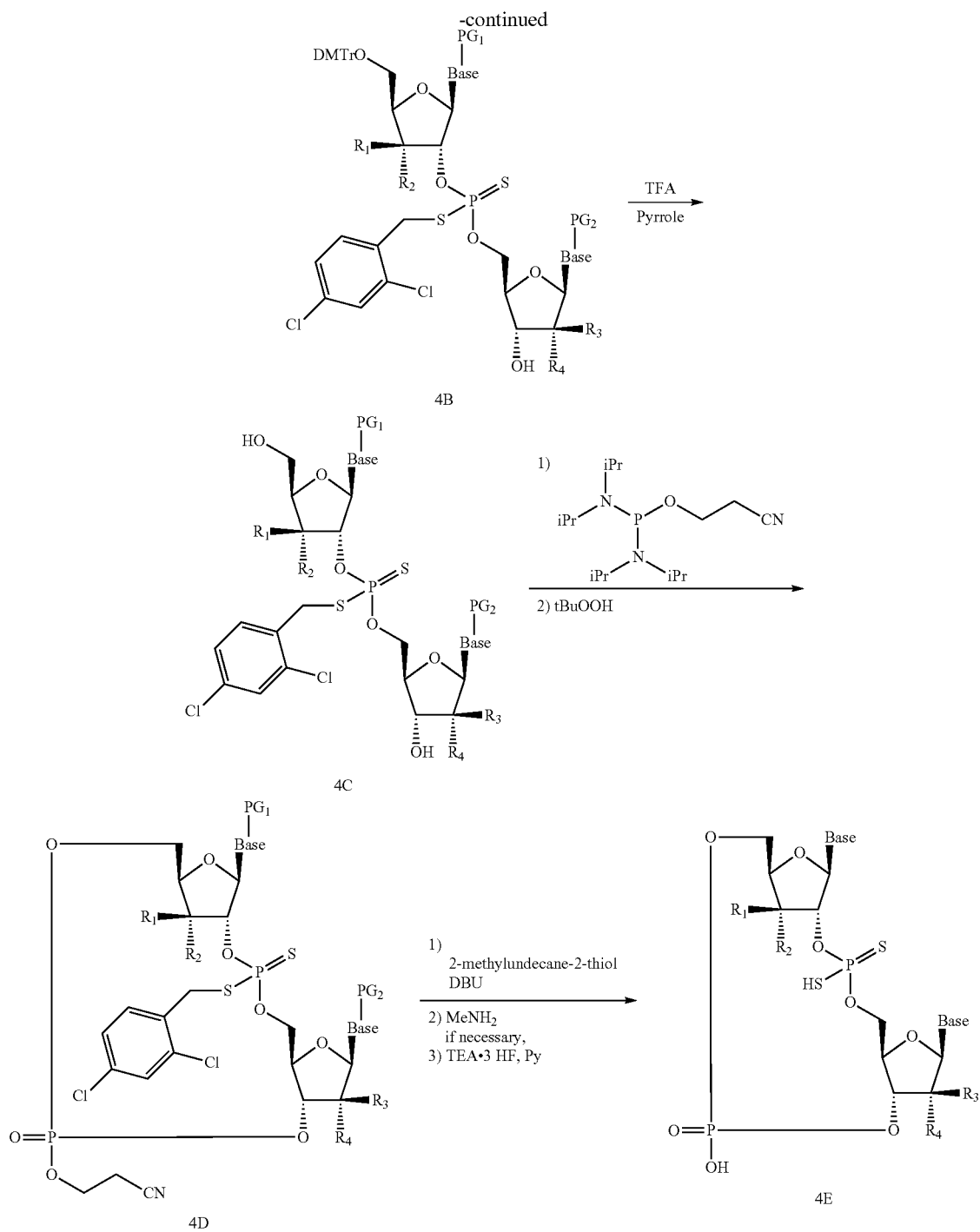

Methods of Use

Compounds described herein having therapeutic applications, such as the compounds of general formula (I), the compounds of the Examples 1 through 27, and pharmaceutically acceptable salts of the foregoing, may be administered to a patient for the purpose of inducing an immune response, inducing STING-dependent cytokine production and/or inducing anti-tumor activity. The term "administration" and variants thereof (e.g., "administering" a compound) means providing the compound to the individual in need of treatment. When a compound is provided in combination with one or more additional active agents (e.g., antiviral agents useful for treating HCV infection or anti-tumor agents for treating cancers), "administration" and its variants are each understood to include concurrent and sequential provision of the compound or salt and other agents.

The compounds disclosed herein may be STING agonists. These compounds are potentially useful in treating diseases or disorders including, but not limited to, cell proliferation disorders. Cell-proliferation disorders include, but are not limited to, cancers, benign papillomatosis, gestational trophoblastic diseases, and benign neoplastic diseases, such as skin papilloma (warts) and genital papilloma.

In specific embodiments, the disease or disorder to be treated is a cell proliferation disorder. In certain embodiments, the cell proliferation disorder is cancer. In particular embodiments, the cancer is selected from brain and spinal cancers, cancers of the head and neck, leukemia and cancers of the blood, skin cancers, cancers of the reproductive system, cancers of the gastrointestinal system, liver and bile duct cancers, kidney and bladder cancers, bone cancers, lung cancers, malignant mesothelioma, sarcomas, lymphomas, glandular cancers, thyroid cancers, heart tumors, germ cell tumors, malignant neuroendocrine (carcinoid) tumors, midline tract cancers, and cancers of unknown primary (i.e., cancers in which a metastasized cancer is found but the original cancer site is not known). In particular embodiments, the cancer is present in an adult patient; in additional embodiments, the cancer is present in a pediatric patient. In particular embodiments, the cancer is AIDS-related.

In specific embodiments, the cancer is selected from brain and spinal cancers. In particular embodiments, the cancer is selected from the group consisting of anaplastic astrocytomas, glioblastomas, astrocytomas, and estheosioneuroblastomas (also known as olfactory blastomas). In particular embodiments, the brain cancer is selected from the group consisting of astrocytic tumor (e.g., pilocytic astrocytoma, subependymal giant-cell astrocytoma, diffuse astrocytoma, pleomorphic xanthoastrocytoma, anaplastic astrocytoma, astrocytoma, giant cell glioblastoma, glioblastoma, secondary glioblastoma, primary adult glioblastoma, and primary pediatric glioblastoma), oligodendroglial tumor (e.g., oligodendroglioma, and anaplastic oligodendroglioma), oligoastrocytic tumor (e.g., oligoastrocytoma, and anaplastic oligoastrocytoma), ependymoma (e.g., myxopapillary ependymoma, and anaplastic ependymoma); medulloblastoma, primitive neuroectodermal tumor, schwannoma, meningioma, atypical meningioma, anaplastic meningioma, pituitary adenoma, brain stem glioma, cerebellar astrocytoma, cerebral astorcytoma/malignant glioma, visual pathway and hypothalmic glioma, and primary central nervous system lymphoma. In specific instances of these embodiments, the brain cancer is selected from the group consisting of glioma, glioblastoma multiforme, paraganglioma, and suprantentorial primordial neuroectodermal tumors (sP-NET).

In specific embodiments, the cancer is selected from cancers of the head and neck, including nasopharyngeal cancers, nasal cavity and paranasal sinus cancers, hypopharyngeal cancers, oral cavity cancers (e.g., squamous cell carcinomas, lymphomas, and sarcomas), lip cancers, oropharyngeal cancers, salivary gland tumors, cancers of the larynx (e.g., laryngeal squamous cell carcinomas, rhabdomyosarcomas), and cancers of the eye or ocular cancers. In particular embodiments, the ocular cancer is selected from the group consisting of intraocular melanoma and retinoblastoma.

In specific embodiments, the cancer is selected from leukemia and cancers of the blood. In particular embodiments, the cancer is selected from the group consisting of myeloproliferative neoplasms, myelodysplastic syndromes, myelodysplastic/myeloproliferative neoplasms, acute myeloid leukemia (AML), myelodysplastic syndrome (MDS), chronic myelogenous leukemia (CML), myeloproliferative neoplasm (MPN), post-MPN AML, post-MDS AML, del(5q)-associated high risk MDS or AML, blast-phase chronic myelogenous leukemia, angioimmunoblastic lymphoma, acute lymphoblastic leukemia, Langerans cell histiocytosis, hairy cell leukemia, and plasma cell neoplasms including plasmacytomas and multiple myelomas. Leukemias referenced herein may be acute or chronic.

In specific embodiments, the cancer is selected from skin cancers. In particular embodiments, the skin cancer is selected from the group consisting of melanoma, squamous cell cancers, and basal cell cancers.

In specific embodiments, the cancer is selected from cancers of the reproductive system. In particular embodiments, the cancer is selected from the group consisting of breast cancers, cervical cancers, vaginal cancers, ovarian cancers, prostate cancers, penile cancers, and testicular cancers. In specific instances of these embodiments, the cancer is a breast cancer selected from the group consisting of ductal carcinomas and phyllodes tumors. In specific instances of these embodiments, the breast cancer may be male breast cancer or female breast cancer. In specific instances of these embodiments, the cancer is a cervical cancer selected from the group consisting of squamous cell carcinomas and adenocarcinomas. In specific instances of these embodiments, the cancer is an ovarian cancer selected from the group consisting of epithelial cancers.

In specific embodiments, the cancer is selected from cancers of the gastrointestinal system. In particular embodiments, the cancer is selected from the group consisting of esophageal cancers, gastric cancers (also known as stomach cancers), gastrointestinal carcinoid tumors, pancreatic cancers, gallbladder cancers, colorectal cancers, and anal cancer. In instances of these embodiments, the cancer is selected from the group consisting of esophageal squamous cell carcinomas, esophageal adenocarcinomas, gastric adenocarcinomas, gastrointestinal carcinoid tumors, gastrointestinal stromal tumors, gastric lymphomas, gastrointestinal lymphomas, solid pseudopapillary tumors of the pancreas, pancreatoblastoma, islet cell tumors, pancreatic carcinomas including acinar cell carcinomas and ductal adenocarcinomas, gallbladder adenocarcinomas, colorectal adenocarcinomas, and anal squamous cell carcinomas.

In specific embodiments, the cancer is selected from liver and bile duct cancers. In particular embodiments, the cancer is liver cancer (also known as hepatocellular carcinoma). In particular embodiments, the cancer is bile duct cancer (also known as cholangiocarcinoma); in instances of these embodiments, the bile duct cancer is selected from the group consisting of intrahepatic cholangiocarcinoma and extrahepatic cholangiocarcinoma.

In specific embodiments, the cancer is selected from kidney and bladder cancers. In particular embodiments, the cancer is a kidney cancer selected from the group consisting of renal cell cancer, Wilms tumors, and transitional cell cancers. In particular embodiments, the cancer is a bladder cancer selected from the group consisting of urethelial carcinoma (a transitional cell carcinoma), squamous cell carcinomas, and adenocarcinomas.

In specific embodiments, the cancer is selected from bone cancers. In particular embodiments, the bone cancer is selected from the group consisting of osteosarcoma, malignant fibrous histiocytoma of bone, Ewing sarcoma, chordoma (cancer of the bone along the spine).

In specific embodiments, the cancer is selected from lung cancers. In particular embodiments, the lung cancer is selected from the group consisting of non-small cell lung cancer, small cell lung cancers, bronchial tumors, and pleuropulmonary blastomas.

In specific embodiments, the cancer is selected from malignant mesothelioma. In particular embodiments, the cancer is selected from the group consisting of epithelial mesothelioma and sarcomatoids.

In specific embodiments, the cancer is selected from sarcomas. In particular embodiments, the sarcoma is selected from the group consisting of central chondrosarcoma, central and periosteal chondroma, fibrosarcoma, clear cell sarcoma of tendon sheaths, and Kaposi's sarcoma.

In specific embodiments, the cancer is selected from lymphomas. In particular embodiments, the cancer is selected from the group consisting of Hodgkin lymphoma (e.g., Reed-Sternberg cells), non-Hodgkin lymphoma (e.g., diffuse large B-cell lymphoma, follicular lymphoma, mycosis fungoides, Sezary syndrome, primary central nervous system lymphoma), cutaneous T-cell lymphomas, primary central nervous system lymphomas.

In specific embodiments, the cancer is selected from glandular cancers. In particular embodiments, the cancer is selected from the group consisting of adrenocortical cancer (also known as adrenocortical carcinoma or adrenal cortical carcinoma), pheochromocytomas, paragangliomas, pituitary tumors, thymoma, and thymic carcinomas.

In specific embodiments, the cancer is selected from thyroid cancers. In particular embodiments, the thyroid cancer is selected from the group consisting of medullary thyroid carcinomas, papillary thyroid carcinomas, and follicular thyroid carcinomas.

In specific embodiments, the cancer is selected from germ cell tumors. In particular embodiments, the cancer is selected from the group consisting of malignant extracranial germ cell tumors and malignant extragonadal germ cell tumors. In specific instances of these embodiments, the malignant extragonadal germ cell tumors are selected from the group consisting of nonseminomas and seminomas.

In specific embodiments, the cancer is selected from heart tumors. In particular embodiments, the heart tumor is selected from the group consisting of malignant teratoma, lymphoma, rhabdomyosacroma, angiosarcoma, chondrosarcoma, infantile fibrosarcoma, and synovial sarcoma.

In specific embodiments, the cell-proliferation disorder is selected from benign papillomatosis, benign neoplastic diseases and gestational trophoblastic diseases. In particular embodiments, the benign neoplastic disease is selected from skin papilloma (warts) and genital papilloma. In particular embodiments, the gestational trophoblastic disease is selected from the group consisting of hydatidiform moles, and gestational trophoblastic neoplasia (e.g., invasive moles, choriocarcinomas, placental-site trophoblastic tumors, and epithelioid trophoblastic tumors).

As used herein, the terms "treatment" and "treating" refer to all processes in which there may be a slowing, interrupting, arresting, controlling, or stopping of the progression of a disease or disorder described herein. The terms do not necessarily indicate a total elimination of all disease or disorder symptoms.

The terms "administration of" and or "administering" a compound should be understood to include providing a compound described herein, or a pharmaceutically acceptable salt thereof, and compositions of the foregoing to a subject.

The amount of a compound administered to a subject is an amount sufficient to induce an immune response and/or to induce STING-dependent type I interferon production in the subject. In an embodiment, the amount of a compound can be an "effective amount" or "therapeutically effective amount," such that the subject compound is administered in an amount that will elicit, respectively, a biological or medical (i.e., intended to treat) response of a tissue, system, animal, or human that is being sought by a researcher, veterinarian, medical doctor, or other clinician. An effective amount does not necessarily include considerations of toxicity and safety related to the administration of a compound.

An effective amount of a compound will vary with the particular compound chosen (e.g., considering the potency, efficacy, and/or half-life of the compound); the route of administration chosen; the condition being treated; the severity of the condition being treated; the age, size, weight, and physical condition of the subject being treated; the medical history of the subject being treated; the duration of the treatment; the nature of a concurrent therapy; the desired therapeutic effect; and like factors and can be routinely determined by the skilled artisan.

The compounds disclosed herein may be administered by any suitable route including oral and parenteral administration. Parenteral administration is typically by injection or infusion and includes intravenous, intramuscular, intratumoral, and subcutaneous injection or infusion.

The compounds disclosed herein may be administered once or according to a dosing regimen where a number of doses are administered at varying intervals of time for a given period of time. For example, doses may be administered one, two, three, or four times per day. Doses may be administered until the desired therapeutic effect is achieved or indefinitely to maintain the desired therapeutic effect. Suitable dosing regimens for a compound disclosed herein depend on the pharmacokinetic properties of that compound, such as absorption, distribution and half-life, that can be determined by a skilled artisan. In addition, suitable dosing regimens, including the duration such regimens are administered, for a compound disclosed herein depend on the disease or condition being treated, the severity of the disease or condition, the age and physical condition of the subject being treated, the medical history of the subject being treated, the nature of concurrent therapy, the desired therapeutic effect, and like factors within the knowledge and expertise of the skilled artisan. It will be further understood by such skilled artisans that suitable dosing regimens may require adjustment given an individual subject's response to the dosing regimen or over time as the individual subject needs change. Typical daily dosages may vary depending upon the particular route of administration chosen.

One embodiment of the present disclosure provides for a method of treating a cell proliferation disorder comprising administration of a therapeutically effective amount of a compound of general formula (I), or a pharmaceutically acceptable salt of the foregoing, to a subject in need of treatment thereof. In embodiments, the disease or disorder to be treated is a cell proliferation disorder. In aspects of these embodiments, the cell proliferation disorder is cancer. In further aspects of these embodiments, the cancer is selected from brain and spinal cancers, cancers of the head and neck, leukemia and cancers of the blood, skin cancers, cancers of the reproductive system, cancers of the gastrointestinal system, liver and bile duct cancers, kidney and bladder cancers, bone cancers, lung cancers, malignant mesothelioma, sarcomas, lymphomas, glandular cancers, thyroid cancers, heart tumors, germ cell tumors, malignant neuroendocrine (carcinoid) tumors, midline tract cancers, and cancers of unknown primary.

In one embodiment, disclosed herein is the use of a compound of general formula (I), or a pharmaceutically acceptable salt of the foregoing, in a therapy. The compound may be useful in a method of inducing an immune response and/or inducing STING-dependent type I interferon production in a subject, such as a mammal in need of such inhibition, comprising administering an effective amount of the compound to the subject.

In one embodiment, disclosed herein is a pharmaceutical composition comprising at least one compound of general formula (I), or at least one pharmaceutically acceptable salt of the foregoing, for use in potential treatment to induce an immune response and/or to induce STING-dependent type I interferon production.

One embodiment disclosed herein is the use of a compound of general formula (I), or a pharmaceutically acceptable salt of the foregoing, in the manufacture of a medicament to induce an immune response and/or to induce STING-dependent type I interferon production. In embodiments, the disease or disorder to be treated is a cell proliferation disorder. In aspects of these embodiments, the cell proliferation disorder is cancer. In further aspects of these embodiments, the cancer is selected from brain and spinal cancers, cancers of the head and neck, leukemia and cancers of the blood, skin cancers, cancers of the reproductive system, cancers of the gastrointestinal system, liver and bile duct cancers, kidney and bladder cancers, bone cancers, lung cancers, malignant mesothelioma, sarcomas, lymphomas, glandular cancers, thyroid cancers, heart tumors, germ cell tumors, malignant neuroendocrine (carcinoid) tumors, midline tract cancers, and cancers of unknown primary.

Compositions

The term "composition" as used herein is intended to encompass a dosage form comprising a specified compound in a specified amount, as well as any dosage form that results, directly or indirectly, from combination of a specified compound in a specified amount. Such term is intended to encompass a dosage form comprising a compound of general formula (I), or a pharmaceutically acceptable salt, hydrate, solvate, or prodrug of the foregoing, and one or more pharmaceutically acceptable carriers or excipients. In embodiments, the dosage form comprises compounds of general structural formula (I), or a pharmaceutically acceptable salt, hydrate, or solvate thereof, and one or more pharmaceutically acceptable carriers or excipients. In specific embodiments, the dosage form comprises compounds of general structural formula (I), or a pharmaceutically acceptable salt thereof, and one or more pharmaceutically acceptable carriers or excipients. Accordingly, the compositions of the present disclosure encompass any composition made by admixing a compound of the present disclosure and one or more pharmaceutically acceptable carrier or excipients. By "pharmaceutically acceptable", it is meant the carriers or excipients are compatible with the compound disclosed herein and with other ingredients of the composition.

For the purpose of inducing an immune response and/or inducing STING-dependent type I interferon production, the compounds of general formula (I), or pharmaceutically acceptable salts of the foregoing, can be administered by means that produces contact of the active agent with the agent's site of action. The compounds can be administered by conventional means available for use in conjunction with pharmaceuticals, either as individual therapeutic agents or in a combination of therapeutic agents. The compounds can be administered alone, but typically are administered with a pharmaceutical carrier selected on the basis of the chosen route of administration and standard pharmaceutical practice.

In one embodiment, disclosed herein is a composition comprising a compound of general formula (I), or a pharmaceutically acceptable salt of the foregoing, and one or more pharmaceutically acceptable carriers or excipients. The composition may be prepared and packaged in bulk form in which a therapeutically effective amount of a compound of the disclosure can be extracted and then given to a subject, such as with powders or syrups. Alternatively, the composition may be prepared and packaged in unit dosage form in which each physically discrete unit contains a therapeutically effective amount of a compound of general formula (I), or a pharmaceutically acceptable salt of the foregoing.

The compounds disclosed herein and a pharmaceutically acceptable carrier or excipient(s) will typically be formulated into a dosage form adapted for administration to a subject by a desired route of administration. For example, dosage forms include those adapted for (1) oral administration, such as tablets, capsules, caplets, pills, troches, powders, syrups, elixirs, suspensions, solutions, emulsions, sachets, and cachets; and (2) parenteral administration, such as sterile solutions, suspensions, and powders for reconstitution. Suitable pharmaceutically acceptable carriers or excipients will vary depending upon the particular dosage form chosen. In addition, suitable pharmaceutically acceptable carriers or excipients may be chosen for a particular function that they may serve in the composition. For example, certain pharmaceutically acceptable carriers or excipients may be chosen for their ability to facilitate the production of uniform dosage forms. Certain pharmaceutically acceptable carriers or excipients may be chosen for their ability to facilitate the production of stable dosage forms. Certain pharmaceutically acceptable carriers or excipients may be chosen for their ability to facilitate the carrying or transporting of a compound disclosed herein, once administered to the subject, from one organ or portion of the body to another organ or another portion of the body. Certain pharmaceutically acceptable carriers or excipients may be chosen for their ability to enhance patient compliance.

Suitable pharmaceutically acceptable excipients include the following types of excipients: diluents, lubricants, binders, disintegrants, fillers, glidants, granulating agents, coating agents, wetting agents, solvents, co-solvents, suspending agents, emulsifiers, sweeteners, flavoring agents, flavor masking agents, coloring agents, anti-caking agents, hemectants, chelating agents, plasticizers, viscosity increasing agents, antioxidants, preservatives, stabilizers, surfactants, and buffering agents.

A skilled artisan possesses the knowledge and skill in the art to select suitable pharmaceutically acceptable carriers and excipients in appropriate amounts for the use in the compositions of the disclosure. In addition, there are a number of resources available to the skilled artisan, which describe pharmaceutically acceptable carriers and excipients and may be useful in selecting suitable pharmaceutically acceptable carriers and excipients. Examples include REMINGTON'S PHARMACEUTICAL SCIENCES (Mack Publishing Company), THE HANDBOOK OF PHARMACEUTICAL ADDITIVES (Gower Publishing Limited), and THE HANDBOOK OF PHARMACEUTICAL EXCIPIENTS (the American Pharmaceutical Association and the Pharmaceutical Press).

The compositions of the disclosure are prepared using techniques and methods known to those skilled in the art. Some methods commonly used in the art are described in REMINGTON'S PHARMACEUTICAL SCIENCES (Mack Publishing Company).

In one embodiment, the disclosure is directed to a solid oral dosage form such as a tablet or capsule comprising a therapeutically effective amount of a compound of general formula (I), or a pharmaceutically acceptable salt of the foregoing, and a diluent or filler. Suitable diluents and fillers include lactose, sucrose, dextrose, mannitol, sorbitol, starch (e.g., corn starch, potato starch, and pre-gelatinized starch), cellulose and its derivatives, (e.g., microcrystalline cellulose), calcium sulfate, and dibasic calcium phosphate. The solid oral dosage form may further comprise a binder. Suitable binders include starch (e.g., corn starch, potato starch, and pre-gelatinized starch) gelatin, acacia, sodium alginate, alginic acid, tragacanth, guar gum, povidone, and cellulose and its derivatives (e.g., microcrystalline cellulose). The solid oral dosage form may further comprise a disintegrant. Suitable disintegrants include crospovidone, sodium starch glycolate, croscarmelose, alginic acid, and sodium carboxymethyl cellulose. The solid oral dosage form may further comprise a lubricant. Suitable lubricants include stearic acid, magnesium stearate, calcium stearate, and talc.

Where appropriate, dosage unit formulations for oral administration can be microencapsulated. The composition can also be prepared to prolong or sustain the release as, for example, by coating or embedding particulate material in polymers, wax, or the like.

The compounds disclosed herein may also be coupled with soluble polymers as targetable drug carriers. Such polymers can include polyvinylpyrrolidone, pyrancopolymer, polyhydroxypropylmethacrylamidephenol, polyhydroxyethylaspartamidephenol, or polyethyleneoxidepolylysine substituted with palmitoyl residues. Furthermore, the compounds of the disclosure may be coupled to a class of biodegradable polymers useful in achieving controlled release of a drug, for example polylactic acid, polepsilon caprolactone, polyhydroxy butyric acid, polyorthoesters, polyacetals, polydihydropyrans, polycyanacrylates, and cross-linked or amphipathic block copolymers of hydrogels.

In one embodiment, the disclosure is directed to a liquid oral dosage form. Oral liquids such as solutions, syrups, and elixirs can be prepared in dosage unit form so that a given quantity contains a predetermined amount of a compound or a pharmaceutically acceptable salt thereof disclosed herein. Syrups can be prepared by dissolving the compound of the disclosure in a suitably flavored aqueous solution; elixirs are prepared through the use of a non-toxic alcoholic vehicle. Suspensions can be formulated by dispersing a compound disclosed herein in a non-toxic vehicle. Solubilizers and emulsifiers such as ethoxylated isostearyl alcohols and polyoxy ethylene sorbitol ethers, preservatives, flavor additives such as peppermint oil, or other natural sweeteners or saccharin or other artificial sweeteners and the like can also be added.

In one embodiment, the disclosure is directed to compositions for parenteral administration. Compositions adapted for parenteral administration include aqueous and non-aqueous sterile injection solutions that may contain anti-oxidants, buffers, bacteriostats, and solutes that render the formulation isotonic with the blood of the intended recipient; and aqueous and non-aqueous sterile suspensions that may include suspending agents and thickening agents. The compositions may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules, and tablets.

Combinations

The compounds of general formula (I), and/or pharmaceutically acceptable salts of the foregoing, may be administered in combination with one or more additional active agents. In embodiments, one or more compounds of general formula (I), or one or more pharmaceutically acceptable salts of the foregoing, and the one or more additional active agents may be co-administered. The additional active agent(s) may be administered in a single dosage form with the compound of general formula (I), or pharmaceutically acceptable salt of the foregoing, or the additional active agent(s) may be administered in separate dosage form(s) from the dosage form containing the compound of general formula (I), or pharmaceutically acceptable salt of the foregoing. The additional active agent(s) may be one or more agents selected from the group consisting of STING agonist compounds, anti-viral compounds, antigens, adjuvants, anti-cancer agents, CTLA-4, LAG-3 and PD-1 pathway antagonists, lipids, liposomes, peptides, cytotoxic agents, chemotherapeutic agents, immunomodulatory cell lines, checkpoint inhibitors, vascular endothelial growth factor (VEGF) receptor inhibitors, topoisomerase II inhibitors, smoothen inhibitors, alkylating agents, anti-tumor antibiotics, anti-metabolites, retinoids, and immunomodulatory agents including but not limited to anti-cancer vaccines. It will be understood the descriptions of the above additional active agents may be overlapping. It will also be understood that the treatment combinations are subject to optimization, and it is understood that the best combination to use of the compounds of general formula (I), or pharmaceutically acceptable salts of the foregoing, and one or more additional active agents will be determined based on the individual patient needs.

A compound disclosed herein may be used in combination with one or more other active agents, including but not limited to, other anti-cancer agents that are used in the prevention, treatment, control, amelioration, or reduction of risk of a particular disease or condition (e.g., cell proliferation disorders). In one embodiment, a compound disclosed herein is combined with one or more other anti-cancer agents for use in the prevention, treatment, control amelioration, or reduction of risk of a particular disease or condition for which the compounds disclosed herein are useful. Such other active agents may be administered, by a route and in an amount commonly used therefor, contemporaneously or sequentially with a compound of the present disclosure.

When a compound disclosed herein is used contemporaneously with one or more other active agents, a composition containing such other active agents in addition to the compound disclosed herein is contemplated. Accordingly, the compositions of the present disclosure include those that also contain one or more other active ingredients, in addition to a compound disclosed herein. A compound disclosed herein may be administered either simultaneously with, or before or after, one or more other active agent(s). A compound disclosed herein may be administered separately, by the same or different route of administration, or together in the same pharmaceutical composition as the other agent(s).

Products provided as combinations may include a composition comprising a compound of general formula (I), or a pharmaceutically acceptable salt of the foregoing, and one or more other active agent(s) together in the same pharmaceutical composition, or may include a composition comprising a compound of general formula (I), or a pharmaceutically acceptable salt of the foregoing, and a composition comprising one or more other active agent(s) in separate form, e.g. in the form of a kit or in any form designed to enable separate administration either concurrently or on separate dosing schedules.

The weight ratio of a compound of general formula (I), or a pharmaceutically acceptable salt of the foregoing, to a second active agent may be varied and will depend upon the therapeutically effective dose of each agent. Generally, a therapeutically effective dose of each will be used. Combinations of a compound disclosed herein and other active agents will generally also be within the aforementioned range, but in each case, a therapeutically effective dose of each active agent should be used. In such combinations, the compound disclosed herein and other active agents may be administered separately or in conjunction. In addition, the administration of one element may be prior to, concurrent to, or subsequent to the administration of other agent(s).

In one embodiment, this disclosure provides a composition comprising a compound of general formula (I), or a pharmaceutically acceptable salt of the foregoing, and at least one other active agent as a combined preparation for simultaneous, separate or sequential use in therapy. In one embodiment, the therapy is the treatment of a cell proliferation disorder, such as cancer.

In one embodiment, the disclosure provides a kit comprising two or more separate pharmaceutical compositions, at least one of which contains a compound of general formula (I), or a pharmaceutically acceptable salt of the foregoing. In one embodiment, the kit comprises means for separately retaining said compositions, such as a container, divided bottle, or divided foil packet. An example of such a kit is a blister pack, as typically used for the packaging of tablets, capsules, and the like.

A kit of this disclosure may be used for administration of different dosage forms, for example, oral and parenteral, for administration of the separate compositions at different dosage intervals, or for titration of the separate compositions against one another. To assist with compliance, a kit of the disclosure typically comprises directions for administration.

Disclosed herein is a use of a compound of general formula (I), or a pharmaceutically acceptable salt of the foregoing, for treating a cell proliferation disorder, where the medicament is prepared for administration with another active agent. The disclosure also provides the use of another active agent for treating a cell proliferation disorder, where the medicament is administered with a compound of general formula (I), or a pharmaceutically acceptable salt of the foregoing.

The disclosure also provides the use of a compound of general formula (I), or a pharmaceutically acceptable salt of the foregoing, for treating a cell proliferation disorder, where the patient has previously (e.g., within 24 hours) been treated with another active agent. The disclosure also provides the use of another active agent for treating a cell proliferation disorder, where the patient has previously (e.g., within 24 hours) been treated with a compound of general formula (I), or a pharmaceutically acceptable salt of the foregoing. The second agent may be administered a week, several weeks, a month, or several months after the administration of a compound disclosed herein.

STING agonist compounds that may be used in combination with the compounds of general formula (I), or pharmaceutically acceptable salts of the foregoing, disclosed herein include but are not limited to cyclic di-nucleotide compounds.

Anti-viral compounds that may be used in combination with the compounds of general formula (I), or pharmaceutically acceptable salts of the foregoing, disclosed herein include hepatitis B virus (HBV) inhibitors, hepatitis C virus (HCV) protease inhibitors, HCV polymerase inhibitors, HCV NS4A inhibitors, HCV NS5A inhibitors, HCV NS5b inhibitors, and human immunodeficiency virus (HIV) inhibitors.

Antigens and adjuvants that may be used in combination with the compounds of general formula (I), or the pharmaceutically acceptable salts of the foregoing, include B7 costimulatory molecule, interleukin-2, interferon-y, GM-CSF, CTLA-4 antagonists, OX-40/OX-40 ligand, CD40/CD40 ligand, sargramostim, levamisol, vaccinia virus, Bacille Calmette-Guerin (BCG), liposomes, alum, Freund's complete or incomplete adjuvant, detoxified endotoxins, mineral oils, surface active substances such as lipolecithin, pluronic polyols, polyanions, peptides, and oil or hydrocarbon emulsions. Adjuvants, such as aluminum hydroxide or aluminum phosphate, can be added to increase the ability of the vaccine to trigger, enhance, or prolong an immune response. Additional materials, such as cytokines, chemokines, and bacterial nucleic acid sequences, like CpG, a toll-like receptor (TLR) 9 agonist as well as additional agonists for TLR 2, TLR 4, TLR 5, TLR 7, TLR 8, TLR9, including lipoprotein, LPS, monophosphoryllipid A, lipoteichoic acid, imiquimod, resiquimod, and in addition retinoic acid-inducible gene I (RIG-I) agonists such as poly I:C, used separately or in combination with the described compositions are also potential adjuvants.

CLTA-4 and PD-1 pathways are important negative regulators of immune response. Activated T-cells up-regulate CTLA-4, which binds on antigen-presenting cells and inhibits T-cell stimulation, IL-2 gene expression, and T-cell proliferation; these anti-tumor effects have been observed in mouse models of colon carcinoma, metastatic prostate cancer, and metastatic melanoma. PD-1 binds to active T-cells and suppresses T-cell activation; PD-1 antagonists have demonstrated anti-tumor effects as well. CTLA-4 and PD-1 pathway antagonists that may be used in combination with the compounds of general formula (Ia), the compounds of general formula (Ib), the compounds of general formula (I), or the pharmaceutically acceptable salts of the foregoing, disclosed herein, include ipilimumab, tremelimumab, nivolumab, pembrolizumab, CT-011, AMP-224, and MDX-1106.

"PD-1 antagonist" or "PD-1 pathway antagonist" means any chemical compound or biological molecule that blocks binding of PD-L1 expressed on a cancer cell to PD-1 expressed on an immune cell (T-cell, B-cell, or NKT-cell) and preferably also blocks binding of PD-L2 expressed on a cancer cell to the immune-cell expressed PD-1. Alternative names or synonyms for PD-1 and its ligands include: PDCD1, PD1, CD279, and SLEB2 for PD-1; PDCD1-L1, PDL1, B7H1, B7-4, CD274, and B7-H for PD-L1; and PDCD1L2, PDL2, B7-DC, Btdc, and CD273 for PD-L2. In any of the treatment method, medicaments and uses of the present disclosure in which a human individual is being treated, the PD-1 antagonist blocks binding of human PD-L1 to human PD-1, and preferably blocks binding of both human PD-L1 and PD-L2 to human PD-1. Human PD-1 amino acid sequences can be found in NCBI Locus No.: NP_005009. Human PD-L1 and PD-L2 amino acid sequences can be found in NCBI Locus No.: NP_054862 and NP_079515, respectively.

PD-1 antagonists useful in any of the treatment method, medicaments and uses of the present disclosure include a monoclonal antibody (mAb), or antigen binding fragment thereof, which specifically binds to PD-1 or PD-L1, and preferably specifically binds to human PD-1 or human PD-L1. The mAb may be a human antibody, a humanized antibody, or a chimeric antibody and may include a human constant region. In some embodiments, the human constant region is selected from the group consisting of IgG1, IgG2, IgG3, and IgG4 constant regions, and in preferred embodiments, the human constant region is an IgG1 or IgG4 constant region. In some embodiments, the antigen binding fragment is selected from the group consisting of Fab, Fab'-SH, F(ab')$_2$, scFv, and Fv fragments.

Examples of mAbs that bind to human PD-1, and useful in the treatment method, medicaments and uses of the present disclosure, are described in U.S. Pat. Nos. 7,488, 802, 7,521,051, 8,008,449, 8,354,509, and 8,168,757, PCT International Patent Application Publication Nos. WO2004/004771, WO2004/072286, and WO2004/056875, and U.S. Patent Application Publication No. US2011/0271358.

Examples of mAbs that bind to human PD-L1, and useful in the treatment method, medicaments and uses of the present disclosure, are described in PCT International Patent Application Nos. WO2013/019906 and WO2010/077634 A1 and in U.S. Pat. No. 8,383,796. Specific anti-human PD-L1 mAbs useful as the PD-1 antagonist in the treatment method, medicaments and uses of the present disclosure include MPDL3280A, BMS-936559, MEDI4736, MSB0010718C, and an antibody that comprises the heavy chain and light chain variable regions of SEQ ID NO:24 and SEQ ID NO:21, respectively, of WO2013/019906.

Other PD-1 antagonists useful in any of the treatment method, medicaments, and uses of the present disclosure include an immune-adhesion that specifically binds to PD-1 or PD-L1, and preferably specifically binds to human PD-1 or human PD-L1, e.g., a fusion protein containing the extracellular or PD-1 binding portion of PD-L1 or PD-L2 fused to a constant region such as an Fc region of an immunoglobulin molecule. Examples of immune-adhesion molecules that specifically bind to PD-1 are described in PCT International Patent Application Publication Nos. WO2010/027827 and WO2011/066342. Specific fusion proteins useful as the PD-1 antagonist in the treatment method, medicaments, and uses of the present disclosure include AMP-224 (also known as B7-DCIg), which is a PD-L2-FC fusion protein and binds to human PD-1.

Examples of cytotoxic agents that may be used in combination with the compounds of general formula (I), or pharmaceutically acceptable salts of the foregoing, include, but are not limited to, arsenic trioxide (sold under the tradename TRISENOX®), asparaginase (also known as L-asparaginase, and Erwinia L-asparaginase, sold under the tradenames ELSPAR® and KIDROLASE®).

Chemotherapeutic agents that may be used in combination with the compounds of general formula (I), or pharmaceutically acceptable salts of the foregoing, disclosed herein include abiraterone acetate, altretamine, anhydrovinblastine, auristatin, bexarotene, bicalutamide, BMS 184476, 2,3,4,5, 6-pentafluoro-N-(3-fluoro-4-methoxyphenyl)benzene sulfonamide, bleomycin, N,N-dimethyl-L-valyl-L-valyl-N-methyl-L-valyl-L-prolyl-1-Lproline-t-butylamide, cachectin, cemadotin, chlorambucil, cyclophosphamide, 3',4'-didehydro-4'deoxy-8'-norvin-caleukoblastine, docetaxol, doxetaxel, cyclophosphamide, carboplatin, carmustine, cisplatin, cryptophycin, cyclophosphamide, cytarabine, dacarbazine (DTIC), dactinomycin, daunorubicin, decitabine dolastatin, doxorubicin (adriamycin), etoposide, 5-fluorouracil, finasteride, flutamide, hydroxyurea and hydroxyurea andtaxanes, ifosfamide, liarozole, lonidamine, lomustine (CCNU), MDV3100, mechlorethamine (nitrogen mustard), melphalan, mivobulin isethionate, rhizoxin, sertenef, streptozocin, mitomycin, methotrexate, taxanes, nilutamide, nivolumab, onapristone, paclitaxel, pembrolizumab, prednimustine, procarbazine, RPR109881, stramustine phosphate, tamoxifen, tasonermin, taxol, tretinoin, vinblastine, vincristine, vindesine sulfate, and vinflunine.

Examples of vascular endothelial growth factor (VEGF) receptor inhibitors include, but are not limited to, bevacizumab (sold under the trademark AVASTIN), axitinib (described in PCT International Patent Publication No. WO01/002369), Brivanib Alaninate ((S)-((R)-1-(4-(4-Fluoro-2-methyl-1H-indol-5-yloxy)-5-methylpyrrolo[2,1-f][1,2,4] triazin-6-yloxy)propan-2-yl)2-aminopropanoate, also known as BMS-582664), motesanib (N-(2,3-dihydro-3,3-dimethyl-1H-indol-6-yl)-2-[(4-pyridinylmethyl)amino]-3-pyridinecarboxamide. and described in PCT International Patent Application Publication No. WO02/068470), pasireotide (also known as SO 230, and described in PCT International Patent Publication No. WO02/010192), and sorafenib (sold under the tradename NEXAVAR).

Examples of topoisomerase II inhibitors, include but are not limited to, etoposide (also known as VP-16 and Etoposide phosphate, sold under the tradenames TOPOSAR, VEPESID, and ETOPOPHOS), and teniposide (also known as VM-26, sold under the tradename VUMON).

Examples of alkylating agents, include but are not limited to, 5-azacytidine (sold under the trade name VIDAZA), decitabine (sold under the trade name of DECOGEN), temozolomide (sold under the trade names TEMCAD, TEMODAR, and TEMODAL), dactinomycin (also known as actinomycin-D and sold under the tradename COSMEGEN), melphalan (also known as L-PAM, L-sarcolysin, and phenylalanine mustard, sold under the tradename ALKERAN), altretamine (also known as hexamethylmelamine (HMNI), sold under the tradename HEXALEN), carmustine (sold under the tradename BCNU), bendamustine (sold under the tradename TREANDA), busulfan (sold under the tradenames BUSULFEX® and MYLERAN®), carboplatin (sold under the tradename PARAPLATIN®), lomustine (also known as CCNU, sold under the tradename CEENU®), cisplatin (also known as CDDP, sold under the tradenames PLATINOL® and PLATINOC®-AQ), chlorambucil (sold under the tradename LEUKERAN®), cyclophosphamide (sold under the tradenames CYTOXAN® and NEOSAR®), dacarbazine (also known as DTIC, DIC and imidazole carboxamide, sold under the tradename DTIC-DOME®), altretamine (also known as hexamethylmelamine (HMM) sold under the tradename HEXALEN®), ifosfamide (sold under the tradename IFEX®), procarbazine (sold under the tradename MATULANE®), mechlorethamine (also known as nitrogen mustard, mustine and mechloroethamine hydrochloride, sold under the tradename MUSTARGEN®), streptozocin (sold under the tradename ZANOSAR®), thiotepa (also known as thiophosphoamide, TESPA and TSPA, and sold under the tradename THIOPLEX®.

Examples of anti-tumor antibiotics include, but are not limited to, doxorubicin (sold under the tradenames ADRIAMYCIN® and RUBEX®), bleomycin (sold under the tradename LENOXANE®), daunorubicin (also known as dauorubicin hydrochloride, daunomycin, and rubidomycin hydrochloride, sold under the tradename CERUBIDINE®), daunorubicin liposomal (daunorubicin citrate liposome, sold under the tradename DAUNOXOME®), mitoxantrone (also known as DHAD, sold under the tradename NOVANTRONE®), epirubicin (sold under the tradename ELLENCE™), idarubicin (sold under the tradenames IDAMYCIN®, IDAMYCIN PFS®), and mitomycin C (sold under the tradename MUTAMYCIN®).

Examples of anti-metabolites include, but are not limited to, claribine (2-chlorodeoxyadenosine, sold under the tradename LEUSTATIN®), 5-fluorouracil (sold under the tradename ADRUCIL®), 6-thioguanine (sold under the tradename PURI- NETHOL®), pemetrexed (sold under the tradename ALIMTA®), cytarabine (also known as arabinosylcytosine (Ara-C), sold under the tradename CYTOSAR-U®), cytarabine liposomal (also known as Liposomal Ara-C, sold under the tradename DEPOCYT™), decitabine (sold under the tradename DACOGEN®), hydroxyurea and (sold under the tradenames HYDREA®, DROXIA™ and MYLOCEL™) fludarabine (sold under the tradename FLUDARA®), floxuridine (sold under the tradename FUDR®), cladribine (also known as 2-chlorodeoxyadenosine (2-CdA) sold under the tradename LEUSTATIN™), methotrexate (also known as amethopterin, methotrexate sodium (MTX), sold under the tradenames RHEUMATREX® and TREXALL™), and pentostatin (sold under the tradename NIPENT®).

Examples of retinoids include, but are not limited to, alitretinoin (sold under the tradename PANRETIN®), tretinoin (all-trans retinoic acid, also known as ATRA, sold under the tradename VESANOID®), Isotretinoin (13-c/s-retinoic acid, sold under the tradenames ACCUTANE®, AMNESTEEM® CLARAVIS®, CLARUS®, DECUTAN®, ISOTANE®, IZOTECH® ORATANE®, ISOTRET®, and SOTRET®), and bexarotene (sold under the tradename TARGRETIN®)

Activity: STING Biochemical [3H]cGAMP Competition Assay

The individual compounds described in the Examples herein are defined as STING agonists by (i) binding to the STING protein as evidenced by a reduction in binding of tritiated cGAMP ligand to the STING protein by at least 20% at 20 uM (concentration of compound being tested) in a STING Biochemical [3H]cGAMP Competition Assay and/or (ii) demonstrating interferon production with a 6% or greater induction of IFN-β secretion at 30 uNT in the THP1 cell assay (where induction caused by cGAMP at 300/1 was set at 100%).

The ability of compounds to bind STING is quantified by the ability to compete with tritiated cGAMP ligand for human STING receptor membrane using a radioactive filter-binding assay. The binding assay employs STING receptor obtained from Hi-Five cell membranes overexpressing full-length HAQ STING prepared in-house and tritiated cGAMP ligand also purified in-house.

The following experimental procedures detail the preparation of specific examples of the instant disclosure. The compounds of the examples are drawn in their neutral forms in the procedures and tables below. In some cases, the compounds were isolated as salts depending on the method used for their final purification and/or intrinsic molecular properties. The examples are for illustrative purposes only and are not intended to limit the scope of the instant disclosure in any way.

EXAMPLES

Abbreviations $^{19}$F-NMR $^{19}$F nuclear magnetic resonance spectroscopy
$^{1}$H-NMR Proton nuclear magnetic resonance spectroscopy
$^{31}$P-NMR $^{31}$P nuclear magnetic resonance spectroscopy
Å Angstrom
AcOH Acetic acid
aq Aqueous
ATP Adenosine 5'-triphosphate
$BF_3$—$OEt_2$ Boron trifluoride diethyl etherate
Bn Benzyl
Bz Benzoyl
BzCl Benzoyl chloride
$CD_3OD$ Deuterium-enriched methyl alcohol, deuterium-enriched methanol
Ci Curie, a non-standard unit of radioactivity; 1Ci=3.7×$10^{10}$Bq, where Bq is Becquerel, the SI unit of radioactivity, equivalent to 1 disintegration per second (dps)
d Doublet
$D_2O$ Deuterium-enriched water
DBU 1,8-diazabicyclo(5.4.0)undec-7-ene
DCA Dichloroacetic acid
DCM, $CH_2Cl_2$ Dichloromethane
ddd Doublet of doublet of doublet
ddt Doublet of doublet of triplet
DIEA N,N-diisopropylethylamine
DMF N,N-dimethylformamide
DMSO Dimethyl sulfoxide
DMTr 4,4'-dimethoxytrityl
DMTrCl 4,4'-dimethoxytrityl chloride
DPCP Diphenyl phosphorochloridate
dq Doublet of quartet
e # Standard exponential notation for #×$10^{\#}$; for example 2e5=2×$10^5$
$EC_{50}$ half maximal effective concentration, concentration of a drug, antibody or toxicant that induces a response halfway between the baseline and maximum after a specified exposure time
EDTA Ethylenediaminetetraacetic acid
eq Equivalents
ES Electron spray
Et Ethyl
$Et_2O$ Diethyl ether
$Et_3N$, TEA Triethylamine
$Et_3N$.3HF Triethylamine trihydrogen floride
$Et_3SiH$, $Si(C_2H_5)_3H$ Triethylsilane
EtOAc Ethyl acetate
EtOH Ethyl alcohol, ethanol
g Gram
GTP Guanosine 5'-triphosphate
h Hour
HEPES 2-[4-(2-hydroxyethyl)piperazin-1-yl]ethanesulfortic acid, a zwitterionic organic chemical buffering agent
hept Heptet
Hex Hexanes
HF-Pyr, HF-Py Hydrogen fluoride pyridine complex
HPLC High performance liquid chromatography
Hz Hertz
iPrMgCl-LiCl Isopropylmagnesium chloride lithium chloride compled
J NMR Coupling constant
L Liter
LCMS Liquid chromatography mass spectroscopy
$Li_2S$ Dilithium sulfide
m Multiplet
M Molar, moles per liter
mCi Millicurie
Me, $CH_3$ Methyl
MeCN, ACN, $CH_3CH$ Acetonitrile
MeMgBr, $CH_3MgBr$ Methylmagnesium bromide
MeNH, $CH_3NH_2$ Methylamine
MeOH Methanol
mg Milligram
$MgCl_2$ Magnesium chloride
MHz Megahertz
min Minute(s)
mL,ml Milliliter
mM Millimole per liter
mm Millimeter
mmol Millimole MOI Multiplicity of infection mol Mole N Normal ng Nanogram(s)

nL Nanoliter nm Nanometer nM Nanomolar pfu Particle-forming units

Ph phenyl

PSI, psi Pounds per square inch

Py Pyridine q Quartet

RPM, rpm Revolutions per minute

RT, rt Room temperature, approximately 25° C.

s Singlet sat Saturated t Triplet tBuOOH t-Butylhydrogen peroxide

TEAA Triethyl ammonium acetate

THF Tetrahydrofuran

TLC Thin layer chromatography

TMSCl Trimethylsilyl chloride, Si(CH$_3$)$_3$Cl

T$_R$ Retention time

TrisCl Tris(hydroxymethyl)aminomethane hydrochloride v/v Volume/volume xg Times gravity; the force applied to a spinning sample in terms of multiples of the gravitational force $\lambda_{em}$ Emission wavelength $\lambda_{ex}$ Excitation wavelength μg Microgram μL, uL Microliter μM, uM Micromolar μm Micrometer, micron μmol Micromole Preparation 1: N-(9-((2R,3S,4S,5R)-5-((bis(4-methoxyphenyl)(phenyl)methoxy)methyl)-4-fluoro-3-hydroxytetrahydrofuran-2-yl)-6-oxo-6,9-dihydro-1H-purin-2-yl)isobutyramide Step 1: N-(9-((2R,3S,4S,5R)-4-fluoro-3-hydroxy-5-(hydroxymethyl)tetrahydrofuran-2-yl)-6-oxo-6,9-dihydro-1H-purin-2-yl)isobutyramide

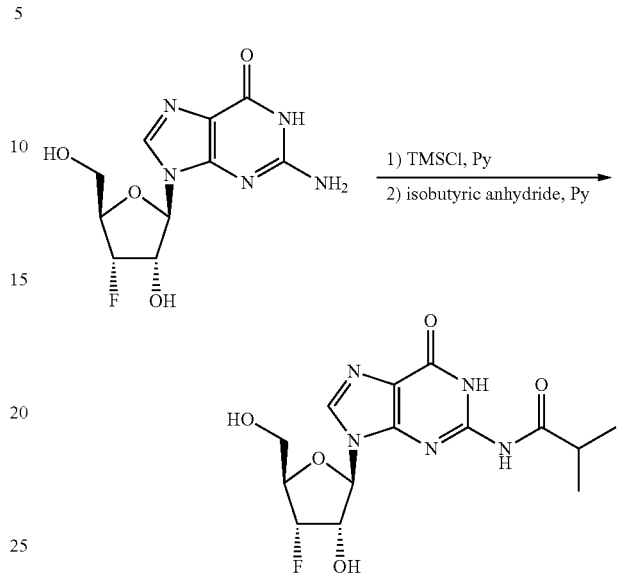

To a suspension of 2-amino-9-((2R,3S,4S,5R)-4-fluoro-3-hydroxy-5-(hydroxymethyl)tetrahydrofuran-2-yl)-1,9-dihydro-6H-purin-6-one (Carbosynth catalog # ND10826, 1.50 g, 5.26 mmol) in Py (30 mL) at 0° C. to 5° C. was added TMSCl (2.86 g, 26.3 mmol), and the mixture was stirred at RT for 30 min. Then, isobutyric anhydride (2.50 g, 15.8 mmol) was added dropwise, and it was stirred for an additional for 2 h. Then, MeOH (5.3 mL) was added. After 5 min, NH$_4$OH (10.5 mL) was added dropwise and stirring was continued for 30 min. The reaction mixture was concentrated under reduced pressure, and MeOH (2 mL) in CH$_2$Cl$_2$ (18 mL) was added to the residue. Insolubles were filtered off, and the filtrate was concentrated and purified by flash column chromatography with 2-10% MeOH in CH$_2$Cl$_2$ to give the product. LCMS (ES, m/z): 356.1 [M+H]$^+$. $^1$H-NMR: (400 MHz, DMSO-d$_6$): δ 12.11 (s, 1H), 11.68 (s, 1H), 8.28 (s, 1H), 5.98 (d, J=6.1 Hz, 1H), 5.85 (d, J=8.0 Hz, 1H), 5.24 (t, J=5.4 Hz, 1H), 5.14 (d, J=4.1 Hz, 0.5H), 5.01 (d, J=4.2 Hz, 0.5H), 4.87-4.69 (m, 1H), 4.26 (t, J=4.4 Hz, 0.5H), 4.19 (t, J=4.4 Hz, 0.5H), 3.61 (t, J=4.9 Hz, 2H), 2.77 (hept, J=6.8 Hz, 1H), 1.13 (d, J=6.7 Hz, 6H). $^{19}$F-NMR: (376 MHz, DMSO-d$_6$): δ –197.5 (s).

Step 2: N-(9-((2R,3S,4S,5R)-5-((bis(4-methoxyphenyl)(phenyl)methoxy)methyl)-4-fluoro-3-hydroxytetrahydrofuran-2-yl)-6-oxo-6,9-dihydro-1H-purin-2-yl)isobutyramide

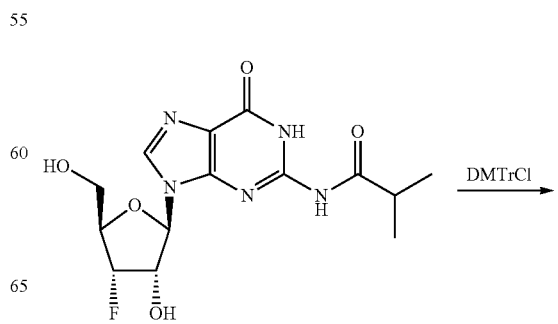

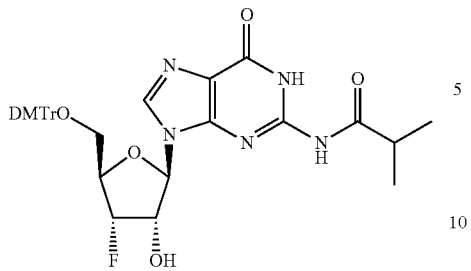

N-(9-((2R,3S,4S,5R)-4-fluoro-3-hydroxy-5-(hydroxymethyl)tetrahydrofuran-2-yl)-6-oxo-6,9-dihydro-1H-purin-2-yl)isobutyramide (1.30 g, 3.66 mmol) was co-evaporated with Py (3×10 mL) and re-dissolved in Py (26 mL). To the solution at 0° C. to 5° C. was added DMTrCl (1.36 g, 4.02 mmol). It was stirred at RT for 3 h and then concentrated. CH$_2$Cl$_2$ (40 mL, with 1% Et$_3$N) was added, and it was washed with sat aq NaHCO$_3$ (15 mL), H$_2$O (10 mL) and brine (10 mL). The organic solution was dried (Na$_2$SO$_4$), concentrated and purified by silica gel column chromatography using 0-10% MeOH in CH$_2$Cl$_2$ (1% Et$_3$N) to give the product. LCMS (ES, m/z): 656.2 [M−H]⁻. $^1$H-NMR: (400 MHz, DMSO-d$_6$): δ 12.10 (s, 1H), 11.61 (s, 1H), 8.14 (s, 1H), 7.40-7.31 (m, 2H), 7.31-7.19 (m, 7H), 6.89-6.78 (m, 4H), 6.08 (d, J=6.1 Hz, 1H), 5.87 (d, J=7.3 Hz, 1H), 5.23 (dd, J=4.1, 1.8 Hz, OH), 5.10 (d, J=4.4 Hz, OH), 4.96 (dq, J=22.4, 5.9 Hz, 1H), 4.30 (dt, J=26.1, 4.6 Hz, 1H), 3.74 (d, J=1.1 Hz, 6H), 3.39 (dd, J=10.6, 5.7 Hz, 1H), 3.22 (dd, J=10.6, 3.8 Hz, 1H), 2.76 (p, J=6.8 Hz, 1H), 1.13 (d, J=6.8 Hz, 6H). $^{19}$F-NMR: (376 MHz, DMSO-d$_6$): δ −198.1 (s, 1F).

Preparation 2: N-(7-((2R,4S,5R)-5-((bis(4-methoxyphenyl)(phenyl)methoxy)methyl)-4-hydroxytetrahydrofuran-2-yl)imidazo[2,1-f][1,2,4]triazin-4-yl)benzamide

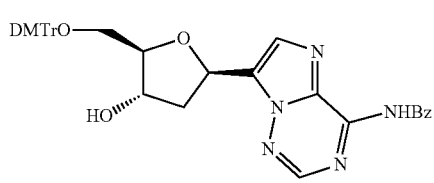

Step 1: (3R,4R,5R)-2-(4-aminoimidazo[2,1-f][1,2,4]triazin-7-yl)-3,4-bis(benzyloxy)-5-((benzyloxy)methyl)tetrahydrofuran-2-ol

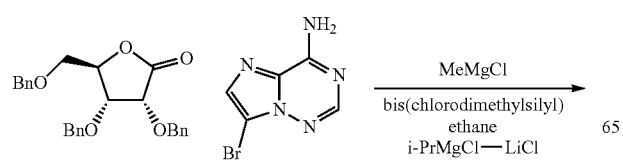

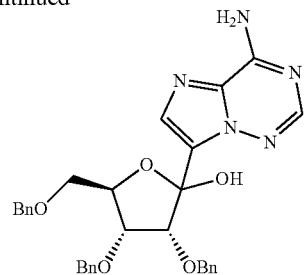

To a stirring mixture of 7-bromoimidazo[2,1-f][1,2,4]triazin-4-amine (41 g, 0.19 mol) in THF (0.50 L) at 0° C. was added MeMgBr (3.0M in THF, 66 mL, 0.19 mol) dropwise to maintain the internal temperature below 10° C. Bis(chlorodimethylsilyl)ethane (41 g, 190 mmol) was added in one portion. MeMgBr (3.0M in Et$_2$O, 66 mL, 0.19 mol) was then added dropwise to maintain the internal temperature below 10° C. i-PrMgCl-LiCl (1.3M in THF, 0.16 L, 0.21 mol) was added while maintaining the internal temperature below 10° C. A mixture of (3R,4R,5R)-3,4-bis(benzyloxy)-5-((benzyloxy)methyl)dihydrofuran-2(3H)-one (160 g, 0.38 mol) in THF was added dropwise at 0° C., and the mixture was then allowed to warm to RT and was stirred for 12 h. The mixture was diluted with sat aq NH$_4$Cl (100 mL) and extracted with EtOAc (3×1000 mL). The combined organic layers were dried over Na$_2$SO$_4$ and concentrated under reduced pressure. The resulting residue was purified by column chromatography (column height: 2500 mm, diameter: 1000 mm, 25% to 75% EtOAc gradient in hex) to afford (3R,4R,5R)-2-(4-aminoimidazo[2,1-f][1,2,4]triazin-7-yl)-3,4-bis(benzyloxy)-5-((benzyloxy)methyl)-tetrahydrofuran-2-ol.

Step 2: 7-((3S,4R,5R)-3,4-bis(benzyloxy)-5-((benzyloxy)methyl)tetrahydrofuran-2-yl)imidazo[2,1-f][1,2,4]triazin-4-amine

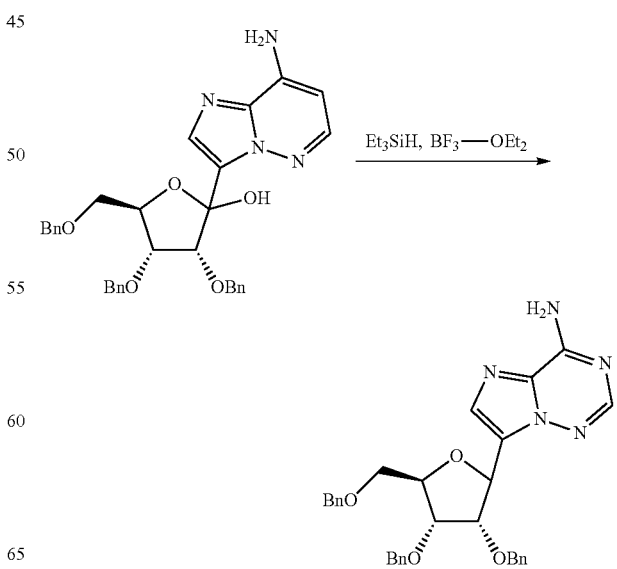

To a stirring mixture of (3R,4R,5R)-2-(4-aminoimidazo[2,1-f][1,2,4]triazin-7-yl)-3,4-bis(benzyloxy)-5-((benzyloxy)methyl)tetrahydrofuran-2-ol (64 g, 0.12 mmol) in DCM (1.3 L) at 0° C. was added Et₃SiH (81 g, 0.69 mol), and then BF₃—OEt₂ (21 g, 0.15 mol). The mixture was then allowed to warm to 25° C., and the mixture was stirred for 1 h. More BF₃—OEt₂ (57 g, 0.40 mol) was added, and the mixture was then heated to 35° C. for 4 h. Upon cooling to RT, the mixture was quenched with sat aq NaHCO₃ (200 mL) and then extracted with EtOAc (3×300 mL). The combined organic layers were dried over Na₂SO₄ and concentrated under reduced pressure. The resulting residue was purified by column chromatography (15-75% EtOAc gradient in hex) to afford 7-((3S,4R,5R)-3,4-bis(benzyloxy)-5-((benzyloxy)methyl)tetrahydrofuran-2-yl)imidazo[2,1-f][1,2,4]triazin-4-amine. MS (ES, m/z)=538 [M+H]⁺.

Step 3: (3R,4S,5R)-2-(4-aminoimidazo[2,1-f][1,2,4]triazin-7-yl)-5-(hydroxymethyl)-tetrahydrofuran-3,4-diol

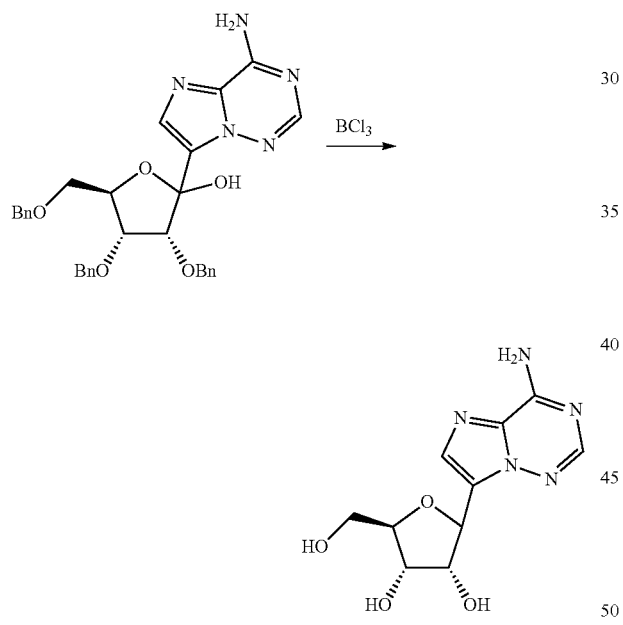

To a stirring mixture of 7-((3S,4R,5R)-3,4-bis(benzyloxy)-5-((benzyloxy)methyl)-tetrahydrofuran-2-yl)imidazo[2,1-f][1,2,4]triazin-4-amine (12 g, 22 mmol) in DCM (850 mL) at −78° C. was added BCl₃ (18 g, 0.16 mol) dropwise. Upon completion, the mixture was stirred at −78° C. for 3 h. After 3 h, the mixture was quenched with MeOH (50 mL) at −78° C., and the mixture was allowed to warm to 25° C. The mixture was concentrated under reduced pressure. The residue was purified by column chromatography (9-25% MeOH gradient in DCM) to afford (3R,4S,5R)-2-(4-aminoimidazo[2,1-f][1,2,4]triazin-7-yl)-5-(hydroxymethyl)tetrahydrofuran-3,4-diol.

Step 4: (6aR,8S,9S,9aS)-8-(4-aminoimidazo[2,1-f][1,2,4]triazin-7-yl)-2,2,4,4-tetraisopropyltetrahydro-6H-furo[3,2-f][1,3,5,2,4]trioxadisilocin-9-ol

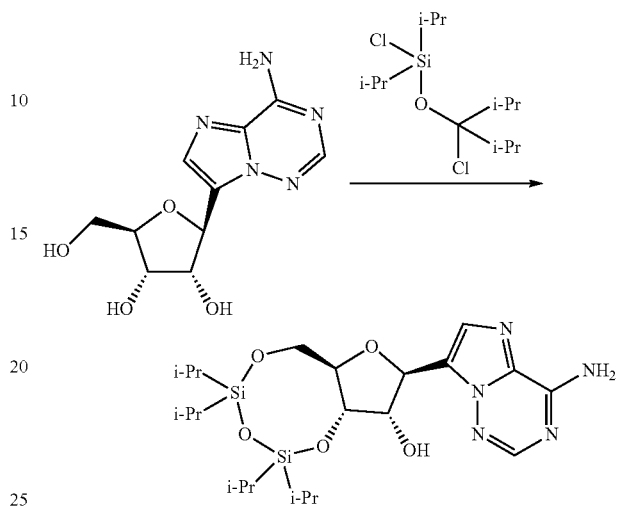

To a stirred mixture of (2S,3R,4S,5R)-2-(4-aminoimidazo[2,1-f][1,2,4]triazin-7-yl)-5-(hydroxymethyl)tetrahydrofuran-3,4-diol (4.0 g, 15 mmol) in Py (0.10 L) was added 1,3-dichloro-1,1,3,3-tetraisopropyldisiloxane (5.8 mL, 18 mmol). After 3 h, the mixture was diluted with toluene (50 mL) and then concentrated. The resulting mixture was taken up in DCM and MeOH, and then silica gel (40 g) was added. The mixture was concentrated, placed under vacuum for 1 h and purified by column chromatography (0-80% EtOAc gradient in hex) to afford (6aR,8S,9S,9aS)-8-(4-aminoimidazo[2,1-f][1,2,4]triazin-7-yl)-2,2,4,4-tetraisopropyltetrahydro-6H-furo[3,2-f][1,3,5,2,4]trioxadisilocin-9-ol. MS (ES, m/z)=510 [M+H]⁺.

Step 5: O-((6aR,8S,9S,9aR)-8-(4-aminoimidazo[2,1-f][1,2,4]triazin-7-yl)-2,2,4,4-tetraisopropyltetrahydro-6H-furo[3,2-f][1,3,5,2,4]trioxadisilocin-9-yl) 1H-imidazole-1-carbothioate

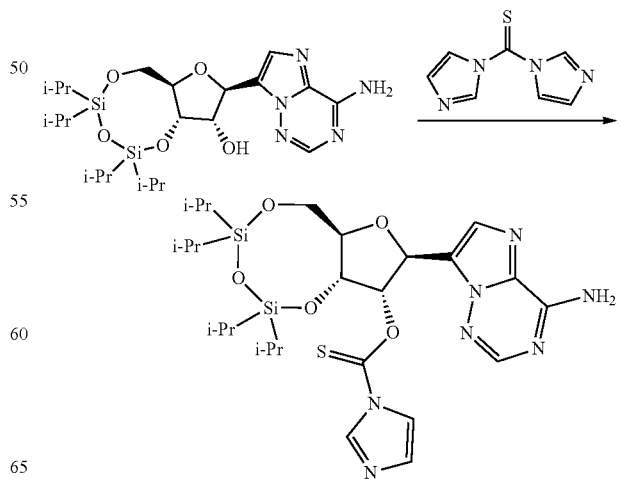

To a mixture of (6aR,8S,9S,9aS)-8-(4-aminoimidazo[2,1-f][1,2,4]triazin-7-yl)-2,2,4,4-tetraisopropyltetrahydro-6H-furo[3,2-f][1,3,5,2,4]trioxadisilocin-9-ol (6.45 g, 12.7 mmol) in CH₃CN (63.0 mL) and Py (63.0 mL) was added 1,1'-thiocarbonyldiimidazole (2.71 g, 15.2 mmol). After 90 min, more 1,1'-thiocarbonyldiimidazole (2.71 g, 15.2 mmol) was added, and the mixture was stirred overnight. After stirring overnight, the mixture was concentrated and purified by column chromatography (0-100% EtOAc gradient in hex) to afford O-((6aR,8S,9S,9aR)-8-(4-aminoimidazo[2,1-f][1,2,4]triazin-7-yl)-2,2,4,4-tetraisopropyltetrahydro-6H-furo[3,2-f][1,3,5,2,4]trioxadisilocin-9-yl) 1H-imidazole-1-carbothioate. MS (ES, m/z)=620 [M+H]±.

Step 6: 7-((6aR,8R,9aS)-2,2,4,4-tetraisopropyltetrahydro-6H-furo[3,2-j][1,3,5,2,4]trioxadisilocin-8-yl)imidazo[2,1-f][1,2,4]triazin-4-amine

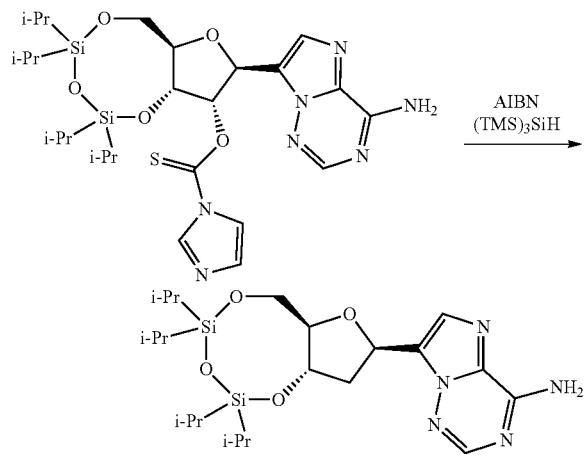

To a mixture of O-((6aR,8S,9S,9aR)-8-(4-aminoimidazo[2,1-f][1,2,4]triazin-7-yl)-2,2,4,4-tetraisopropyltetrahydro-6H-furo[3,2-f][1,3,5,2,4]trioxadisilocin-9-yl) (5.65 g, 9.11 mmol) in toluene (91.0 mL) was added 2,2'-azobis(2-methylpropionitrile) (0.300 g, 1.82 mmol) and tris(trimethylsilyl)silane ((TMS)₃SiH, 4.22 mL, 13.7 mmol). The mixture was heated to 85° C. for 30 min. After 30 min, the mixture was allowed to cool to RT and placed directly on the column and purified (0-80% EtOAc gradient in hex) to afford 7-((6aR,8R,9aS)-2,2,4,4-tetraisopropyl-tetrahydro-6H-furo[3,2-f][1,3,5,2,4]trioxadisilocin-8-yl)imidazo[2,1-f][1,2,4]triazin-4-amine. MS (ES, m/z)=494 [M+H]⁺ 494.

Step 7: N-benzoyl-N-(7-((6aR,8R,9aS)-2,2,4,4-tetraisopropyltetrahydro-6H-furo[3,2-f][1,3,5,2,4]trioxadisilocin-8-yl)imidazo[2,1-f][1,2,4]triazin-4-yl)benzamide

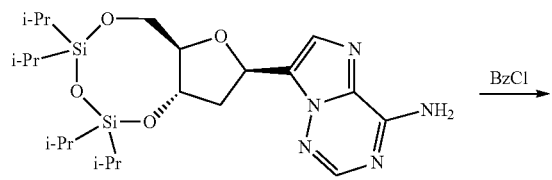

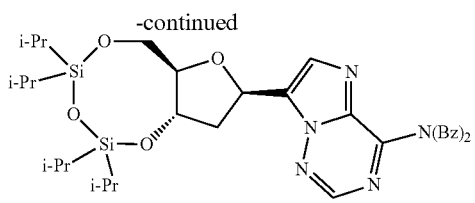

To a mixture of 7-((6aR,8R,9aS)-2,2,4,4-tetraisopropyltetrahydro-6H-furo[3,2-f][1,3,5,2,4]trioxadisilocin-8-yl)imidazo[2,1-f][1,2,4]triazin-4-amine (15.7 g, 31.8 mmol) in Py (64.0 mL) was added BzCl (11.0 mL, 95.0 mmol), and the mixture was heated to 50° C. for 45 min. After 45 min, the mixture was allowed to cool to RT. After cooling, a precipitate formed and was filtered off. The filtrate was diluted with DCM (50 mL) and toluene (50 mL). The mixture was concentrated to about 50 mL. The mixture was filtered, and the solids were washed with DCM. The filtrate and washes were combined, loaded onto a column, and purified (0-50% EtOAc gradient in hex) to afford N-benzoyl-N-(7-((6aR,8R,9aS)-2,2,4,4-tetraisopropyltetrahydro-6H-furo[3,2-f][1,3,5,2,4]trioxadisilocin-8-yl)imidazo[2,1-f][1,2,4]triazin-4-yl)benzamide. MS (ES, m/z)=702 [M+H]⁺.

Step 8: N-(7-((2R,4S,5R)-4-hydroxy-5-(hydroxymethyl)tetrahydrofuran-2-yl)imidazo[2,1-f][1,2,4]triazin-4-yl)benzamide

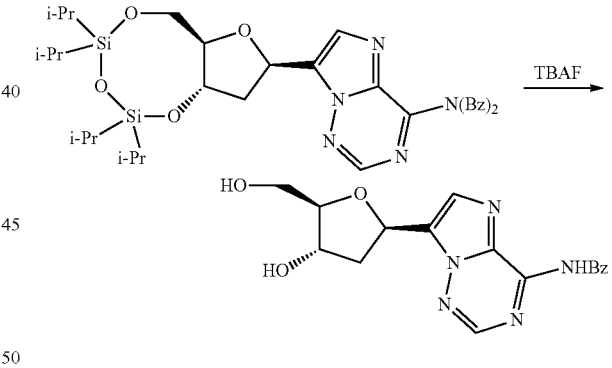

To a mixture of N-(7-((2R,4S,5R)-4-hydroxy-5-(hydroxymethyl)tetrahydrofuran-2-yl)imidazo[2,1-f][1,2,4]triazin-4-yl)benzamide (6.1 g, 17 mmol) in Py (86 mL) at 0° C. was added 4,4'-(chloro(phenyl)methylene)bis(methoxybenzene) (5.8 g, 17 mmol), and the mixture was allowed to warm to RT overnight. After stirring overnight, the mixture was diluted with toluene and then concentrated under reduced pressure to afford the crude product. The crude product was purified by silica gel chromatography (0-100% EtOAc gradient in hex) to afford N-(7-((2R,4S,5R)-5-((bis(4-methoxyphenyl)(phenyl)-methoxy)methyl)-4-hydroxytetrahydrofuran-2-yl)imidazo[2,1-f][1,2,4]triazin-4-yl)benzamide. MS (ES, m/z)=658 [M+H]⁺.

Preparation 3: Ammonium (2R,3R,4S,5R)-5-((bis(4-methoxyphenyl)(phenyl)methoxy)methyl)-4-((tert-butyldimethylsilyl)oxy)-2-(2-isobutyramido-6-oxo-1,6-dihydro-9H-purin-9-yl)tetrahydrothiophen-3-yl phosphonate

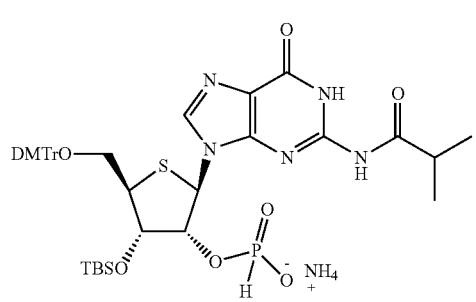

Step 1: N-(9-((2R,3R,4S,5R)-3,4-dihydroxy-5-(hydroxymethyl)tetrahydrothiophen-2-yl)-6-oxo-6,9-dihydro-1H-purin-2-yl)isobutyramide

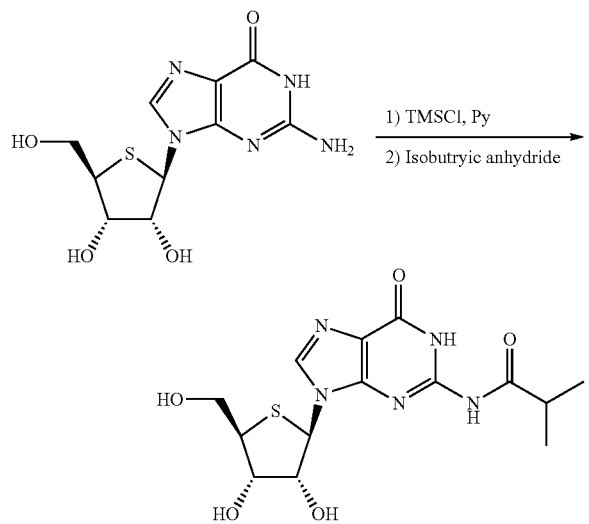

2-amino-9-((2R,3R,4S,5R)-3,4-dihydroxy-5-(hydroxymethyl)tetrahydrothiophen-2-yl)-1,9-dihydro-6H-purin-6-one (1.7 g, 5.7 mmol) was co-evaporated with Py (3×5 mL) and then, re-dissolved in Py (34 mL). To the mixture at 0° C. was added TMSCl (4.32 g, 39.8 mmol) dropwise. It was stirred at RT for 1 h and then, cooled to 0° C. again. Isobutyric anhydride (1.348 g, 8.52 mmol) was added dropwise, and it was stirred at RT for 3 h. It was quenched by the addition of H$_2$O (8.5 mL). After 5 min, NH$_4$OH (ca. 29%, 17 mL) was added, and the mixture was stirred for 30 min. It was concentrated and purified by column chromatography eluted with 1 to 30% MeOH in CH$_2$Cl$_2$ to give the product. LCMS (ES, m/z): 396.9 [M+H]$^+$. $^1$H-NMR (400 MHz, DMSO-d$_6$): δ 9.52 (br s, 2H), 8.39 (s, 1H), 5.79 (d, J=7.1 Hz, 1H), 5.59 (s, 1H), 5.40 (s, 1H), 5.22 (s, 1H), 4.55 (d, J=6.7 Hz, 1H), 4.21 (s, 1H), 3.77 (t, J=9.3 Hz, 1H), 3.61 (s, 1H), 3.30 (dt, J=6.4, 3.3 Hz, 1H), 2.78 (p, J=6.9 Hz, 1H), 1.13 (d, J=6.8 Hz, 6H).

Step 2: N-(9-((2R,3R,4S,5R)-5-((bis(4-methoxyphenyl)(phenyl)methoxy)methyl)-3,4-dihydroxytetrahydrothiophen-2-yl)-6-oxo-6,9-dihydro-1H-purin-2-yl) isobutyramide

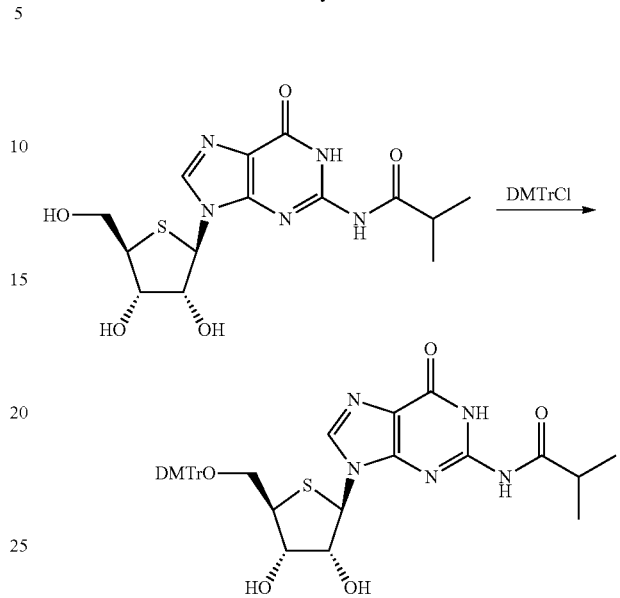

To a mixture of N-(9-((2R,3R,4S,5R)-3,4-dihydroxy-5-(hydroxymethyl)-tetrahydrothiophen-2-yl)-6-oxo-6,9-dihydro-1H-purin-2-yl)isobutyramide (480 mg, 1.299 mmol) in pyridine (10 mL) was added 4,4'-(chloro(phenyl)methylene)-bis(methoxybenzene) (484 mg, 1.43 mmol). It was stirred at RT for 16 h and then, concentrated. The crude product was purified by column chromatography on silica gel eluted with 1 to 30% MeOH in CH$_2$Cl$_2$ (containing 1% Et$_3$N) to give the product. LCMS (ES, m/z): 672.2 [M+H]$^+$. $^1$H-NMR (400 MHz, DMSO-d$_6$+D$_2$O): δ 8.08 (s, 1H), 7.39 (d, J=7.2 Hz, 2H), 7.32 (t, J=7.6 Hz, 2H), 7.26 (dt, J=9.1, 3.3 Hz, 5H), 6.94-6.87 (m, 4H), 5.75 (d, J=5.9 Hz, 1H), 4.39 (dd, J=5.9, 3.5 Hz, 1H), 4.14 (t, J=3.9 Hz, 1H), 3.74 (s, 6H), 3.49-3.37 (m, 2H), 3.33 (dd, J=14.5, 7.3 Hz, 1H), 2.87-2.67 (m, 1H), 1.11 (dd, J=6.8, 1.6 Hz, 6H).

Step 3: N-(9-((2R,3R,4S,5R)-5-((bis(4-methoxyphenyl)(phenyl)methoxy)methyl)-4-((tert-butyldimethylsilyl)oxy)-3-hydroxytetrahydrothiophen-2-yl)-6-oxo-6,9-dihydro-1H-purin-2-yl)isobutyramide and N-(9-((2R,3R,4S,5R)-5-((bis (4-methoxyphenyl)(phenyl)methoxy)methyl)-3-((tert-butyldimethylsilyl)oxy)-4-hydroxytetrahydrothiophen-2-yl)-6-oxo-6,9-dihydro-1H-purin-2-yl)isobutyramide

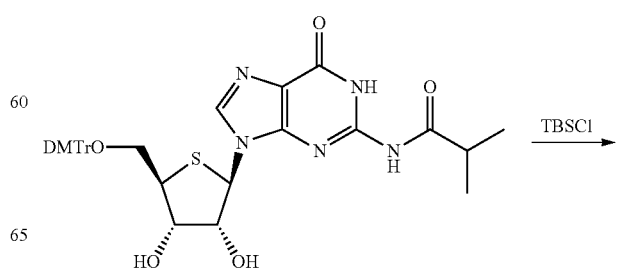

-continued

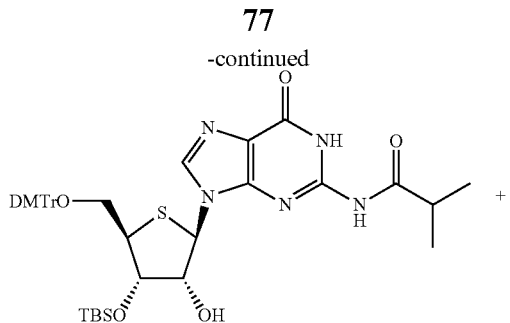

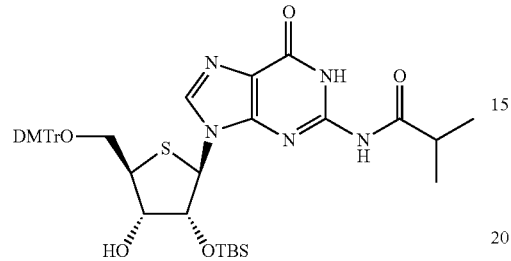

To a solution of N-(9-((2R,3R,4S,5R)-5-((bis(4-methoxyphenyl)(phenyl)-methoxy)methyl)-3,4-dihydroxytetrahydrothiophen-2-yl)-6-oxo-6,9-dihydro-1H-purin-2-yl)isobutyramide (580 mg, 0.863 mmol) in DMF (5 mL) at RT was added 1H-imidazole (147 mg, 2.16 mmol) and tert-butylchlorodimethylsilane (156 mg, 1.04 mmol). After 6 h, the mixture was diluted with EtOAc (50 mL) and washed with sat aq NaHCO$_3$ (2×20 mL) and brine (20 mL). It was dried (Na$_2$SO$_4$), concentrated, and purified by reverse phase (C18) chromatography eluted with 0 to 95% ACN in H$_2$O to give the products. LCMS (ES, m/z): 786.3 [M+H]$^+$.

Step 4: (2R,3R,4S,5R)-5-((bis(4-methoxyphenyl)(phenyl)methoxy)methyl)-4-((tert-butyldimethylsilyl)oxy)-2-(2-isobutyramido-6-oxo-1,6-dihydro-9H-purin-9-yl)tetrahydrothiophen-3-yl phenyl phosphonate and (2R,3S,4R,5R)-2-((bis(4-methoxyphenyl)(phenyl)methoxy)methyl)-4-((tert-butyldimethylsilyl)oxy)-5-(2-isobutyramido-6-oxo-1,6-dihydro-9H-purin-9-yl)tetrahydrothiophen-3-yl phenyl phosphonate

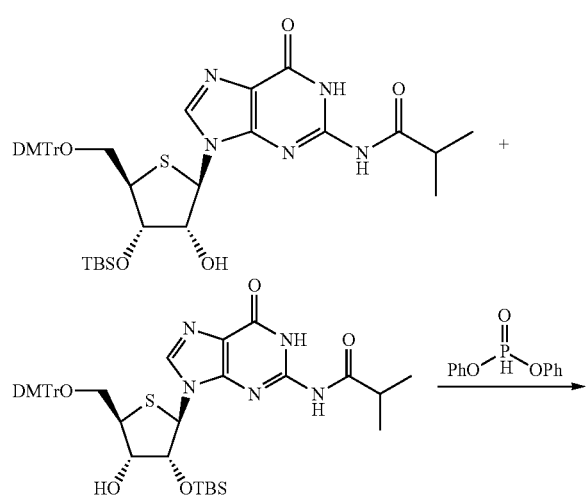

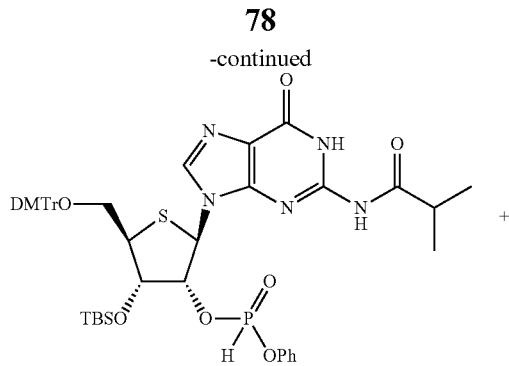

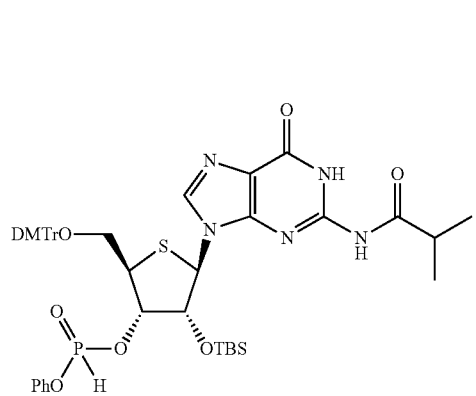

To a solution of a mixture of N-(9-((2R,3R,4S,5R)-5-((bis(4-methoxyphenyl) (phenyl)-methoxy)methyl)-4-((tert-butyldimethylsilyl)oxy)-3-hydroxytetrahydrothiophen-2-yl)-6-oxo-6,9-dihydro-1H-purin-2-yl)isobutyramide and N-(9-((2R,3R,4S,5R)-5-((bis(4-methoxyphenyl)(phenyl)methoxy)methyl)-3-((tert-butyldimethylsilyl)oxy)-4-hydroxytetrahydrothiophen-2-yl)-6-oxo-6,9-dihydro-1H-purin-2-yl)isobutyramide (220 mg, 0.280 mmol) in Py (2 mL) at 0° C. was added diphenyl phosphonate (98 mg, 0.420 mmol). The resulting mixture was stirred at RT for 20 min. It was used in the next reaction step without purification. LCMS (ES, m/z): 926.2 [M+H]$^+$.

Step 5: ammonium (2R,3R,4S,5R)-5-((bis(4-methoxyphenyl)(phenyl)methoxy)methyl)-4-((tert-butyldimethylsilyl)oxy)-2-(2-isobutyramido-6-oxo-1,6-dihydro-9H-purin-9-yl)tetrahydrothiophen-3-yl phosphonate

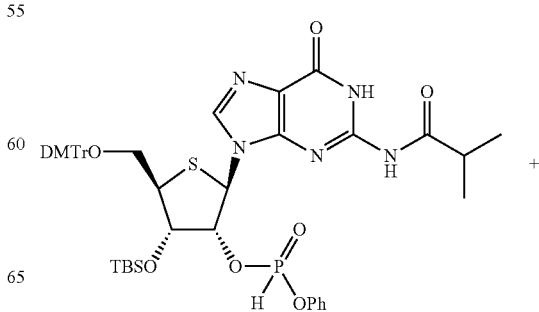

-continued

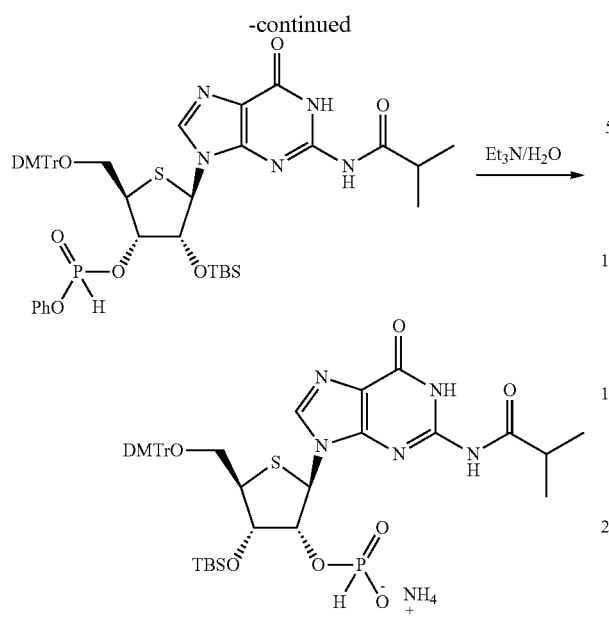

To the reaction mixture from Step 4 at 0° C. was added Et₃N (0.28 mL, 2.0 mmol) and H₂O (0.28 mL). It was stirred at RT for 30 min. It was concentrated, and the residue was partitioned between CH₂Cl₂ (40 mL) and aq NaHCO₃ (5%, 30 mL). The organic layer was washed with aq NaHCO₃ (5%, 2×30 mL), dried (Na₂SO₄), concentrated and purified by silica gel column chromatography using 0-10% MeOH in CHCl₃ containing 1% Et₃N to give a mixture. The mixture was further purified by Prep-HPLC (XBridge Shield RP18 OBD Column, 19×150 mm) eluted with 46 to 79% ACN in aq NH₄HCO₃ (10 mM) over 7 min to give the product. LCMS (ES, m/z): 850.2 [M+H]⁺. ¹H-NMR (400 MHz, CD₃OD): δ 8.18 (s, 1H), 7.68 (s, 0.5H), 7.59-7.49 (m, 2H), 7.45-7.36 (m, 4H), 7.37-7.30 (m, 2H), 7.28-7.22 (m, 1H), 6.95-6.87 (m, 4H), 6.16-6.07 (m, 2H), 4.88-4.87 (m, 1H), 4.69 (dd, J=7.3, 3.3 Hz, 1H), 3.81 (s, 6H), 3.51 (dd, J=4.9, 1.9 Hz, 2H), 3.37 (s, 1H), 2.67 (p, J=6.9 Hz, 1H), 1.21 (dd, J=6.9, 0.9 Hz, 6H), 0.77 (s, 9H), 0.01 (s, 3H), −0.28 (s, 3H). ³¹P-NMR (162 MHz, DMSO-d₆): δ−0.74 (s).

Preparation 4: (2R,3S,4S,5R)-5-((bis(4-methoxyphenyl)(phenyl)methoxy)methyl)-4-fluoro-2-(2-isobutyramido-6-oxo-1,6-dihydro-9H-purin-9-yl)tetrahydrofuran-3-yl hydrogen phosphonate Step 1: (2R,3S,4S,5R)-5-((bis(4-methoxyphenyl)(phenyl)methoxy)methyl)-4-fluoro-2-(2-isobutyramido-6-oxo-1,6-dihydro-9H-purin-9-yl)tetrahydrofuran-3-yl phenyl phosphonate

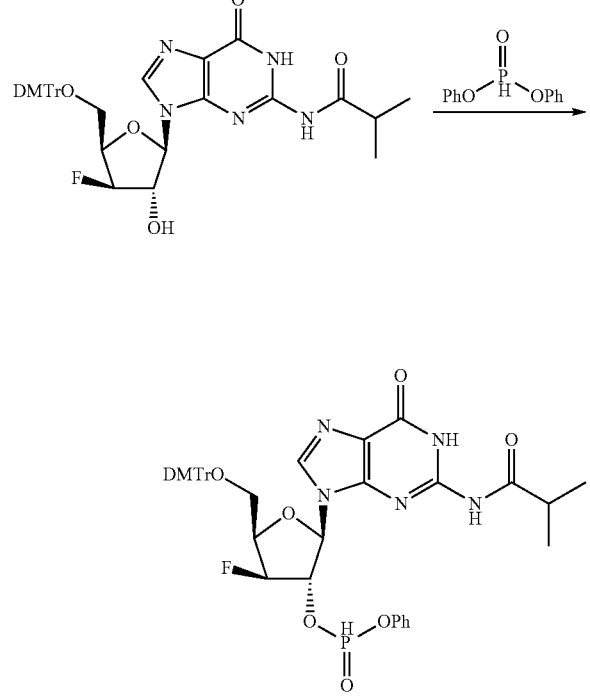

To a solution of N-(9-((2R,3S,4R,5R)-5-((bis(4-methoxyphenyl)(phenyl)methoxy) methyl)-4-fluoro-3-hydroxytetrahydrofuran-2-yl)-6-oxo-6,9-dihydro-1H-purin-2-yl)isobutyramide (prepared according to published procedures: *Tetrahedron Letters*, 1989, 30, 3171-3174. 630 mg, 0.96 mmol) in Py (5 mL) under Ar was added diphenyl phosphonate (1.07 g, 4.56 mmol), and the mixture was stirred at RT for 20 min. It was used for the next reaction step without purification. LCMS (ES, m/z): 798.3 [M+H]⁺.

Step 2: (2R,3S,4S,5R)-5-((bis(4-methoxyphenyl)(phenyl)methoxy)methyl)-4-fluoro-2-(2-isobutyramido-6-oxo-1,6-dihydro-9H-purin-9-yl)tetrahydrofuran-3-yl phosphonate

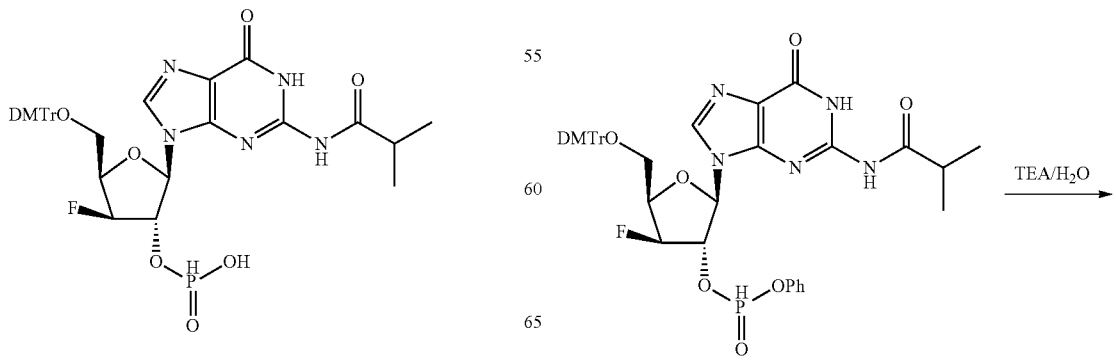

-continued

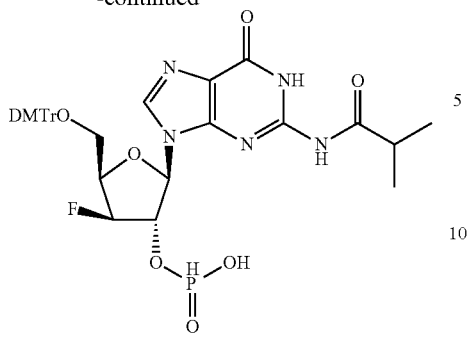

To the reaction mixture from Step 1 at 0° C. was added H₂O (1 mL), Et₃N (1 mL). The resulting mixture was stirred at RT for 20 min. Then, it was concentrated, and the residue was partitioned between CH₂Cl₂ (50 mL) and aq NaHCO₃ (5%, 20 mL). The organic layer was washed with aq NaHCO₃ (5%, 20 mL), dried (Na₂S₂O₄), concentrated and purified by silica gel column chromatography using 0-7% MeOH in CH₂Cl₂ (1% Et₃N) to give the product. LCMS (ES, m/z): 722.2 [M+H]⁺. ¹H-NMR (400 MHz, CD₃OD): δ 7.76 (s, 1H), 7.74 (s, 0.5H), 7.51 (d, J=1.5 Hz, 1H), 7.48 (q, J=2.4, 1.9 Hz, 1H), 7.41-7.34 (m, 4H), 7.34-7.27 (m, 2H), 7.26-7.21 (m, 1H), 6.92-6.85 (m, 4H), 6.22 (s, 1H), 6.15 (s, 0.5H), 5.37 (d, J=2.7 Hz, 0.5H), 5.28-5.19 (m, 1.5H), 4.73-4.69 (m, 0.5H), 4.66-4.62 (m, 1H), 3.80 (s, 6H), 3.65-3.55 (m, 1H), 3.53-3.44 (m, 1H), 3.12 (q, J=7.3 Hz, 8H), 2.75 (p, J=6.8 Hz, 1H), 1.33-1.22 (m, 18H). ³¹P-NMR: (162 MHz, CD₃OD): δ 2.67 (s, 1P).

Examples 1 and 2: 2-amino-9-[(5R,7R,8S,12aR, 14R,15S,15aR,16R)-14-(6-amino-9H-purin-9-yl)-15, 16-difluoro-10-hydroxy-2-sulfanyl-2,10-disulfidooc-tahydro-12H-5,8-methanofuro[3,2-l][1,3,6,9,11,2,10] pentaoxadiphosphacyclotetradecin-7-yl]-1,9-dihydro-6H-purin-6-one (Diastereomer 1) and 2-amino-9-[(5R,7R,8S,12aR,14R,15S,15aR,16R)-14-(6-amino-9H-purin-9-yl)-15,16-difluoro-10-hydroxy-2-sulfanyl-2,10-disulfidooctahydro-12H-5,8-methanofuro[3,2-l][1,3,6,9,11,2,10] pentaoxadiphosphacyclotetradecin-7-yl]-1,9-dihydro-6H-purin-6-one (Diastereomer 2)

Diastereomer 1

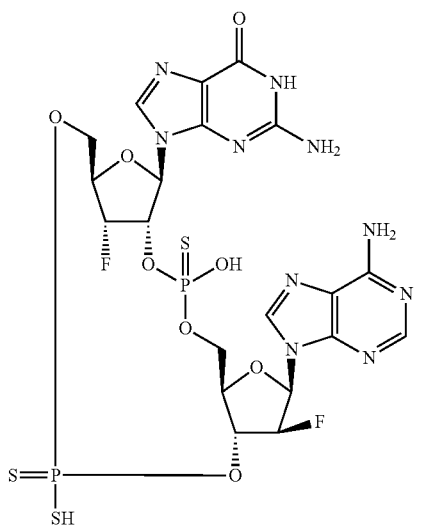

Diastereomer 2

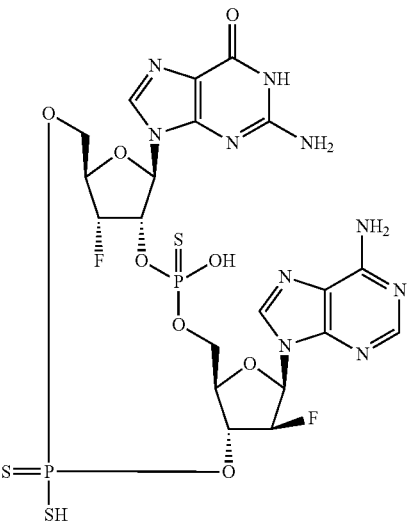

Step 1: (2R,3R,4S,5R)-5-(6-benzamido-9H-purin-9-yl)-2-((bis(4-methoxyphenyl)(phenyl)methoxy) methyl)-4-fluorotetrahydrofuran-3-yl phenyl phosphonate

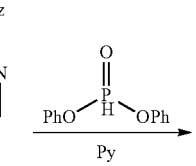

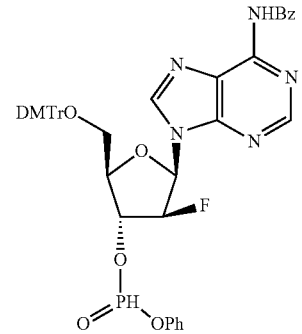

To a solution of N-(9-((2R,3S,4R,5R)-5-((bis(4-methoxyphenyl)(phenyl) methoxy)methyl)-3-fluoro-4-hydroxytetrahydrofuran-2-yl)-9H-purin-6-yl)benzamide (2.1 g, 3.1 mmol) in anhydrous Py (14 mL) was added diphenyl phosphonate (7.28 g, 31.1 mmol). The mixture was stirred at RT for 20 min and was used for the next reaction step without purification. LCMS (ES, m/z): 816.3 [M+H]⁺.

Step 2: Ammonium O-((2R,3R,4S,5R)-5-(6-benzamido-9H-purin-9-yl)-2-((bis(4-methoxyphenyl)(phenyl)methoxy)methyl)-4-fluorotetrahydrofuran-3-yl)phosphonothioate Step 3: pyridin-1-ium O-((2R,3R,4S,5R)-5-(6-benzamido-9H-purin-9-yl)-4-fluoro-2-(hydroxymethyl)tetrahydrofuran-3-yl) phosphonothioate

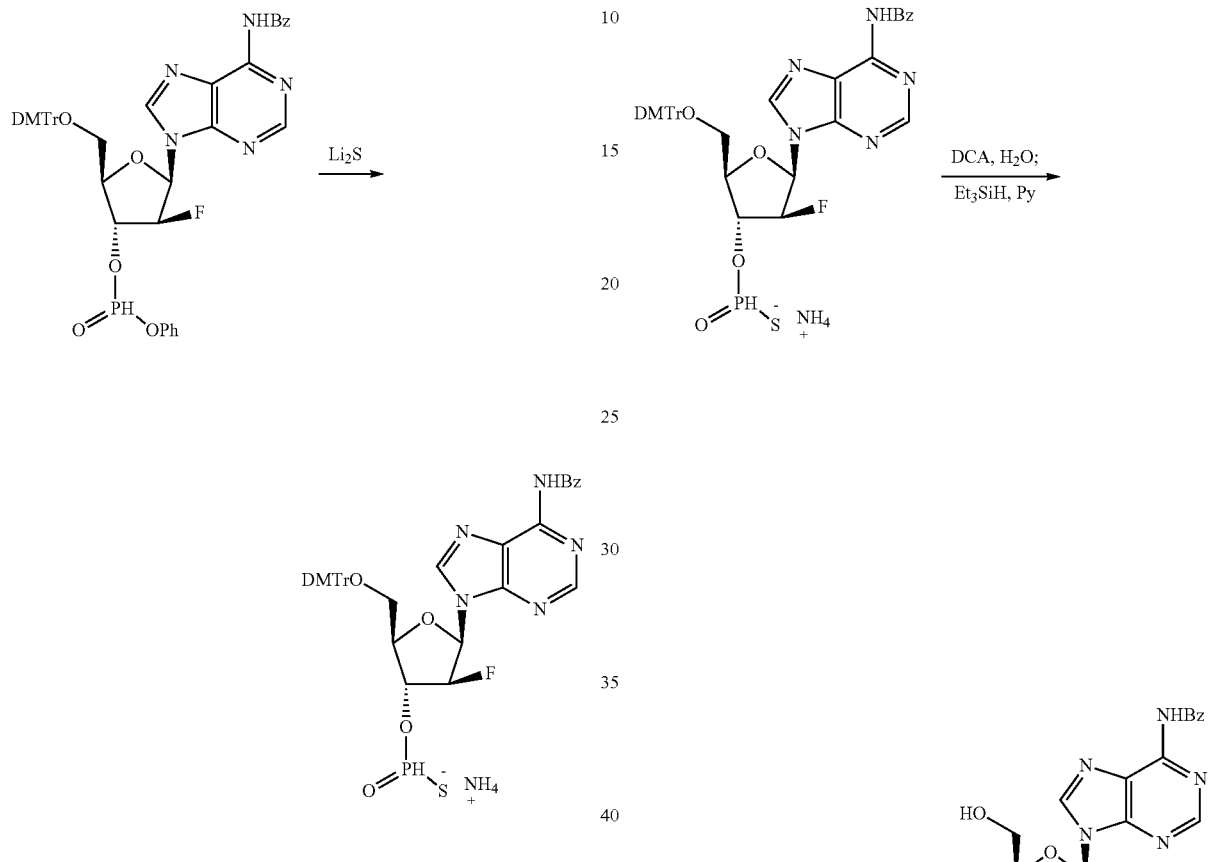

To the reaction mixture from Step 1 at 0° C. was added Li$_2$S (714 mg, 15.5 mmol), and the mixture was stirred at RT for 15 h. The mixture was concentrated under reduced pressure. The residue was partitioned between CH$_2$Cl$_2$ (200 mL) and aq NaHCO$_3$ (5%, 100 mL). The organic layer was washed with aq NaHCO$_3$ (5%, 2×50 mL), dried (Na$_2$SO$_4$) and concentrated to give a crude product. The residue was purified by reverse phase (C18) chromatography eluted with 0 to 95% ACN in aq NH$_4$HCO$_3$ (5 mM) to give the product. LCMS (ES, m/z): 756.2 [M+H]$^+$. $^1$H-NMR (400 MHz, DMSO-d$_6$): δ 11.25 (s, 2H), 8.76 (d, J=9.9 Hz, 3H), 8.25 (d, J=4.1 Hz, 2H), 8.03 (d, J=7.6 Hz, 4H), 7.58 (dt, J=29.5, 7.6 Hz, 6H), 7.41 (d, J=7.7 Hz, 4H), 7.32-7.13 (m, 14H), 6.94 (d, J=5.9 Hz, 1H), 6.84 (d, J=8.4 Hz, 8H), 6.57 (d, J=4.0 Hz, 1H), 6.51 (s, 1H), 5.54 (s, 1H), 5.37 (s, 1H), 5.10 (d, J=15.3 Hz, 2H), 4.24 (d, J=14.1 Hz, 2H), 3.70 (s, 13H), 2.48 (d, J=1.3 Hz, 2H), 2.36 (s, 1H), 2.05 (s, 6H), 1.24-1.09 (m, 2H). $^{31}$P-NMR: (162 MHz, DMSO-d$_6$): δ 48.82 (s).

To a solution of ammonium O-((2R,3R,4S,5R)-5-(6-benzamido-9H-purin-9-yl)-2-((bis(4-methoxyphenyl)(phenyl)methoxy)methyl)-4-fluorotetrahydrofuran-3-yl) phosphonothioate (400 mg, 0.467 mmol) in CH$_2$Cl$_2$ (7 mL) at RT was added H$_2$O (84 mg, 4.9 mmol) and 2,2-dichloroacetic acid in CH$_2$Cl$_2$ (6%, 7 mL). The mixture was stirred at RT for 15 min, and then Et$_3$SiH (5 mL) was added. After 40 min, Py (660 mg, 8.4 mmol) was added, and the mixture was stirred for 5 min. The mixture was concentrated, and the residue was used for the next reaction step without purification. LCMS (ES, m/z): 452.0 [M−H]$^−$.

85

Step 4: pyridin-1-ium O-((2R,3R,4S,5R)-5-(6-benzamido-9H-purin-9-yl)-2-((((((2R,3S,4R,5R)-5-((bis(4-methoxyphenyl)(phenyl)methoxy)methyl)-4-fluoro-2-(2-isobutyramido-6-oxo-1,6-dihydro-9H-purin-9-yl)tetrahydrofuran-3-yl)oxy)(2-cyanoethoxy)phosphanyl)oxy)methyl)-4-fluorotetrahydrofuran-3-yl) phosphonothioate

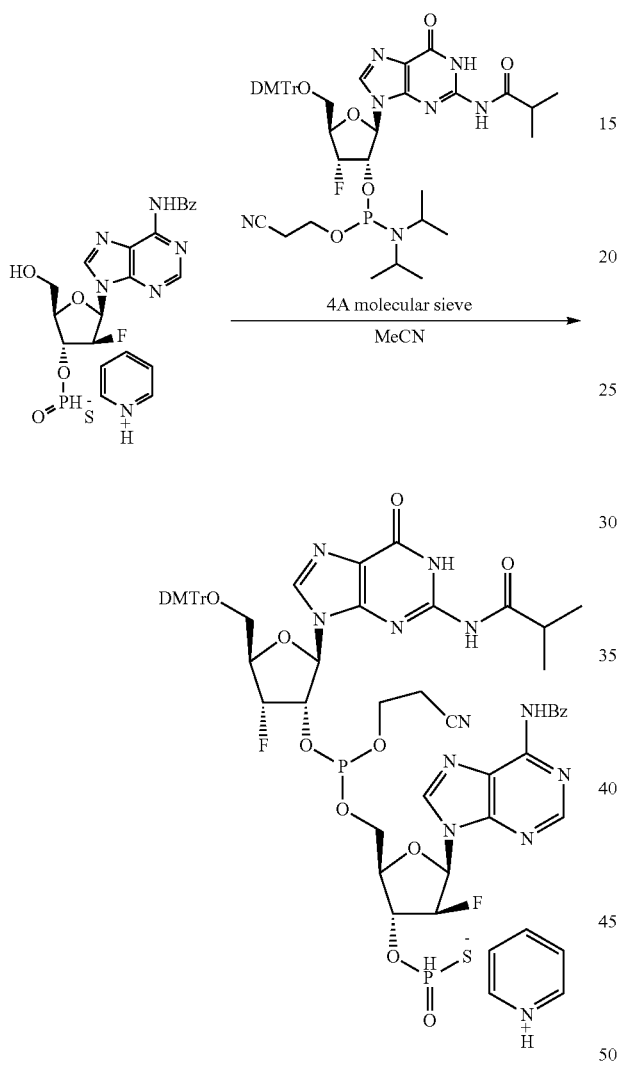

The crude product of Step 3 was co-evaporated with MeCN (3×4 mL), re-dissolved in MeCN (2 mL), and dried by adding activated 4Å molecular sieve (50 mg). (2R,3S,4R,5R)-5-((bis(4-methoxyphenyl)(phenyl)methoxy)methyl)-4-fluoro-2-(2-isobutyramido-6-oxo-1,6-dihydro-9H-purin-9-yl)tetrahydrofuran-3-yl (2-cyanoethyl) diisopropylphosphoramidite (0.48 g, 0.56 mmol) was co-evaporated with MeCN (3×4 mL), re-dissolved in MeCN (2 mL), and dried by adding activated 4Å molecular sieve (50 mg). After 30 min, it was added to the previously prepared mixture containing pyridin-1-ium O-((2R,3R,4S,5R)-5-(6-benzamido-9H-purin-9-yl)-4-fluoro-2-(hydroxymethyl)tetrahydrofuran-3-yl) phosphonothioate. The resulting mixture was stirred at RT for 30 min and was used in the next reaction step without purification. LCMS (ES, m/z): 1208.2 [M−H]⁻.

86

Step 5: pyridin-1-ium O-((2R,3R,4S,5R)-5-(6-benzamido-9H-purin-9-yl)-2-((((((2R,3S,4R,5R)-5-((bis(4-methoxyphenyl)(phenyl)methoxy)methyl)-4-fluoro-2-(2-isobutyramido-6-oxo-1,6-dihydro-9H-purin-9-yl)tetrahydrofuran-3-yl)oxy)(2-cyanoethoxy)phosphorothioyl)oxy)methyl)-4-fluorotetrahydrofuran-3-yl) phosphonothioate

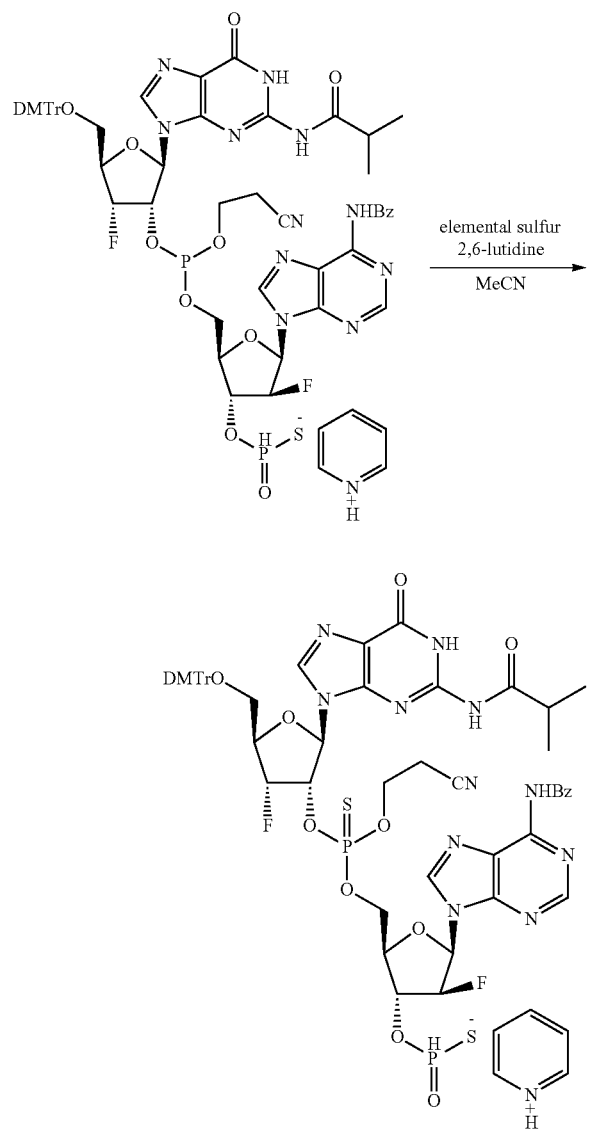

To the mixture from Step 4 was added sulfur (1.50 g, 46.7 mmol) in one portion and 2,6-dimethylpyridine (0.541 ml, 4.67 mmol). The resulting mixture was stirred at RT for 2 h. Then, the mixture was concentrated, and the crude product was used for the next step without purification. LCMS (ES, m/z): 1240.2 [M−H]⁻.

87

Step 6: ammonium O-((2R,3R,4S,5R)-5-(6-benzamido-9H-purin-9-yl)-2-((((2-cyanoethoxy)(((2R,3S,4R,5R)-4-fluoro-5-(hydroxymethyl)-2-(2-isobutyramido-6-oxo-1,6-dihydro-9H-purin-9-yl)tetrahydrofuran-3-yl)oxy)phosphorothioyl)oxy)methyl)-4-fluorotetrahydrofuran-3-yl)phosphonothioate

88

Step 7: pyridinium (5R,7R,8S,12aR,14R,15S,15aR,16R)-10-(2-cyanoethoxy)-15,16-difluoro-7-{2-[(2-methylpropanoyl)amino]-6-oxo-1,6-dihydro-9H-purin-9-yl}-14-{6-[(phenylcarbonyl)amino]-9H-purin-9-yl}octahydro-12H-5,8-methanofuro[3,2-l][1,3,6,9,11,2,10]pentaoxadiphosphacyclotetradecine-2-thiolate 10-sulfide

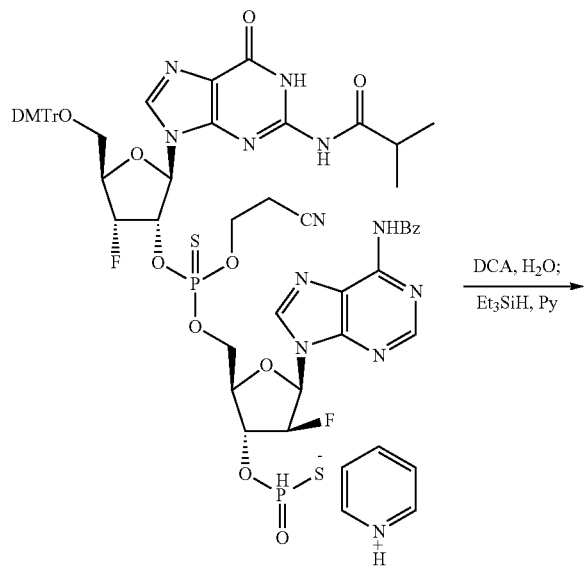

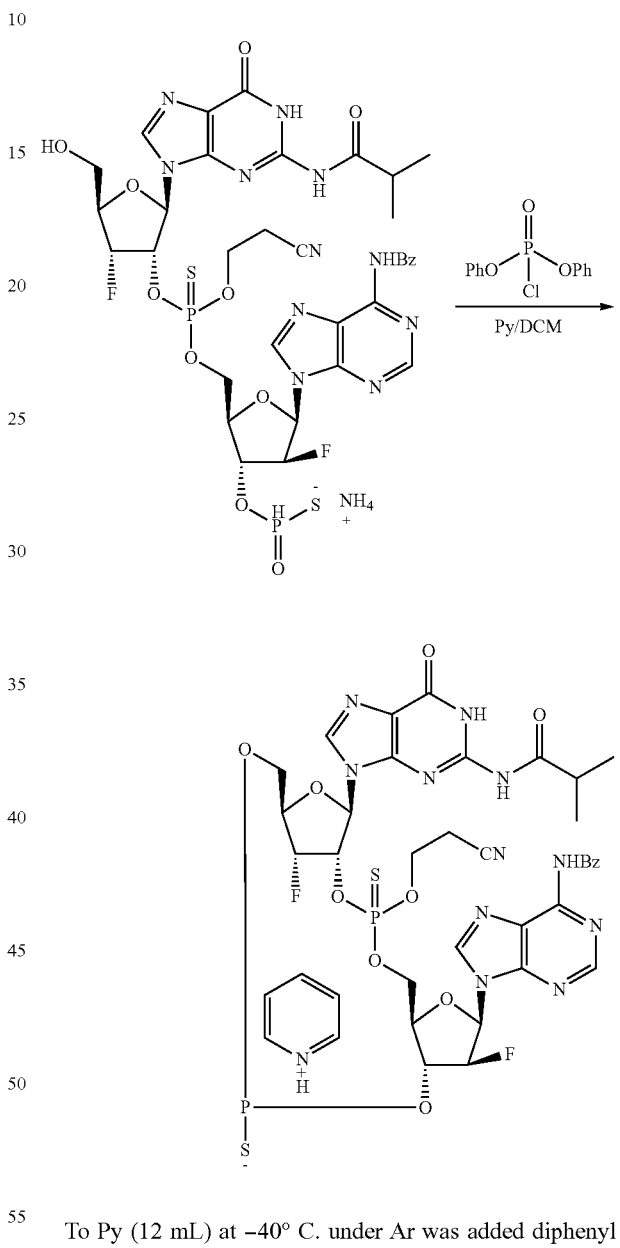

To a solution of the crude product of Step 5 in CH$_2$Cl$_2$ (7 mL) at RT was added H$_2$O (93 mg, 5.2 mmol) and 2,2-dichloroacetic acid in CH$_2$Cl$_2$ solution (6%, 7.7 mL, 4.6 mmol). After 15 min, Et$_3$SiH (15 mL) was added, and the mixture was stirred for additional 40 min. Then, Py (665 mg, 8.5 mmol) was added, and the mixture was concentrated. The residue was purified by reverse phase (C18) chromatography eluted with 0 to 95% ACN in aq NH$_4$HCO$_3$ (0.04%) to give the product. LCMS (ES, m/z): 938.1 [M+H]$^+$.

To Py (12 mL) at −40° C. under Ar was added diphenyl phosphorochloridate (657 mg, 2.44 mmol) and then, a solution of ammonium O-((2R,3R,4S,5R)-5-(6-benzamido-9H-purin-9-yl)-2-((((2-cyanoethoxy)(((2R,3 S,4R,5R)-4-fluoro-5-(hydroxymethyl)-2-(2-isobutyramido-6-oxo-1,6-dihydro-9H-purin-9-yl)tetrahydrofuran-3-yl)oxy)phosphorothioyl) oxy)methyl)-4-fluorotetrahydrofuran-3-yl) phosphonothioate (150 mg, 0.122 mmol, co-evaporated with Py 3×5 mL) in CH$_2$Cl$_2$ (30 mL) over 20 min. The resulting mixture was stirred at −40° C. for 20 min. It was used in the next step immediately without purification. LCMS (ES, m/z): 922.2 [M+H]$^+$.

Step 8: ammonium (5R,7R,8S,12aR,14R,15S,15aR, 16R)-10-(2-cyanoethoxy)-15,16-difluoro-7-{2-[(2-methylpropanoyl)amino]-6-oxo-1,6-dihydro-9H-purin-9-yl}-14-{6-[(phenylcarbonyl)amino]-9H-purin-9-yl}octahydro-12H-5,8-methanofuro[3,2-l][1,3,6,9,11,2,10]pentaoxadiphosphacyclotetradecine-2-thiolate 2,10-disulfide Step 9: 2-amino-9-[(5R,7R,8S,12aR,14R,15S,15aR, 16R)-14-(6-amino-9H-purin-9-yl)-15,16-difluoro-10-hydroxy-2-sulfanyl-2,10-disulfidooctahydro-12H-5,8-methanofuro[3,2-l][1,3,6,9,11,2,10]pentaoxachphosphacyclotetradecin-7-yl]-1,9-dihydro-6H-purin-6-one (Diastereomers 1-2)

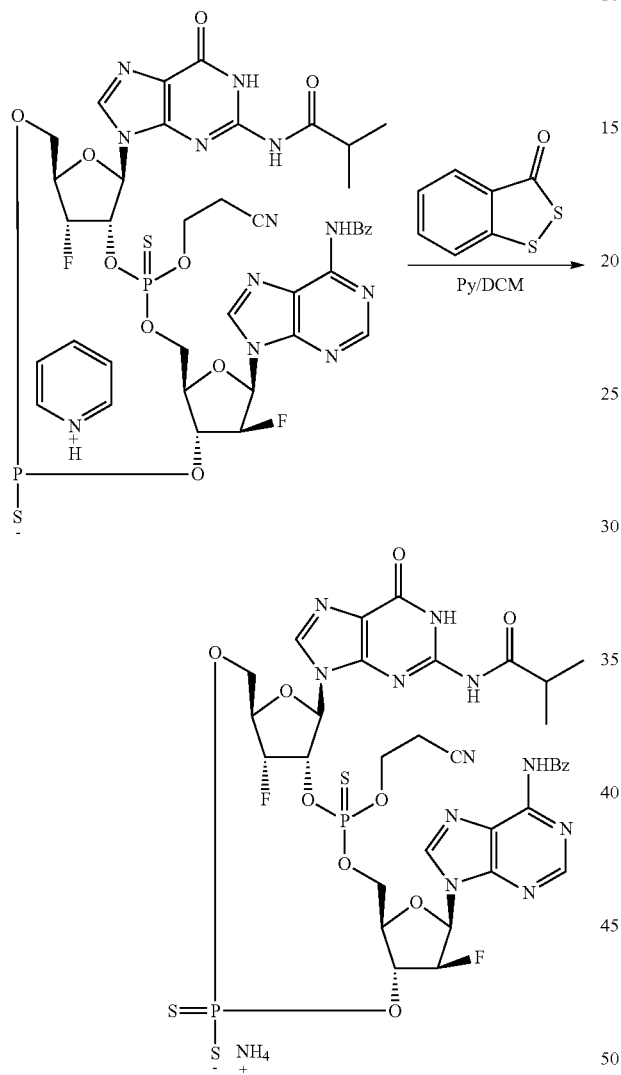

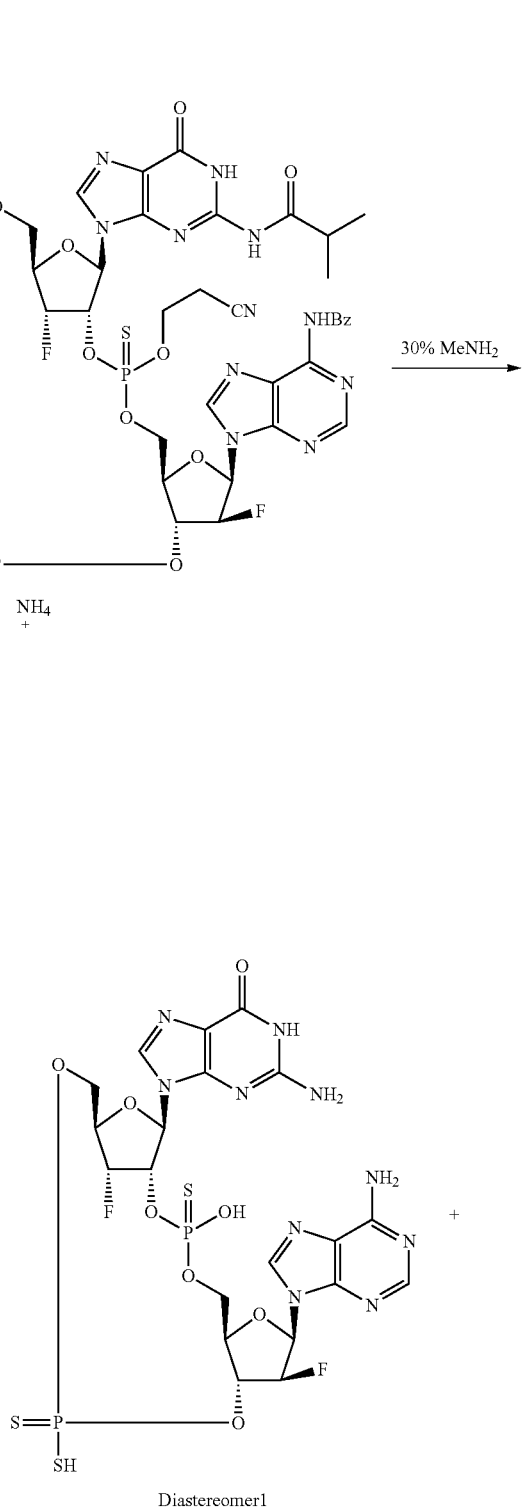

Diastereomer1

To the solution from Step 7 at −40° C. was added 3H-benzo[c][1,2]dithiol-3-one (0.031 g, 0.18 mmol) and H$_2$O (8.1 g, 450 mmol). The mixture was stirred at RT for 40 min. Then, the mixture was concentrated, and the residue was purified by reverse phase (C18) chromatography eluted with 0 to 95% ACN in aq NH$_4$HCO$_3$ (0.04%) to give the product. LCMS (ES, m/z): 954.2 [M+H]$^+$. $^1$H-NMR: (400 MHz, CD$_3$OD) δ 8.77 (d, J=7.7 Hz, 1H), 8.20-8.03 (m, 3H), 7.71-7.64 (m, 1H), 7.64-7.51 (m, 3H), 7.35-7.17 (m, 4H), 7.07 (t, J=7.3 Hz, 1H), 6.30 (dd, J=15.9, 8.0 Hz, 1H), 5.85-5.33 (m, 2H), 4.59-4.37 (m, 2H), 4.32 (t, J=11.7 Hz, 1H), 4.24-3.99 (m, 2H), 3.86-3.65 (m, 3H), 2.90 (t, J=6.9 Hz, 1H), 2.82-2.69 (m, 1H), 2.63 (ddd, J=21.0, 7.1, 5.1 Hz, 1H), 1.43-1.28 (m, 7H). $^{31}$P-NMR: (162 MHz, CD$_3$OD): δ 115.38 (s), 63.59 (s).

-continued

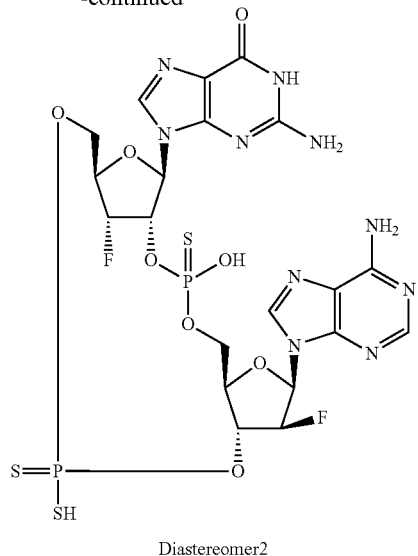

Diastereomer 2

Ammonium (5R,7R,8 S,12aR,14R,15 S,15aR,16R)-10-(2-cyanoethoxy)-15,16-difluoro-7-{2-[(2-methylpropanoyl)amino]-6-oxo-1,6-dihydro-9H-purin-9-yl}-14-{6-[(phenylcarbonyl)amino]-9H-purin-9-yl}octahydro-12H-5,8-methanofuro[3,2-l][1,3,6,9,11,2,10]pentaoxadiphosphacyclotetradecine-2-thiolate 2,10-disulfide (40 mg, 0.064 mmol) was dissolved in a solution of MeNH₂ in EtOH (30%, 5 mL). The resulting solution was stirred at RT for 3 h, then the solution was concentrated. The residue was suspended in EtOAc (10 mL) and stirred for 1 h. The mixture was filtered and washed with cold EtOAc (2×10 mL). The solid was purified by prep-HPLC (Atlantis Prep RP C18 OBD Column, 19 mm×250 mm) eluted with 0 to 27% ACN in aq NH₄HCO₃ (50 mM) over 25 min to afford two diastereomers of 2-amino-9-[(5R,7R,8S,12aR,14R,15S,15aR,16R)-14-(6-amino-9H-purin-9-yl)-15,16-difluoro-10-hydroxy-2-sulfanyl-2,10-disulfidooctahydro-12H-5,8-methanofuro[3,2-l][1,3,6,9,11,2,10]pentaoxadiphosphacyclotetradecin-7-yl]-1,9-dihydro-6H-purin-6-one:

Example 1 (diastereomer 1) (T$_R$: 13.58 min): LCMS (ES, m/z): 727.3 [M+H]$^+$. $^1$H-NMR: (400 MHz, D₂O) δ 8.33 (s, 1H), 8.27 (d, J=2.4 Hz, 1H), 8.20 (s, 1H), 6.63-6.46 (m, 1H), 6.08 (d, J=8.7 Hz, 1H), 5.78-5.24 (m, 4H), 4.55 (s, 1H), 4.46-4.01 (m, 4H), 3.67-3.44 (m, 1H). $^{31}$P-NMR: (162 MHz, D₂O) δ 113.21 (s), 54.13 (s).

Example 2 (diastereomer 2) (T$_R$: 12.77 min): LCMS (ES, m/z): 727.3 [M+H]$^+$. $^1$H-NMR: (400 MHz, D₂O) δ 8.54 (s, 1H), 8.28 (d, J=2.9 Hz, 1H), 8.20 (s, 1H), 6.53 (dd, J=22.7, 2.6 Hz, 1H), 6.10 (d, J=8.5 Hz, 1H), 5.74-5.49 (m, 2H), 5.42-5.13 (m, 2H), 4.49-4.27 (m, 3H), 4.07 (s, 2H). $^{31}$P-NMR: (162 MHz, D₂O) δ 113.30 (s), 60.84 (s).

Examples 3 through 9, as shown in Table 1 below, were prepared according to procedures analogous to those outlined in Examples 1 and 2 above using appropriate monomers, described as Preparations or as obtained from commercial sources, in the coupling step.

TABLE 1

| Example | Structure | Name | Mass [M + H]$^+$ |
|---|---|---|---|
| 3 | 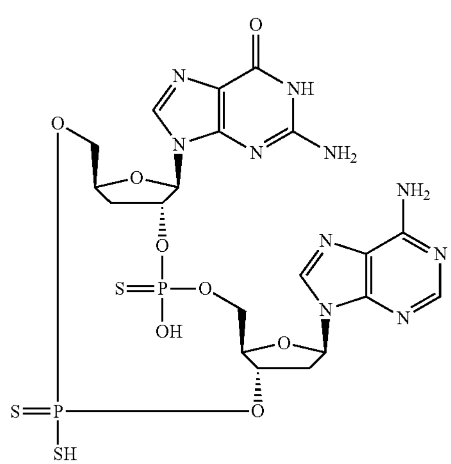 [SMILES: Nc1nc2c(ncn2[C@@H]2O[C@@H]3COP(=S)(S)O[C@H]4C[C@H](n5cnc6c(N)ncnc65)O[C@@H]4COP(O)(=S)O[C@@H]2C3)c(=O)[nH]1] | 2-amino-9-[(5S,7R,8R,12aR,14R,15aS)-14-(6-amino-9H-purin-9-yl)-10-hydroxy-2-sulfanyl-2,10-disulfidooctahydro-12H-5,8-methanofuro[3,2-l][1,3,6,9,11,2,10]pentaoxadiphosphacyclotetradecin-7-yl]-1,9-dihydro-6H-purin-6-one (Diastereomer 1) | 691 |

TABLE 1-continued

| Example | Structure | Name | Mass [M + H]+ |
|---|---|---|---|
| 4 | 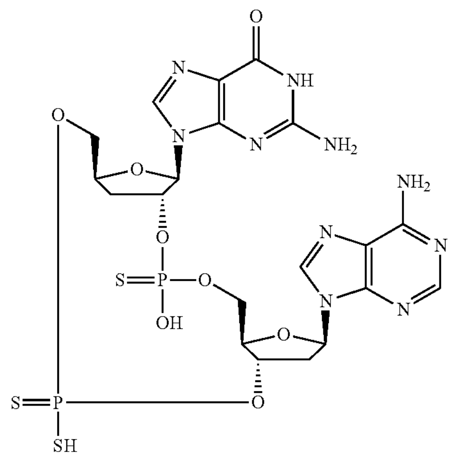 [SMILES: Nc1nc2c(ncn2[C@@H]2O[C@@H]3COP(=S)(S)O[C@H]4C[C@H](n5cnc6c(N)ncnc65)O[C@@H]4COP(O)(=S)O[C@@H]2C3)c(=O)[nH]1] | 2-amino-9-[(5S,7R,8R,12aR,14R,15aS)-14-(6-amino-9H-purin-9-yl)-10-hydroxy-2-sulfanyl-2,10-disulfidooctahydro-12H-5,8-methanofuro[3,2-l][1,3,6,9,11,2,10]pentaoxadiphosphacyclotetradecin-7-yl]-1,9-dihydro-6H-purin-6-one (Diastereomer 2) | 691 |
| 5 | 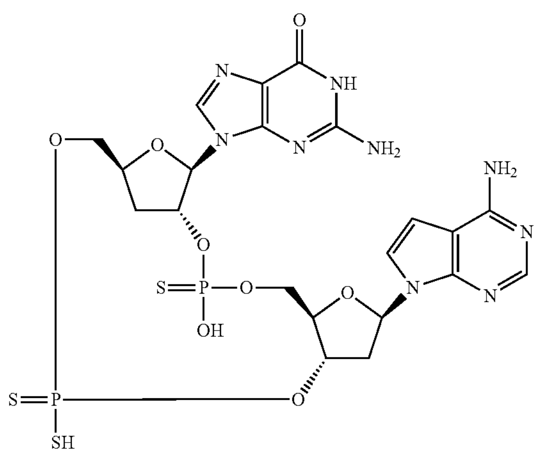 [SMILES: Nc1nc2c(ncn2[C@@H]2O[C@@H]3COP(=S)(S)O[C@H]4C[C@H](n5ccc6c(N)ncnc65)O[C@@H]4COP(O)(=S)O[C@@H]2C3)c(=O)[nH]1] | 2-amino-9-[(5S,7R,8R,12aR,14R,15aS)-14-(4-amino-7H-pyrrolo[2,3-d]pyrimidin-7-yl)-10-hydroxy-2-sulfanyl-2,10-disulfidooctahydro-12H-5,8-methanofuro[3,2-l][1,3,6,9,11,2,10]pentaoxadiphosphacyclotetradecin-7-yl]-1,9-dihydro-6H-purin-6-one (Diastereomer 1) | 690 |
| 6 | 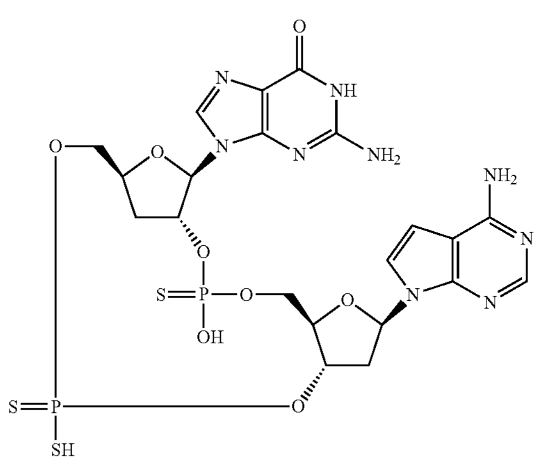 [SMILES: Nc1nc2c(ncn2[C@@H]2O[C@@H]3COP(=S)(S)O[C@H]4C[C@H](n5ccc6c(N)ncnc65)O[C@@H]4COP(O)(=S)O[C@@H]2C3)c(=O)[nH]1] | 2-amino-9-[(5S,7R,8R,12aR,14R,15aS)-14-(4-amino-7H-pyrrolo[2,3-d]pyrimidin-7-yl)-10-hydroxy-2-sulfanyl-2,10-disulfidooctahydro-12H-5,8-methanofuro[3,2-l][1,3,6,9,11,2,10]pentaoxadiphosphacyclotetradecin-7-yl]-1,9-dihydro-6H-purin-6-one (Diastereomer 2) | 690 |

TABLE 1-continued

| Example | Structure | Name | Mass [M + H]+ |
|---|---|---|---|
| 7 | 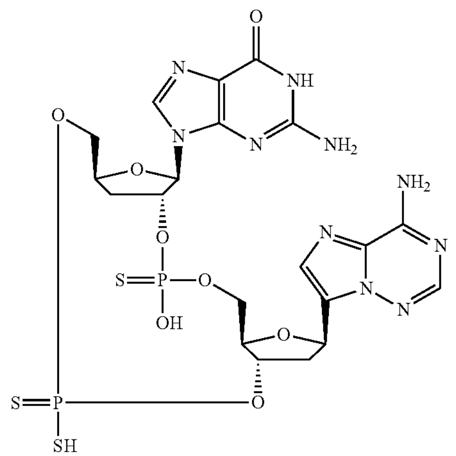 [SMILES: Nc1nc2c(ncn2[C@@H]2O[C@@H]3COP(=S)(S)O[C@H]4C[C@H](c5cnc6c(N)ncnn56)O[C@@H]4COP(O)(=S)O[C@@H]2C3)c(=O)[nH]1] | 2-amino-9-[(5S,7R,8R,12aR,14R,15aS)-14-(4-aminoimidazo[2,1-f][1,2,4]triazin-7-yl)-10-hydroxy-2-sulfanyl-2,10-disulfidooctahydro-12H-5,8-methanofuro[3,2-1][1,3,6,9,11,2,10]pentaoxadiphosphacyclotetradecin-7-yl]-1,9-dihydro-6H-purin-6-one (Diastereomer 1) | 691 |
| 8 | 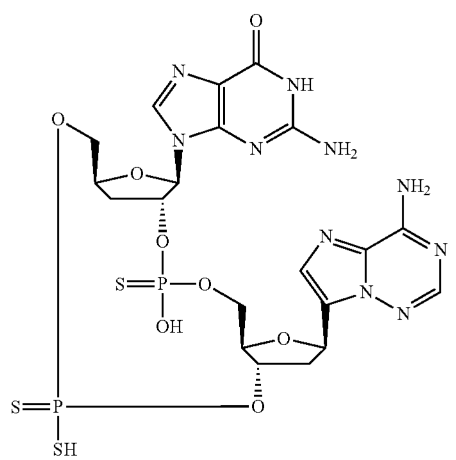 [SMILES: Nc1nc2c(ncn2[C@@H]2O[C@@H]3COP(=S)(S)O[C@H]4C[C@H](c5cnc6c(N)ncnn56)O[C@@H]4COP(O)(=S)O[C@@H]2C3)c(=O)[nH]1] | 2-amino-9-[(5S,7R,8R,12aR,14R,15aS)-14-(4-aminoimidazo[2,1-f][1,2,4]triazin-7-yl)-10-hydroxy-2-sulfanyl-2,10-disulfidooctahydro-12H-5,8-methanofuro[3,2-1][1,3,6,9,11,2,10]pentaoxadiphosphacyclotetradecin-7-yl]-1,9-dihydro-6H-purin-6-one (Diastereomer 2) | 691 |
| 9 | 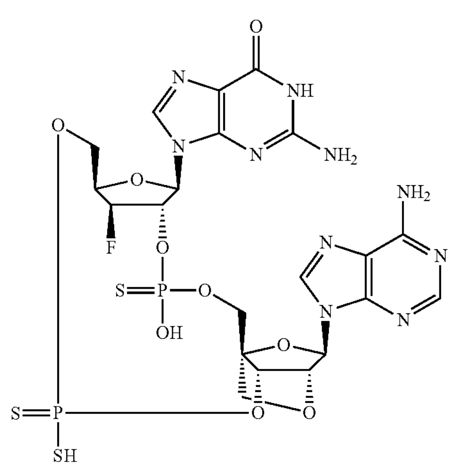 | 2-amino-9-[(5R,7R,8S,12aR,14R,15R,15aS,18S)-14-(6-amino-9H-purin-9-yl)-18-fluoro-10-hydroxy-2-sulfanyl-2,10-disulfidohexahydro-14H-15,12a-(epoxymethano)-5,8-methanofuro[3,2-1][1,3,6,9,11,2,10] pentaoxadiphosphacyclotetradecin-7(12H)-yl]-1,9-dihydro-6H-purin-6-one | 737 |

Examples 10 and 11: 2-amino-9-[(5S,7R,8R,12aR,14R,15aS)-14-(6-amino-9H-purin-9-yl)-2-hydroxy-10-sulfanyl-2,10-disulfidooctahydro-12H-5,8-methanofuro[3,2-l][1,3,6,9,11,2,10]pentaoxadiphosphacyclotetradecin-7-yl]-1,9-dihydro-6H-purin-6-one (Diastereomer 1) and 2-amino-9-[(5S,7R,8R,12aR,14R,15aS)-14-(6-amino-9H-purin-9-yl)-2-hydroxy-10-sulfanyl-2,10-disulfidooctahydro-12H-5,8-methanofuro[3,2-l][1,3,6,9,11,2,10]pentaoxadiphosphacyclotetradecin-7-yl]-1,9-dihydro-6H-purin-6-one (Diastereomer 2)

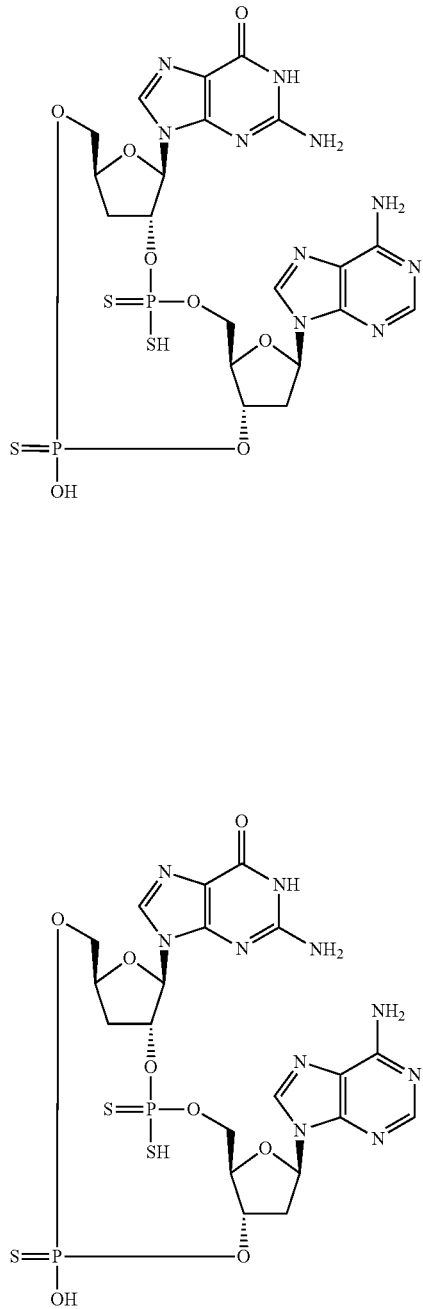

Step 1: Ammonium O-((2R,3R,5S)-5-((bis(4-methoxyphenyl)(phenyl)methoxy)methyl)-2-(2-isobutyramido-6-oxo-1,6-dihydro-9H-purin-9-yl)tetrahydrofuran-3-yl) phosphonothioate

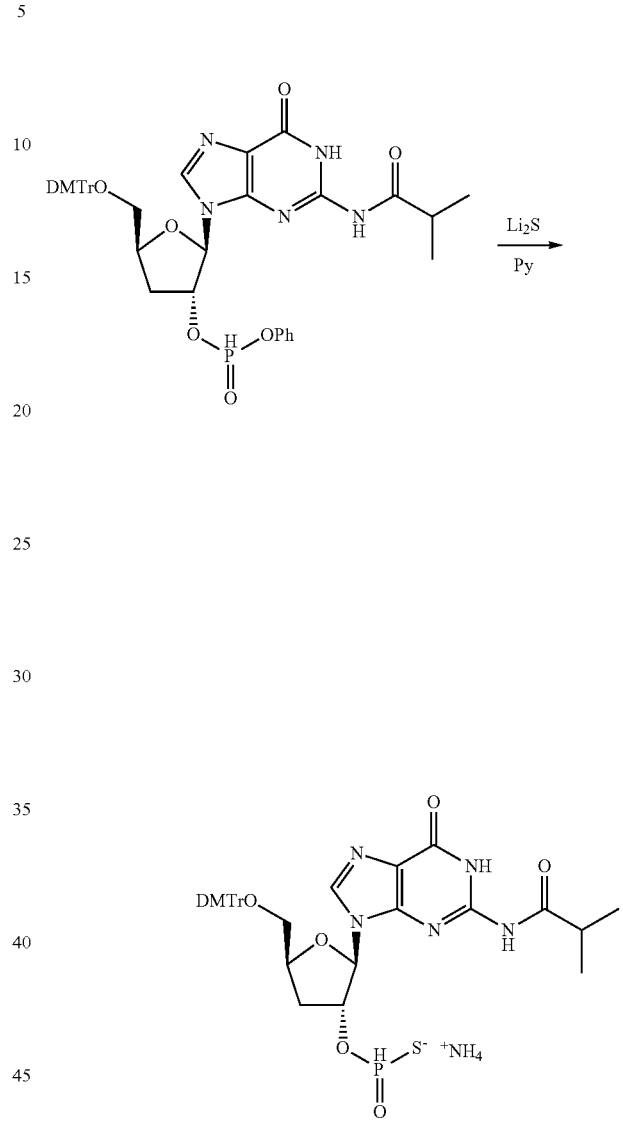

To a solution of (2R,3R,5S)-5-((bis(4-methoxyphenyl)(phenyl)methoxy)methyl)-2-(2-isobutyramido-6-oxo-1,6-dihydro-9H-purin-9-yl)tetrahydrofuran-3-yl phenyl phosphonate (2.35 mmol) in Py (12 ml) at 0° C. was added Li$_2$S (539 mg, 11.7 mmol). The mixture was stirred at RT for 1 h. Then, the mixture was concentrated. DCM (50 mL) was added, and the mixture was washed with sat aq NaHCO$_3$ (20 mL). The layers were separated, and the aq layer was extracted with DCM (3×80 mL). The combined organic layers were washed with brine (30 mL), dried (Na$_2$SO$_4$), concentrated, and purified by reverse phase (C18) chromatography eluted with 0-50% ACN in aq NH$_4$HCO$_3$ (0.4%) to give the product. LCMS (ES, m/z): 720.2 [M+H]$^+$. $^1$H-NMR: (400 MHz, DMSO-d$_6$): δ 12.11 (s, 1H), 11.75-11.70 (m, 1H), 8.15 (s, 1H), 7.32-7.12 (m, 9H), 7.00 (s, 1H), 6.82-6.78 (m, 4H), 6.14 (s, 1H), 5.30 (d, J=12 Hz, 1H), 4.51-4.47 (m, 1H), 3.72 (s, 6H), 3.15-3.14 (m, 2H), 2.83-2.76 (m, 1H), 2.21-2.16 (m, 1H), 1.13 (d, J=8 Hz, 1H). $^{31}$P-NMR: (162 MHz, DMSO-d$_6$): δ 48.27 (s).

Step 2: Pyridin-1-ium O-((2R,3R,5S)-5-(hydroxymethyl)-2-(2-isobutyramido-6-oxo-1,6-dihydro-9H-purin-9-yl)tetrahydrofuran-3-yl) phosphonothioate

Step 3: Pyridin-1-ium O-((2R,3R,5S)-5-(((((2R,3S,5R)-5-(6-benzamido-9H-purin-9-yl)-2-((bis(4-methoxyphenyl)(phenyl)methoxy)methyl)tetrahydrofuran-3-yl)oxy)(2-cyanoethoxy)phosphanyl)oxy)methyl)-2-(2-isobutyramido-6-oxo-1,6-dihydro-9H-purin-9-yl)tetrahydrofuran-3-yl) phosphonothioate

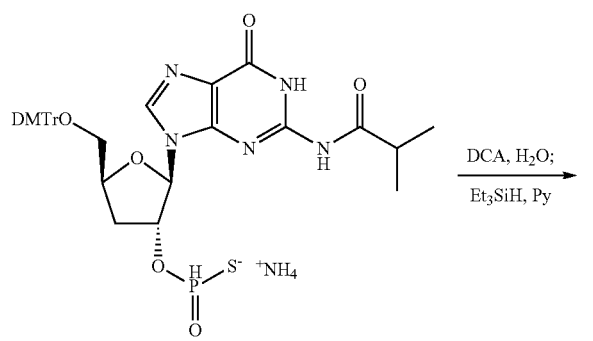

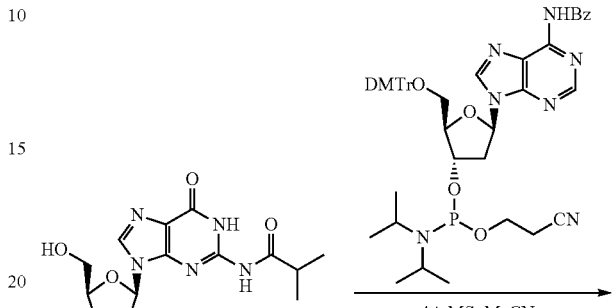

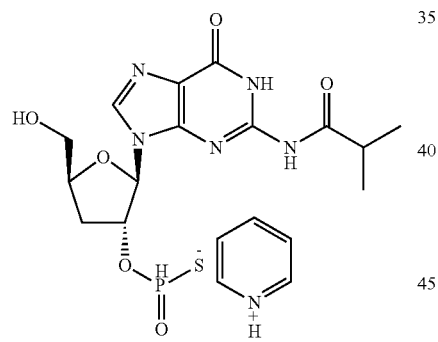

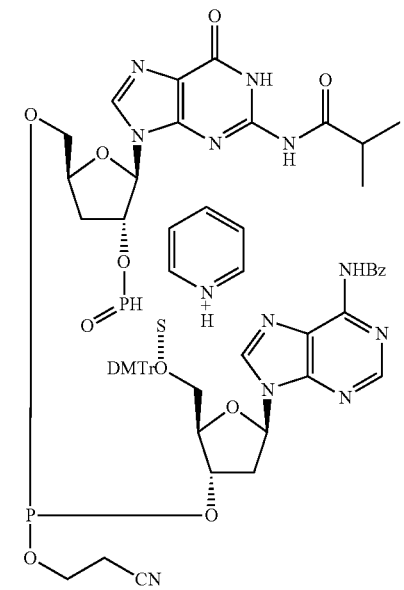

To a solution of ammonium O-((2R,3R,5S)-5-((bis(4-methoxyphenyl)(phenyl) methoxy)methyl)-2-(2-isobutyramido-6-oxo-1,6-dihydro-9H-purin-9-yl)tetrahydrofuran-3-yl) phosphonothioate (400 mg, 0.543 mmol) in DCM (6 ml) was added H₂O (98 mg, 5.4 mmol) and 2,2-dichloroacetic acid in DCM (6%, 6 mL). The mixture was stirred at RT for 20 min, and then Et₃SiH (6 mL) was added. After 2 h, Py (773 mg, 9.77 mmol) was added, and the mixture was stirred for 10 min. Then, the mixture was concentrated, and the residue was co-evaporated with MeCN and toluene (1:1, 3×4 mL) to give the crude product, which was used for the next reaction step without purification. LCMS (ES, m/z): 418.1 [M+H]⁺.

To the crude product from Step 3 in MeCN (4 mL) under Ar was added activated 4Å molecular sieve (100 mg). (2R,3S,5R)-5-(6-benzamido-9H-purin-9-yl)-2-((bis(4-methoxyphenyl)(phenyl)methoxy)methyl)tetrahydrofuran-3-yl (2-cyanoethyl) diisopropylphosphoramidite (0.466 g, 0.543 mmol) was co-evaporated with MeCN (3×4 mL), re-dissolved in MeCN (4 mL), and dried by adding 4Å molecular sieve (100 mg). After 30 min, it was transferred into a solution containing pyridin-1-ium O-((2R,3R,5S)-5-(hydroxymethyl)-2-(2-isobutyramido-6-oxo-1,6-dihydro-9H-purin-9-yl)tetrahydrofuran-3-yl) phosphonothioate, and the mixture was stirred at RT for 1 h. It was used for the next reaction step. LCMS (ES, m/z): 1174.5 [M+H]⁺.

101

Step 4: Pyridin-1-ium O-((2R,3R,5S)-5-(((((2R,3S, 5R)-5-(6-benzamido-9H-purin-9-yl)-2-((bis(4-methoxyphenyl)(phenyl)methoxy)methyl)tetrahydrofuran-3-yl)oxy)(2-cyanoethoxy)phosphorothioyl)oxy)methyl)-2-(2-isobutyramido-6-oxo-1,6-dihydro-9H-purin-9-yl)tetrahydrofuran-3-yl) phosphonothioate

102

Step 5: Ammonium O-((2R,3R,5S)-5-(((((2R,3S, 5R)-5-(6-benzamido-9H-purin-9-yl)-2-(hydroxymethyl)tetrahydrofuran-3-yl)oxy)(2-cyanoethoxy)phosphorothioyl)oxy)methyl)-2-(2-isobutyramido-6-oxo-1,6-dihydro-9H-purin-9-yl)tetrahydrofuran-3-yl) phosphonothioate

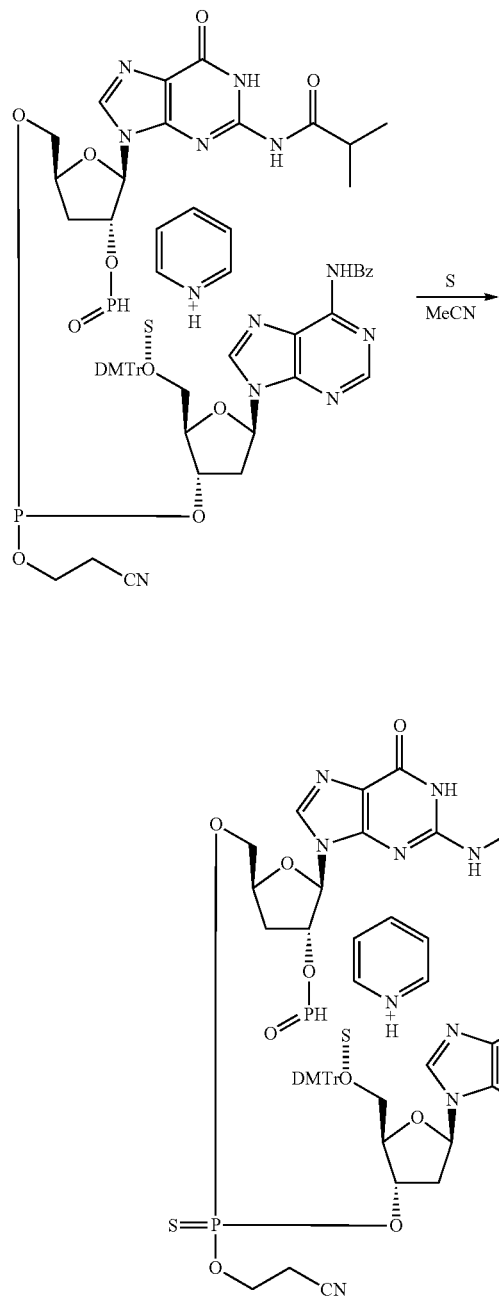

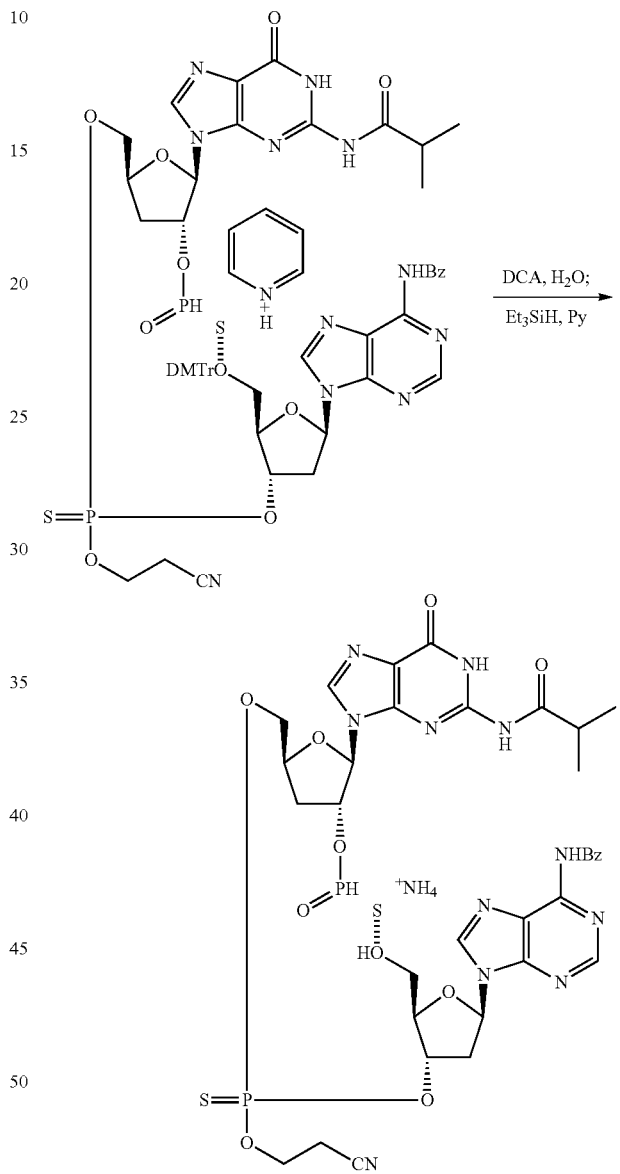

To the reaction mixture from Step 3 at RT was added sulfur (0.174 g, 5.43 mmol), and the mixture was stirred at RT for 3 h. The reaction mixture was filtered, and the filtrate was concentrated to give a residue. It was co-evaporated with toluene (3×5 ml) and CH₃CN (3×5 ml), and the crude product was used for the next reaction step without purification. LCMS (ES, m/z): 1206.3 [M+H]⁺.

To a solution of the crude product from Step 4 in DCM (6 ml) at RT was added H₂O (98 mg, 5.4 mmol) and 2,2-dichloroacetic acid in DCM (6%, 6 mL). After 20 min, Et₃SiH (6 mL) was added, and the mixture was stirred for 1.5 h. Then, Py (773 mg, 9.77 mmol) was added. The mixture was stirred for 10 min, then concentrated, and the residue was purified by reverse phase (C18) chromatography eluted with 0-35% ACN in aq NH₄HCO₃ (0.04%) to give the product. LCMS (ES, m/z): 904.2 [M+H]⁺. ¹H-NMR (400 MHz, DMSO-d₆): δ 12.11 (s, 1H), 11.73 (s, 1H), 11.23 (s, 1H), 8.75-8.70 (m, 2H), 8.17-8.05 (m, 3H), 7.68-7.55 (m, 4H), 7.20-7.14 (m, 3H), 6.56-6.51 (m, 1H), 6.10-6.05 (m, 1H), 5.32-5.18 (m, 3H), 4.58 (s, 1H), 4.36-4.32 (m, 1H), 4.27-4.20 (m, 4H), 3.62-3.57 (m, 2H), 3.13-3.10 (m, 1H), 2.98-2.93 (m, 1H), 2.80-2.69 (m, 2H), 1.21 (d, J=8 Hz, 1H), 1.13-1.10 (m, 6H). P-NMR: (162 MHz, DMSO-d$_6$): δ 66.02 (s, 1P), 47.44-47.30 (m, 1P).

Step 6: Pyridinium (5S,7R,8R,12aR,14R,15aS)-2-(2-cyanoethoxy)-7-{2-[(2-methylpropanoyl) amino]-6-oxo-1,6-dihydro-9H-purin-9-yl}-14-{6-[(phenylcarbonyl)amino]-9H-purin-9-yl}octahydro-12H-5,8-methanofuro[3,2-l][1,3,6,9,11,2,10] pentaoxadiphosphacyclotetradecine-10-thiolate 2-sulfide mL) in DCM (8 mL) dropwise over 5 min. The resulting mixture was stirred at −40° C. for 1 h. The reaction mixture was used for the next without purification. LCMS (ES, m/z): 886.2 [M+H]$^+$.

Step 7: Ammonium (5S,7R,8R,12aR,14R,15aS)-2-(2-cyanoethoxy)-7-{2-[(2-methylpropanoyl) amino]-6-oxo-1,6-dihydro-9H-purin-9-yl}-14-{6-[(phenylcarbonyl)amino]-9H-purin-9-yl}octahydro-12H-5,8-methanofuro[3,24][1,3,6,9,11,2,10] pentaoxadiphosphacyclotetradecine-10-thiolate 2,10-disulfide

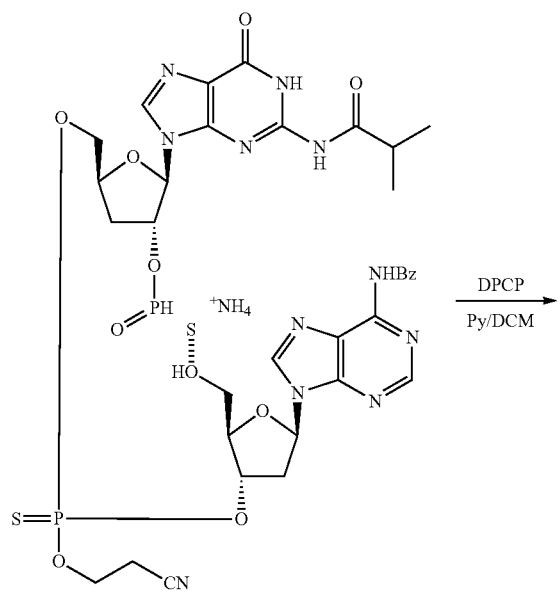

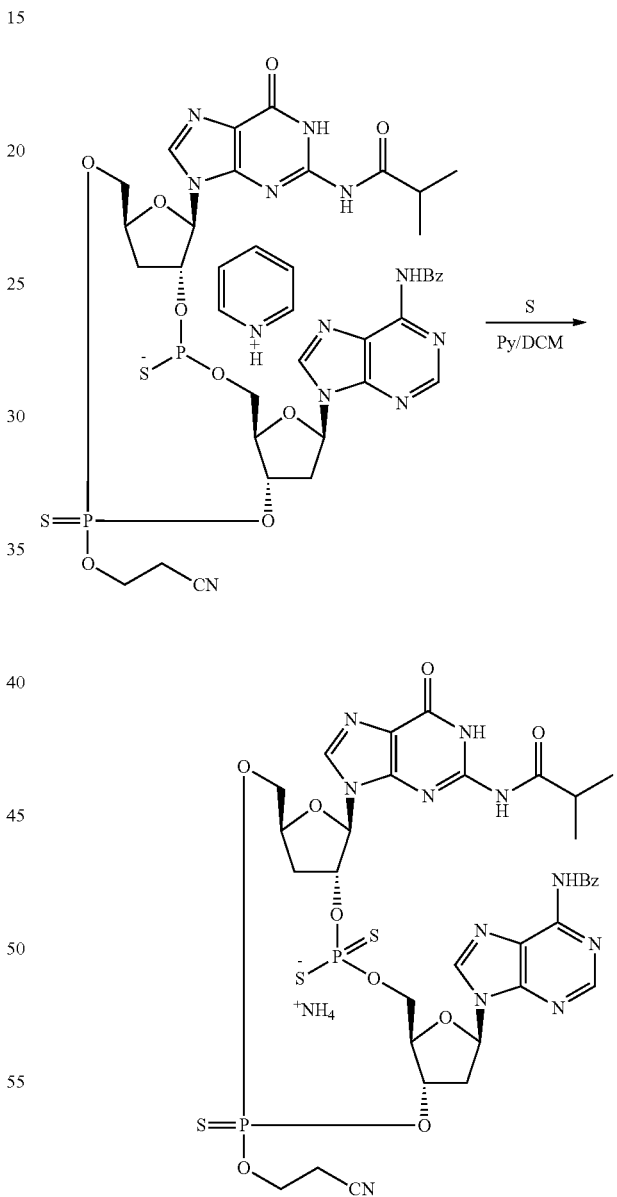

To Py (8 mL) at −40° C. under Ar was added DPCP (467 mg, 1.74 mmol), and a solution of ammonium O-((2R,3R,5S)-5-(((((2R,3S,5R)-5-(6-benzamido-9H-purin-9-yl)-2-(hydroxymethyl)tetrahydrofuran-3-yl)oxy)(2-cyanoethoxy) phosphorothioyl)oxy)methyl)-2-(2-isobutyramido-6-oxo-1,6-dihydro-9H-purin-9-yl) tetrahydrofuran-3-yl) phosphonothioate (80 mg, 0.087 mmol) (co-evaporated with Py 3×4

To the solution at −40° C. from Step 6 was added sulfur (27.9 mg, 0.870 mmol) in one portion. After stirring at RT for 3 h, the reaction mixture was concentrated and purified by reverse phase (C18) chromatography eluted with 0-35% ACN in aq NH$_4$HCO$_3$ (0.4%) to give the product. LCMS (ES, m/z): 918.2 [M+H]$^+$.

Step 8: 2-amino-9-[(5S,7R,8R,12aR,14R,15aS)-14-(6-amino-9H-purin-9-yl)-2-hydroxy-10-sulfanyl-2,10-disulfidooctahydro-12H-5,8-methanofuro[3,2-l][1,3,6,9,11,2,10]pentaoxachphosphacyclotetradecin-7-yl]-1,9-dihydro-6H-purin-6-one

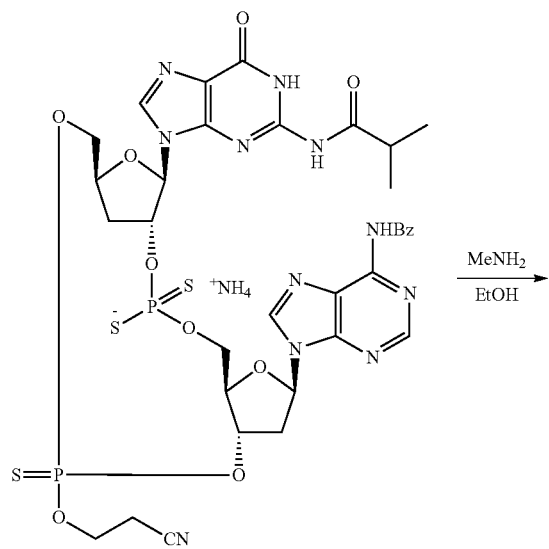

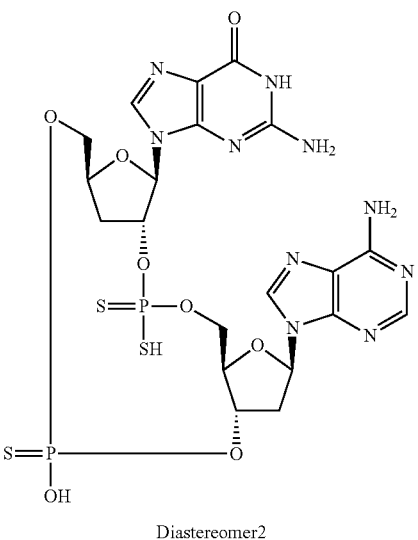

Diastereomer2

Ammonium (5S,7R,8R,12aR,14R,15aS)-2-(2-cyanoethoxy)-7-{2-[(2-methylpropanoyl)amino]-6-oxo-1,6-dihydro-9H-purin-9-yl}-14-{6-[(phenylcarbonyl)amino]-9H-purin-9-yl}octahydro-12H-5,8-methanofuro[3,2-l][1,3,6,9,11,2,10]pentaoxadiphosphacyclotetradecine-10-thiolate 2,10-disulfide (20 mg, 0.020 mmol) was dissolved in a solution of MeNH$_2$ in EtOH (30%, 1 mL). The mixture was stirred at RT for 2 h, then concentrated. The residue was purified by prep-HPLC (XBridge Shield RP C18 OBD Column, 19 mm×250 mm) eluted with 4-12% ACN in aq NH$_4$HCO$_3$ (10 mM) over 26 min to afford two diastereomers of 2-amino-9-[(5S,7R,8R,12aR,14R,15aS)-14-(6-amino-9H-purin-9-yl)-2-hydroxy-10-sulfanyl-2,10-disulfidooctahydro-12H-5,8-methanofuro[3,2-l][1,3,6,9,11,2,10]pentaoxadiphosphacyclotetradecin-7-yl]-1,9-dihydro-6H-purin-6-one:

Example 10 (diastereomer 1) (T$_R$: 13.88 min): LCMS (ES, m/z): 689.0 [M–H]$^-$. $^1$H-NMR (300 MHz, D$_2$O): δ 8.33 (s, 1H), 8.07 (s, 1H), 8.78 (s, 1H), 6.35-6.33 (m, 1H), 5.73-5.69 (m, 1H), 5.57-5.56 (m, 1H), 5.30-5.27 (m, 1H), 4.49-4.69 (m, 1H), 4.25-4.08 (m, 3H), 3.98-3.81 (m, 2H), 2.91-2.72 (m, 2H), 2.56-2.34 (m, 2H). $^{31}$P-NMR: (121 MHz, D$_2$O): δ 113.61 (s), 55.67-55.58 (m).

Example 11 (diastereomer 2) (T$_R$: 20.67 min): LCMS (ES, m/z): 689.0 [M–H]$^-$. $^1$H-NMR: (300 MHz, D$_2$O): δ 8.29 (s, 1H), 8.27 (s, 1H), 8.24 (s, 1H), 6.37-6.33 (m, 1H), 5.74 (d, J=7.2 Hz, 1H), 5.51-5.43 (m, 1H), 5.33-5.29 (m, 1H), 4.50-4.47 (m, 1H), 4.32-4.29 (m, 1H), 4.22-4.12 (m, 1H), 3.98-3.96 (m, 2H), 3.84-3.78 (m, 1H), 3.00-2.87 (m, 2H), 2.56-2.38 (m, 2H). $^{31}$P-NMR: (121 MHz, D$_2$O): δ 115.35 (s), 54.08 (s).

Examples 12 through 15, as shown in Table 2 below, were prepared according to procedures analogous to those outlined in Examples 10 and 11 above using the appropriate monomers, described as Preparations or as obtained from commercial sources, in the coupling step.

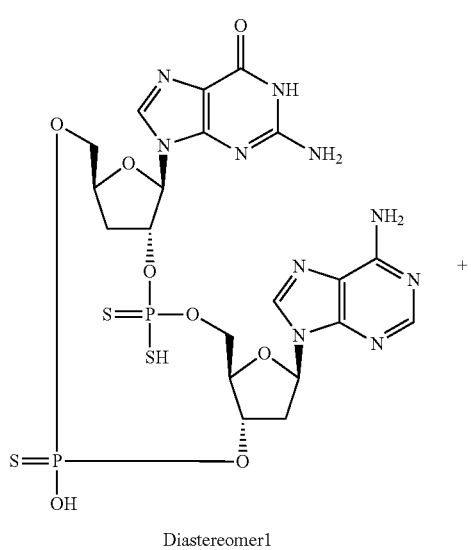

Diastereomer1

TABLE 2

| Example | Structure | Name | Mass [M + H]+ |
|---|---|---|---|
| 12 | 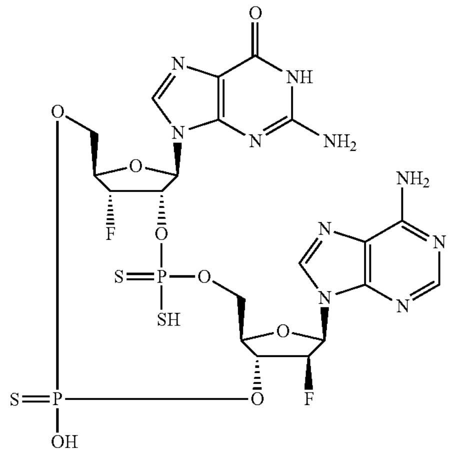 [SMILES: Nc1nc2c(ncn2[C@@H]2O[C@@H]3COP(O)(=S)O[C@H]4[C@H](F)[C@H](n5cnc6c(N)ncnc65)O[C@@H]4COP(=S)(S)O[C@@H]2[C@@H]3F)c(=O)[nH]1] | 2-amino-9-[(5R,7R,8S,12aR,14R,15S,15aR,16R)-14-(6-amino-9H-purin-9-yl)-15,16-difluoro-2-hydroxy-10-sulfanyl-2,10-disulfidooctahydro-12H-5,8-methanofuro[3,2-l][1,3,6,9,11,2,10]pentaoxadiphosphacyclotetradecin-7-yl]-1,9-dihydro-6H-purin-6-one (Diastereomer 1) | 727 |
| 13 | 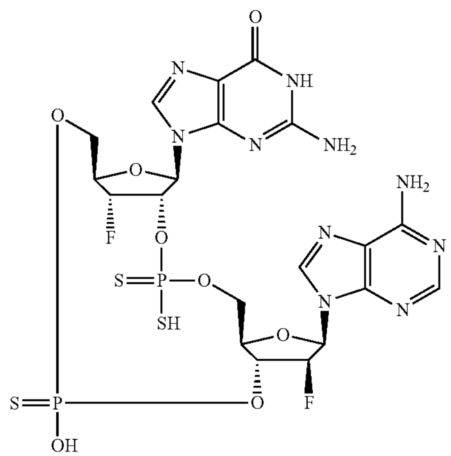 [SMILES: Nc1nc2c(ncn2[C@@H]2O[C@@H]3COP(O)(=S)O[C@H]4[C@H](F)[C@H](n5cnc6c(N)ncnc65)O[C@@H]4COP(=S)(S)O[C@@H]2[C@@H]3F)c(=O)[nH]1] | 2-amino-9-[(5R,7R,8S,12aR,14R,15S,15aR,16R)-14-(6-amino-9H-purin-9-yl)-15,16-difluoro-2-hydroxy-10-sulfanyl-2,10-disulfidooctahydro-12H-5,8-methanofuro[3,2-l][1,3,6,9,11,2,10]pentaoxadiphosphacyclotetradecin-7-yl]-1,9-dihydro-6H-purin-6-one (Diastereomer 2) | 727 |
| 14 | 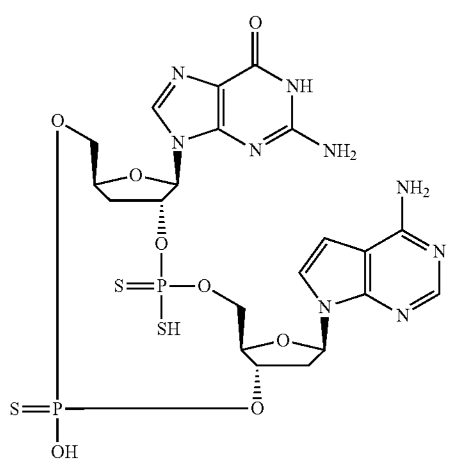 [SMILES: Nc1nc2c(ncn2[C@@H]2O[C@@H]3COP(O)(=S)O[C@H]4C[C@H](n5ccc6c(N)ncnc65)O[C@@H]4COP(=S)(S)O[C@@H]2C3)c(=O)[nH]1] | 2-amino-9-[(5S,7R,8R,12aR,14R,15aS)-14-(4-amino-7H-pyrrolo[2,3-d]pyrimidin-7-yl)-2-hydroxy-10-sulfanyl-2,10-disulfidooctahydro-12H-5,8-methanofuro[3,2-l][1,3,6,9,11,2,10]pentaoxadiphosphacyclotetradecin-7-yl]-1,9-dihydro-6H-purin-6-one (Diastereomer 1) | 690 |

TABLE 2-continued

| Example | Structure | Name | Mass [M + H]+ |
|---|---|---|---|
| 15 | 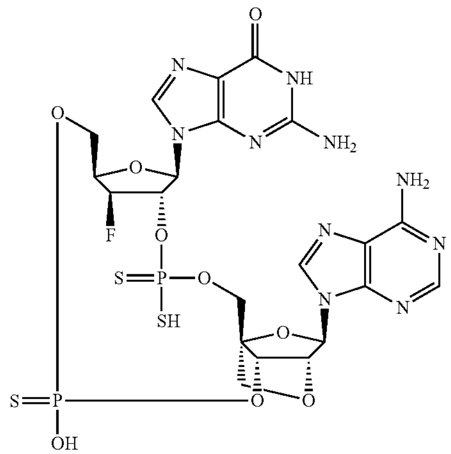 [SMILES: Nc1nc2c(ncn2[C@@H]2O[C@@H]3COP(O)(=S)O[C@H]4[C@H]5OC[C@]4(COP(=S)(S)O[C@@H]2[C@H]3F)O[C@H]5n2cnc3c(N)ncnc32)c(=O)[nH]1] | 2-amino-9-[(5R,7R,8S,12aR,14R,15R, 15aS,18S)-14-(6-amino-9H-purin-9-yl)-18-fluoro-2-hydroxy-10-sulfanyl-2,10-disulfidohexahydro-14H-15,12a-(epoxymethano)-5,8-methanofuro[3,2-1][1,3,6,9,11,2,10] pentaoxadiphosphacyclotetradecin-7(12H)-yl]-1,9-dihydro-6H-purin-6-one (Diastereomer 1) | 737 |

Example 16: 2-amino-9-[(5R,7R,8R,12aR,14R,15S, 15aR,16S)-14-(6-amino-9H-purin-9-yl)-15-fluoro-10,16-dihydroxy-2-sulfanyl-2,10-disulfidoocta-hydro-12H-5,8-methanofuro[3,2-1][1,3,9,11,6,2,10] tetraoxathiadiphosphacyclotetradecin-7-yl]-1,9-dihydro-6H-purin-6-one Step 1: (2R,3R,4S,5R)-5-(6-(N-benzoylbenzamido)-9H-purin-9-yl)-2-((bis(4-methoxyphenyl)(phenyl) methoxy)methyl)-4-fluorotetrahydrofuran-3-yl benzoate To a solution of N-(9-((2R,3S,4R,5R)-5-((bis(4-methoxyphenyl)(phenyl) methoxy)methyl)-3-fluoro-4-hydroxytetrahydrofuran-2-yl)-9H-purin-6-yl)benzamide (2.00 g, 2.96 mmol) in Py (20 ml) at 0° C. was added BzCl (0.832 g, 5.92 mmol) dropwise, and the resulting mixture was stirred at RT for 3 h. Then, the mixture was concentrated to give a crude product, which was used for next reaction step without purification. LCMS (ES, m/z): 884.2 [M+H]+. Step 2: (2R, 3R,4S,5R)-5-(6-benzamido-9H-purin-9-yl)-2-((bis(4-methoxyphenyl)(phenyl)methoxy)methyl)-4-fluorotetrahydrofuran-3-yl benzoate

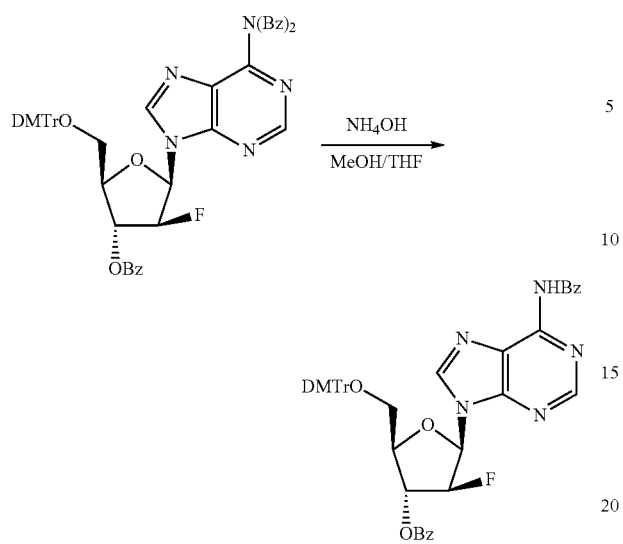

using 0-10% MeOH in DCM to the product. LCMS (ES, m/z): 478.1 [M+H]⁺. ¹H-NMR: (400 MHz, DMSO-d₆) δ 11.26 (s, 1H), 8.79 (s, 1H), 8.65 (d, J=2.6 Hz, 1H), 8.12-8.00 (m, 4H), 7.76-7.69 (m, 1H), 7.67-7.61 (m, 1H), 7.60-7.53 (m, 4H), 6.72 (dd, J=17.8, 3.9 Hz, 1H), 5.79 (d, J=4.0 Hz, 2H), 5.74 (s, 0.5H), 5.66 (s, 0.5H), 5.23 (t, J=5.9 Hz, 1H), 4.32 (d, J=4.6 Hz, 1H), 3.79 (m, 2H).

Step 4: pyridin-1-ium O-(((2R,3R,4S,5R)-5-(6-benzamido-9H-purin-9-yl)-3-(benzoyloxy)-4-fluorotetrahydrofuran-2-yl)methyl)O-((2R,3R,4S,5R)-5-((bis(4-methoxyphenyl)(phenyl)methoxy)methyl)-4-((tert-butyldimethylsilyl)oxy)-2-(2-isobutyramido-6-oxo-1,6-dihydro-9H-purin-9-yl)tetrahydrothiophen-3-yl) phosphorothioate To a solution of the crude product from Step 1 in MeOH (20 ml) and THF (10 ml) was added NH₄OH (5 ml) dropwise, and the resulting mixture was stirred at RT for 30 min. Then, the mixture was concentrated to give a crude product, which was used for next reaction step without purification. LCMS (ES, m/z): 780.3 [M+H]⁺.

Step 3: (2R,3R,4S,5R)-5-(6-benzamido-9H-purin-9-yl)-4-fluoro-2-(hydroxymethyl)tetrahydrofuran-3-yl benzoate

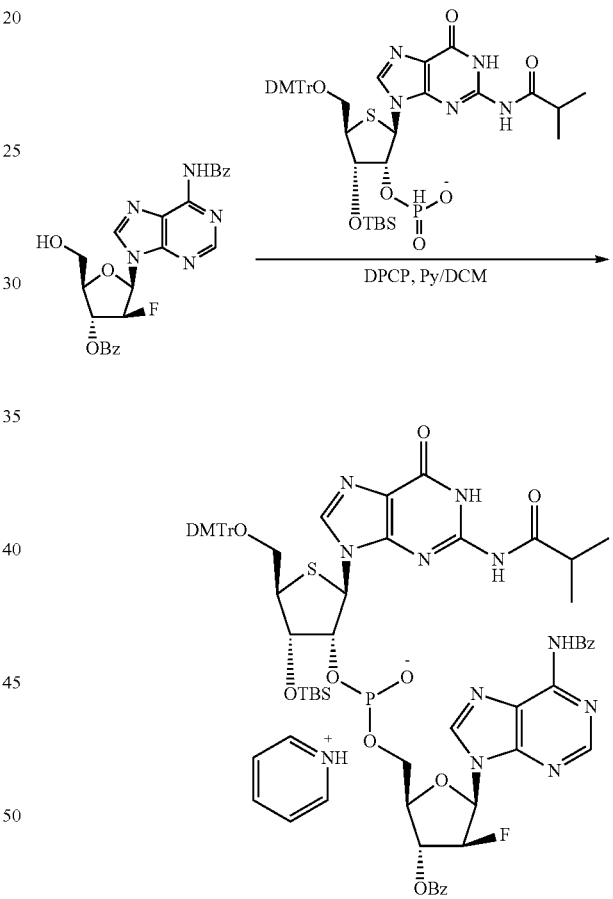

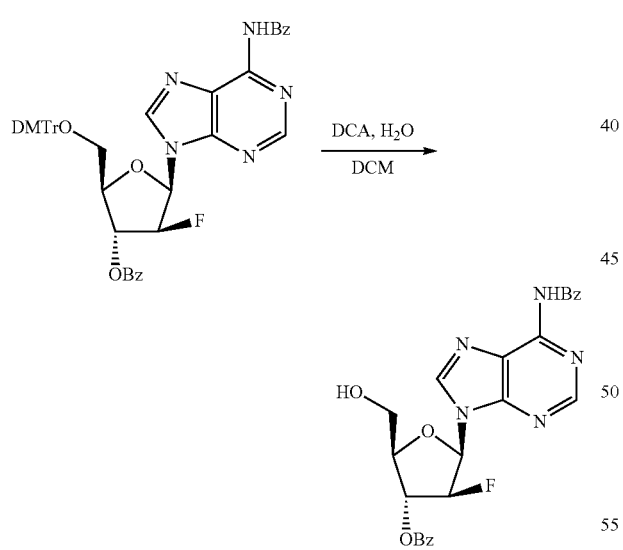

To a solution of the crude product from Step 2 in DCM (45 mL) was added H₂O (533 mg, 29.6 mmol) and 2,2-dichloroacetic acid in DCM (6%, 44.4 mL, 26.6 mmol). The mixture was stirred at RT for 10 min. Then, Et₃SiH (70 mL) was added to the reaction. After 1 h, the reaction mixture (at 0° C. to 5° C.) was treated with Py (4.2 g, 53 mmol) and stirred at RT for 5 min. The resulting solution was concentrated, and EtOAc (300 mL) was added. The solution was washed with H₂O (3×50 mL) and brine (50 mL), dried (Na₂SO₄), and purified by chromatography on silica gel To a solution of (2R,3R,4S,5R)-5-(6-benzamido-9H-purin-9-yl)-4-fluoro-2-(hydroxymethyl)tetrahydrofuran-3-yl benzoate (275 mg, 0.577 mmol) and ammonium (2R,3R,4S,5R)-5-((bis(4-methoxyphenyl)(phenyl)methoxy)methyl)-4-((tert-butyldimethylsilyl)oxy)-2-(2-isobutyramido-6-oxo-1,6-dihydro-9H-purin-9-yl)tetrahydrothiophen-3-yl phosphonate (500 mg, 0.577 mmol) in Py (7 mL) and DCM (3 mL) at −40° C. under Ar was added DPCP (3098 mg, 11.53 mmol) over 5 min. The resulting mixture was stirred at −20° C. to −40° C. for 40 min. The reaction mixture was used for the next step without work-up. LCMS (ES, m/z): 1309.4 [M+H]⁺.

Step 5: ammonium O-(((2R,3R,4S,5R)-5-(6-benzamido-9H-purin-9-yl)-3-(benzoyloxy)-4-fluorotetrahydrofuran-2-yl)methyl) O-((2R,3R,4S,5R)-4-((tert-butyldimethylsilyl)oxy)-5-(hydroxymethyl)-2-(2-isobutyramido-6-oxo-1,6-dihydro-9H-purin-9-yl)tetrahydrothiophen-3-yl)phosphorothioate Step 6: ammonium O-(((2R,3R,4S,5R)-5-(6-benzamido-9H-purin-9-yl)-3-(benzoyloxy)-4-fluorotetrahydrofuran-2-yl)methyl) O-((2R,3R,4S,5R)-4-((tert-butyldimethylsilyl)oxy)-5-(hydroxymethyl)-2-(2-isobutyramido-6-oxo-1,6-dihydro-9H-purin-9-yl)tetrahydrothiophen-3-yl)phosphorothioate

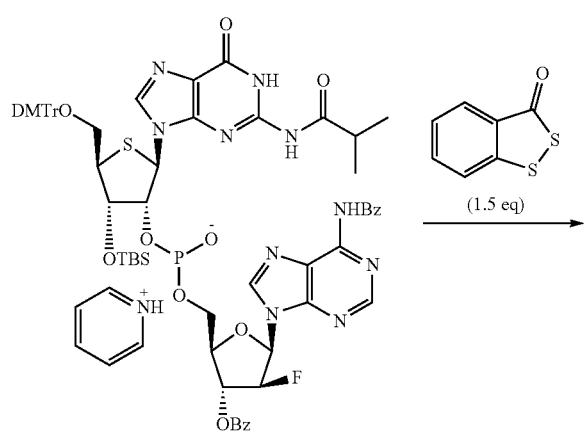

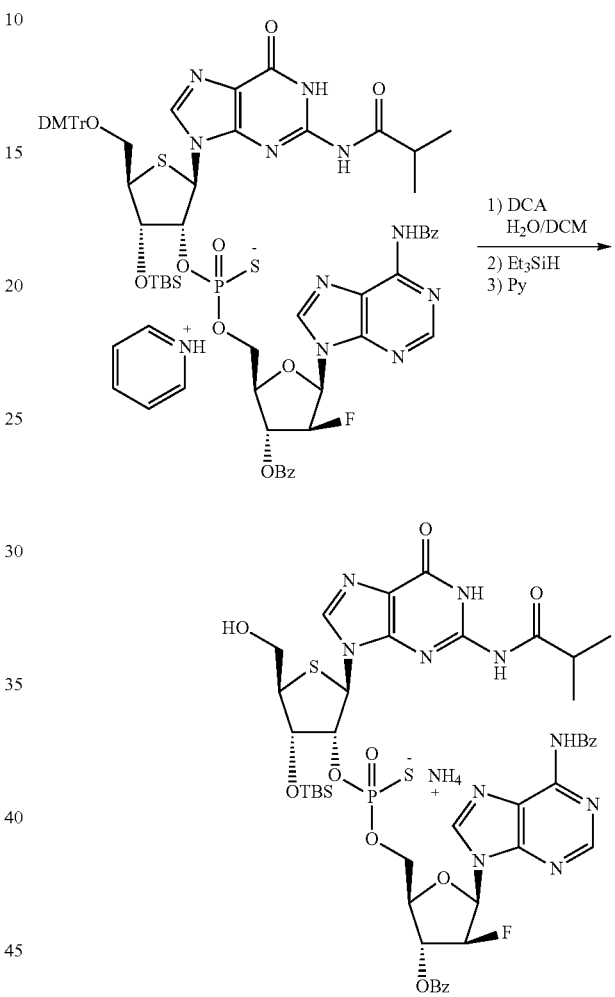

To the reaction mixture from Step 4 at −20° C. was added 3H-benzo[c][1,2]dithiol-3-one (0.146 g, 0.866 mmol) and H₂O (250 mg). The mixture was stirred at RT for 1 h. Then, the reaction mixture was concentrated to give a crude product, which was used for the next reaction step without purification. LCMS (ES, m/z): 1341.2 [M+H]⁺.

To a solution of the crude product from Step 5 in DCM (9 mL) was added H₂O (104 mg, 5.77 mmol) and 2,2-dichloroacetic acid in DCM (6%, 10 mL, 5.2 mmol). The mixture was stirred at RT for 10 min and then, Et₃SiH (15 mL) was added. After 1 h, the mixture was treated with Py (1.0 g) and stirred for 5 min. The resulting solution was concentrated and purified by reverse phase (C18) chromatography eluted with 0-95% ACN in aq NH₄HCO₃ (5 mM) to give the product. LCMS (ES, m/z): 1039.3 [M+H]⁺. ¹H-NMR (400 MHz, DMSO-d₆) δ 12.06-12.01 (m, 1H), 11.62-11.59 (m, 1H), 11.27-11.26 (m, 1H), 8.78-8.77 (m, 1H), 8.68-8.64 (m, 1H), 8.39 (s, 1H), 8.15-8.00 (m, 4H), 7.78-7.51 (m, 6H), 7.31-6.93 (m, 4H), 6.76-6.55 (m, 1H), 5.89-5.86 (m, 1H), 5.77-5.53 (m, 2H), 5.41-5.22 (m, 2H), 4.67-4.64 (m, 1H), 4.42-4.24 (m, 1H), 4.12-4.09 (m, 1H), 3.89-3.74 (m, 1H), 3.69-3.50 (m, 1H), 3.22 (t, J=6.8 Hz, 1H), 2.85-2.73 (m, 1H), 1.16-1.02 (m, 6H), 0.90-0.85 (m, 9H), 0.19-0.10 (m, 6H). ³¹P-NMR: (162 MHz, DMSO-d₆): δ 54.64-53.95 (m).

Step 7: ammonium O-(((2R,3R,4S,5R)-5-(6-ben-zamido-9H-purin-9-yl)-4-fluoro-3-hydroxytetrahy-drofuran-2-yl)methyl) O-((2R,3R,4S,5R)-4-((tert-butyldimethylsilyl)oxy)-5-(hydroxymethyl)-2-(2-isobutyramido-6-oxo-1,6-dihydro-9H-purin-9-yl)tetrahydrothiophen-3-yl)phosphorothioate

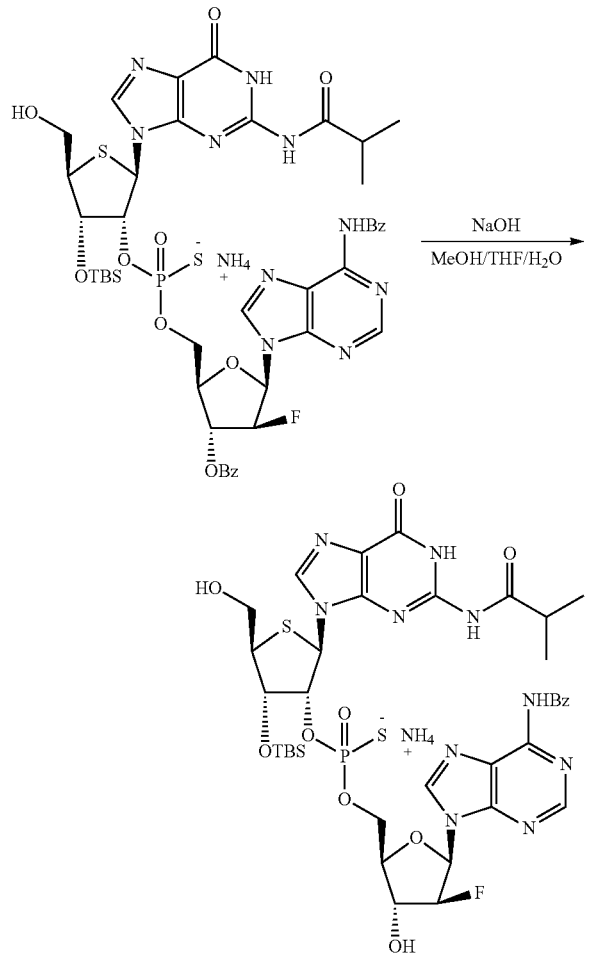

To a solution of ammonium O-(((2R,3R,4S,5R)-5-(6-benzamido-9H-purin-9-yl)-3-(benzoyloxy)-4-fluorotetrahydrofuran-2-yl)methyl) O-((2R,3R,4S,5R)-4-((tert-butyl dim ethyl silyl)oxy)-5-(hydroxymethyl)-2-(2-isobutyramido-6-oxo-1,6-dihydro-9H-purin-9-yl)tetrahydrothiophen-3-yl) phosphorothioate (400 mg, 0.379 mmol) in MeOH (15 mL), THF (12 mL), and H$_2$O (3 mL) at 0° C. was added aq NaOH (2M, 3 mL, 6 mmol) over 3 min. After 10 min, the reaction mixture was neutralized with AcOH and then concentrated. The residue was purified by reverse phase (C18) chromatography eluted with 0-95% ACN in aq NH$_4$HCO$_3$ (5 mM) to give the product. LCMS (ES, m/z): 935.2 [M+H]$^+$. $^1$H-NMR: (400 MHz, DMSO-d$_6$) δ 12.08-12.06 (m, 1H), 11.61-11.59 (m, 1H), 11.23 (br s, 1H), 8.76-8.75 (m, 1H), 8.56-8.54 (m, 1H), 8.37-8.35 (m, 1H), 8.06 (d, J=7.9 Hz, 2H), 7.66 (t, J=7.4 Hz, 1H), 7.56 (t, J=7.6 Hz, 2H), 7.28-6.94 (m, 4H), 6.64-6.44 (m, 1H), 6.16-5.83 (m, 2H), 5.41-5.10 (m, 3H), 4.71-4.64 (m, 1H), 4.36-4.32 (m, 1H), 4.06-3.85 (m, 1H), 3.82-3.52 (m, 4H), 3.23-3.19 (m, 1H), 2.85-2.71 (m, 1H), 1.15-1.04 (m, 6H), 0.90-0.89 (m, 9H), 0.17-0.15 (m, 6H). $^{31}$P-NMR: (162 MHz, DMSO-d$_6$): δ 54.41 (s).

Step 8: ammonium (5R,7R,8R,12aR,14R,15S,15aR,16S)-16-{[tert-butyl(dimethyl)silyl]oxy}-2-[(2,4-dichlorobenzyl)sulfanyl]-15-fluoro-7-{2-[(2-methylpropanoyl)amino]-6-oxo-1,6-dihydro-9H-purin-9-yl}-14-{6-[(phenylcarbonyl)amino]-9H-purin-9-yl}octahydro-12H-5,8-methanofuro[3,2-l][1,3,9,11,6,2,10]tetraoxathiadiphosphacyclotetradecine-10-thiolate 10-oxide 2-sulfide

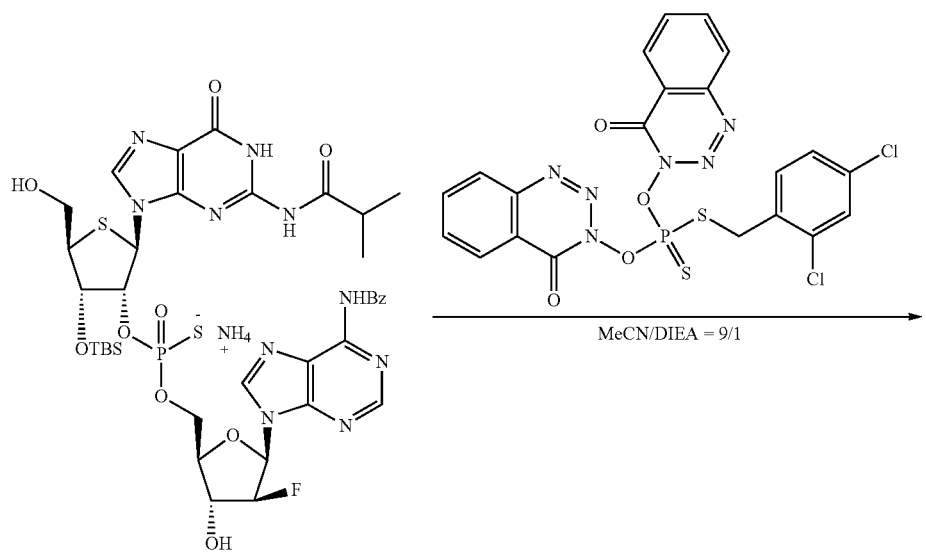

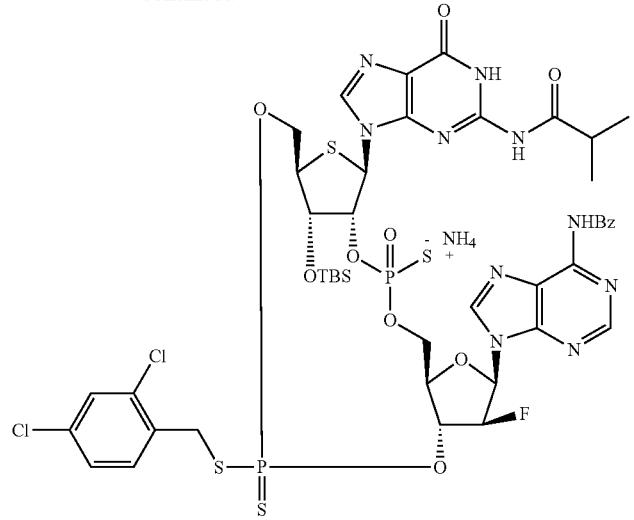

To a solution of ammonium O-(((2R,3R,4S,5R)-5-(6-benzamido-9H-purin-9-yl)-4-fluoro-3-hydroxytetrahydrofuran-2-yl)methyl) O-((2R,3R,4S,5R)-4-((tert-butyldimethylsilyl)oxy)-5-(hydroxymethyl)-2-(2-isobutyramido-6-oxo-1,6-dihydro-9H-purin-9-yl) tetrahydrothiophen-3-yl) phosphorothioate (360 mg, 0.378 mmol, co-evaporated with Py 3×5 mL) in CH$_3$CN (36 mL) and DIEA (4 mL) was added a solution of S-2,4-dichlorobenzyl O,O-bis(4-oxobenzo[d][1,2,3]triazin-3(4H)-yl) phosphorodithioate (548 mg, 0.945 mmol) in 1,4-dioxane (4 mL) dropwise over 3 min. The mixture was stirred at RT for 16 h and then concentrated. The residue was purified by reverse phase (C18) chromatography eluted with 0 to 95% ACN in aq NH$_4$HCO$_3$ (5 mM) to give a crude product. The crude product was further purified with prep-TLC (developed by 3% MeOH in DCM) to give the product. LCMS (ES, m/z): 1189.0 [M+H]$^+$. $^{31}$P-NMR: (162 MHz, CD$_3$OD): δ 96.19-95.17 (m), 61.86-59.92 (m).

Step 9: diammonium (5R,7R,8R,12aR,14R,15S,15aR,16S)-16-{[tert-butyl(dimethyl)silyl]oxy}-15-fluoro-7-{2-[(2-methylpropanoyl)amino]-6-oxo-1,6-dihydro-9H-purin-9-yl}-14-{6-[(phenylcarbonyl)amino]9H-purin-9-yl}octahydro-12H-5,8-methanofuro[3,2-l][1,3,9,11,6,2,10]tetraoxathiadiphosphacyclotetradecine-2,10-bis(thiolate) 10-oxide 2-sulfide

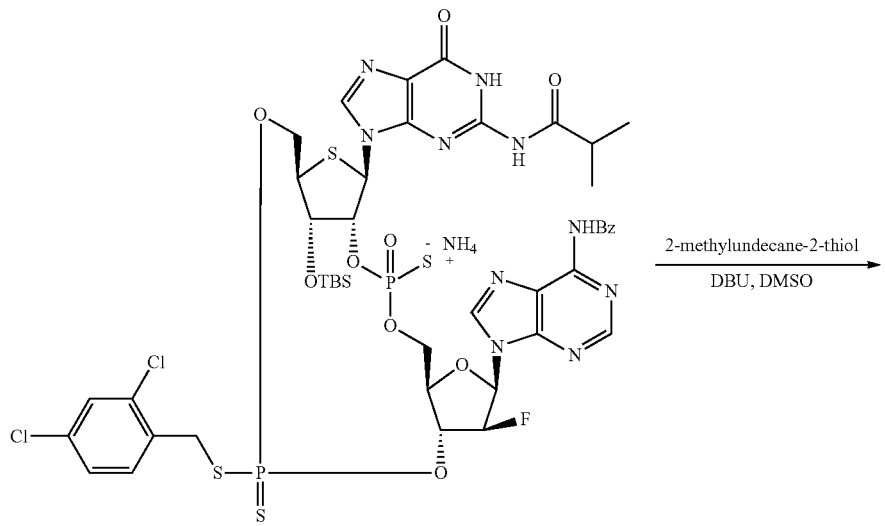

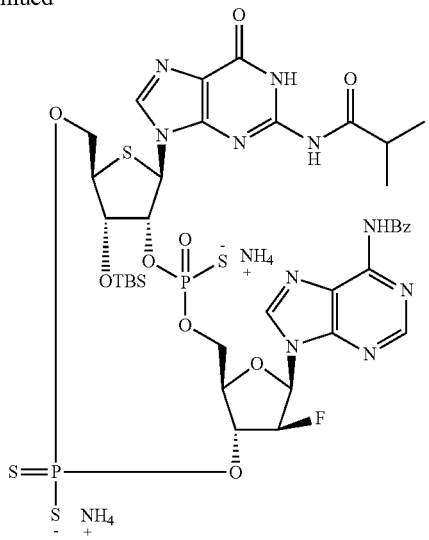

To a stirred solution of ammonium (5R,7R,8R,12aR,14R,15S,15aR,16S)-16-{[tert-butyl(dimethyl)silyl]oxy}-2-[(2,4-dichlorobenzyl)sulfanyl]-15-fluoro-7-{2-[(2-methylpropanoyl)amino]-6-oxo-1,6-dihydro-9H-purin-9-yl}-14-{6-[(phenylcarbonyl)amino]-9H-purin-9-yl}octahydro-12H-5,8-methanofuro[3,2-l][1,3,9,11,6,2,10]tetraoxathiadiphosphacyclotetradecine-10-thiolate 10-oxide 2-sulfide (100 mg, 0.082 mmol) (co-evaporated with CH₃CN 3×5 mL) in DMSO (15 mL) were added 2-methylundecane-2-thiol (99 mg, 0.49 mmol) and 2,3,4,6,7,8,9,10-octahydropyrimido[1,2-a]azepine (100 mg, 0.65 mmol). The resulting mixture was stirred at RT for 3 h. The mixture was purified by reverse phase (C18) chromatography eluted with 0 to 95% ACN in aq NH₄HCO₃ (5 mM) to give the product. LCMS (ES, m/z): 1029.3 [M+H]⁺. ³¹P-NMR: (162 MHz, CD₃OD): δ 113.80 (s), 61.35 (s).

Step 10: diethanaminium (5R,7R,8R,12aR,14R,15S,15aR,16S)-7-(2-amino-6-oxo-1,6-dihydro-9H-purin-9-yl)-14-(6-amino-9H-purin-9-yl)-16-{[tert-butyl(dimethyl)silyl]oxy}-15-fluorooctahydro-12H-5,8-methanofuro[3,2-l][1,3,9,11,6,2,10]tetraoxathiadiphosphacyclotetradecine-2,10-bis(thiolate) 10-oxide 2-sulfide

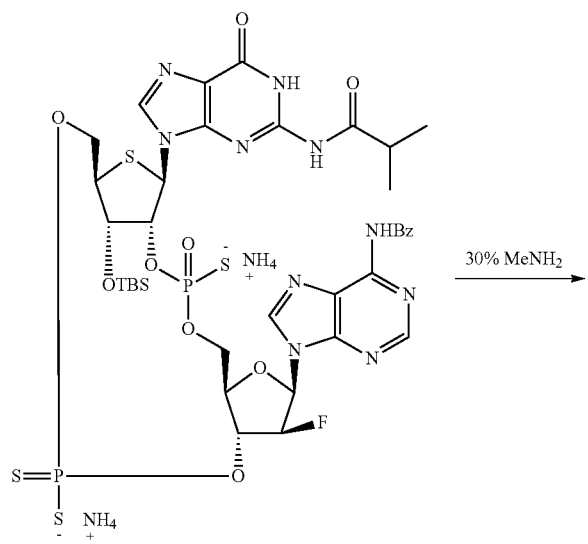

30% MeNH₂ →

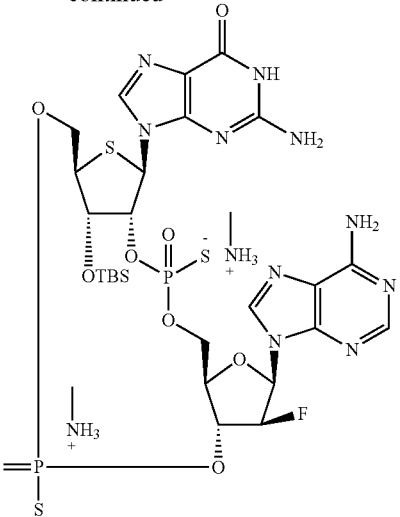

Diammonium (5R,7R,8R,12aR,14R,15S,15aR,16S)-16-{[tert-butyl(dimethyl) silyl]oxy}-15-fluoro-7-{2-[(2-methylpropanoyl)amino]-6-oxo-1,6-dihydro-9H-purin-9-yl}-14-{6-[(phenylcarbonyl)amino]-9H-purin-9-yl}octahydro-12H-5,8-methanofuro[3,2-l][1,3,9,11,6,2,10]tetraoxathiadiphosphacyclotetradecine-2,10-bis(thiolate) 10-oxide 2-sulfide (40 mg, 0.037 mmol) was dissolved in a solution of CH₃NH₂ in EtOH (33%, 10 mL). The mixture was stirred at RT for 3 h, then was concentrated to give a crude product, which was used for next step without purification. LCMS (ES, m/z): 855.2 [M+H]⁺.

Step 11: 2-amino-9-[(5R,7R,8R,12aR,14R,15S, 15aR,16S)-14-(6-amino-9H-purin-9-yl)-15-fluoro-10,16-dihydroxy-2-sulfanyl-2,10-disulfidooctahydro-12H-5,8-methanofuro[3,2-l][1,3,9,11,6,2,10]tetraoxathiadiphosphacyclotetradecin-7-yl]-1,9-dihydro-6H-purin-6-one

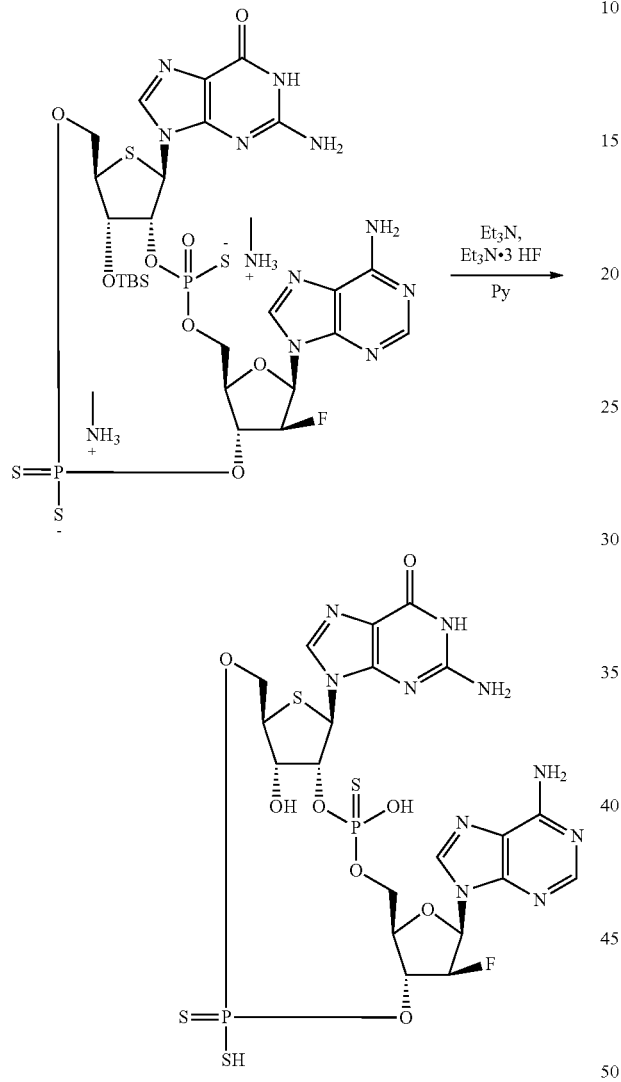

To a stirred solution of the crude product from Step 10 in Py (1.5 mL) were added Et₃N (0.37 g, 3.7 mmol) and Et₃N.3HF (0.30 g, 1.85 mmol). The resulting mixture was heated at 50° C. for 24 h. The mixture then was concentrated and purified by prep-HPLC (Atlantis Prep T3 OBD Column, 19 mm×250 mm) eluted with 7-25% ACN in aq NH₄HCO₃ (10 mM) over 14 min to afford a crude product (T$_R$: 11.58 min). The crude product was further purified by prep-HPLC (XBridge Prep Phenyl OBD Column, 19 mm×250 mm) eluted with 6-8% ACN in aq NH₄HCO₃ (20 mM) over 15 min to afford the product (T$_R$: 13.5 min). LCMS (ES, m/z): 741.2 [M+H]⁺. ¹H-NMR: (400 MHz, D₂O) δ 8.61 (s, 1H), 8.25 (d, J=3.0 Hz, 1H), 8.19 (s, 1H), 6.52 (dd, J=23.3, 2.6 Hz, 1H), 5.96 (d, J=8.7 Hz, 1H), 5.73-5.62 (m, 1H), 5.59 (m, 0.5H), 5.46 (m, 0.5H), 5.40 (m, 1H), 4.55 (d, J=3.4 Hz, 1H), 4.46-4.28 (m, 2H), 4.25 (m, 2H), 4.00 (m, 1H), 3.63 (m, 1H). ³¹P-NMR: (162 MHz, D₂O) δ 112.91 (s), 60.45 (s).

Example 17: 2-amino-9-[(5R,7R,8S,12aR,14R,15R, 15aS,18S)-14-(6-amino-9H-purin-9-yl)-18-fluoro-10-hydroxy-10-oxido-2-sulfanyl-2-sulfidohexahydro-14H-15,12a-(epoxymethano)-5,8-methanofuro[3,2-l][1,3,6,9,11,2,10]pentaoxadiphosphacyclotetradecin-7(12H)-yl]-1,9-dihydro-6H-purin-6-one

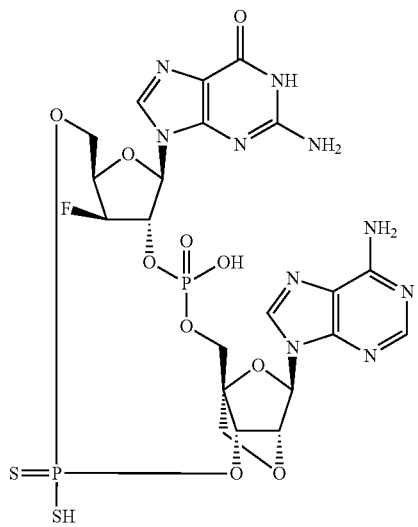 [SMILES: Nc1nc2c(ncn2[C@@H]2O[C@@H]3COP(=S)(S)O[C@H]4[C@H]5OC[C@]4(COP(=O)(O)O[C@@H]2[C@H]3F)O[C@H]5n2cnc3c(N)ncnc32)c(=O)[nH]1]

Step 1: N-(9-((1R,3R,4R,7S)-1-((bis(4-methoxyphenyl)(phenyl)methoxy)methyl)-7-((tert-butyldimethylsilyl)oxy)-2,5-dioxabicyclo[2.2.1]heptan-3-yl)-9H-purin-6-yl)benzamide

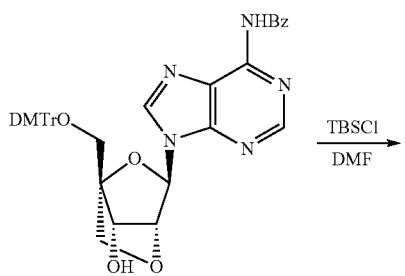

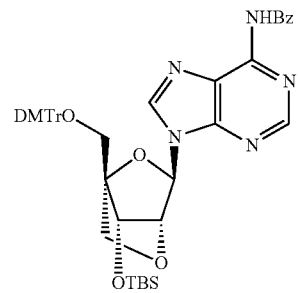

N-(9-((1R,3R,4R,7S)-1-((bis(4-methoxyphenyl)(phenyl)methoxy)methyl)-7-hydroxy-2,5-dioxabicyclo[2.2.1]heptan-3-yl)-9H-purin-6-yl)benzamide (800 mg, 1.17 mmol)

was co-evaporated with Py (3×5 mL) and then re-dissolved in DMF (5 ml) under Ar. To the solution was added imidazole (397 mg, 5.84 mmol) and tert-butylchlorodimethylsilane (440 mg, 2.92 mmol), and the solution was stirred at RT for 5 h. Then, sat aq NaHCO₃ (5 mL), H₂O (30 ml) and EtOAc (50 mL) were added. The layers were separated, and the aq layer was extracted with EtOAc (2×50 mL). The combined organic solution was washed with brine (3×60 mL), concentrated, and purified by silica gel column chromatography eluted with 1 to 10% MeOH in DCM (0.3% Et₃N) to give the product. LCMS (ES, m/z): 801.3 [M+H]⁺. ¹H-NMR: (400 MHz, DMSO-d₆) δ 11.26 (s, 1H), 8.79 (s, 1H), 8.60 (s, 1H), 8.10-8.03 (m, 2H), 7.71-7.62 (m, 1H), 7.59-7.55 (m, 2H), 7.44-7.36 (m, 2H), 7.37-7.18 (m, 7H), 6.94-6.84 (m, 4H), 6.20 (s, 1H), 4.85 (s, 1H), 4.73 (s, 1H), 4.02 (d, J=8.0 Hz, 1H), 3.87 (d, J=7.9 Hz, 1H), 3.73 (s, 6H), 3.47 (d, J=10.9 Hz, 1H), 3.33-3.30 (m, 1H), 0.72 (s, 9H), −0.01 (s, 3H), −0.07 (s, 3H).

Step 2: N-(9-((1S,3R,4R,7S)-7-((tert-butyldimethylsilyl)oxy)-1-(hydroxymethyl)-2,5-dioxabicyclo[2.2.1]heptan-3-yl)-9H-purin-6-yl)benzamide

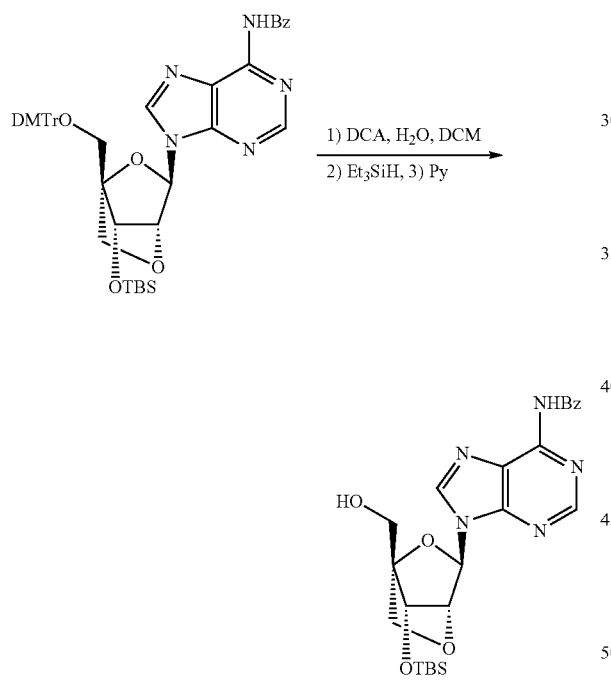

To a solution of N-(9-((1R,3R,4R,7S)-1-((bis(4-methoxyphenyl)(phenyl) methoxy)methyl)-7-((tert-butyldimethylsilyl)oxy)-2,5-dioxabicyclo[2.2.1]heptan-3-yl)-9H-purin-6-yl)benzamide (850 mg, 0.956 mmol) in DCM (5 ml) was added H₂O (172 mg, 9.56 mmol) and 2,2-dichloroacetic acid in DCM (6%, 12 ml, 7.20 mmol). After 20 min, Et₃SiH (20 mL, 124 mmol) was added. The resulting solution was stirred at RT for 1 h. Then, Py (1.36 g, 17.2 mmol) was added to the mixture, which was stirred for 10 min. The mixture was concentrated, and the residue was purified by reverse phase (C18) chromatography eluted with 0-100% ACN in aq NH₄HCO₃ (5 mM) to give the product. LCMS (ES, m/z): 498.2 [M+H]⁺. ¹H-NMR: (400 MHz, DMSO-d₆) δ 11.23 (s, 1H), 8.77 (s, 1H), 8.56 (s, 1H), 8.09-8.02 (m, 2H), 7.71-7.62 (m, 1H), 7.59-7.55 m, 2H), 6.09 (s, 1H), 5.10-5.07 (m, 1H), 4.68 (s, 1H), 4.59 (s, 1H), 3.96 (d, J=7.9 Hz, 1H), 3.88-3.73 (m, 3H), 0.87 (s, 9H), 0.10 (d, J=1.3 Hz, 6H).

Step 3: pyridin-1-ium ((1R,3R,4R,7S)-3-(6-benzamido-9H-purin-9-yl)-7-((tert-butyldimethylsilyl)oxy)-2,5-dioxabicyclo[2.2.1]heptan-1-yl)methyl ((2R,3S,4S,5R)-5-((bis(4-methoxyphenyl)(phenyl)methoxy)methyl)-4-fluoro-2-(2-isobutyramido-6-oxo-1,6-dihydro-9H-purin-9-yl)tetrahydrofuran-3-yl) phosphite

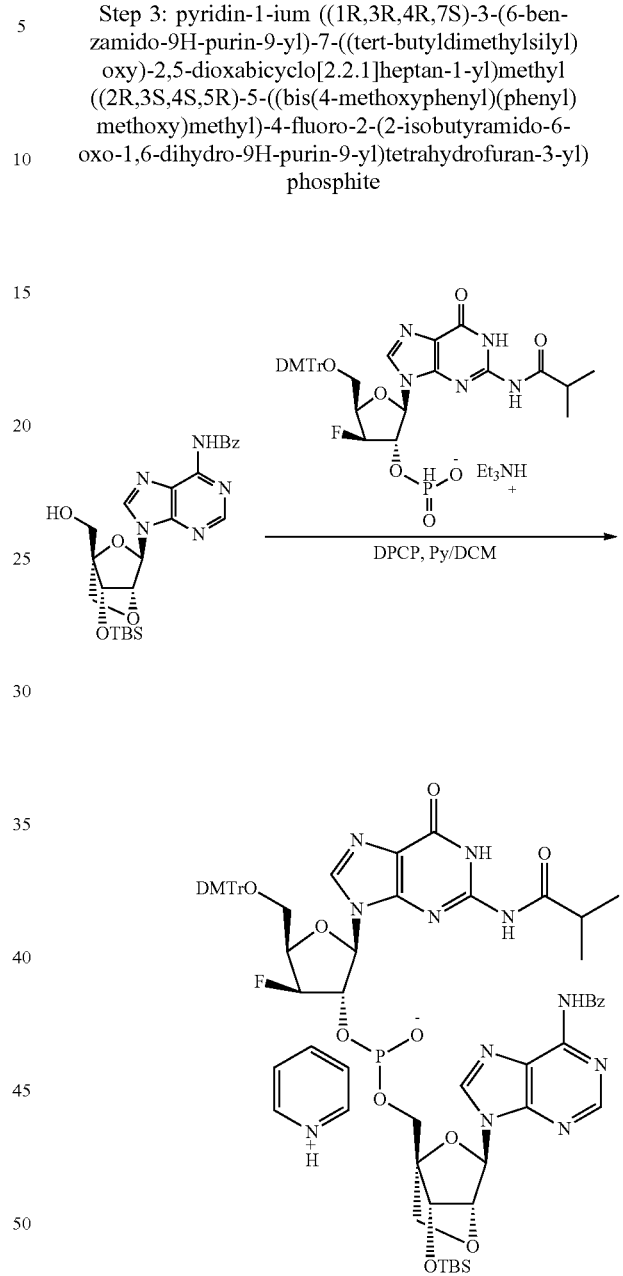

To a solution of DPCP (3.66 g, 13.7 mmol) in Py (10 ml) at −40° C. was under Ar added a solution of N-(9-((1S,3R,4R,7S)-7-((tert-butyldimethylsilyl)oxy)-1-(hydroxymethyl)-2,5-dioxabicyclo[2.2.1]heptan-3-yl)-9H-purin-6-yl)benzamide (340 mg, 0.684 mmol, co-evaporated with Py 3×1 ml) and triethylammonium (2R,3S,4S,5R)-5-((bis(4-methoxyphenyl) (phenyl)methoxy)methyl)-4-fluoro-2-(2-isobutyramido-6-oxo-1,6-dihydro-9H-purin-9-yl)tetrahydrofuran-3-yl phosphonate (560 mg, 0.684 mmol, co-evaporated with Py 3×1 ml) in Py (3 ml) and DCM (3 ml). The mixture was stirred for 40 min. The reaction mixture was used for the next step immediately without purification. LCMS (ES, m/z): 1201.4 [M+H]⁺.

Step 4: pyridin-1-ium ((1R,3R,4R,7S)-3-(6-benzamido-9H-purin-9-yl)-7-((tert-butyldimethylsilyl)oxy)-2,5-dioxabicyclo[2.2.1]heptan-1-yl)methyl ((2R,3S,5R)-5-((bis(4-methoxyphenyl)(phenyl)methoxy)methyl)-4-fluoro-2-(2-isobutyramido-6-oxo-1,6-dihydro-9H-purin-9-yl)tetrahydrofuran-3-yl) phosphate Step 5: ammonium ((1R,3R,4R,7S)-3-(6-benzamido-9H-purin-9-yl)-7-((tert-butyldimethylsilyl)oxy)-2,5-dioxabicyclo[2.2.1]heptan-1-yl)methyl ((2R,3S,4S,5R)-4-fluoro-5-(hydroxymethyl)-2-(2-isobutyramido-6-oxo-1,6-dihydro-9H-purin-9-yl)tetrahydrofuran-3-yl)phosphate

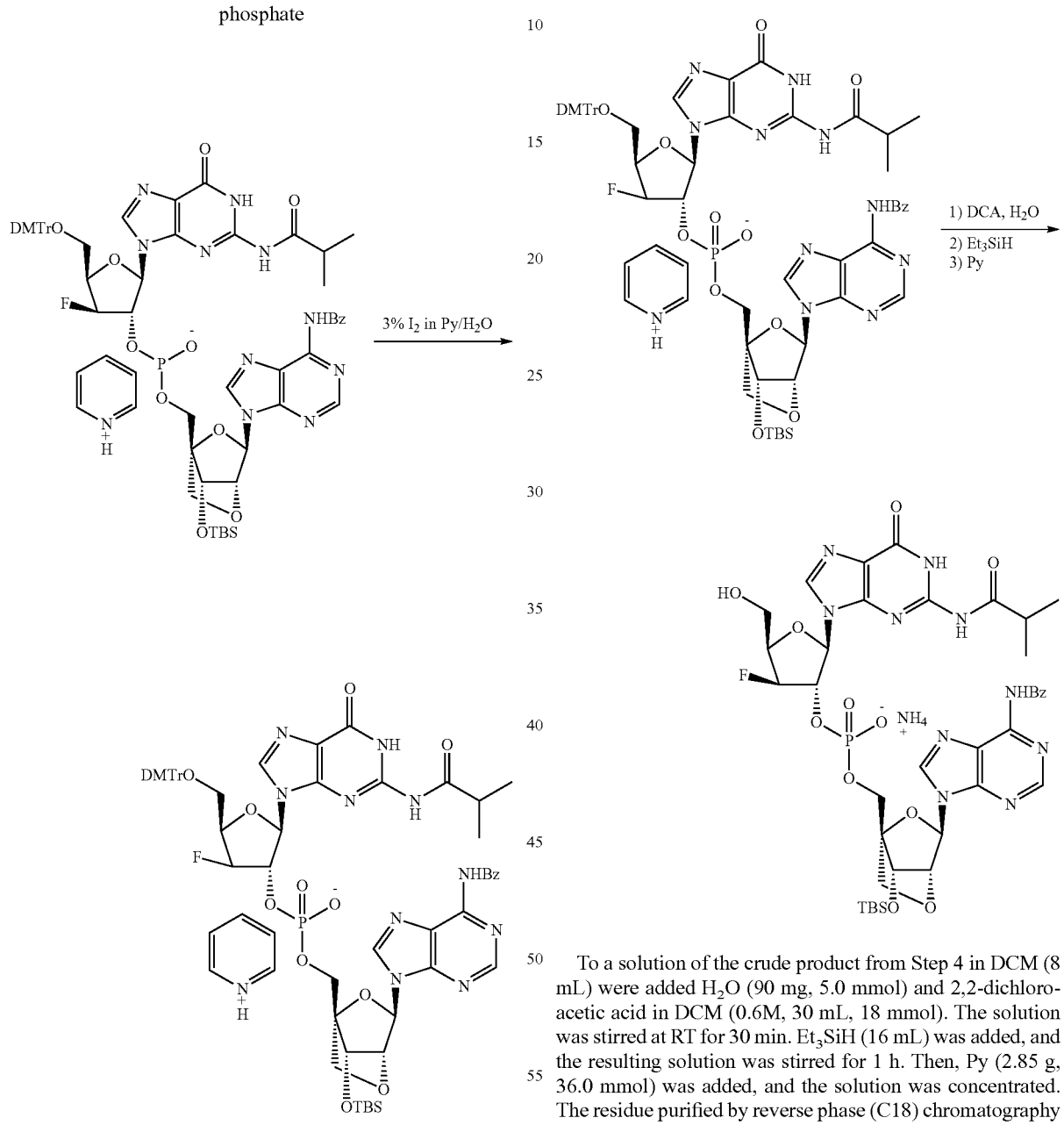

To the reaction mixture from Step 3 at −40° C., was added 3% I$_2$ in Py/H$_2$O (9/1, 6 mL). The mixture was stirred at RT for 1 h. Then, 1.6 g Na$_2$S$_2$O$_3$.5H$_2$O (1.6 g) in H$_2$O (8 ml) was added. After 5 min, the mixture was concentrated to give a crude product, which was used in next reaction step directly. LCMS (ES, m/z): 1217.3 [M+H]$^+$.

To a solution of the crude product from Step 4 in DCM (8 mL) were added H$_2$O (90 mg, 5.0 mmol) and 2,2-dichloroacetic acid in DCM (0.6M, 30 mL, 18 mmol). The solution was stirred at RT for 30 min. Et$_3$SiH (16 mL) was added, and the resulting solution was stirred for 1 h. Then, Py (2.85 g, 36.0 mmol) was added, and the solution was concentrated. The residue purified by reverse phase (C18) chromatography eluted with 0 to 95% ACN in aq NH$_4$HCO$_3$ (5 mM) to give the product. LCMS (ES, m/z): 915.2 [M+H]$^+$. $^1$H NMR: (400 MHz, MeOH-d$_4$) δ 8.70 (s, 1H), 8.41 (s, 1H), 8.18-8.11 (m, 2H), 7.92 (s, 1H), 7.73-7.66 (m, 1H), 7.61 (dd, J=8.3, 6.9 Hz, 2H), 6.25 (s, 1H), 5.93 (s, 1H), 5.43-5.26 (m, 2H), 4.67 (s, 1H), 4.62 (s, 1H), 4.57-4.43 (m, 1H), 4.26 (t, J=4.5 Hz, 2H), 4.11 (d, J=7.9 Hz, 1H), 3.96-3.82 (m, 3H), 2.73 (p, J=6.9 Hz, 1H), 1.25 (dd, J=9.3, 6.9 Hz, 6H), 0.91 (s, 9H), 0.14 (d, J=9.5 Hz, 6H). $^{31}$P-NMR: (162 MHz, MeOH-d$_4$): δ −1.84 (s).

Step 6: Ammonium ((1R,3R,4R,7S)-3-(6-benzamido-9H-purin-9-yl)-7-hydroxy-2,5-dioxabicyclo[2.2.1]heptan-1-yl)methyl ((2R,3S,4S,5R)-4-fluoro-5-(hydroxymethyl)-2-(2-isobutyramido-6-oxo-1,6-dihydro-9H-purin-9-yl)tetrahydrofuran-3-yl) phosphate

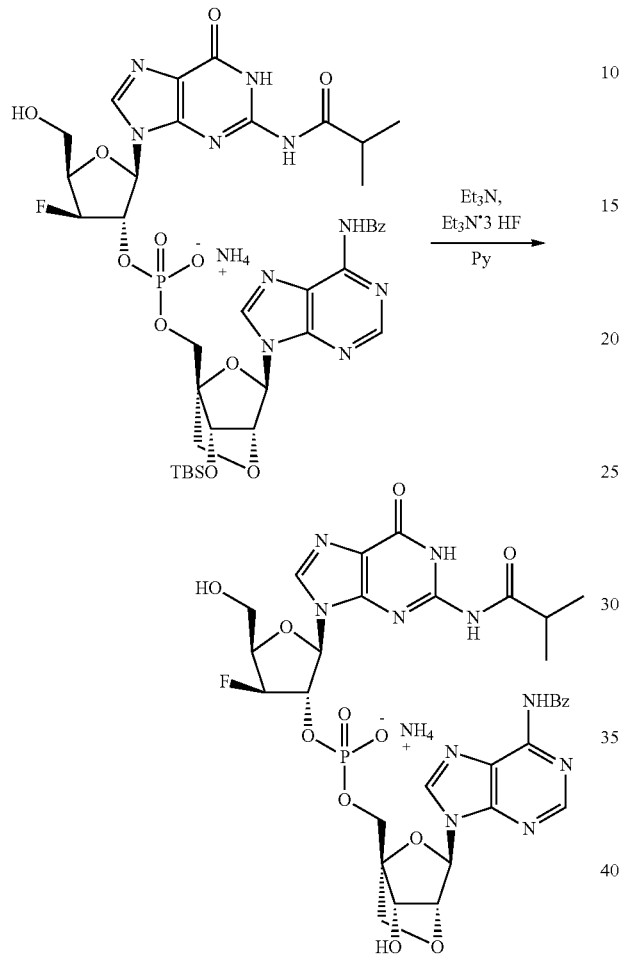

To a solution of ammonium ((1R,3R,4R,7S)-3-(6-benzamido-9H-purin-9-yl)-7-(((tert-butyldimethylsilyl)oxy)-2,5-dioxabicyclo[2.2.1]heptan-1-yl)methyl ((2R,3S,4S,5R)-4-fluoro-5-(hydroxymethyl)-2-(2-isobutyramido-6-oxo-1,6-dihydro-9H-purin-9-yl) tetrahydrofuran-3-yl) phosphate (320 mg, 0.343 mmol) in Py (5 ml) were added Et$_3$N.3HF (2768 mg, 17.17 mmol) and Et$_3$N (1737 mg, 17.17 mmol). The resulting mixture was heated at 50° C. for 15 h. Then, the mixture was concentrated and purified by reverse phase (C18) chromatography eluted with 0 to 95% ACN in aq NH$_4$HCO$_3$ (5 mM) to give the product. LCMS (ES, m/z): 801.1 [M+H]$^+$. $^1$H NMR: (400 MHz, MeOH-d$_4$) δ 8.69 (s, 1H), 8.42 (s, 1H), 8.13 (dd, J=7.4, 1.8 Hz, 2H), 7.93 (s, 1H), 7.74-7.65 (m, 1H), 7.60 (dd, J=8.4, 7.0 Hz, 2H), 6.26 (s, 1H), 5.98 (s, 1H), 5.48-5.26 (m, 2H), 4.54 (s, 1H), 4.47 (s, 1H), 4.30 (dd, J=14.7, 5.5 Hz, 2H), 4.11 (d, J=8.0 Hz, 1H), 3.97-3.85 (m, 3H), 2.74 (p, J=6.9 Hz, 1H), 1.25 (dd, J=9.7, 6.9 Hz, 6H). $^{31}$P NMR: (162 MHz, MeOH-d$_4$) δ−1.42 (s, 1).

Step 7: N-{9-[(5R,7R,8S,12aR,14R,15R,15aS,18S)-2-[(2,4-dichlorobenzyl)sulfanyl]-18-fluoro-10-hydroxy-7-{2-[(2-methylpropanoyl)amino]-6-oxo-1,6-dihydro-9H-purin-9-yl}-10-oxido-2-sulfidohexahydro-14H-15,12a-(epoxymethano)-5,8-methanofuro[3,2-l][1,3,6,9,11,2,10]pentaoxadiphosphacyclotetradecin-14(12H)-yl]-9H-purin-6-yl}benzamide

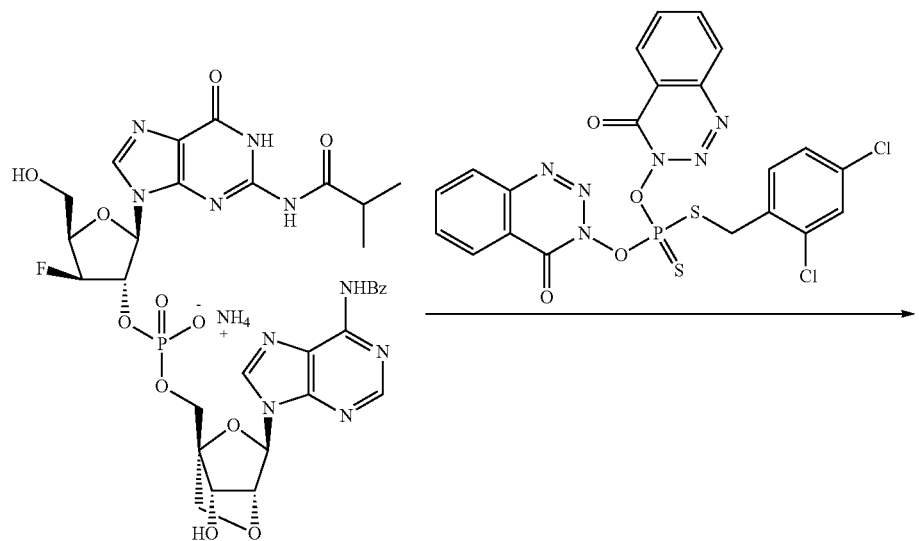

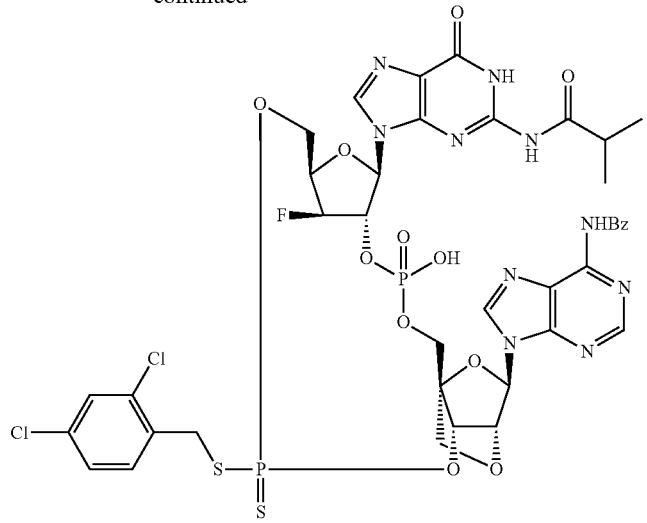

To a solution of ammonium ((1R,3R,4R,7S)-3-(6-benzamido-9H-purin-9-yl)-7-hydroxy-2,5-dioxabicyclo[2.2.1]heptan-1-yl)methyl ((2R,3S,4S,5R)-4-fluoro-5-(hydroxymethyl)-2-(2-isobutyramido-6-oxo-1,6-dihydro-9H-purin-9-yl)tetrahydrofuran-3-yl) phosphate (268 mg, 0.328 mmol, co-evaporated with MeCN 3×2 mL) in MeCN (30 mL) under Ar added DIEA (3.3 mL) and a solution of S-2,4-dichlorobenzyl-O,O-bis(4-oxobenzo[d][1,2,3]triazin-3(4H)-yl) phosphorodithioate (613 mg, 1.06 mmol) in 1,4-dioxane (3.5 mL). The mixture was stirred at RT for 18 h, then concentrated. The residue was purified by reverse phase (C18) chromatography eluted with 0 to 95% ACN in aq $NH_4HCO_3$ (5 mM) to give the product. LCMS (ES, m/z): 1053.1 [M−H]$^-$. $^{31}$P NMR: (162 MHz, MeOH-$d_4$) δ 95.72(s), 95.02 (s); −1.96(s), −3.17 (s).

Step 8: dipyridinium (5R,7R,8S,12aR,14R,15R,15aS,18S)-7-(2-amino-6-oxo-1,6-dihydro-9H-purin-9-yl)-18-fluoro-14-{6-[(phenylcarbonyl)amino]-9H-purin-9-yl}-2-sulfidohexahydro-14H-15,12a-(epoxymethano)-5,8-methanofuro[3,2-l][1,3,6,9,11,2,10]pentaoxadiphosphacyclotetradecin-10(12H)-olate 10-oxide 2-sulfide

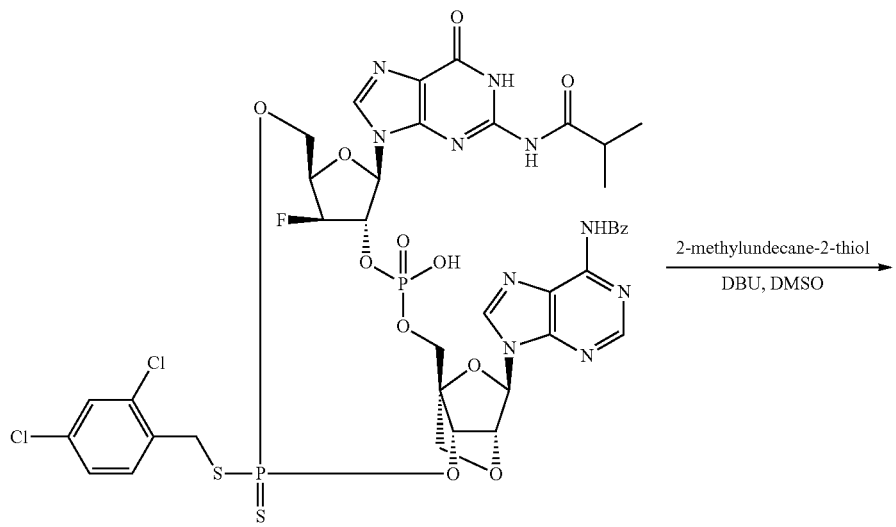

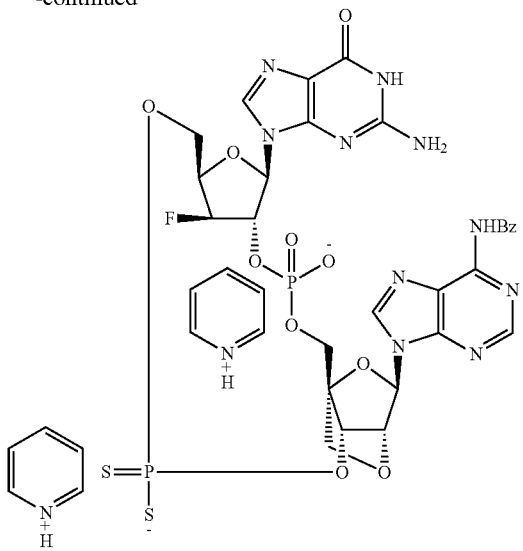

To a solution of N-{9-[(5R,7R,8S,12aR,14R,15R,15aS, 18S)-2-[(2,4-dichlorobenzyl)sulfanyl]-18-fluoro-10-hydroxy-7-{2-[(2-methylpropanoyl)amino]-6-oxo-1,6-dihydro-9H-purin-9-yl}-10-oxido-2-sulfidohexahydro-14H-15,12a-(epoxymethano)-5,8-methanofuro[3,2-l][1,3,6,9,11,2,10]pentaoxadiphosphacyclotetradecin-14(12H)-yl]-9H-purin-6-yl}benzamide (35 mg, 0.033 mmol, co-evaporated with MeCN 3×2 mL) in DMSO (6.3 mL) were added 2-methylundecane-2-thiol (26.7 mg, 0.132 mmol) and 2,3,4,6,7,8,9,10-octahydropyrimido[1,2-a]azepine (30.1 mg, 0.198 mmol). The mixture was stirred at RT for 3 h. The mixture was used for the next step without purification. LCMS (ES, m/z): 895.2 [M+H]$^+$.

Step 9: 2-Amino-9-[(5R,7R,8S,12aR,14R,15R,15aS, 18S)-14-(6-amino-9H-purin-9-yl)-18-fluoro-10-hydroxy-10-oxido-2-sulfanyl-2-sulfidohexahydro-14H-15,12a-(epoxymethano)-5,8-methanofuro[3,2-l][1,3,6,9,11,2,10]pentaoxadiphosphacyclotetradecin-7(12H)-yl]-1,9-dihydro-6H-purin-6-one

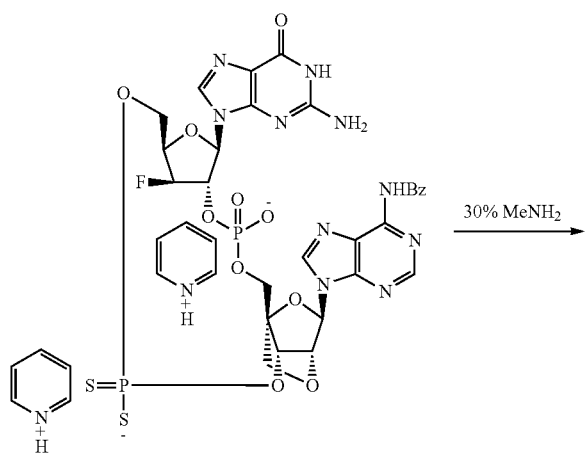

30% MeNH$_2$ →

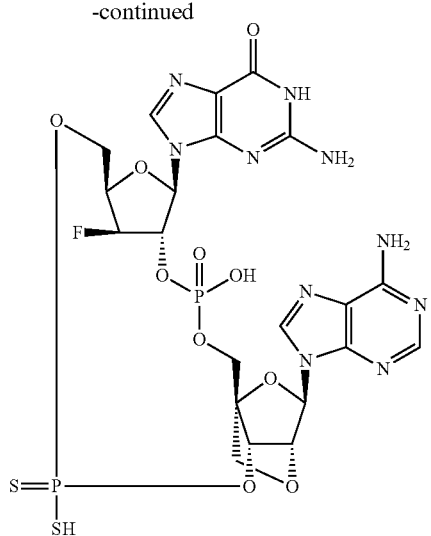

To the reaction mixture from Step 8 was added a solution of MeNH$_2$ in EtOH (30%, 8 mL). The resulting solution was stirred at RT for 3 h. The solution was concentrated, and the residue was purified prep-HPLC (XBridge Prep Phenyl OBD Column, 19 mm×250 mm) eluted with 2-14% ACN in aq NH$_4$HCO$_3$ (10 mM) over 15 min to afford the product (T$_R$: 9.13 min). LCMS (ES, m/z): 721.2 [M+H]$^+$. $^1$H-NMR: (400 MHz, D$_2$O) δ 8.36 (d, J=1.9 Hz, 2H), 8.16 (s, 1H), 7.72 (s, 1H), 6.14 (s, 1H), 6.08 (s, 1H), 5.60-5.44 (m, 2H), 5.02 (d, J=9.5 Hz, 1H), 4.78 (d, J=6.5 Hz, 1H), 4.67-4.50 (m, 1H), 4.36-4.21 (m, 2H), 4.17-4.06 (m, 2H), 4.00 (d, J=8.5 Hz, 1H). $^{31}$P-NMR: (162 MHz, D$_2$O) δ 114.34 (s), −3.21 (s).

Examples 18 through 19, as shown in Table 3 below, were prepared according to procedures analogous to those outlined in Example 17 above using the appropriate monomers, described as Preparations or as obtained from commercial sources, in the coupling step.

TABLE 3
| Example | Structure | Name | Mass [M + H]+ |
|---|---|---|---|
| 18 | 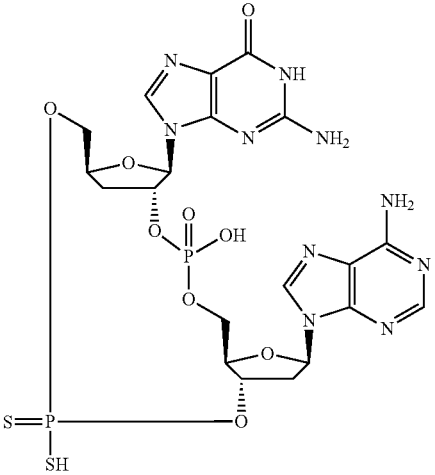 [SMILES: Nc1nc2c(ncn2[C@@H]2O[C@@H]3COP(=S)(S)O[C@H]4C[C@H](n5cnc6c(N)ncnc65)O[C@@H]4COP(=O)(O)O[C@@H]2C3)c(=O)[nH]1] | 2-amino-9-[(5S,7R,8R,12aR,14R,15aS)-14-(6-amino-9H-purin-9-yl)-10-hydroxy-10-oxido-2-sulfanyl-2-sulfidooctahydro-12H-5,8-methanofuro[3,2-1][1,3,6,9,11,2,10]pentaoxadiphosphacyclotetradecin-7-yl]-1,9-dihydro-6H-purin-6-one | 673 |
| 19 | 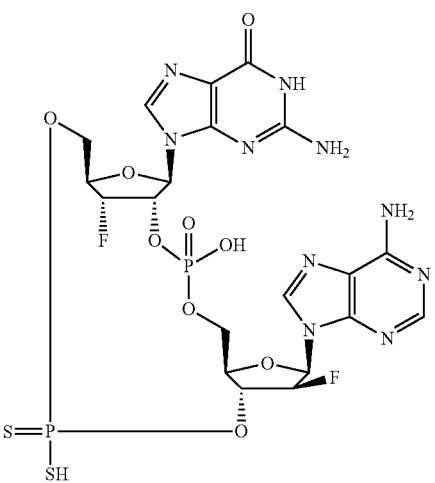 [SMILES: Nc1nc2c(ncn2[C@@H]2O[C@@H]3COP(=S)(S)O[C@H]4[C@H](F)[C@H](n5cnc6c(N)ncnc65)O[C@@H]4COP(=O)(O)O[C@@H]2[C@@H]3F)c(=O)[nH]1] | 2-amino-9-[(5R,7R,8S,12aR,14R,15S,15aR,16R)-14-(6-amino-9H-purin-9-yl)-15,16-difluoro-10-hydroxy-10-oxido-2-sulfanyl-2-sulfidooctahydro-12H-5,8-methanofuro[3,2-1][1,3,6,9,11,2,10]pentaoxadiphosphacyclotetradecin-7-yl]-1,9-dihydro-6H-purin-6-one | 709 |

Example 20: 2-amino-9-[(5R,7R,8R,12aR,14R,15S, 15aR,16S)-14-(6-amino-9H-purin-9-yl)-15-fluoro-10,16-dihydroxy-10-oxido-2-sulfanyl-2-sulfidooctahydro-12H-5,8-methanofuro[3,2-l][1,3,9,11,6,2,10]tetraoxathiadiphosphacyclotetradecin-7-yl]-1,9-dihydro-6H-purin-6-one

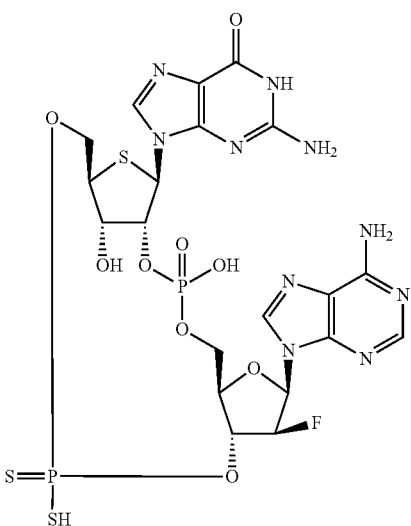 [SMILES: Nc1nc2c(ncn2[C@@H]2S[C@@H]3COP(=S)(S)O[C@H]4[C@H](F)[C@H](n5cnc6c(N)ncnc65)O[C@@H]4COP(=O)(O)O[C@@H]2[C@@H]3O)c(=O)[nH]1]

Step 1: ((2R,3R,4S,5R)-5-(6-benzamido-9H-purin-9-yl)-3-(benzoyloxy)-4-fluorotetrahydrofuran-2-yl) methyl ((2R,3R,4S,5R)-5-((bis(4-methoxyphenyl)(phenyl)methoxy)methyl)-4-((tert-butyldimethylsilyl)oxy)-2-(2-isobutyramido-6-oxo-1,6-dihydro-9H-purin-9-yl)tetrahydrothiophen-3-yl) phosphate

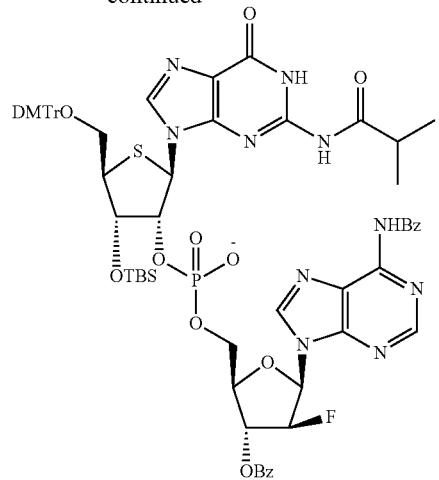

To a mixture containing crude pyridin-1-ium ((2R,3R,4S,5R)-5-(6-benzamido-9H-purin-9-yl)-3-(benzoyloxy)-4-fluorotetrahydrofuran-2-yl)methyl ((2R,3R,4S,5R)-5-((bis(4-methoxyphenyl)(phenyl)methoxy)methyl)-4-((tert-butyldimethylsilyl)oxy)-2-(2-isobutyramido-6-oxo-1,6-dihydro-9H-purin-9-yl)tetrahydrothiophen-3-yl) phosphite (~0.607 mmol) in DCM (4 mL) and Py (4 mL) was added 3% I$_2$ in Py (1.8 ml) and H$_2$O (0.2 ml) over 5 min. The mixture was stirred at RT for 30 min. A solution of Na$_2$S$_2$O$_3$.5H$_2$O (0.5 g) in H$_2$O (5 ml) was added. After 5 min, the mixture was concentrated to give a crude product. LCMS (ES, m/z): 1325.3 [M+H]$^+$.

Step 2: ((2R,3R,4S,5R)-5-(6-benzamido-9H-purin-9-yl)-3-(benzoyloxy)-4-fluorotetrahydrofuran-2-yl) methyl ((2R,3R,4S,5R)-4-((tert-butyldimethylsilyl)oxy)-5-(hydroxymethyl)-2-(2-isobutyramido-6-oxo-1,6-dihydro-9H-purin-9-yl)tetrahydrothiophen-3-yl) phosphate

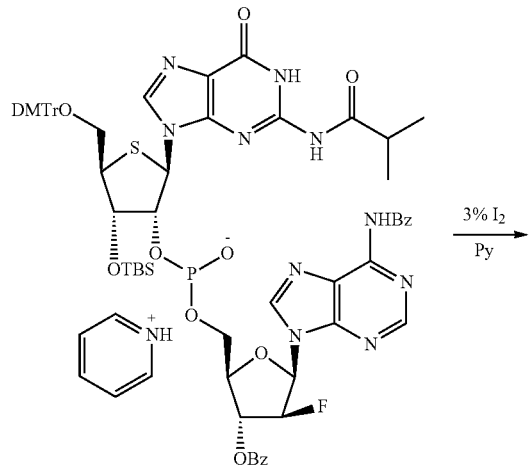

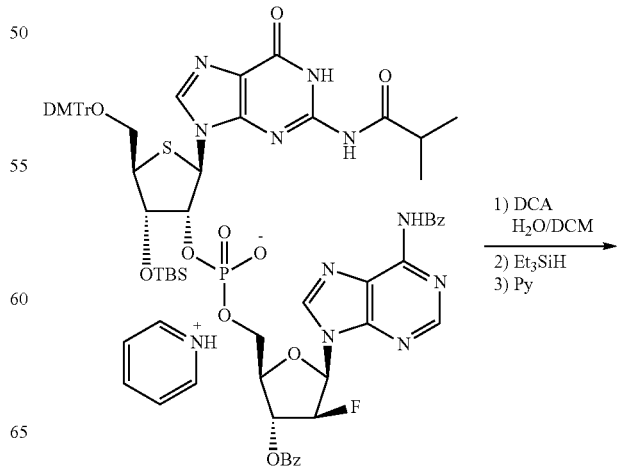

-continued

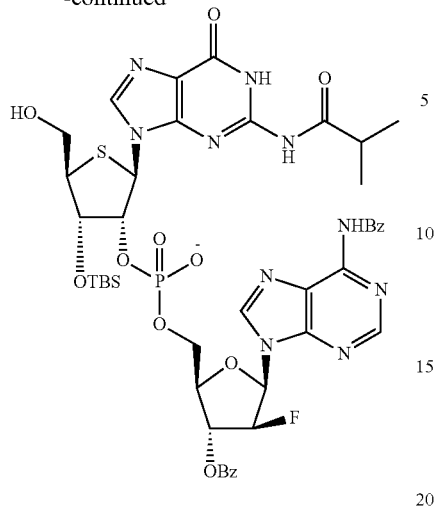

To a solution of the crude product from Step 1 in DCM (8 ml) at RT were added H₂O (110 mg, 6.0 mmol) and 2,2-dichloroacetic acid in DCM (0.6M, 36 ml, 22 mmol). The solution was stirred at RT for 30 min. Then, Et₃SiH (16 ml) was added. The resulting solution was stirred for 1 h, and then, Py (3.42 g, 43.2 mmol) was added. The solution was concentrated, and the residue was purified by reverse phase (C18) chromatography eluted with 0-95% ACN in aq NH₄HCO₃ (5 mM) to give the product. LCMS (ES, m/z): 1023.1 [M+H]⁺.

Step 3: ((2R,3R,4S,5R)-5-(6-benzamido-9H-purin-9-yl)-4-fluoro-3-hydroxytetrahydrofuran-2-yl)methyl ((2R,3R,4S,5R)-4-((tert-butyldimethylsilyl)oxy)-5-(hydroxymethyl)-2-(2-isobutyramido-6-oxo-1,6-dihydro-9H-purin-9-yl)tetrahydrothiophen-3-yl) phosphate

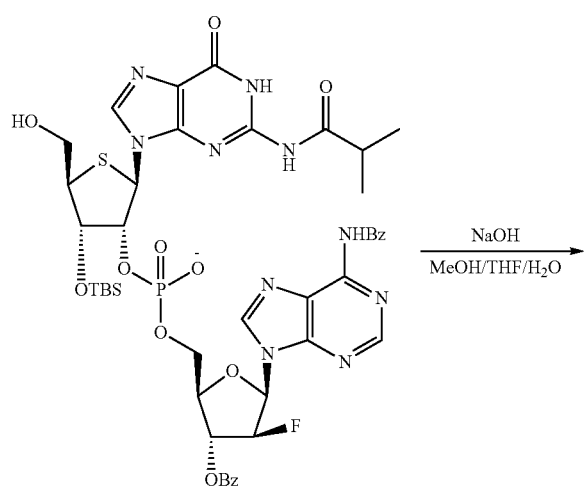

-continued

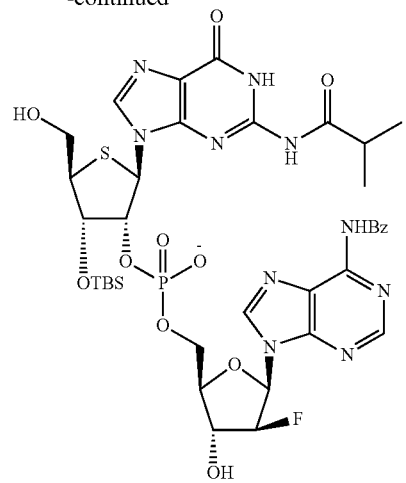

To a solution of ((2R,3R,4S,5R)-5-(6-benzamido-9H-purin-9-yl)-3-(benzoyloxy)-4-fluorotetrahydrofuran-2-yl) methyl ((2R,3R,4S,5R)-4-((tert-butyldimethylsilyl)oxy)-5-(hydroxymethyl)-2-(2-isobutyramido-6-oxo-1,6-dihydro-9H-purin-9-yl)tetrahydrothiophen-3-yl) phosphate (280 mg, 0.193 mmol) in MeOH (10 ml), THF (8 ml) and H₂O (2 mL) at 0° C. was added aq NaOH (2N, 2 ml, 4 mmol) over 3 min. After 10 min, the reaction mixture was neutralized with AcOH and concentrated under vacuum. The residue was purified by reverse phase (C18) chromatography eluted with 0-95% ACN in aq NH₄HCO₃ (5 mM) to give the product. LCMS (ES, m/z): 919.1 [M+H]⁺. ¹H-NMR: (400 MHz, DMSO-d₆) δ 8.76 (s, 1H), 8.57 (d, J=1.7 Hz, 1H), 8.42 (s, 1H), 8.12-8.04 (m, 2H), 7.66 (t, J=7.4 Hz, 1H), 7.56 (t, J=7.6 Hz, 2H), 6.52 (dd, J=13.2, 4.7 Hz, 1H), 6.35 (s, 1H), 5.84 (d, J=8.8 Hz, 1H), 5.36-5.22 (m, 2H), 5.21-5.01 (m, 2H), 4.63 (d, J=3.4 Hz, 1H), 4.36 (d, J=19.2 Hz, 1H), 3.78 (d, J=5.3 Hz, 1H), 3.68 (d, J=11.7 Hz, 2H), 3.56 (d, J=5.9 Hz, 1H), 3.22 (t, J=7.1 Hz, 1H), 2.79 (p, J=6.8 Hz, 1H), 1.10 (dd, J=6.8, 4.7 Hz, 6H), 0.92 (s, 9H), 0.17 (d, J=4.7 Hz, 6H). ³¹P-NMR: (162 MHz, DMSO-d₆) δ−1.15 (s).

Step 4: (5R,7R,8R,12aR,14R,15S,15aR,16S)-16-
{[tert-butyl(dimethyl)silyl]oxy}-2-[(2,4-dichloroben-
zyl)sulfanyl]-15-fluoro-7-{2-[(2-methylpropanoyl)
amino]-6-oxo-1,6-dihydro-9H-purin-9-yl}-14-{6-
[(phenylcarbonyl)amino]-9H-purin-9-yl}octahydro-
12H-5,8-methanofuro[3,2-l][1,3,9,11,6,2,10]
tetraoxathiadiphosphacyclotetradecin-10-olate
10-oxide 2-sulfide
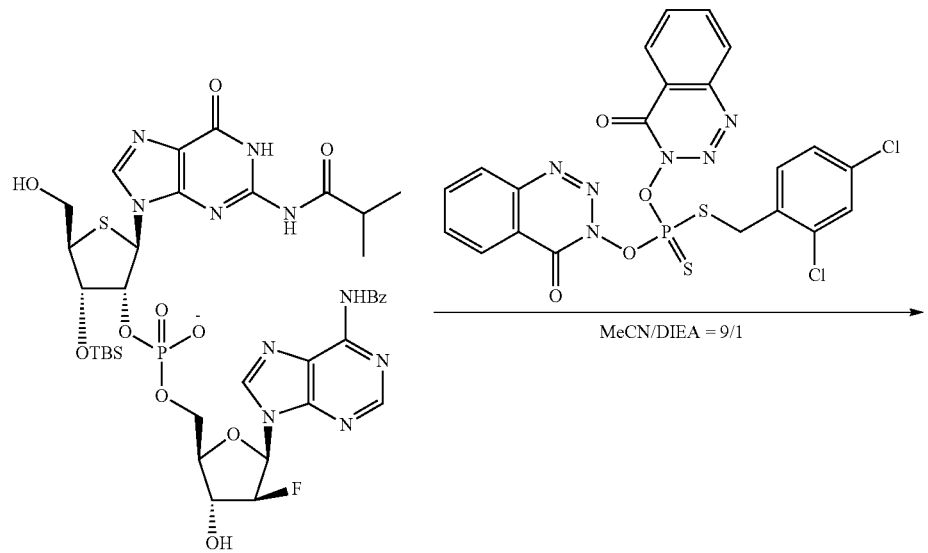
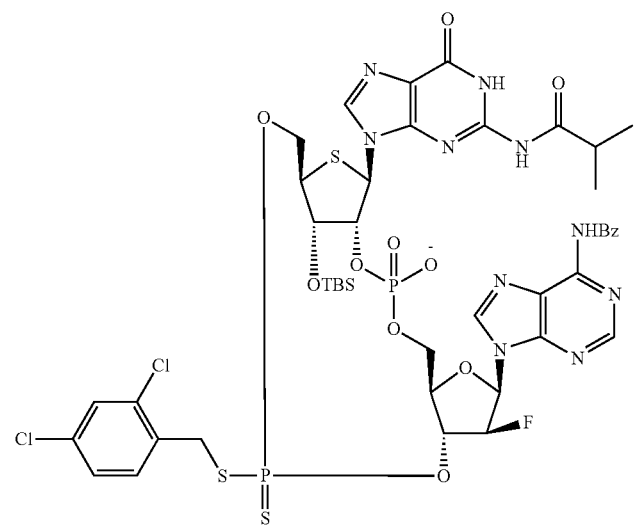

To a solution of ((2R,3R,4S,5R)-5-(6-benzamido-9H-purin-9-yl)-4-fluoro-3-hydroxytetrahydrofuran-2-yl)methyl ((2R,3R,4S,5R)-4-((tert-butyldimethylsilyl)oxy)-5-(hydroxymethyl)-2-(2-isobutyramido-6-oxo-1,6-dihydro-9H-purin-9-yl)tetrahydrothiophen-3-yl) phosphate (180 mg, 0.196 mmol, co-evaporated with Py 3×4 ml) in MeCN (18 ml) was added diisopropylamine (2 ml) and S-2,4-dichlorobenzyl O,O-bis(4-oxobenzo[d][1,2,3]triazin-3(4H)-yl) phosphorodithioate in 1,4-dioxane (213 mg, 0.369 mmol). The resulting mixture was stirred at RT for 16 h. The mixture was concentrated, and the residue was purified by reverse phase (C18) chromatography eluted with 0 to 95% ACN in aq NH$_4$HCO$_3$ (5 mM) to give a crude product. It was further purified by prep-TLC developed with 5% MeOH in DCM (0.2% Et$_3$N) to give the product. LCMS (ES, m/z): 1173.0 [M+H]$^+$.

Step 5: (5R,7R,8R,12aR,14R,15S,15aR,16S)-16-{[tert-butyl(dimethyl)silyl]oxy}-15-fluoro-7-{2-[(2-methylpropanoyl)amino]-6-oxo-1,6-dihydro-9H-purin-9-yl}-14-{6-[(phenylcarbonyl)amino]-9H-purin-9-yl}-2-sulfidooctahydro-12H-5,8-methanofuro[3,2-l][1,3,9,11,6,2,10]tetraoxathiadiphosphacyclotetradecin-10-olate 10-oxide 2-sulfide

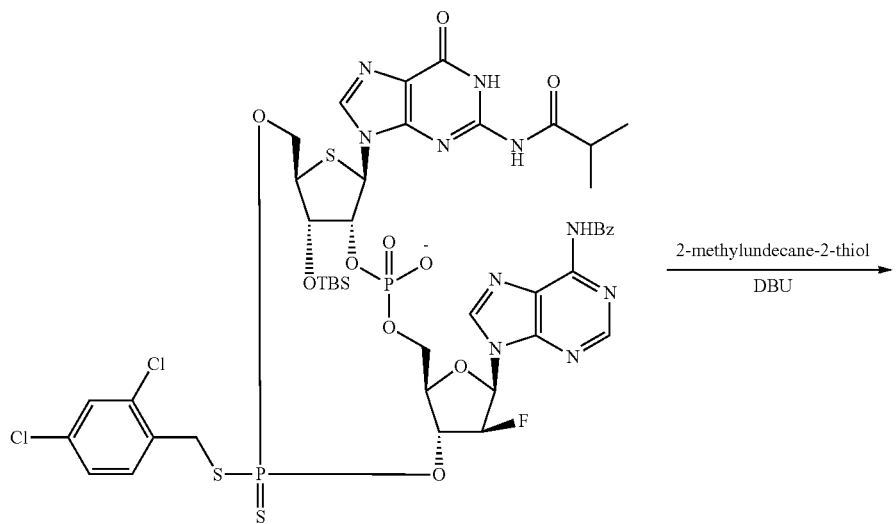

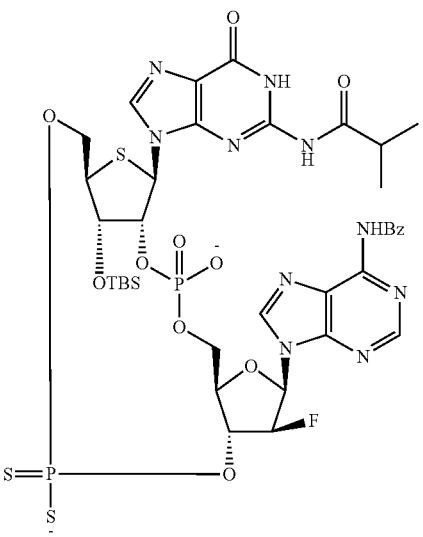

To a stirred solution of (5R,7R,8R,12aR,14R,15S,15aR,16S)-16-{[tert-butyl(dimethyl)silyl]oxy}-2-[(2,4-dichlorobenzyl)sulfanyl]-15-fluoro-7-{2-[(2-methylpropanoyl)amino]-6-oxo-1,6-dihydro-9H-purin-9-yl}-14-{6-[(phenylcarbonyl)amino]-9H-purin-9-yl}octahydro-12H-5,8-methanofuro[3,2-l][1,3,9,11,6,2,10]tetraoxathiadiphosphacyclotetradecin-10-olate 10-oxide 2-sulfide triethylammonium salt (30 mg, 0.025 mmol, co-evaporated with MeCN 3×2 mL) in DMSO (2.5 mL) were added 2-methylundecane-2-thiol (30 mg, 0.15 mmol) and 2,3,4,6,7,8,9,10-octahydropyrimido[1,2-a]azepine (30 mg, 0.20 mmol). The resulted mixture was stirred at RT for 3 h. The reaction mixture was used for next step without purification. LCMS (ES, m/z): 1013.2 [M+H]⁺.

Step 6: (5R,7R,8R,12aR,14R,15S,15aR,16S)-7-(2-amino-6-oxo-1,6-dihydro-9H-purin-9-yl)-14-(6-amino-9H-purin-9-yl)-16-{[tert-butyl(dimethyl)silyl]oxy}-15-fluoro-2-sulfidooctahydro-12H-5,8-methanofuro[3,2-l][1,3,9,11,6,2,10]tetraoxathiadiphosphacyclotetradecin-10-olate 10-oxide 2-sulfide

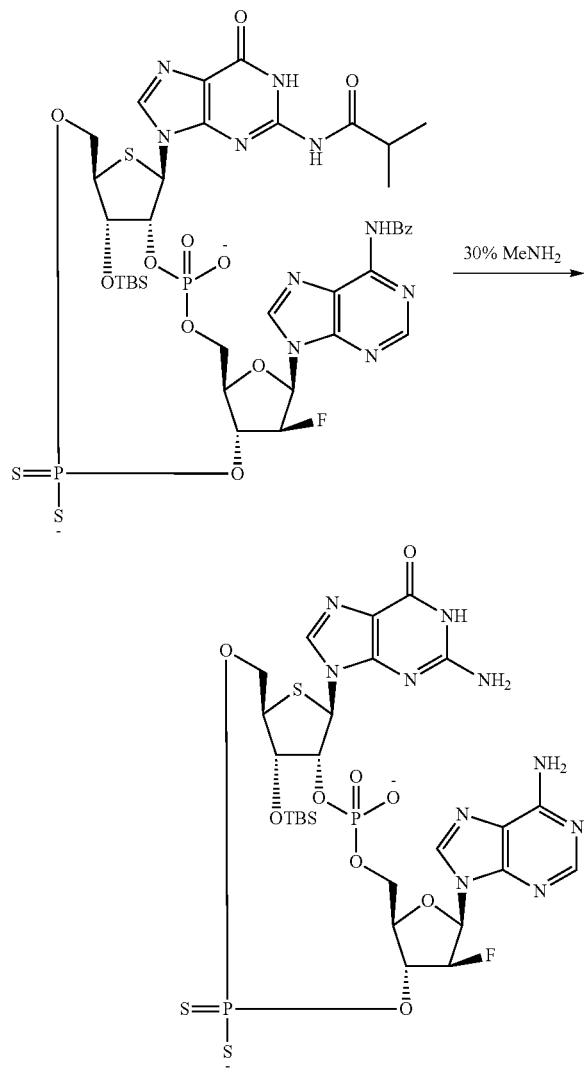

To the reaction mixture from Step 5 was added MeNH₂ in EtOH (33%, 3.65 ml). The resulting solution was stirred at ET for 3 h. The solution was concentrated, and the residue was purified by reverse phase (C18) chromatography eluted with 0-95% ACN in aq NH₄HCO₃ (5 mM) to give the product. LCMS (ES, m/z): 839.2 [M+H]⁺.

Step 7: 2-amino-9-[(5R,7R,8R,12aR,14R,15S,15aR,16S)-14-(6-amino-9H-purin-9-yl)-15-fluoro-10,16-dihydroxy-10-oxido-2-sulfanyl-2-sulfidooctahydro-12H-5,8-methanofuro[3,2-l][1,3,9,11,6,2,10]tetraoxathiadiphosphacyclotetradecin-7-yl]-1,9-dihydro-6H-purin-6-one

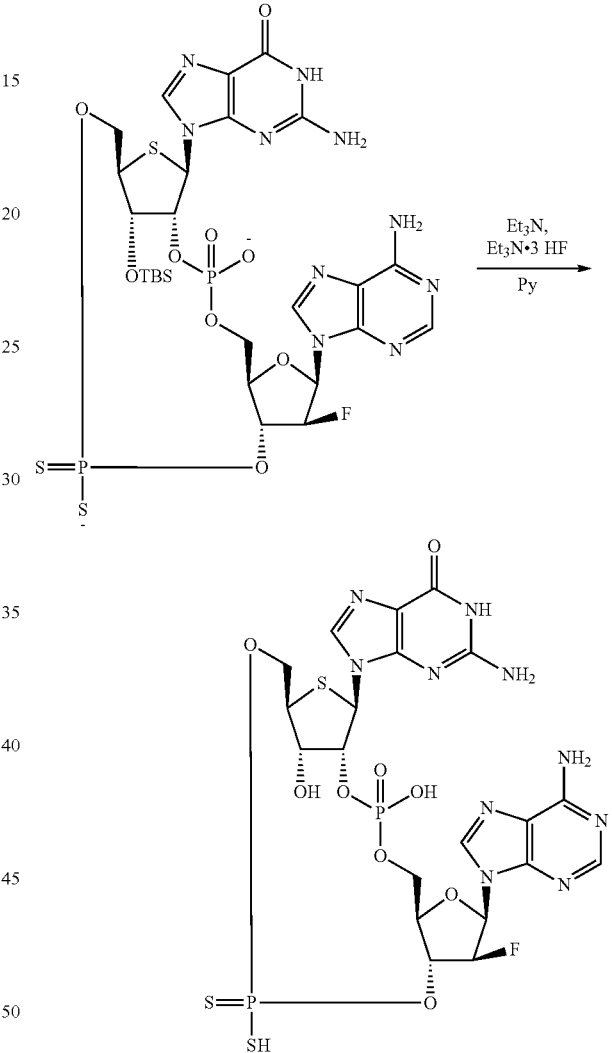

(5R,7R,8R,12aR,14R,15S,15aR,16S)-7-(2-amino-6-oxo-1,6-dihydro-9H-purin-9-yl)-14-(6-amino-9H-purin-9-yl)-16-{[tert-butyl(dimethyl)silyl]oxy}-15-fluoro-2-sulfidooctahydro-12H-5,8-methanofuro[3,2-l][1,3,9,11,6,2,10]tetraoxathiadiphosphacyclotetradecin-10-olate 10-oxide 2-sulfide (12 mg, 0.013 mmol) was suspended in Py (1.5 mL) under Ar, and Et₃N (121 mg, 1.20 mmol) and Et₃N.3HF (144 mg, 0.896 mmol) were added. The mixture was warmed at 50° C. for 16 h. Then, the mixture was concentrated and purified by prep-HPLC (Atlantis Prep T3 OBD Column, 19 mm×250 mm) eluted with 6-15% ACN in aq NH₄HCO₃ (10 mM) over 11 min to afford the product (T$_R$: 8.87 min). LCMS (ES, m/z): 725.1 [M+H]⁺. ¹H-NMR: (400 MHz, D₂O): δ 8.40 (s, 1H), 8.27 (d, J=2.6 Hz, 1H), 8.22 (s, 1H), 6.53 (dd, J=19.9, 3.3 Hz, 1H), 5.96 (d, J=8.7 Hz, 1H), 5.71-5.59 (m, 1H), 5.44-5.27 (m, 2H), 4.64 (d, J=3.4 Hz, 1H), 4.42-4.38 (m, 2H), 4.33-4.25 (m, 1H), 4.09 (t, J=6.2 Hz, 2H), 3.67-3.65 (m, 1H). $^{31}$P-NMR: (162 MHz, D$_2$O) δ 112.88 (s), 0.90 (s).

Example 21, as shown in Table 4 below, was prepared according to procedures analogous to those outlined in Example 20 above using the appropriate monomers, described as Preparations or as obtained from commercial sources, in the coupling step.

TABLE 4

| Example | Structure | Name | Mass [M + H]$^+$ |
|---|---|---|---|
| 21 | 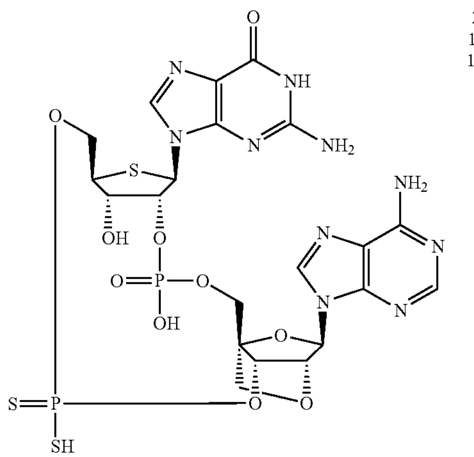 | 2-amino-9-[(5R,7R,8R,12aR,14R,15R, 15aS,18S)-14-(6-amino-9H-purin-9-yl)-10,18-dihydroxy-10-oxido-2-sulfanyl-2-sulfidohexahydro-14H-15,12a-(epoxymethano)-5,8-methanofuro[3,2-l][1,3,9,11,6,2,10]tetraoxathiadiphosphacyclotetradecin-7(12H)-yl]-1,9-dihydro-6H-purin-6-one | 735 |

Example 22: 2-amino-9-[(5R,7R,8S,12aR,14R,15S, 15aR,16R)-14-(6-amino-9H-purin-9-yl)-15,16-difluoro-2-hydroxy-2-oxido-10-sulfanyl-10-sulfidooctahydro-12H-5,8-methanofuro[3,2-l][1,3,6,9,11,2,10]pentaoxadiphosphacyclotetradecin-7-yl]-1,9-dihydro-6H-purin-6-one

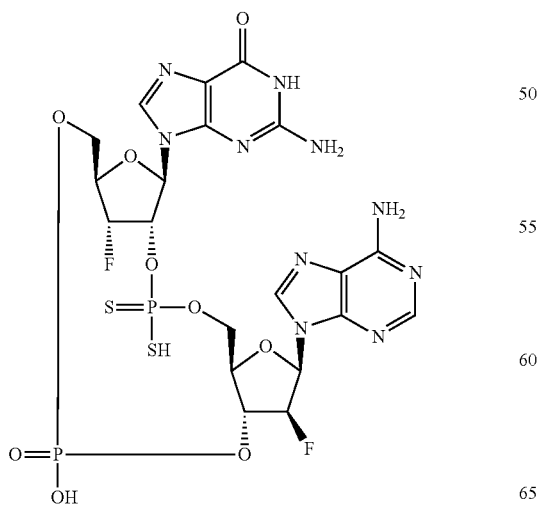

Step 1: O-(((2R,3R,4S,5R)-5-(6-benzamido-9H-purin-9-yl)-4-fluoro-3-hydroxytetrahydrofuran-2-yl)methyl) O-((2R,3S,4R,5R)-5-((bis(4-methoxyphenyl)(phenyl)methoxy)methyl)-4-fluoro-2-(2-isobutyramido-6-oxo-1H-purin-9(6H)-yl)tetrahydrofuran-3-yl)S-2,4-dichlorobenzyl phosphorodithioate

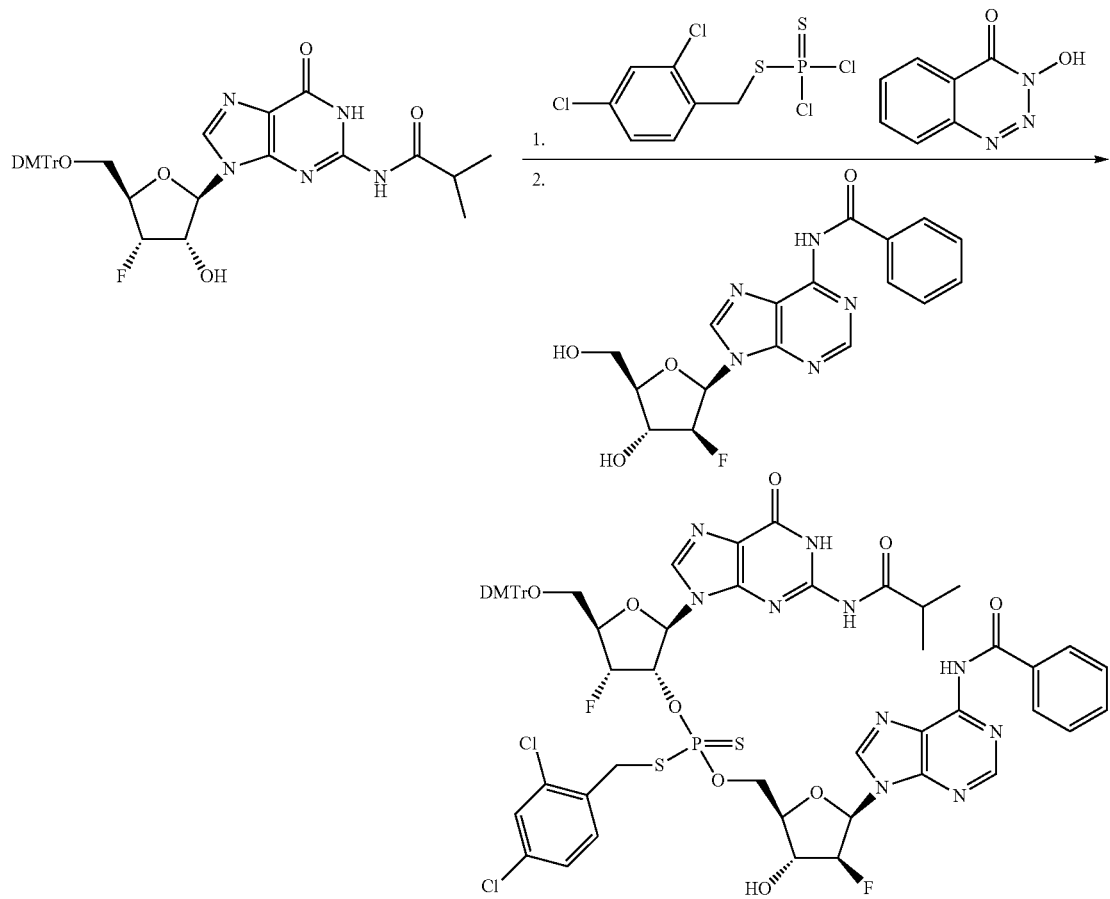

2,4-dichlorobenzyl phosphorodichloridodithioate (714 mg, 2.19 mmol) and 3-hydroxybenzo[d][1,2,3]triazin-4(3H)-one (734 mg, 4.50 mmol) were kept under high vacuum for 2 h, then added 1,4-dioxane (4 ml) and Py (0.492 ml, 6.08 mmol). The mixture was stirred at RT for 2 h, and resulting solid was filtered off. The solid was washed with 1,4-dioxane (3 ml), and the combined filtrate was concentrated. DMF (5 ml), activated 4Å molecular sieve (300 mg) and Py (0.492 ml, 6.08 mmol) were added to the residue. The mixture was stirred for 20 min, and N-(9-((2R,3S,4S,5R)-5-((bis(4-methoxyphenyl)(phenyl)m ethoxy)methyl)-4-fluoro-3-hydroxytetrahydrofuran-2-yl)-6-oxo-6,9-dihydro-1H-purin-2-yl)isobutyramide (800 mg, 1.22 mmol) was added. After 5 h, N-(9-((2R,3S,4R,5R)-3-fluoro-4-hydroxy-5-(hydroxymethyl)tetrahydrofuran-2-yl)-9H-purin-6-yl)benzamide (454 mg, 1.22 mmol), Py (1 ml) and 1-methylimidazole (0.97 ml, 12 mmol) were added. The mixture was stirred at RT overnight. Then, EtOAc (30 ml) and H$_2$O (20 ml) were added. The layers were separated, and the organic layer was dried (Na$_2$SO$_4$) and purified by column chromatography on silica gel eluted with 0 to 4% MeOH in DCM with (1% Et$_3$N) to give the product. LCMS (ES, m/z): 1285 [M+H]$^+$.

Step 2: O-(((2R,3R,4S,5R)-5-(6-benzamido-9H-purin-9-yl)-4-fluoro-3-hydroxytetrahydrofuran-2-yl)methyl)S-2,4-dichlorobenzyl O-((2R,3S,4R,5R)-4-fluoro-5-(hydroxymethyl)-2-(2-isobutyramido-6-oxo-1H-purin-9(6H)-yl)tetrahydrofuran-3-yl) phosphorodithioate

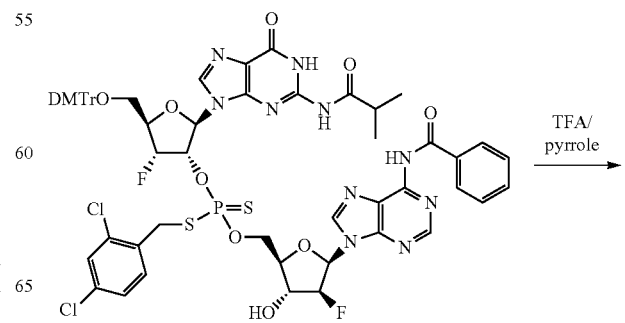

TFA/pyrrole

149

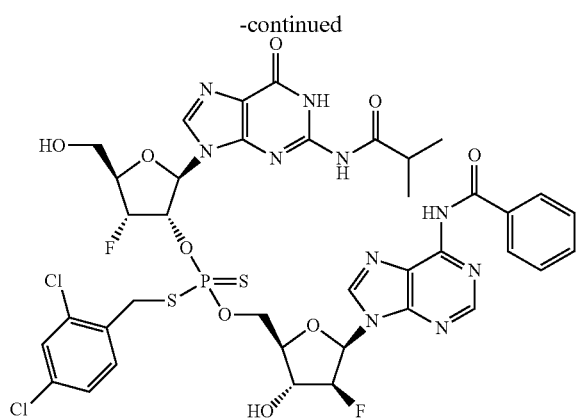

To a solution of O-(((2R,3R,4S,5R)-5-(6-benzamido-9H-purin-9-yl)-4-fluoro-3-hydroxytetrahydrofuran-2-yl)meth

150 yl) O-((2R,3 S,4R,5R)-5-((bis(4-methoxyphenyl)(phenyl)methoxy)methyl)-4-fluoro-2-(2-isobutyramido-6-oxo-1H-purin-9(6H)-yl)tetrahydrofuran-3-yl) S-2,4-dichlorobenzyl phosphorodithioate (1.2 g, 0.37 mmol) in MeCN (15 ml) was added pyrrole (0.078 ml, 1.1 mmol) and trifluoroacetic acid (0.288 ml, 3.74 mmol). The resulting mixture was stirred at RT for 30 min. The mixture was concentrated, and the residue was purified by column chromatography on silica gel, eluted with 0-5% MeOH in DCM to give the product. LCMS (ES, m/z): 982 [M+H]$^+$.

Step 3: N—O-[(5R,7R,8S,12aR,14R,15S,15aR,16R)-2-(2-cyanoethoxy)-10-[(2,4-dichlorobenzyl)sulfanyl]-15,16-difluoro-7-{2-[(2-methylpropanoyl)amino]-6-oxo-1,6-dihydro-9H-purin-9-yl}-2-oxido-10-sulfidooctahydro-12H-5,8-methanofuro[3,2-l][1,3,6,9,11,2,10]pentaoxadiphosphacyclotetradecin-14-yl]-9H-purin-6-yl)benzamide

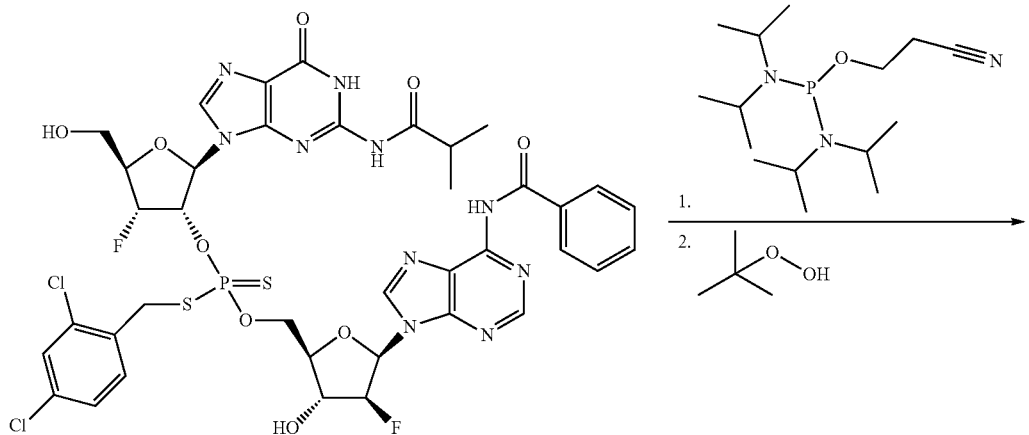

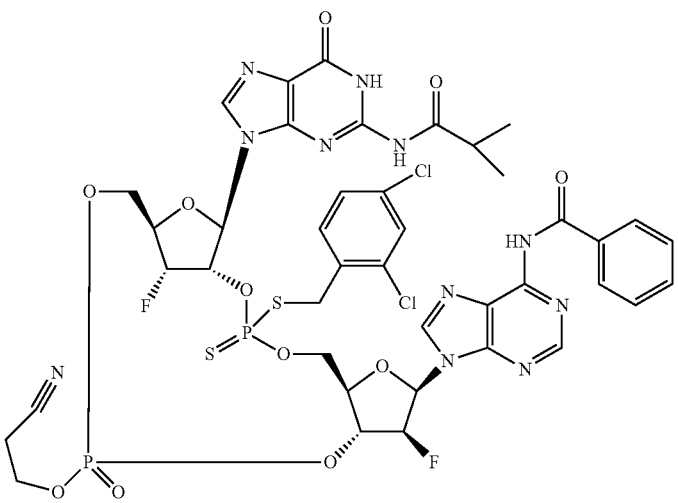

Diisopropylammonium tetrazolide (59.3 mg, 0.346 mmol) and O-(((2R,3R,4S,5R)-5-(6-benzamido-9H-purin-9-yl)-4-fluoro-3-hydroxytetrahydrofuran-2-yl)methyl)S-2,4-dichlorobenzyl O-((2R,3S,4R,5R)-4-fluoro-5-(hydroxymethyl)-2-(2-isobutyramido-6-oxo-1H-purin-9(6H)-yl)tetrahydrofuran-3-yl) phosphorodithioate (170 mg, 0.173 mmol) were co-evaporated with CH$_3$CN (3×5 ml) and kept under high vacuum for 30 min. To the residue was added MeCN (10 ml), DMF (1 mL), and activated 4Å molecular sieve (300 mg), and the mixture was stirred at RT for 20 min. Then, cyanoethyl N,N,N',N'-tetraisopropylphosphorodiamidite (67.8 mg, 0.225 mmol) in CH$_3$CN (1 ml) was added to the mixture. After 20 min, 1H-tetrazole (60.7 mg, 0.866 mmol) was added. The reaction was stirred at RT for 1.5 h, and then, tert-butyl hydroperoxide (5.0M in decane, 0.104 ml, 0.519 mmol) was added. The mixture was stirred at RT for 1 h. Then, EtOAc (30 ml) and aq Na$_2$S$_2$O$_3$ (5%, 10 ml) were added. The layers were separated, and the organic layer was washed with brine, dried (Na$_2$SO$_4$) and purified by column chromatography on silica gel eluted with 0-10% MeOH in DCM to give the product. LCMS (ES, m/z): 1096 [M+H]$^+$.

Step 4: 2-Amino-9-[(5R,7R,8S,12aR,14R,15S,15aR,16R)-14-(6-amino-9H-purin-9-yl)-15,16-difluoro-2-hydroxy-2-oxido-10-sulfanyl-10-sulfidooctahydro-12H-5,8-methanofuro[3,2-l][1,3,6,9,11,2,10]pentaoxadiphosphacyclotetradecin-7-yl]-1,9-dihydro-6H-purin-6-one

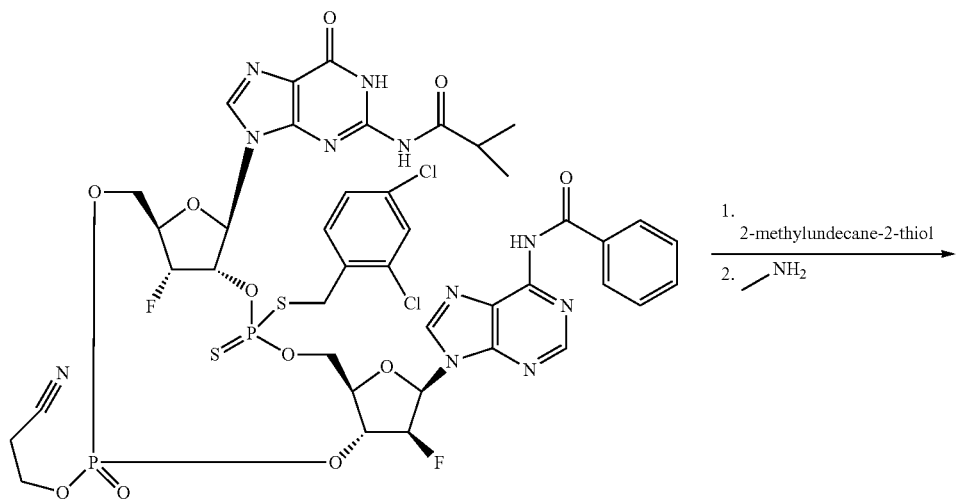

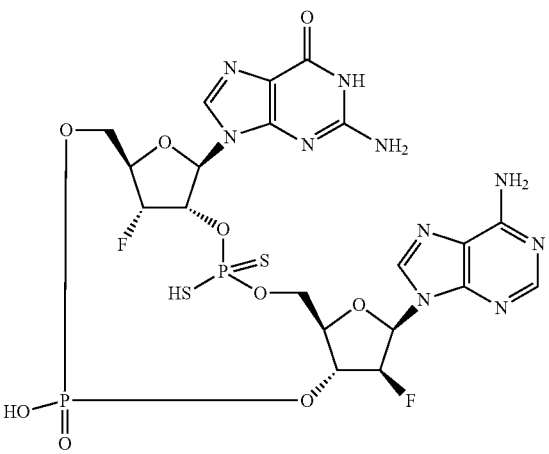

To a solution of N-{9-[(5R,7R,8S,12aR,14R,15S,15aR,16R)-2-(2-cyanoethoxy)-10-[(2,4-dichlorobenzyl)sulfanyl]-15,16-difluoro-7-{2-[(2-methylpropanoyl)amino]-6-oxo-1,6-dihydro-9H-purin-9-yl}-2-oxido-10-sulfidooctahydro-12H-5,8-methanofuro[3,2-l][1,3,6,9,11,2,10]pentaoxadiphosphacyclotetradecin-14-yl]-9H-purin-6-yl}benzamide (70 mg, 0.064 mmol) in DMSO (1 ml) was added 2,3,4,6,7,8,9,10-octahydropyrimido[1,2-a]azepine (0.038 ml, 0.25 mmol) and 2-methylundecane-2-thiol (0.090 ml, 0.38 mmol). The resulting mixture was stirred at RT for 3 h, and then, MeNH$_2$ in EtOH (30%, 2 ml) was added. It was stirred at RT for 2 h. The reaction mixture was concentrated and purified by prep-HPLC (X-Bridge BEH 150 Prep C18) eluted with ACN in aq NH$_4$HCO$_3$ (100 mM) to give the product. LCMS (ES, m/z): 709 [M−H]$^−$. $^1$H-NMR (500 MHz, D$_2$O): δ 8.36 (1H, s), 8.23 (1H, s), 8.10 (1H, s), 6.53 (1H, dd, J=21.0, 2.9 Hz), 6.10 (1H, d, J=8.6 Hz), 5.44 (1H, d, J=49.5 Hz), 5.33-5.22 (2H, m), 4.65 (2H, m), 4.44 (1H, d, J=9.9 Hz), 4.38-4.26 (2H, m), 4.14 (1H, d, J=12.1 Hz), 4.06 (1H, d, J=9.6 Hz). $^{31}$P-NMR: (202 MHz, D$_2$O): δ 118, −1.4.

Example 23, as shown in Table 5 below, was prepared according to procedures analogous to those outlined in Example 22 above using the appropriate monomers, described as Preparations or as obtained from commercial sources, in the coupling step.

Example 24: 2-amino-9-[(5S,7R,8R,12aR,14R,15aS)-10-hydroxy-14-(6-oxo-1,6-dihydro-9H-purin-9-yl)-2-sulfanyl-2,10-disulfidooctahydro-12H-5,8-methanofuro[3,2-l][1,3,6,9,11,2,10]pentaoxadiphosphacyclotetradecin-7-yl]-1,9-dihydro-6H-purin-6-one (Diastereomer 1)

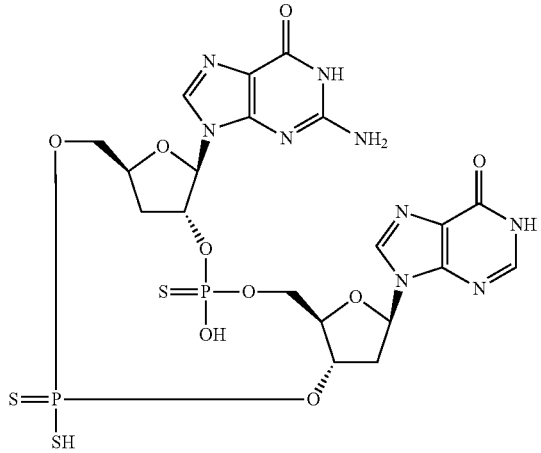

To 2-amino-9-[(5S,7R,8R,12aR,14R,15aS)-14-(6-amino-9H-purin-9-yl)-10-hydroxy-2-sulfanyl-2,10-disulfidooctahydro-12H-5,8-methanofuro[3,2-l][1,3,6,9,11,2,10]pentaoxadiphosphacyclotetradecin-7-yl]-1,9-dihydro-6H-purin-6-one (Example 3) (4.2 mg, 6.0 μmol) were added NaPO$_4$H$_2$ buffer (pH 6.8, 50 mM, 1 mL) and adenosine monphosphate deaminase (5 mg). The reaction mixture was left to stir overnight, filtered, and purified by reverse phase HPLC (eluting MeCN/H$_2$O gradient with 100 mM TEAA modifier, linear gradient) to afford the product. LCMS (ES, m/z): 690 [M−H]$^−$. $^1$H NMR (600 MHz, D$_2$O): δ 8.62 (s, 1H), 8.33 (s, 1H), 8.21 (s, 1H), 6.54 (m, 1H), 5.92 (d, J=7.3 Hz, 1H), 5.65 (m, 1H), 5.42 (m, 1H), 4.67 (d, J=8.4 Hz, 1H), 4.48 (m, 1H), 4.41 (m, 1H), 4.24 (m, 1H), 4.10 (m, 1H), 3.97 (m, 1H), 3.08 (m, 2H), 2.64 (m, 1H), 2.52 (m, 1H).

TABLE 5

| Example | Structure | Name | Mass [M + H]$^+$ |
|---|---|---|---|
| 23 | 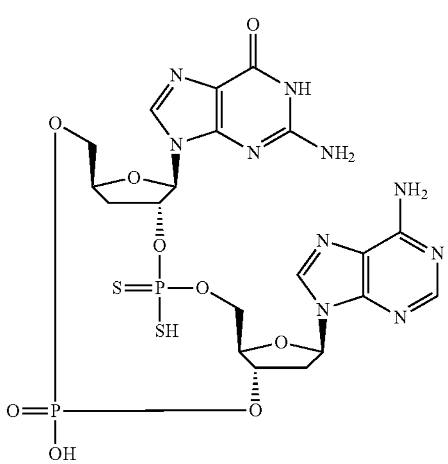 [SMILES: Nc1nc2c(ncn2[C@@H]2O[C@@H]3COP(=O)(O)O[C@H]4C[C@H](n5cnc6c(N)ncnc65)O[C@@H]4COP(=S)(S)O[C@@H]2C3)c(=O)[nH]1] | 2-amino-9-[(5S,7R,8R,12aR,14R,15aS)-14-(6-amino-9H-purin-9-yl)-2-hydroxy-2-oxido-10-sulfanyl-10-sulfidooctahydro-12H-5,8-methanofuro[3,2-l][1,3,6,9,11,2,10]pentaoxadiphosphacyclotetradecin-7-yl]-1,9-dihydro-6H-purin-6-one | 673 |

Examples 25 through 27, as shown in Table 6 below, were prepared according to procedures analogous to those outlined in Example 24 above using the appropriate monomers, described as Preparations or Examples, or as obtained from commercial sources, in the coupling step.

TABLE 6

| Example | Structure | Name | Mass [M + H]+ |
|---|---|---|---|
| 25 | 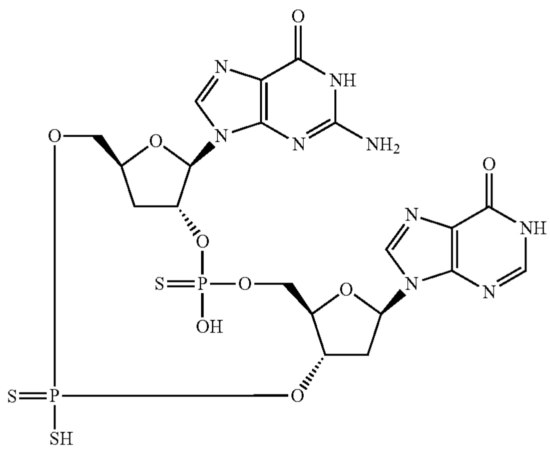 [SMILES: Nc1nc2c(ncn2[C@@H]2O[C@@H]3COP(=S)(S)O[C@H]4C[C@H](n5cnc6c(=O)[nH]cnc65)O[C@@H]4COP(O)(=S)O[C@@H]2C3)c(=O)[nH]1] | 2-amino-9-[(5S,7R,8R,12aR,14R,15aS)-10-hydroxy-14-(6-oxo-1,6-dihydro-9H-purin-9-yl)-2-sulfanyl-2,10-disulfidooctahydro-12H-5,8-methanofuro[3,2-l][1,3,6,9,11,2,10]pentaoxadiphosphacyclotetradecin-7-yl]-1,9-dihydro-6H-purin-6-one (Diastereomer 2) | 690 |
| 26 | 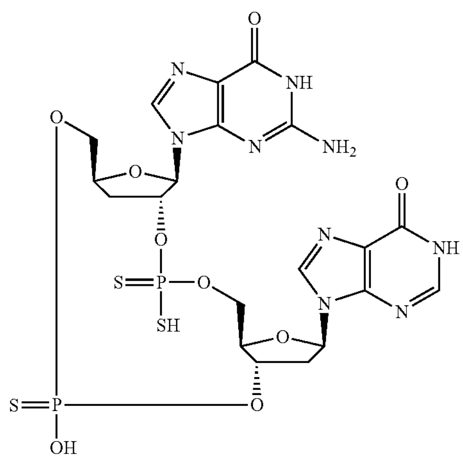 [SMILES: Nc1nc2c(ncn2[C@@H]2O[C@@H]3COP(O)(=S)O[C@H]4C[C@H](n5cnc6c(=O)[nH]cnc65)O[C@@H]4COP(=S)(S)O[C@@H]2C3)c(=O)[nH]1] | 2-amino-9-[(5S,7R,8R,12aR,14R,15aS)-2-hydroxy-14-(6-oxo-1,6-dihydro-9H-purin-9-yl)-10-sulfanyl-2,10-disulfidooctahydro-12H-5,8-methanofuro[3,2-l][1,3,6,9,11,2,10]pentaoxadiphosphacyclotetradecin-7-yl]-1,9-dihydro-6H-purin-6-one | 690 |
| 27 | 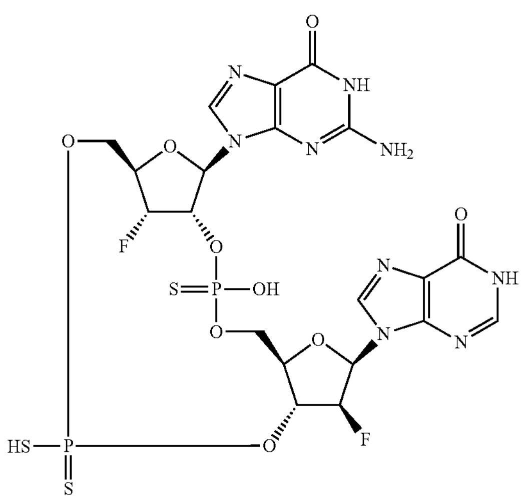 [SMILES: Nc1nc2c(ncn2[C@@H]2O[C@@H]3COP(=S)(S)O[C@H]4[C@H](F)[C@H](n5cnc6c(=O)[nH]cnc65)O[C@@H]4COP(O)(=S)O[C@@H]2[C@@H]3F)c(=O)[nH]1] | 2-amino-9-[(5R,7R,8S,12aR,14R,15S,15aR,16R)-15,16-difluoro-10-hydroxy-14-(6-oxo-1,6-dihydro-9H-purin-9-yl)-2-sulfanyl-2,10-disulfidooctahydro-12H-5,8-methanofuro[3,2-l][1,3,6,9,11,2,10]pentaoxadiphosphacyclotetradecin-7-yl]-1,9-dihydro-6H-purin-6-one | 726 |

BIOLOGICAL EVALUATION

The individual compounds described in the Examples herein are defined as STING agonists by (i) binding to the STING protein as evidenced by a reduction in binding of tritiated cGAMP ligand to the STING protein by at least 20% at 20 uM (concentration of compound being tested) in a STING Biochemical [3H]cGAMP Competition Assay and/or (ii) demonstrating interferon production with a 6% or greater induction of IFN-β secretion at 30 uM in the TFLP1 cell assay (where induction caused by cGAMP at 30 uM was set at 100%).

[$^3$H]-cGAMP Synthesis 2.3 mL of buffer solution containing 80 mM TrisCl, 200 mM $MgCl_2$, and 20 mM NaCl followed by 0.32 mL of a 10 mM aq solution of GTP was added to a plastic 50 mL AMICON tube. A solution of [$^3$H]ATP (21 Ci/mmol, 45 mCi) in 0.5 mL $H_2O$ was then added followed by 1 mL of a 1 mg/mL solution of DNA (Herring testes activator DNA, Sigma, #D6898) and 53 uL of a 47 mM solution of cGAS enzyme. Additional $H_2O$ was added to bring the total volume to 10 mL.

The reaction was stirred for 2 h at 37° C. and then added directly to an Amicon Ultra-15 10K centrifuge tube and spun for 1 h at 4,000 g. The collected solution was then purified on a semi-prep Mono Q column using the following mobile phases:

A: 0.05M TrisCl pH 8.5 adjusted with 1M NaOH
B: 0.05M TrisCl, 0.5M NaCl pH 8.5 adjusted with 1M NaOH Gradient: 100% A for 5 min followed by a linear gradient to 50:50 (A:B) over 25 min, 3 mL/min, 254 nm.

The collected product fractions were pooled and adjusted to a total volume of 30 mL with buffer A. A total yield of 15.5 mCi of [$^3$H]cGAMP was isolated at a radiochemical purity of 98.0% at a specific activity of 21.5 Ci/mmol.

cGAS Enzyme

A recombinant DNA vector was chemically synthesized to express the truncated human cGAS enzyme (residues 161-522). To aid in expression and purification, the amino terminus contains a hexahistidine tag, SUMO tag and TEV cleavage site. The recombinant enzyme was overexpressed in ROSETTA™ 2(DE3) Single Competent Cells (Novagen). Affinity purification was carried out using HIS-Select HF Nickel Affinity Gel (Sigma) followed by size exclusion chromatography using a Hi-Load 26/60 SUPERDEX200 prep grade column (GE Healthcare). Fractions were pooled, concentrated, flash-frozen in liquid nitrogen and stored at −80° C. until needed.

Example 28: $^3$H-cGAMP Filtration Binding Assay (HAQ STING)

The ability of compounds to bind STING is quantified by their ability to compete with tritiated cGAMP ligand for human STING receptor membrane using a radioactive filter-binding assay. The binding assay employs STING receptor obtained from *Trichoplusia ni* cell membranes (*T.ni*; Expression Systems, cat #94-002F, www.expressionsystems.com) overexpressing full-length HAQ STING and tritiated cGAMP ligand.

The basic HAQ STING filtration assay protocol is as follows:

The compounds were serially titrated by the Hamilton STARPlus CORE in a 96-well plate (Greiner, #651201) using a 1:3 ten-point dose response format. After compound preparation, a 2.2 ug/ml working concentration of STING membrane (SEQ. ID. No. 1) was prepared by diluting concentrated membrane into assay buffer (1x PBS; Invitrogen #SH30028.02) and douncing 7× using a manual tissue homogenizer (Wheaton, #357546). 148 uL of prepared membrane was then manually added to each well of a 96-well deep-well polypropylene plate (Fisher Scientific, #12-566-121). Following membrane addition, 2 uL of either titrated test compound, DMSO control (Sigma #276855), or cold cGAMP control was added to the appropriate wells using a BIOMEK FX. Compound and membrane then preincubated for 60 min at RT to allow compound binding to equilibrate. Following equilibration, 8 nM of [$^3$H]c-GAMP ligand was prepared by diluting into assay buffer, and 50 uL of this working stock was then manually added to each well of the assay plate. Plates were then incubated at RT for 60 min, and the contents of each assay plate were then filtered through a 96-well GF/B filter plate (PerkinElmer, #6005250) using a TOMTEC MACH III Cell Harvester equipped with 20 mM HEPES buffer (Fisher Scientific, #BP299500). The filter plates were then dried at 55° C. for 30 min using a pressurized oven before 30 uL of ULTIMA GOLD F scintillate was added to each well. Tritium levels for each reaction well were then measured using a PerkinElmer TopCount plate reader.

After normalization to controls, the percent activity for each compound concentration was calculated by measuring the amount of remaining radioactivity. The plot of percent activity versus the log of compound concentration was fit with a 4-parameter dose response equation to calculate $EC_{50}$ values.

The final reaction conditions were:

| Component | Volume (uL) | Final Concentration |
|---|---|---|
| STING membrane | 148 | 1.5 ug/ml |
| $^3$H-cGAMP | 50 | 2.0 nM |
| Low Control (cold cGAMP) | 2 | 10 uM |
| Test compound/DMSO | 2 | 10 uM |

Compound concentrations tested were 20.000, 637.00, 2.200, 0.740, 0.247, 0.082, 0.027, 0.009, 0.003, and 0.001 µM with 1.0% residual DMSO.

Full-Length STING (HAQ) Virus Generation

STING virus was generated using an insect cell baculovirus system. *Spodoptera frugiperda* Sf21 cells (Kempbio, Inc.) were diluted to 5e5 cells/ml in Sf-900II SFM media (LifeTechnologies #10902088) without antibiotics. The cell suspension was added to each well of a treated 6-well plate (2 mL per well, 1e6 cells total), and the cells were allowed to adhere for at least 30 min. Meanwhile, a 1 mL co-transfection mix was assembled by combining 500 ng of HAQ STING [STING(1-379)R71H,G230A,H232R,R293Q-GG-AviTag-GS-HRV3C-HIS8/pBAC1] DNA (Genewiz custom synthesis) with 1 mL Sf-900II SFM media containing 104, Cellfectin® II Reagent (Invitrogen #10362100) and 100 ng viral backbone BestBac 2.0, v-cath/chiA Deleted Linearized Baculovirus DNA (Expression Systems #91-002). The transfection mixtures were allowed to incubate for 30 min. After incubation, media was gently removed from the adhered cells in the 6-well plate, the 1 mL transfection mixtures were added (1 mL per well), and the plate was placed in a humidified incubator at 27° C. The following day, 1 mL Sf-900II SFM media (no antibiotics) was added to each well of the 6-well plate. After media addition, the cells were allowed to incubate with DNA (SEQ. ID. No. 2) at 27° C. for 5-7 days to generate the P0 viral stock. To generate P1 viral stocks, 0.5 mL of P0 viral supernatant was added to 50 mL uninfected Sf21 cells (seeded the day prior to infection at a density of 5×10$^5$ cells/mL to allow for one overnight doubling) in Sf-900II SFM media containing 5 µg/mL gentamicin (Invitrogen #15710072). The infected cells were then incubated at 27° C. for 3 days while shaking at 110 rpm (ATR Biotech Multitron Infors HT #AJ118). On day 3, P1 cultures were counted using a ViCell XR (Beckman Coulter Life Sciences #383556) to confirm infection had occurred (cell size ≥3 μm larger than uninfected cells and viability approximately 85-95%). Cultures were harvested in 50 mL conical tubes and centrifuged at 2000×g for 10 min at 4° C. The P1 viral supernatants were poured off into clean 50 ml centrifuge tubes, and the remaining P1 cell pellets were used to generate Baculovirus Infected Insect Cells (BIICs). Cryopreservation media containing Sf-900II SFM media with 10% heat inactivated FBS, 10% DMSO (Sigma #D2650), and 5 μg/ml gentamicin was prepared and sterilized through 0.22 μM filter immediately prior to use. P1 cell pellets were resuspended to a density of 2e7 cells/ml and aliquoted into cryovials (1 mL per vial). Cryovials were placed in MR. FROSTY™ cell freezers O/N at −80° C. and transferred to liquid nitrogen for long term storage the following day. To generate P2 viral stock, 0.5 mL of the P1 viral supernatant was added to 50 mL uninfected Sf21 cells (seeded the day prior to infection at a density of 5×10$^5$ cells/mL to allow for one overnight doubling) in Sf-900II SFM media containing 5 μg/mL gentamicin. These cells were incubated at 27° C. for 3 days while shaking at 110 rpm before harvesting P2 stock with centrifugation at 2000×g for 10 min at 4° C. The P2 viral supernatants were poured off and discarded, while the P2 cell pellets were used to generate P2 BIICs following the same protocol described above. The baculovirus generation protocol has been validated to consistently produce P1/P2 BIICs with titers of 2e9 pfu/mL (2e7 cells/mL×100 pfu/cell).

Full-Length STING (HAQ) Expression

To generate STING (HAQ) membranes, P1/P2 BIICs were amplified overnight by adding thawed BIICs to Sf21 cells seeded at a density of 1.0×10$^6$ cells/mL. The volume of BIIC used to infect the culture was calculated using an assumed BIIC titer of 2e9 pfu/ml to achieve an MOI of 10 in the overnight amplification. After culturing overnight, the cells were counted on a ViCell XR to confirm infection had occurred (cell size ≥3 μm larger than uninfected cells and viability approximately 80-90%). The volume of infected Sf21 cells from the overnight amplification used to infect the large-scale expression of Trichoplusia ni (T.ni; Expression Systems, cat #94-002F, www.expressionsystems.com) seeded at a density of 1.0×10$^6$ in cell media (ESF921 SFM containing 5 μg/mL gentamicin) at MOI=2.0 was calculated based on (100 pfu/infected Sf21 cell). The cells were allowed to express for 48 h at 27° C. before harvesting the cell pellet, by centrifugation at 3,400×g for 10 min at 4° C. T ni cells were counted on a ViCell XR to confirm infection had occurred (cell size ≥3 μm larger than uninfected cells and viability approximately 80-90%) prior to harvest.

Full-Length STING (HAQ) Membrane Generation

Buffer stock reagents:
1) 1M HEPES pH 7.5, Teknova, Cat #H1035
2) 5M NaCl, Sigma Aldrich, Cat #55150-1L
3) KCl, Sigma Aldrich, Cat #319309-500ML
4) Complete EDTA-free protease inhibitor tablets, Roche Diagnostics, Cat #11873580001
5) Benzonase, Universal Nuclease, Pierce, Cat #88702

Lysis buffer [25 mM HEPES pH 7.5, 10 mM MgCl$_2$, 20 mM KCl, (Benzonase 1:5000, Complete Protease Inhibitor tab/50 mL)] was added to the pellet of cells expressing full-length STING (HAQ) prepared above at 5 mL Lysis buffer per g of cell pellet. The pellet was resuspended and dounced twenty times using a Wheaton Dounce Homogenizer to disrupt the cell membrane. Homogenized lysate was then passed through the EMULSIFLEX-C5 microfluidizer at a pressure close to 5000PSI. The resuspended pellet was centrifuged at 36,000 rpm (100,000×g) in a 45Ti rotor ultra-high speed centrifuge for 45 min, 4° C. The supernatant was removed. The pellet then was resuspended in wash buffer [(25 mM HEPES pH7.5, 1 mM MgCl$_2$, 20 mM KCl, 1M NaCl (Complete Protease Inhibitor tab/50 mL)] at a volume of 50 mL pellet/centrifuge tube. The pellet/wash buffer mixture was then homogenized, using a glass homogenizer on ice (20 strokes), followed by centrifugation at 36,000 rpm for 45 min at 4° C. The supernatant was removed. The wash step was repeated once more. The resulting membrane was resuspended in 20 mM HEPES pH 7.5, 500 mM NaCl, 10% glycerol, EDTA-free Protease Inhibitors (1tablet/50 mL). The protein concentration was measured by Bradford assay (Bio-Rad Protein Assay, Cat #500-0006), and protein enrichment was determined by SDS-PAGE and confirmed by Western blot. The resuspended membranes were stored at −80° C.

Full-Length HAQ STING [STING(1-379)R71H, G230A, H232R, R293Q-GG-AviTag-GS-HRV3C-HIS8]Amino Acid Sequence:
(SEQ. ID. No. 1)
MPHSSLHPSIPCPRGHGAQKAALVLLSACLVTLWGLGEPPEHTLRYLVLH

LASLQLGLLLNGVCSLAEELHHIHSRYRGSYWRTVRACLGCPLRRGALLL

LSIYFYYSLPNAVGPPFTWMLALLGLSQALNILLGLKGLAPAEISAVCEK

GNFNVAHGLAWSYYIGYLRLILPELQARIRTYNQHYNNLLRGAVSQRLYI

LLPLDCGVPDNLSMADPNIRFLDKLPQQTADRAGIKDRVYSNSIYELLEN

GQRAGTCVLEYATPLQTLFAMSQYSQAGFSREDRLEQAKLFCQTLEDILA

DAPESQNNCRLIAYQEPADDSSFSLSQEVLRHLRQEEKEEVTVGSLKTSA

VPSTSTMSQEPELLISGMEKPLPLRTDFSGGGLNDIFEAQKIEWHEGSLE

VLFQGPHHHHHHHH

Full-length HAQ [STING(1-379)R71H, G230A, H232R, R293Q-GG-AviTag-GS-HRV3C-HIS8/pBAC1] Plasmid DNA Sequence:
(SEQ. ID. No. 2)
GGAACGGCTCCGCCCACTATTAATGAAATTAAAAATTCCAATTTTAAAA

ACGCAGCAAGAGAAACATTTGTATGAAAGAATGCGTAGAAGGAAAGAAAA

ATGTCGTCGACATGCTGAACAACAAGATTAATATGCCTCCGTGTATAAAA

AAAATATTGAACGATTTGAAAGAAAACAATGTACCGCGCGGCGGTATGTA

CAGGAAGAGGTTTATACTAAACTGTTACATTGCAAACGTGGTTTCGTGTG

CCAAGTGTGAAAACCGATGTTTAATCAAGGCTCTGACGCATTTCTACAAC

CACGACTCCAAGTGTGTGGGTGAAGTCATGCATCTTTTAATCAAATCCCA

AGATGTGTATAAACCACCAAACTGCCAAAAAATGAAAACTGTCGACAAGC

TCTGTCCGTTTGCTGGCAACTGCAAGGGTCTCAATCCTATTTGTAATTAT

TGAATAATAAAACAATTATAAATGCTAAATTTGTTTTTTATTAACGATAC

AAACCAAACGCAACAAGAACATTTGTAGTATTATCTATAATTGAAAACGC

GTAGTTATAATCGCTGAGGTAATATTTAAAATCATTTTCAAATGATTCAC

AGTTAATTTGCGACAATATAATTTTATTTTCACATAAACTAGACGCCTTG

TCGTCTTCTTCTTCGTATTCCTTCTCTTTTTCATTTTTCTCTTCATAAAA

ATTAACATAGTTATTATCGTATCCATATATGTATCTATCGTATAGAGTAA

ATTTTTTGTTGTCATAAATATATATGTCTTTTTTAATGGGGTGTATAGTA

CCGCTGCGCATAGTTTTTCTGTAATTTACAACAGTGCTATTTTCTGGTAG

TTCTTCGGAGTGTGTTGCTTTAATTATTAAATTTATATAATCAATGAATT

TGGGATCGTCGGTTTTGTACAATATGTTGCCGGCATAGTACGCAGCTTCT

TCTAGTTCAATTACACCATTTTTTAGCAGCACCGGATTAACATAACTTTC

CAAATGTTGTACGAACCGTTAAACAAAAACAGTTCACCTCCCTTTTCTA

-continued
```
TACTATTGTCTGCGAGCAGTTGTTTGTTGTTAAAAATAACAGCCATTGTA
ATGAGACGCACAAACTAATATCACAAACTGGAAATGTCTATCAATATATA
GTTGCTGATCAGATCTGATCATGGAGATAATTAAAATGATAACCATCTCG
CAAATAAATAAGTATTTTACTGTTTTCGTAACAGTTTTGTAATAAAAAAA
CCTATAAATATAGGATCCATGCCCCACTCCAGCCTGCATCCATCCATCCC
GTGTCCCAGGGGTCACGGGGCCCAGAAGGCAGCCTTGGTTCTGCTGAGTG
CCTGCCTGGTGACCCTTTGGGGGCTAGGAGAGCCACCAGAGCACACTCTC
CGGTACCTGGTGCTCCACCTAGCCTCCCTGCAGCTGGGACTGCTGTTAAA
CGGGGTCTGCAGCCTGGCTGAGGAGCTGCACCACATCCACTCCAGGTACC
GGGGCAGCTACTGGAGGACTGTGCGGGCCTGCCTGGGCTGCCCCCTCCGC
CGTGGGGCCCTGTTGCTGCTGTCCATCTATTTCTACTACTCCCTCCCAAA
TGCGGTCGGCCCGCCCTTCACTTGGATGCTTGCCCTCCTGGGCCTCTCGC
AGGCACTGAACATCCTCCTGGGCCTCAAGGGCCTGGCCCCAGCTGAGATC
TCTGCAGTGTGTGAAAAAGGGAATTTCAACGTGGCCCATGGGCTGGCATG
GTCATATTACATCGGATATCTGCGGCTGATCCTGCCAGAGCTCCAGGCCC
GGATTCGAACTTACAATCAGCATTACAACAACCTGCTACGGGGTGCAGTC
AGCCAGCGGCTGTATATTCTCCTCCCATTGGACTGTGGGGTGCCTGATAA
CCTGAGTATGGCTGACCCCAACATTCGCTTCCTGGATAAACTGCCCCAGC
AGACCGCTGACCGTGCTGGCATCAAGGATCGGGTTTACAGCAACAGCATC
TATGAGCTTCTGGAGAACGGGCAGCGGGCGGGCACCTGTGTCCTGGAGTA
CGCCACCCCCTTGCAGACTTTGTTTGCCATGTCACAATACAGTCAAGCTG
GCTTTAGCCGGGAGGATAGGCTTGAGCAGGCCAAACTCTTCTGCCAGACA
CTTGAGGACATCCTGGCAGATGCCCCTGAGTCTCAGAACAACTGCCGCCT
CATTGCCTACCAGGAACCTGCAGATGACAGCAGCTTCTCGCTGTCCCAGG
AGGTTCTCCGGCACCTGCGGCAGGAGGAAAAGGAAGAGGTTACTGTGGGC
AGCTTGAAGACCTCAGCGGTGCCCAGTACCTCCACGATGTCCCAAGAGCC
TGAGCTCCTCATCAGTGGAATGGAAAAGCCCCTCCCTCTCCGCACGGATT
TCTCTGGCGGTGGCCTGAACGACATCTTCGAAGCCCAGAAAATCGAATGG
CATGAAGGCAGCCTGGAAGTGCTGTTCCAGGGCCCACACCACCATCATCA
CCATCACCATTAATGAGCGGCCGCACTCGAGCACCACCACCACCACCACT
AACCTAGGTAGCTGAGCGCATGCAAGCTGATCCGGGTTATTAGTACATTT
ATTAAGCGCTAGATTCTGTGCGTTGTTGATTTACAGACAATTGTTGTACG
TATTTTAATAATTCATTAAATTTATAATCTTTAGGGTGGTATGTTAGAGC
GAAAATCAAATGATTTTCAGCGTCTTTATATCTGAATTTAAATATTAAAT
CCTCAATAGATTTGTAAAATAGGTTTCGATTAGTTTCAAACAAGGGTTGT
TTTTCCGAACCGATGGCTGGACTATCTAATGGATTTTCGCTCAACGCCAC
AAAACTTGCCAAATCTTGTAGCAGCAATCTAGCTTTGTCGATATTCGTTT
GTGTTTTGTTTTGTAATAAAGGTTCGACGTCGTTCAAATATTATGCGCT
TTTGTATTTCTTTCATCACTGTCGTTAGTGTACAATTGACTCGACGTAAA
CACGTTAAATAGAGCTTGGACATATTTAACATCGGGCGTGTTAGCTTTAT
TAGGCCGATTATCGTCGTCGTCCCAACCCTCGTCGTTAGAAGTTGCTTCC
```
-continued
```
GAAGACGATTTTGCCATAGCCACACGACGCCTATTAATTGTGTCGGCTAA
CACGTCCGCGATCAAATTTGTAGTTGAGCTTTTTGGAATTATTTCTGATT
GCGGGCGTTTTTGGGCGGGTTTCAATCTAACTGTGCCCGATTTTAATTCA
GACAACACGTTAGAAAGCGATGGTGCAGGCGGTGGTAACATTTCAGACGG
CAAATCTACTAATGGCGGCGGTGGTGGAGCTGATGATAAATCTACCATCG
GTGGAGGCGCAGGCGGGGCTGGCGGCGGAGGCGGAGGCGGAGGTGGTGGC
GGTGATGCAGACGGCGGTTTAGGCTCAAATGTCTCTTTAGGCAACACAGT
CGGCACCCTCAACTATTGTACTGGTTTCGGGCGCCGTTTTGGTTTGACCG
GTCTGAGACGAGTGCGATTTTTTTCGTTTCTAATAGCTTCCAACAATTGT
TGTCTGTCGTCTAAAGGTGCAGCGGGTTGAGGTTCCGTCGGCATTGGTGG
AGCGGGCGGCAATTCAGACATCGATGGTGGTGGTGGTGGTGGAGGCGCTG
GAATGTTAGGCACGGGAGAAGGTGGTGGCGGCGGTGCCGCCGGTATAATT
TGTTCTGGTTTAGTTTGTTCGCGCACGATTGTGGGCACCGGCGCAGGCGC
CGCTGGCTGCACAACGGAAGGTCGTCTGCTTCGAGGCAGCGCTTGGGGTG
GTGGCAATTCAATATTATAATTGGAATACAAATCGTAAAAATCTGCTATA
AGCATTGTAATTTCGCTATCGTTTACCGTGCCGATATTTAACAACCGCTC
AATGTAAGCAATTGTATTGTAAAGAGATTGTCTCAAGCTCGGATCGATCC
CGCACGCCGATAACAAGCCTTTTCATTTTTACTACAGCATTGTAGTGGCG
AGACACTTCGCTGTCGTCGAGGTTTAAACGCTTCCTCGCTCACTGACTCG
CTGCGCTCGGTCGTTCGGCTGCGGCGAGCGGTATCAGCTCACTCAAAGGC
GGTAATACGGTTATCCACAGAATCAGGGGATAACGCAGGAAAGAACATGT
GAGCAAAAGGCCAGCAAAAGGCCAGGAACCGTAAAAAGGCCGCGTTGCTG
GCGTTTTTCCATAGGCTCCGCCCCCCTGACGAGCATCACAAAAATCGACG
CTCAAGTCAGAGGTGGCGAAACCCGACAGGACTATAAAGATACCAGGCGT
TTCCCCCTGGAAGCTCCCTCGTGCGCTCTCCTGTTCCGACCCTGCCGCTT
ACCGGATACCTGTCCGCCTTTCTCCCTTCGGGAAGCGTGGCGCTTTCTCA
TAGCTCACGCTGTAGGTATCTCAGTTCGGTGTAGGTCGTTCGCTCCAAGC
TGGGCTGTGTGCACGAACCCCCCGTTCAGCCCGACCGCTGCGCCTTATCC
GGTAACTATCGTCTTGAGTCCAACCCGGTAAGACACGACTTATCGCCACT
GGCAGCAGCCACTGGTAACAGGATTAGCAGAGCGAGGTATGTAGGCGGTG
CTACAGAGTTCTTGAAGTGGTGGCCTAACTACGGCTACACTAGAAGGACA
GTATTTGGTATCTGCGCTCTGCTGAAGCCAGTTACCTTCGGAAAAAGAGT
TGGTAGCTCTTGATCCGGCAAACAAACCACCGCTGGTAGCGGTGGTTTTT
TTGTTTGCAAGCAGCAGATTACGCGCAGAAAAAAAGGATCTCAAGAAGAT
CCTTTGATCTTTTCTACGGGGTCTGACGCTCAGTGGAACGAAAACTCACG
TTAAGGGATTTTGGTCATGAGATTATCAAAAAGGATCTTCACCTAGATCC
TTTTAAATTAAAAATGAAGTTTTAAATCAATCTAAAGTATATATGAGTAA
ACTTGGTCTGACAGTTACCAATGCTTAATCAGTGAGGCACCTATCTCAGC
GATCTGTCTATTTCGTTCATCCATAGTTGCCTGACTCCCCGTCGTGTAGA
TAACTACGATACGGGAGGGCTTACCATCTGGCCCCAGTGCTGCAATGATA
```

-continued
```
CCGCGAGACCCACGCTCACCGGCTCCAGATTTATCAGCAATAAACCAGCC

AGCCGGAAGGGCCGAGCGCAGAAGTGGTCCTGCAACTTTATCCGCCTCCA

TCCAGTCTATTAATTGTTGCCGGGAAGCTAGAGTAAGTAGTTCGCCAGTT

AATAGTTTGCGCAACGTTGTTGCCATTGCTACAGGCATCGTGGTGTCACG

CTCGTCGTTTGGTATGGCTTCATTCAGCTCCGGTTCCCAACGATCAAGGC

GAGTTACATGATCCCCCATGTTGTGCAAAAAAGCGGTTAGCTCCTTCGGT

CCTCCGATCGTTGTCAGAAGTAAGTTGGCCGCAGTGTTATCACTCATGGT

TATGGCAGCACTGCATAATTCTCTTACTGTCATGCCATCCGTAAGATGCT

TTTCTGTGACTGGTGAGTACTCAACCAAGTCATTCTGAGAATAGTGTATG

CGGCGACCGAGTTGCTCTTGCCCGGCGTCAATACGGGATAATACCGCGCC

ACATAGCAGAACTTTAAAAGTGCTCATCATTGGAAAACGTTCTTCGGGGC

GAAAACTCTCAAGGATCTTACCGCTGTTGAGATCCAGTTCGATGTAACCC

ACTCGTGCACCCAACTGATCTTCAGCATCTTTTACTTTCACCAGCGTTTC

TGGGTGAGCAAAAACAGGAAGGCAAAATGCCGCAAAAAAGGGAATAAGGG

CGACACGGAAATGTTGAATACTCATACTCTTCCTTTTTCAATATTATTGA

AGCATTTATCAGGGTTATTGTCTCATGAGCGGATACATATTTGAATGTAT

TTAGAAAAATAAACAAATAGGGGTTCCGCGCACATTTCCCCGAAAAGTGC

CACCTGACGCGCCCTGTAGCGGCGCATTAAGCGCGGCGGGTGTGGTGGTT

ACGCGCAGCGTGACCGCTACACTTGCCAGCGCCCTAGCGCCCGCTCCTTT

CGCTTTCTTCCCTTCCTTTCTCGCCACGTTCGCCGGCTTTCCCCGTCAAG

CTCTAAATCGGGGCTCCCTTTAGGGTTCCGATTTAGTGCTTTACGGCAC

CTCGACCCCAAAAAACTTGATTAGGGTGATGGTTCACGTAGTGGGCCATC

GCCCTGATAGACGGTTTTTCGCCCTTTGACGTTGGAGTCCACGTTCTTTA

ATAGTGGACTCTTGTTCCAAACTGGAACAACACTCAACCCTATCTCGGTC

TATTCTTTTGATTTATAAGGGATTTTGCCGATTTCGGCCTATTGGTTAAA

AAATGAGCTGATTTAACAAAAATTTAACGCGAATTTTAACAAAATATTAA

CGTTTACAATTTCCCATTCGCCATTCAGGCTGCGCAACTGTTGGGAAGGG

CGATCGGTGCGGGCCTCTTCGCTATTACGCCA
```

Certain compounds of the disclosure were evaluated in HAQ STING in vitro binding assay as described above. The following table tabulates the biological data for these compounds as $EC_{50}$ values.

TABLE 7

$^3$H-cGAMP filtration binding assay for HAQ STING

| Compound | $EC_{50}$ (nM) |
|---|---|
| Example 1 | <1 |
| Example 2 | 2 |
| Example 3 | 2 |
| Example 5 | <1 |
| Example 6 | 28 |
| Example 7 | <1 |
| Example 8 | 7 |
| Example 9 | 349 |
| Example 16 | 5 |
| Example 17 | 15 |
| Example 20 | 1 |
| Example 21 | 217 |
| Example 27 | <1 |

Example 29: $^3$H-cGAMP Filtration Binding Assay (WT STING)

The ability of compounds to bind STING is quantified by their ability to compete with tritiated cGAMP ligand for human STING receptor membrane using a radioactive filter-binding assay. The binding assay employs STING receptor obtained from *Trichoplusia ni* cell membranes (*T.ni*; Expression Systems, cat #94-002F, overexpressing full-length WT STING and tritiated cGAMP ligand.

The basic WT STING filtration assay protocol is as follows:

16 nM of [$^3$H] c-GAMP ligand was prepared by diluting into assay buffer, and 50 uL of this working stock was manually added to each well of the assay plate. After ligand addition, 2 uL of either titrated test compound, DMSO control (Sigma #276855), or cold cGAMP control was added to the appropriate wells using a BIOMEK FX. The serially titrated compound was prepared on a Hamilton STARPlus CORE in a 96-well plate (Greiner, #651201) using a 1:3 ten-point dose response format. Following compound addition, a 2.2 ug/ml working concentration of STING membrane (SEQ. ID. No. 3) was prepared by diluting concentrated membrane into assay buffer (1×PBS; Invitrogen #SH30028.02) and douncing 7× using a manual tissue homogenizer (Wheaton, #357546). 148 uL of this prepared membrane was then manually added to each well of a 96-well deep-well polypropylene plate (Fisher Scientific, #12-566-121). Compound, ligand, and membrane then incubated for 60 min at RT before the contents of each assay plate were filtered through a 96-well GF/B filter plate (PerkinElmer, #6005250) using a TOMTEC MACH III Cell Harvester equipped with 20 mM HEPES buffer (Fisher Scientific, #BP299500). The filter plates were then dried at 55° C. for 30 min using a pressurized VWR oven before 30 uL of ULTIMA GOLD F scintillate was added to each well. Tritium levels for each reaction well were then measured using a PerkinElmer TopCount plate reader.

After normalization to controls, the percent activity for each compound concentration was calculated by measuring the amount of remaining radioactivity. The plot of percent activity versus the log of compound concentration was fit with a 4-parameter dose response equation to calculate $EC_{50}$ values.

The final reaction conditions were:

| Component | Volume (uL) | Final Concentration |
|---|---|---|
| STING membrane | 148 | 1.5 ug/ml |
| $^3$H-cGAMP | 50 | 4.0 nM |
| Low Control (cold cGAMP) | 2 | 10 uM |
| Test compound/DMSO | 2 | 10 uM |

Compound concentrations tested were 20.000, 637.00, 2.200, 0.740, 0.247, 0.082, 0.027, 0.009, 0.003, and 0.001 μM with 1.0% residual DMSO.

Full-Length STING (WT) Virus Generation

STING virus was generated using an insect cell baculovirus system. *Spodoptera frugiperda* Sf21 cells (Kempbio, Inc.) were diluted to 5e5 cells/ml in Sf-900II SFM media (LifeTechnologies #10902088) without antibiotics. The cell suspension was added to each well of a treated 6-well plate (2 mL per well, 1e6 cells total), and the cells were allowed to adhere for at least 30 min. Meanwhile, a 1 mL co-transfection mix was assembled by combining 500 ng of WT STING[STING(1-379)H232R-gg-AviTag-gs-HRV3C-HIS8/pBAC1] (Genewiz custom synthesis) with 1 mL Sf-900II SFM media containing 10 μL CELLFECTIN® II Reagent (Invitrogen #10362100) and 100 ng viral backbone BestBac 2.0, v-cath/chiA Deleted Linearized Baculovirus DNA (Expression Systems #91-002). The transfection mixtures were allowed to incubate for 30 min. After incubation, media was gently removed from the adhered cells in the 6-well plate, the 1 mL transfection mixtures were added (1 mL per well), and the plate was placed in a humidified incubator at 27° C. The following day, 1 mL Sf-900II SFM media (no antibiotics) was added to each well of the 6-well plate. After media addition, the cells were allowed to incubate with DNA [(SEQ. ID. No. 4) and linearized viral backbone BestBac 2.0] at 27° C. for 5-7 days to generate the P0 viral stock. To generate Pb viral stocks, 0.5 mL of P0 viral supernatant was added to 50 mL uninfected Sf21 cells (seeded the day prior to infection at a density of $5 \times 10^5$ cells/mL to allow for one overnight doubling) in Sf-900II SFM media containing 5 µg/mL gentamicin (Invitrogen #15710072). The infected cells were then incubated at 27° C. for 3 days while shaking at 110 rpm (ATR Biotech Multitron Infors HT #AJ118). On day 3, P1 cultures were counted using a ViCell XR (Beckman Coulter Life Sciences #383556) to confirm infection had occurred (cell size ≥3 µm larger than uninfected cells and viability approximately 85-95%). Cultures were harvested in 50 mL conical tubes and centrifuged at 2000×g for 10 min at 4° C. The P1 viral supernatants were poured off into clean 50 ml centrifuge tubes, and the remaining P1 cell pellets were used to generate Baculovirus Infected Insect Cells (BIICs). Cryo-preservation media containing Sf-900II SFM media with 10% heat inactivated FBS, 10% DMSO (Sigma #D2650), and 5 µg/ml gentamicin was prepared and sterilized through 0.22 µM filter immediately prior to use. P1 cell pellets were resuspended to a density of 2e7 cells/ml and aliquoted into cryovials (1 mL per vial). Cryovials were placed in Mr. Frosty™ cell freezers O/N at −80° C. and transferred to liquid nitrogen for long term storage the following day. To generate P2 viral stock, 0.5 mL of the P1 viral supernatant was added to 50 mL uninfected Sf21 cells (seeded the day prior to infection at a density of $5 \times 10^5$ cells/mL to allow for one overnight doubling) in Sf-900II SFM media containing 5 µg/mL gentamicin. These cells were incubated at 27° C. for 3 days while shaking at 110 rpm before harvesting P2 stock with centrifugation at 2000×g for 10 min at 4° C. The P2 viral supernatants were poured off and discarded, while the P2 cell pellets were used to generate P2 BIICs following the same protocol described above. The baculovirus generation protocol has been validated to consistently produce P1/P2 BIICs with titers of 2e9 pfu/mL (2e7 cells/mL×100 pfu/cell).

Full-Length STING (WT) Expression

To generate STING membranes, P1/P2 BIICs were amplified overnight by adding thawed BIICs to Sf21 cells seeded at a density of $1.0 \times 10^6$ cells/mL. The volume of BIIC used to infect the culture was calculated using an assumed BIIC titer of 2e9 pfu/ml to achieve an MOI of 10 in the overnight amplification. After culturing overnight, the cells were counted on a ViCell XR to confirm infection had occurred (cell size ≥3 µm larger than uninfected cells and viability approximately 80-90%). The volume of infected Sf21 cells from the overnight amplification used to infect the large-scale expression of *Trichoplusia ni* (*T.ni*; Expression Systems, cat #94-002F, www.expressionsystems.com) seeded at a density of $1.0 \times 10^6$ in cell media (ESF921 SFM containing 5 µg/mL gentamicin) at MOI=2.0 was calculated based on (100 pfu/infected Sf21 cell). The cells were allowed to express for 48 h at 27° C. before harvesting the cell pellet, by centrifugation at 3,400×g for 10 min at 4° C. *T ni* cells were counted on a ViCell XR to confirm infection had occurred (cell size ≥3 µm larger than uninfected cells and viability approximately 80-90%) prior to harvest.

Full-Length STING (WT) Membrane Generation

Buffer stock reagents:
1) 1 M HEPES pH 7.5, Teknova, Cat #H1035
2) 5 M NaCl, Sigma Aldrich, Cat #S5150-1L
3) KCl, Sigma Aldrich, Cat #319309-500ML
4) Complete EDTA-free protease inhibitor tablets, Roche Diagnostics, Cat #11873580001
5) Benzonase, Universal Nuclease, Pierce, Cat #88702

Lysis buffer [25 mM HEPES pH 7.5, 10 mM MgCl$_2$, 20 mM KCl, (Benzonase 1:5000, Complete Protease Inhibitor tab/50 mL)] was added to the pellet of cells expressing full-length STING (WT) prepared above at 5 mL Lysis buffer per g of cell pellet. The pellet was resuspended and dounced twenty times using a Wheaton Dounce Homogenizer to disrupt the cell membrane. Homogenized lysate was then passed through the emulsiflex-05 microfluidizer at a pressure close to 5000 PSI. The resuspended pellet was centrifuged at 36,000 rpm (100,000×g) in a 45Ti rotor ultra-high speed centrifuge for 45 min, 4° C. The supernatant was removed. The pellet then was resuspended in wash buffer [(25 mM HEPES pH 7.5, 1 mM MgCl$_2$, 20 mM KCl, 1M NaCl (Complete Protease Inhibitor tab/50 mL)] at a volume of 50 mL/pellet/centrifuge tube. The pellet/wash buffer mixture was then homogenized, using a glass homogenizer on ice (20 strokes), followed by centrifugation at 36,000 rpm for 45 min at 4° C. The supernatant was removed. The wash step was repeated once more. The resulting membrane was resuspended in 20 mM HEPES pH 7.5, 500 mM NaCl, 10% glycerol, EDTA-free Protease Inhibitors (1 tablet/50 mL). The protein concentration was measured by Bradford assay (Bio-Rad Protein Assay, Cat #500-0006), and protein enrichment was determined by SDS-PAGE and confirmed by Western blot. The resuspended membranes were stored at −80° C.

Full-Length STING WT [STING(1-379)H232R-gg-AviTag-gs-HRV3C-HIS8] Amino Acid Sequence:
(SEQ. ID. No. 3)
MPHSSLHPSIPCPRGHGAQKAALVLLSACLVTLWGLGEPPEHTLRYLVLH

LASLQLGLLLNGVCSLAEELRHIHSRYRGSYWRTVRACLGCPLRRGALLL

LSIYFYYSLPNAVGPPFTWMLALLGLSQALNILLGLKGLAPAEISAVCEK

GNFNVAHGLAWSYYIGYLRLILPELQARIRTYNQHYNNLLRGAVSQRLYI

LLPLDCGVPDNLSMADPNIRFLDKLPQQTGDRAGIKDRVYSNSIYELLEN

GQRAGTCVLEYATPLQTLFAMSQYSQAGFSREDRLEQAKLFCRTLEDILA

DAPESQNNCRLIAYQEPADDSSFSLSQEVLRHLRQEEKEEVTVGSLKTSA

VPSTSTMSQEPELLISGMEKPLPLRTDFSGGGLNDIFEAQKIEWHEGSLE

VLFQGPHHHHHHHH

Full-length WT STING [STING(1-379)H232R-gg-AviTag-gs-HRV3C-HIS8/pBAC1] plasmid sequence:
(SEQ. ID. No. 4)
GGAACGGCTCCGCCCACTATTAATGAAATTAAAAATTCCAATTTTAAAAA

ACGCAGCAAGAGAAACATTTGTATGAAAGAATGCGTAGAAGGAAAGAAAA

ATGTCGTCGACATGCTGAACAACAAGATTAATATGCCTCCGTGTATAAAA

AAAATATTGAACGATTTGAAAGAAAACAATGTACCGCGCGGCGGTATGTA

CAGGAAGAGGTTTATACTAAACTGTTACATTGCAAACGTGGTTTCGTGTG

CCAAGTGTGAAAACCGATGTTTAATCAAGGCTCTGACGCATTTCTACAAC

CACGACTCCAAGTGTGTGGGTGAAGTCATGCATCTTTTAATCAAATCCCA

AGATGTGTATAAACCACCAAACTGCCAAAAAATGAAAACTGTCGACAAGC

TCTGTCCGTTTGCTGGCAACTGCAAGGGTCTCAATCCTATTTGTAATTAT

TGAATAATAAAACAATTATAAATGTCAAATTTGTTTTTTATTAACGATAC

AAACCAAACGCAACAAGAACATTTGTAGTATTATCTATAATTGAAAACGC

-continued

GTAGTTATAATCGCTGAGGTAATATTTAAAATCATTTTCAAATGATTCAC

AGTTAATTTGCGACAATATAATTTTATTTTCACATAAACTAGACGCCTTG

TCGTCTTCTTCTTCGTATTCCTTCTCTTTTTCATTTTTCTCTTCATAAAA

ATTAACATAGTTATTATCGTATCCATATATGTATCTATCGTATAGAGTAA

ATTTTTTGTTGTCATAAATATATATGTCTTTTTTAATGGGGTGTATAGTA

CCGCTGCGCATAGTTTTTCTGTAATTTACAACAGTGCTATTTTCTGGTAG

TTCTTCGGAGTGTGTTGCTTTAATTATTAAATTTATATAATCAATGAATT

TGGGATCGTCGGTTTTGTACAATATGTTGCCGGCATAGTACGCAGCTTCT

TCTAGTTCAATTACACCATTTTTTAGCAGCACCGGATTAACATAACTTTC

CAAAATGTTGTACGAACCGTTAAACAAAAACAGTTCACCTCCCTTTTCTA

TACTATTGTCTGCGAGCAGTTGTTTGTTGTTAAAAATAACAGCCATTGTA

ATGAGACGCACAAACTAATATCACAAACTGGAAATGTCTATCAATATATA

GTTGCTGATCAGATCTGATCATGGAGATAATTAAAATGATAACCATCTCG

CAAATAAATAAGTATTTTACTGTTTTCGTAACAGTTTTGTAATAAAAAAA

CCTATAAATATAGGATCCATGCCCCACTCCAGCCTGCATCCATCCATCCC

GTGTCCCAGGGGTCACGGGGCCCAGAAGGCAGCCTTGGTTCTGCTGAGTG

CCTGCCTGGTGACCCTTTGGGGGCTAGGAGAGCCACCAGAGCACACTCTC

CGGTACCTGGTGCTCCACCTAGCCTCCCTGCAGCTGGGACTGCTGTTAAA

CGGGGTCTGCAGCCTGGCTGAGGAGCTGCGCCACATCCACTCCAGGTACC

GGGGCAGCTACTGGAGGACTGTGCGGGCCTGCCTGGGCTGCCCCCTCCGC

CGTGGGGCCCTGTTGCTGCTGTCCATCTATTTCTACTACTCCCTCCCAAA

TGCGGTCGGCCCGCCCTTCACTTGGATGCTTGCCCTCCTGGGCCTCTCGC

AGGCACTGAACATCCTCCTGGGCCTCAAGGGCCTGGCCCCAGCTGAGATC

TCTGCAGTGTGTGAAAAAGGGAATTTCAACGTGGCCCATGGGCTGGCATG

GTCATATTACATCGGATATCTGCGGCTGATCCTGCCAGAGCTCCAGGCCC

GGATTCGAACTTACAATCAGCATTACAACAACCTGCTACGGGGTGCAGTG

AGCCAGCGGCTGTATATTCTCCTCCCATTGGACTGTGGGGTGCCTGATAA

CCTGAGTATGGCTGACCCCAACATTCGCTTCCTGGATAAACTGCCCCAGC

AGACCGGTGACCGTGCTGGCATCAAGGATCGGGTTTACAGCAACAGCATC

TATGAGCTTCTGGAGAACGGGCAGCGGGCGGGCACCTGTGTCCTGGAGTA

CGCCACCCCCTTGCAGACTTTGTTTGCCATGTCACAATACAGTCAAGCTG

GCTTTAGCCGGGAGGATAGGCTTGAGCAGGCCAAACTCTTCTGCCGGACA

CTTGAGGACATCCTGGCAGATGCCCCTGAGTCTCAGAACAACTGCCGCCT

CATTGCCTACCAGGAACCTGCAGATGACAGCAGCTTCTCGCTGTCCCAGG

AGGTTCTCCGGCACCTGCGGCAGGAGGAAAAGGAAGAGGTTACTGTGGGC

AGCTTGAAGACCTCAGCGGTGCCCAGTACCTCCACGATGTCCCAAGAGCC

TGAGCTCCTCATCAGTGGAATGGAAAAGCCCCTCCCTCTCCGCACGGATT

TCTCTGGCGGTGGCCTGAACGACATCTTCGAAGCCCAGAAAATCGAATGG

CATGAAGGCAGCCTGGAAGTGCTGTTCCAGGGCCCACACCACCATCATCA

CCATCACCATTAATGAGCGGCCGCACTCGAGCACCACCACCACCACCACT

AACCTAGGTAGCTGAGCGCATGCAAGCTGATCCGGGTTATTAGTACATTT

ATTAAGCGCTAGATTCTGTGCGTTGTTGATTTACAGACAATTGTTGTACG

TATTTTAATAATTCATTAAATTTATAATCTTTAGGGTGGTATGTTAGAGC

GAAAATCAAATGATTTTCAGCGTCTTTATATCTGAATTTAAATATTAAAT

CCTCAATAGATTTGTAAAATAGGTTTCGATTAGTTTCAAACAAGGGTTGT

TTTTCCGAACCGATGGCTGGACTATCTAATGGATTTTCGCTCAACGCCAC

AAAACTTGCCAAATCTTGTAGCAGCAATCTAGCTTTGTCGATATTCGTTT

GTGTTTTGTTTTGTAATAAAGGTTCGACGTCTTCAAAATATTATGCGCT

TTTGTATTTCTTTCATCACTGTCGTTAGTGTACAATTGACTCGACGTAAA

CACGTTAAATAGAGCTTGGACATATTTAACATCGGGCGTGTTAGCTTTAT

TAGGCCGATTATCGTCGTCGTCCCAACCCTCGTCGTTAGAAGTTGCTTCC

GAAGACGATTTTGCCATAGCCACACGACGCCTATTAATTGTGTCGGCTAA

CACGTCCGCGATCAAATTTGTAGTTGAGCTTTTTGGAATTATTTCTGATT

GCGGGCGTTTTTGGGCGGGTTTCAATCTAACTGTGCCCGATTTTAATTCA

GACAACACGTTAGAAAGCGATGGTGCAGGCGGTGGTAACATTTCAGACGG

CAAATCTACTAATGGCGGCGGTGGTGGAGCTGATGATAAATCTACCATCG

GTGGAGGCGCAGGCGGGGCTGGCGGCGGAGGCGGAGGCGGAGGTGGTGGC

GGTGATGCAGACGGCGGTTTAGGCTCAAATGTCTCTTTAGGCAACACAGT

CGGCACCTCAACTATTGTACTGGTTTCGGGCGCCGTTTTGGTTTGACCG

GTCTGAGACGAGTGCGATTTTTTTCGTTTCTAATAGCTTCCAACAATTGT

TGTCTGTCGTCTAAAGGTGCAGCGGGTTGAGGTTCCGTCGGCATTGGTGG

AGCGGGCGGCAATTCAGACATCGATGGTGGTGGTGGTGGAGGCGCTG

GAATGTTAGGCACGGGAGAAGGTGGTGGCGGCGGTGCCGCCGGTATAATT

TGTTCTGGTTTAGTTTGTTCGCGCACGATTGTGGGCACCGGCGCAGGCGC

CGCTGGCTGCACAACGGAAGGTCGTCTGCTTCGAGGCAGCGCTTGGGGTG

GTGGCAATTCAATATTATAATTGGAATACAAATCGTAAAAATCTGCTATA

AGCATTGTAATTTCGCTATCGTTTACCGTGCCGATATTTAACAACCGCTC

AATGTAAGCAATTGTATTGTAAAGAGATTGTCTCAAGCTCGGATCGATCC

CGCACGCCGATAACAAGCCTTTTCATTTTTACTACAGCATTGTAGTGGCG

AGACACTTCGCTGTCGTCGAGGTTTAAACGCTTCCTCGCTCACTGACTCG

CTGCGCTCGGTCGTTCGGCTGCGGCGAGCGGTATCAGCTCACTCAAAGGC

GGTAATACGGTTATCCACAGAATCAGGGGATAACGCAGGAAAGAACATGT

GAGCAAAAGGCCAGCAAAAGGCCAGGAACCGTAAAAAGGCCGCGTTGCTG

GCGTTTTTCCATAGGCTCCGCCCCCCTGACGAGCATCACAAAAATCGACG

CTCAAGTCAGAGGTGGCGAAACCCGACAGGACTATAAAGATACCAGGCGT

TTCCCCCTGGAAGCTCCCTCGTGCGCTCTCCTGTTCCGACCCTGCCGCTT

ACCGGATACCTGTCCGCCTTTCTCCCTTCGGGAAGCGTGGCGCTTTCTCA

TAGCTCACGCTGTAGGTATCTCAGTTCGGTGTAGGTCGTTCGCTCCAAGC

TGGGCTGTGTGCACGAACCCCCCGTTCAGCCCGACCGCTGCGCCTTATCC

GGTAACTATCGTCTTGAGTCCAACCCGGTAAGACACGACTTATCGCCACT

GGCAGCAGCCACTGGTAACAGGATTAGCAGAGCGAGGTATGTAGGCGGTG

-continued

CTACAGAGTTCTTGAAGTGGTGGCCTAACTACGGCTACACTAGAAGGACA

GTATTTGGTATCTGCGCTCTGCTGAAGCCAGTTACCTTCGGAAAAAGAGT

TGGTAGCTCTTGATCCGGCAAACAAACCACCGCTGGTAGCGGTGGTTTTT

TTGTTTGCAAGCAGCAGATTACGCGCAGAAAAAAAGGATCTCAAGAAGAT

CCTTTGATCTTTTCTACGGGGTCTGACGCTCAGTGGAACGAAAACTCACG

TTAAGGGATTTTGGTCATGAGATTATCAAAAAGGATCTTCACCTAGATCC

TTTTAAATTAAAAATGAAGTTTTAAATCAATCTAAAGTATATATGAGTAA

ACTTGGTCTGACAGTTACCAATGCTTAATCAGTGAGGCACCTATCTCAGC

GATCTGTCTATTTCGTTCATCCATAGTTGCCTGACTCCCCGTCGTGTAGA

TAACTACGATACGGGAGGGCTTACCATCTGGCCCCAGTGCTGCAATGATA

CCGCGAGACCCACGCTCACCGGCTCCAGATTTATCAGCAATAAACCAGCC

AGCCGGAAGGGCCGAGCGCAGAAGTGGTCCTGCAACTTTATCCGCCTCCA

TCCAGTCTATTAATTGTTGCCGGGAAGCTAGAGTAAGTAGTTCGCCAGTT

AATAGTTTGCGCAACGTTGTTGCCATTGCTACAGGCATCGTGGTGTCACG

CTCGTCGTTTGGTATGGCTTCATTCAGCTCCGGTTCCCAACGATCAAGGC

GAGTTACATGATCCCCATGTTGTGCAAAAAAGCGGTTAGCTCCTTCGGT

CCTCCGATCGTTGTCAGAAGTAAGTTGGCCGCAGTGTTATCACTCATGGT

TATGGCAGCACTGCATAATTCTCTTACTGTCATGCCATCCGTAAGATGCT

TTTCTGTGACTGGTGAGTACTCAACCAAGTCATTCTGAGAATAGTGTATG

CGGCGACCGAGTTGCTCTTGCCCGGCGTCAATACGGGATAATACCGCGCC

ACATAGCAGAACTTTAAAAGTGCTCATCATTGGAAAACGTTCTTCGGGGC

GAAAACTCTCAAGGATCTTACCGCTGTTGAGATCCAGTTCGATGTAACCC

ACTCGTGCACCCAACTGATCTTCAGCATCTTTTACTTTCACCAGCGTTTC

TGGGTGAGCAAAAACAGGAAGGCAAAATGCCGCAAAAAAGGGAATAAGGG

CGACACGGAAATGTTGAATACTCATACTCTTCCTTTTTCAATATTATTGA

AGCATTTATCAGGGTTATTGTCTCATGAGCGGATACATATTTGAATGTAT

TTAGAAAAATAAACAAATAGGGGTTCCGCGCACATTTCCCCGAAAAGTGC

CACCTGACGCGCCCTGTAGCGGCGCATTAAGCGCGGCGGGTGTGGTGGTT

ACGCGCAGCGTGACCGCTACACTTGCCAGCGCCCTAGCGCCCGCTCCTTT

CGCTTTCTTCCCTTCCTTTCTCGCCACGTTCGCCGGCTTTCCCCGTCAAG

CTCTAAATCGGGGGCTCCCTTTAGGGTTCCGATTTAGTGCTTTACGGCAC

CTCGACCCCAAAAAACTTGATTAGGGTGATGGTTCACGTAGTGGGCCATC

GCCCTGATAGACGGTTTTTCGCCCTTTGACGTTGGAGTCCACGTTCTTTA

ATAGTGGACTCTTGTTCCAAACTGGAACAACACTCAACCCTATCTCGGTC

TATTCTTTTGATTTATAAGGGATTTTGCCGATTTCGGCCTATTGGTTAAA

AAATGAGCTGATTTAACAAAAATTTAACGCGAATTTTAACAAAATATTAA

CGTTTACAATTTCCCATTCGCCATTCAGGCTGCGCAACTGTTGGGAAGGG

CGATCGGTGCGGGCCTCTTCGCTATTACGCCA

Certain compounds of the disclosure were evaluated in WT STING in vitro binding assay as described above. The following table tabulates the biological data for these compounds as $EC_{50}$ values.

TABLE 8

$^3$H-cGAMP filtration binding assay for WT STING

| Compound | $EC_{50}$ (nM) |
|---|---|
| Example 1 | <1 |
| Example 2 | 9 |
| Example 3 | 4 |
| Example 4 | <1 |
| Example 5 | 8 |
| Example 6 | 115 |
| Example 7 | <1 |
| Example 8 | 13 |
| Example 9 | 4393 |
| Example 10 | 6 |
| Example 11 | 34 |
| Example 12 | 171 |
| Example 13 | 223 |
| Example 14 | 244 |
| Example 15 | 79 |
| Example 16 | 18 |
| Example 18 | 1 |
| Example 19 | 1 |
| Example 20 | 3 |
| Example 21 | 1554 |
| Example 22 | 517 |
| Example 23 | 69 |
| Example 24 | 19 |
| Example 25 | 2 |
| Example 26 | 409 |

Example 30: IFN-β Secretion in THP1 Cell Culture (5 h)

The ability of compounds to stimulate the secretion of interferon-beta from THP1 cells was measured using a human IFN-β AlphaLISA kit (Perkin Elmer, Cat. No. AL265F). The basic protocol is as follows:

A Labcyte Echo 550 acoustic dispenser was used to transfer 120 nL of compound dissolved in DMSO into the wells of an empty, sterile 384-well microplate, (Corning, Cat. No. 3712). THP1 cells (American Type Culture Collection, Cat. No. TIB202) previously frozen in Recovery Medium (Life Technologies, Cat. No. 12648-010) were thawed and immediately diluted 10-fold into 37° C. assay medium (RPMI 1640+L-Glutamine & phenol red, Life Technologies, Cat. No. 11875-085; 0.5% heat inactivated fetal bovine serum, Sigma Aldrich, Cat. No. F4135; 1 mM Sodium Pyruvate, Life Technologies, Cat. No. 11360-070; lx non-essential amino acids; Life Technologies, Cat. No. 11140-050). The cell viability and count was ascertained using a Beckman Coulter V-Cell XR cell counter. The cell suspension was centrifuged at 200×g for 5 min at RT. Cells were resuspended to a density of $0.8×10^6$/mL in 37° C. assay medium. Subsequent liquid transfers were performed using either a Matrix electronic multichannel pipette or an Agilent Bravo Automated Liquid Handling Platform.

The assay was started by dispensing 40 µL of the previously prepared cell suspension into the wells of the plate containing compounds. After 5 h incubation at 37° C., 5% $CO_2$ in a humidified atmosphere, the plate of cells and compounds was centrifuged at 200×g for 5 min at RT. From each well, 5 µL of supernatant was transferred into corresponding wells of a white 384-well plate (Perkin Elmer, Cat. No. 6005620). To these supernatant-containing wells was added 10 µL of 5× Anti-Analyte Acceptor beads (50 µg/mL of AlphaLISA HiBlock Buffer) and incubated for 30 min at RT while shaking on an orbital plate shaker. To each well was added 10 µL of 5× Biotinylated Antibody Anti-analyte (5 nM in AlphaLISA HiBlock Buffer) and incubated on an orbital plate shaker for 60 min at RT or overnight at 4° C. To each well was added 25 µL of 2×SA-Donor beads (80 µg/mL in AlphaLISA HiBlock Buffer) and incubated for 30-45 min at RT in the dark while shaking on an orbital plate shaker. The plate was then read on a Perkin Elmer Envision ($\lambda_{ex}$=680 nm, $\lambda_{em}$=570 nm). The percent effect of the AlphaLISA signal at each compound concentration was calculated based on 30 uM cGAMP positive controls and 0.3% DMSO negative controls. The plot of percent effect versus the log of compound concentration was fit with a 4-parameter concentration response equation to calculate $EC_{50}$ values. The test compounds were tested at concentrations 30000, 10000, 3333, 1111, 370.4, 123.4, 41.2, 13.7, 4.6, and 1.5 nM with 0.3% residual DMSO. The control compound, cGAMP was tested at concentrations 100000, 33333, 11111, 3704, 1235, 412, 137, 46, and 15 nM with 0.3% residual DMSO.

Compounds of the disclosure were evaluated for IFN-β secretion in THP1 cell culture as described above. The following table tabulates the biological data for these compounds as percent activation relative to 2'3'-cGAMP at the 30 μM concentration.

TABLE 9

IFN-β secretion in THP1 cell culture (5 h)

| Compound | % Effect at 30 μM relative to 2'3'-cGAMP |
|---|---|
| Example 1 | 165 |
| Example 2 | 175 |
| Example 3 | 128 |
| Example 4 | 146 |
| Example 5 | 95 |
| Example 6 | 91 |
| Example 7 | 173 |
| Example 8 | 110 |
| Example 9 | 26 |
| Example 10 | 91 |
| Example 11 | 51 |
| Example 12 | 116 |
| Example 13 | 95 |
| Example 14 | 422 |
| Example 15 | 357 |
| Example 16 | 107 |
| Example 17 | 145 |
| Example 18 | 153 |
| Example 19 | 250 |
| Example 20 | 137 |
| Example 21 | 45 |
| Example 22 | 117 |
| Example 23 | 152 |
| Example 24 | 168 |
| Example 25 | 281 |
| Example 26 | 75 |
| Example 27 | 164 |

It will be appreciated that various of the above-discussed and other features and functions, or alternatives thereof, may be desirably combined into many other different systems or applications. It also will be appreciated that various presently unforeseen or unanticipated alternatives, modifications, variations or improvements therein may be subsequently made by those skilled in the art and are also intended to be encompassed by the following claims.

What is claimed is:

1. A compound of formula (I):

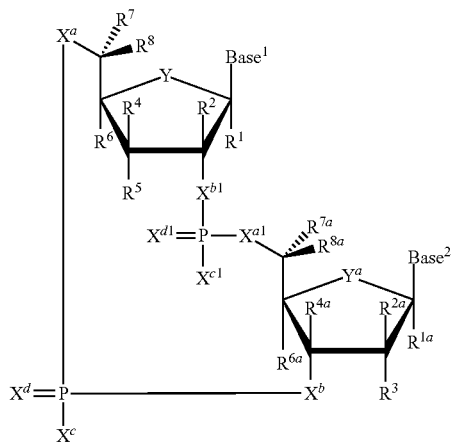

or a pharmaceutically acceptable salt thereof, wherein Base$^1$ and Base$^2$ are each independently selected from the group consisting of

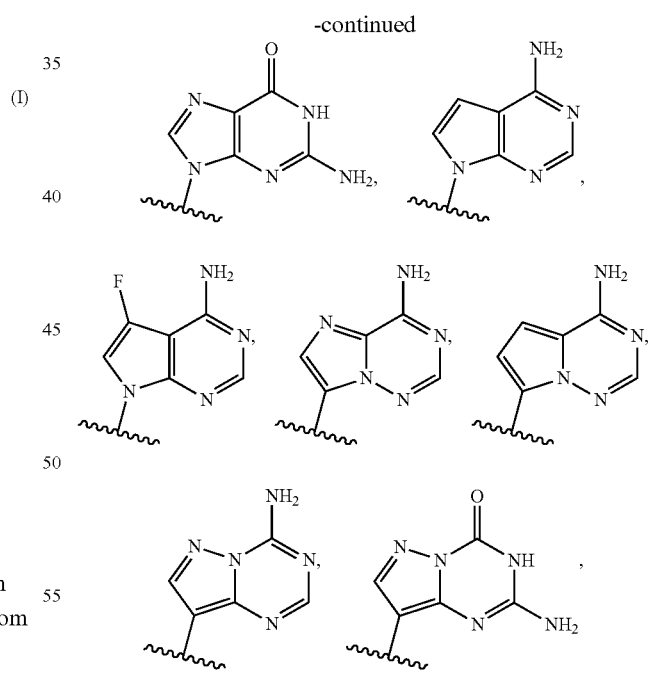

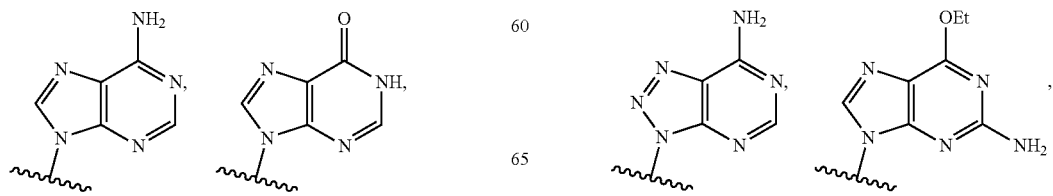

189
-continued
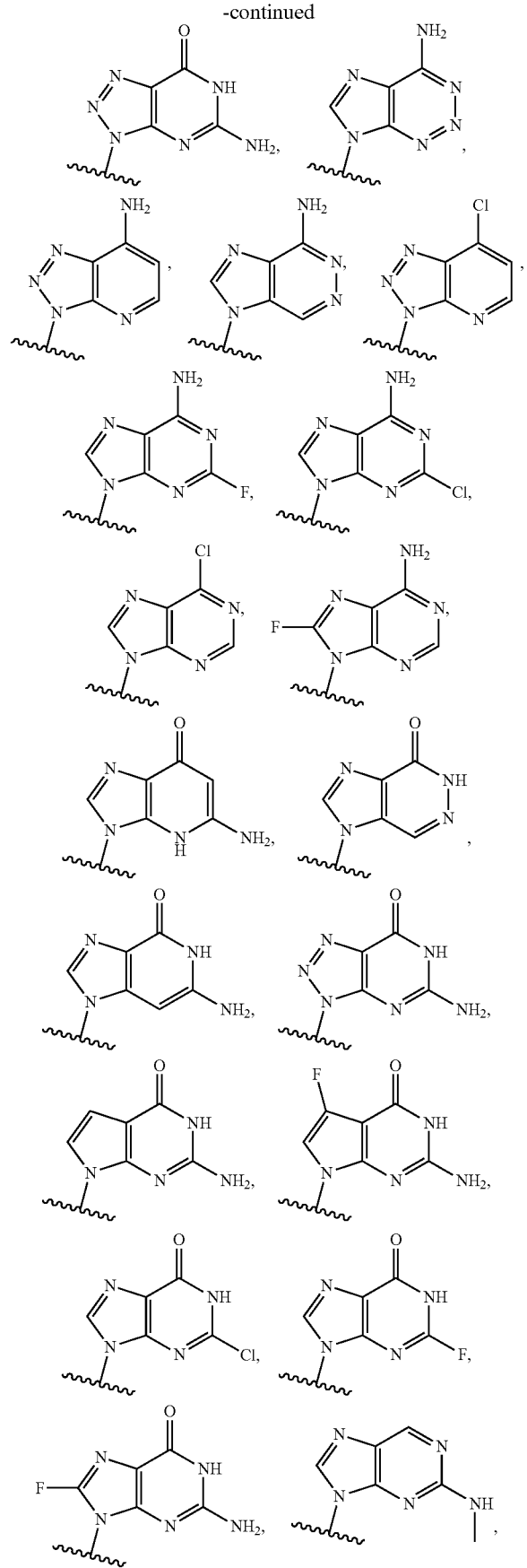
190
-continued
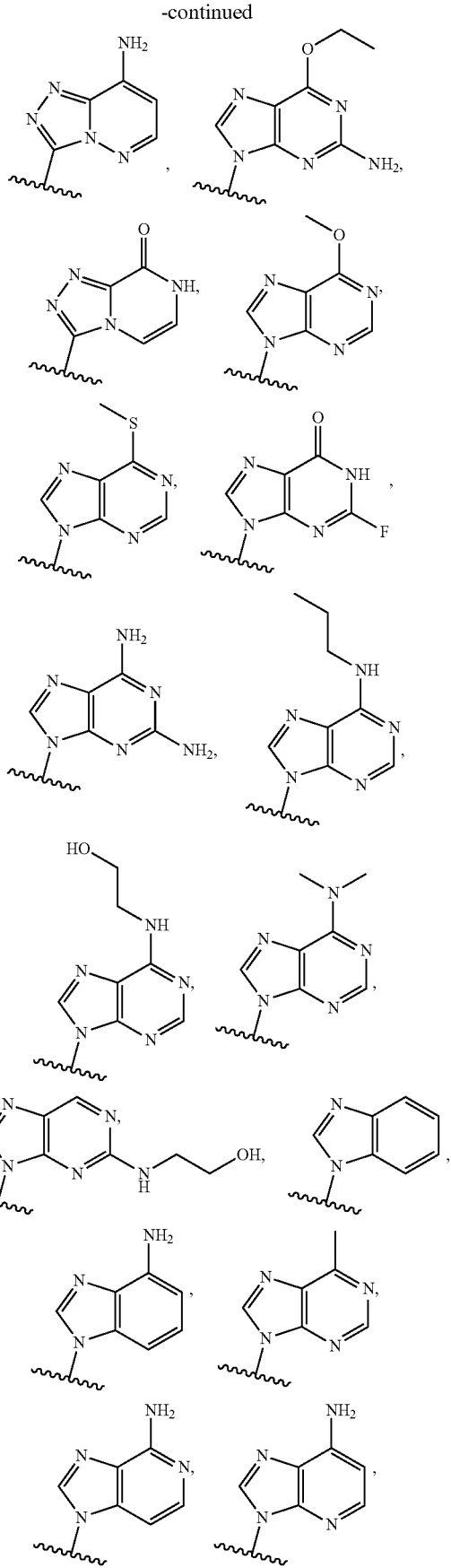

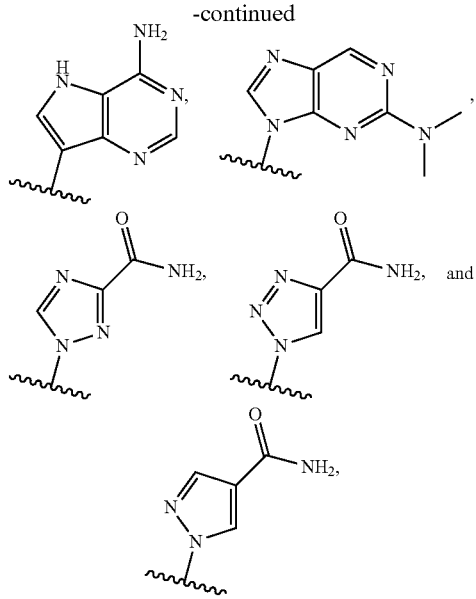

where Base¹ and Base² each may be independently substituted by 0-3 substituents $R^{10}$, where each $R^{10}$ is independently selected from the group consisting of F, Cl, I, Br, OH, SH, $NH_2$, $C_{1-3}$ alkyl, $C_{3-6}$ cycloalkyl, $O(C_{1-3}$ alkyl), $O(C_{3-6}$ cycloalkyl), $S(C_{1-3}$ alkyl), $S(C_{3-6}$ cycloalkyl), $NH(C_{1-3}$ alkyl), $NH(C_{3-6}$ cycloalkyl), $N(C_{1-3}$ alkyl)$_2$, and $N(C_{3-6}$ cycloalkyl)$_2$;

Y and $Y^a$ are each independently selected from the group consisting of —O—, —S—, —$SO_2$—, —$CH_2$—, and —$CF_2$—;

$X^a$ and $X^{a1}$ are each independently selected from the group consisting of —O—, —S—, and —$CH_2$—;

$X^b$ and $X^{b1}$ are each independently selected from the group consisting of —O—, —S—, and —$CH_2$—;

$X^c$ and $X^{c1}$ are each independently selected from the group consisting of $SR^9$, $OR^9$, and $NR^9R^9$;

$X^d$ and $X^{d1}$ are each independently selected from the group consisting of O and S;

$R^1$ and $R^{1a}$ are each independently selected from the group consisting of H, F, Cl, Br, I, OH, CN, $N_3$, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl, where said $R^2$ and $R^{2a}$ $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl are substituted by 0 to 3 substituents selected from the group consisting of F, Cl, Br, I, OH, CN, and $N_3$;

$R^2$ and $R^{2a}$ are each independently selected from the group consisting of H, F, Cl, Br, I, OH, CN, $N_3$, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl, where said $R^2$ and $R^{2a}$ $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl are substituted by 0 to 3 substituents selected from the group consisting of F, Cl, Br, I, OH, CN, and $N_3$;

$R^3$ is selected from the group consisting of H, F, Cl, Br, I, OH, CN, $N_3$, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl, where said $R^3$ $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl are substituted by 0 to 3 substituents selected from the group consisting of F, Cl, Br, I, OH, CN, and $N_3$;

$R^4$ and $R^{4a}$ are each independently selected from the group consisting of H, F, Cl, Br, I, OH, CN, $N_3$, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl, where said $R^4$ and $R^{4a}$ $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl are substituted by 0 to 3 substituents selected from the group consisting of F, Cl, Br, I, OH, CN, and $N_3$;

$R^5$ is selected from the group consisting of H, F, Cl, Br, I, OH, CN, $N_3$, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl, where said $R^5$ $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl are substituted by 0 to 3 substituents selected from the group consisting of F, Cl, Br, I, OH, CN, and $N_3$;

$R^6$ and $R^{6a}$ are each independently selected from the group consisting of H, F, Cl, Br, I, OH, CN, $N_3$, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl, where said $R^6$ and $R^{6a}$ $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl are substituted by 0 to 3 substituents selected from the group consisting of F, Cl, Br, I, OH, CN, and $N_3$;

$R^7$ and $R^{7a}$ are each independently selected from the group consisting of H, F, Cl, Br, I, OH, CN, $N_3$, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl, where said $R^7$ and $R^{7a}$ $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl are substituted by 0 to 3 substituents selected from the group consisting of F, Cl, Br, I, OH, CN, and $N_3$;

$R^8$ and $R^{8a}$ are each independently selected from the group consisting of H, F, Cl, Br, I, OH, CN, $N_3$, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl, where said $R^8$ and $R^{8a}$ $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl are substituted by 0 to 3 substituents selected from the group consisting of F, Cl, Br, I, OH, CN, and $N_3$;

each $R^9$ is independently selected from the group consisting of H, $C_1$-$C_{20}$ alkyl,

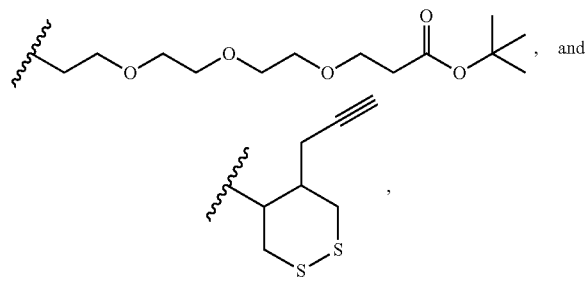

where each $R^9$ $C_1$-$C_{20}$ alkyl is optionally substituted by 0 to 3 substituents independently selected from the group consisting of OH, —O—$C_1$-$C_{20}$ alkyl, —S—C(O)$C_1$-$C_6$ alkyl, and C(O)O$C_1$-$C_6$ alkyl;

optionally $R^{1a}$ and $R^3$ are connected to form $C_1$-$C_6$ alkylene, $C_2$-$C_6$ alkenylene, —O—$C_1$-$C_6$ alkylene, or —O—$C_2$-$C_6$ alkenylene, such that where $R^{1a}$ and $R^3$ are connected to form —O—$C_1$-$C_6$ alkylene, or —O—$C_2$-$C_6$ alkenylene, said O is bound at the $R^3$ position;

optionally $R^{2a}$ and $R^3$ are connected to form $C_1$-$C_6$ alkylene, $C_2$-$C_6$ alkenylene, —O—$C_1$-$C_6$ alkylene, or —O—$C_2$-$C_6$ alkenylene, such that where $R^{2a}$ and $R^3$ are connected to form —O—$C_1$-$C_6$ alkylene, or —O—$C_2$-$C_6$ alkenylene, said O is bound at the $R^3$ position;

optionally $R^3$ and $R^{6a}$ are connected to form $C_1$-$C_6$ alkylene, $C_2$-$C_6$ alkenylene, —O—$C_1$-$C_6$ alkylene, or —O—$C_2$-$C_6$ alkenylene, such that where $R^3$ and $R^{6a}$ are connected to form —O—$C_1$-$C_6$ alkylene, or —O—$C_2$-$C_6$ alkenylene, said O is bound at the $R^3$ position;

optionally $R^4$ and $R^5$ are connected to form $C_1$-$C_6$ alkylene, $C_2$-$C_6$ alkenylene, —O—$C_1$-$C_6$ alkylene, or —O—$C_2$-$C_6$ alkenylene, such that where $R^4$ and $R^5$ are connected to form —O—$C_1$-$C_6$ alkylene, or —O—$C_2$-$C_6$ alkenylene, said O is bound at the $R^5$ position;

optionally $R^5$ and $R^6$ are connected to form —O—$C_1$-$C_6$ alkylene, —O—$C_2$-$C_6$ alkenylene, or —O—$C_2$-$C_6$ alkynylene, such that where $R^5$ and $R^6$ are connected to form —O—$C_1$-$C_6$ alkylene, —O—$C_2$-$C_6$ alkenylene, or —O—$C_2$-$C_6$ alkynylene, said O is bound at the $R^5$ position;

optionally $R^7$ and $R^8$ are connected to form $C_1$-$C_6$ alkylene or $C_2$-$C_6$ alkenylene; and optionally $R^{7a}$ and $R^{8a}$ are connected to form $C_1$-$C_6$ alkylene or $C_2$-$C_6$ alkenylene; and provided that at least one of

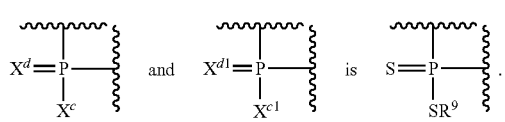

2. The compound according to claim 1, or a pharmaceutically acceptable salt thereof, wherein Base¹ and Base² are each independently selected from the group consisting of

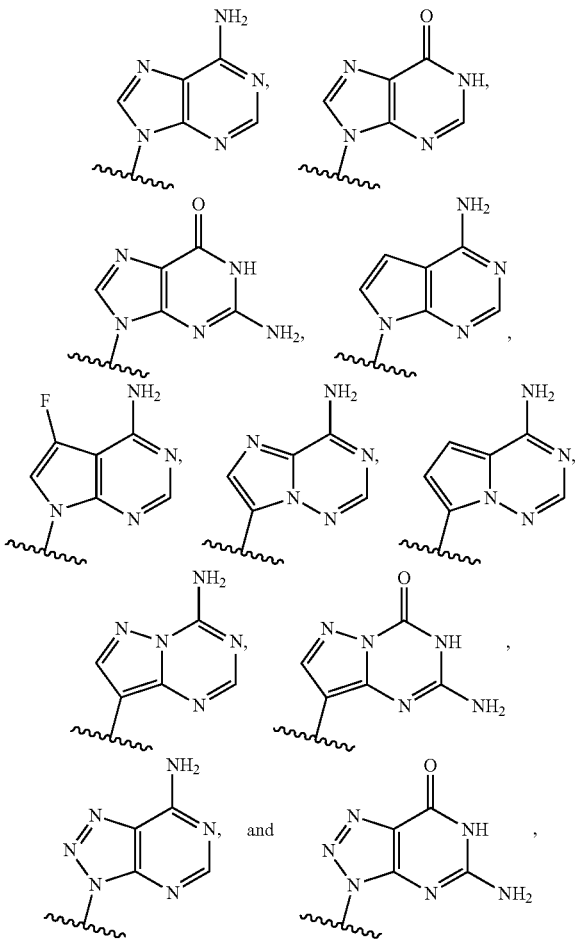

where Base¹ and Base² each may be independently substituted by 0-3 substituents $R^{10}$, where each $R^{10}$ is independently selected from the group consisting of F, Cl, I, Br, OH, SH, $NH_2$, $C_{1-3}$ alkyl, $C_{3-6}$ cycloalkyl, O($C_{1-3}$ alkyl), O($C_{3-6}$ cycloalkyl), S($C_{1-3}$ alkyl), S($C_{3-6}$ cycloalkyl), NH($C_{1-3}$ alkyl), NH($C_{3-6}$ cycloalkyl), N($C_{1-3}$ alkyl)$_2$, and N($C_{3-6}$ cycloalkyl)$_2$;

Y and $Y^a$ are each independently selected from the group consisting of —O— and —S—;

$X^a$ and $X^{a1}$ are each independently selected from the group consisting of O and S;

$X^b$ and $X^{b1}$ are each independently selected from the group consisting of O and S;

$X^c$ and $X^{c1}$ are each independently selected from the group consisting of $SR^9$, $OR^9$, and $NR^9R^9$;

$X^d$ and $X^{d1}$ are each independently selected from the group consisting of O and S;

$R^1$ and $R^{1a}$ are each H;

$R^2$ and $R^{2a}$ are each independently selected from the group consisting of H, F, Cl, Br, I, OH, CN, $N_3$, $C_1$-$C_6$ alkyl, and $C_1$-$C_6$ haloalkyl, where said $R^2$ and $R^{2a}$ $C_1$-$C_6$ alkyl or $C_1$-$C_6$ haloalkyl are substituted by 0 to 3 substituents selected from the group consisting of OH, CN, and $N_3$;

$R^3$ is selected from the group consisting of H, F, Cl, Br, I, OH, CN, $N_3$, $C_1$-$C_6$ alkyl, and $C_1$-$C_6$ haloalkyl, where said $R^3$ $C_1$-$C_6$ alkyl or $C_1$-$C_6$ haloalkyl are substituted by 0 to 3 substituents selected from the group consisting of OH, CN, and $N_3$;

R⁴ and R⁴ᵃ are each independently selected from the group consisting of H, F, Cl, I, Br, CN, OH, N₃, C₁-C₆ alkyl, and C₁-C₆ haloalkyl, where said R⁴ and R⁴ᵃ C₁-C₆ alkyl or C₁-C₆ haloalkyl are substituted by 0 to 3 substituents selected from the group consisting of OH, CN, and N₃;

R⁵ is selected from the group consisting of H, F, Cl, Br, I, OH, N₃, C₁-C₆ alkyl, and C₁-C₆ haloalkyl, where said R⁵ C₁-C₆ alkyl or C₁-C₆ haloalkyl are substituted by 0 to 3 substituents selected from the group consisting of F, Cl, Br, I, OH, CN, and N₃;

R⁶ and R⁶ᵃ are each independently selected from the group consisting of H, F, Cl, I, Br, OH, CN, N₃, C₁-C₆ alkyl, C₂-C₆ alkenyl, and C₂-C₆ alkynyl, where said R⁶ and R⁶ᵃ C₁-C₆ alkyl, C₂-C₆ alkenyl, and C₂-C₆ alkynyl are substituted by 0 to 3 substituents selected from the group consisting of F, Cl, Br, I, OH, CN, and N₃;

R⁷ and R⁷ᵃ are each independently selected from the group consisting of H, C₁-C₆ alkyl, and C₁-C₆ haloalkyl, where said R⁷ and R⁷ᵃ C₁-C₆ alkyl or C₁-C₆ haloalkyl are substituted by 0 to 3 substituents selected from the group consisting of OH, CN, and N₃;

R⁸ and R⁸ᵃ are each independently selected from the group consisting of H, C₁-C₆ alkyl, and C₁-C₆ haloalkyl, where said R⁸ and R⁸ᵃ C₁-C₆ alkyl or C₁-C₆ haloalkyl are substituted by 0 to 3 substituents selected from the group consisting of OH, CN, and N₃;

each R⁹ is independently selected from the group consisting of H, C₁-C₆ alkyl,

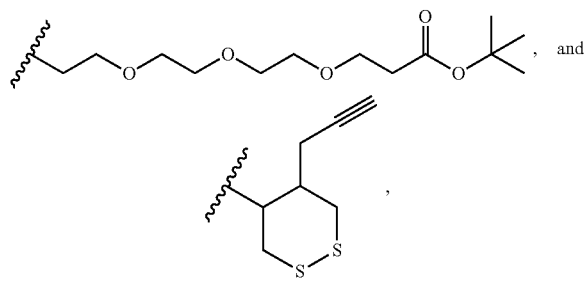, and where each R⁹ C₁-C₆ alkyl is optionally substituted by 1 to 2 substituents independently selected from the group consisting of OH, —O—C₁-C₂₀ alkyl, —S—C(O)C₁-C₆ alkyl, and —C(O)OC₁-C₆ alkyl;

optionally R³ and R⁶ᵃ are connected to form C₂-C₆ alkylene, C₂-C₆ alkenylene, —O—C₁-C₆ alkylene, or —O—C₂-C₆ alkenylene, such that where R³ and R⁶ᵃ are connected to form —O—C₁-C₆ alkylene or —O—C₂-C₆ alkenylene, said O is bound at the R³ position; and optionally R⁵ and R⁶ are connected to form C₁-C₆ alkylene, C₂-C₆ alkenylene, —O—C₁-C₆ alkylene, or

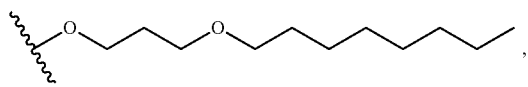

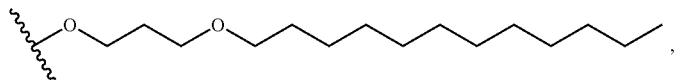

—O—C₂-C₆ alkenylene, such that where R⁵ and R⁶ are connected to form —O—C₁-C₆ alkylene or —O—C₂-C₆ alkenylene, said O is bound at the R⁵ position.

3. The compound according to claim 1, or a pharmaceutically acceptable salt thereof, wherein Base¹ and Base² are each independently selected from the group consisting of

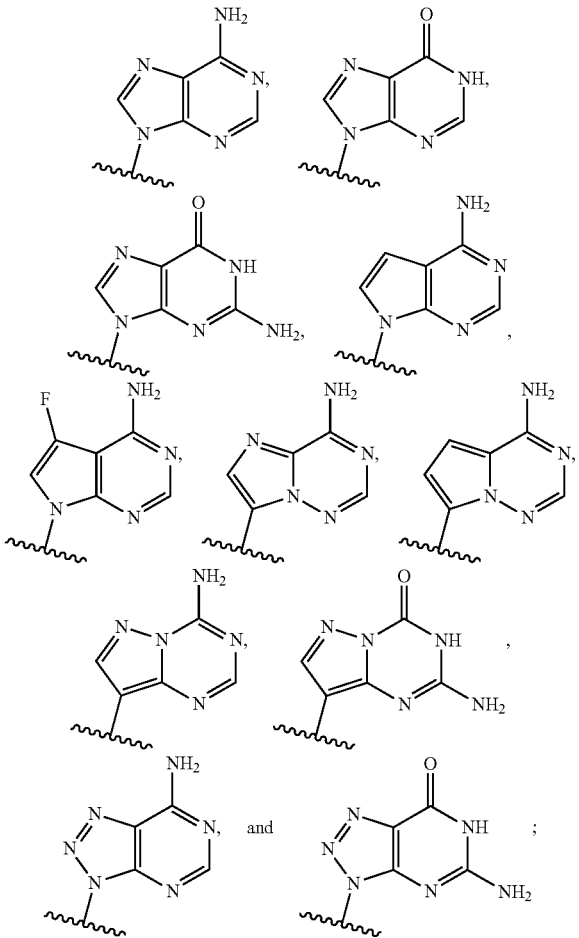

Y and Yᵃ are each independently selected from the group consisting of —O— and —S—;

Xᵃ and Xᵃ¹ are each independently selected from the group consisting of O and S;

Xᵇ and Xᵇ¹ are each independently selected from the group consisting of O and S;

Xᶜ and Xᶜ¹ are each independently selected from the group consisting of —OH, —SH,

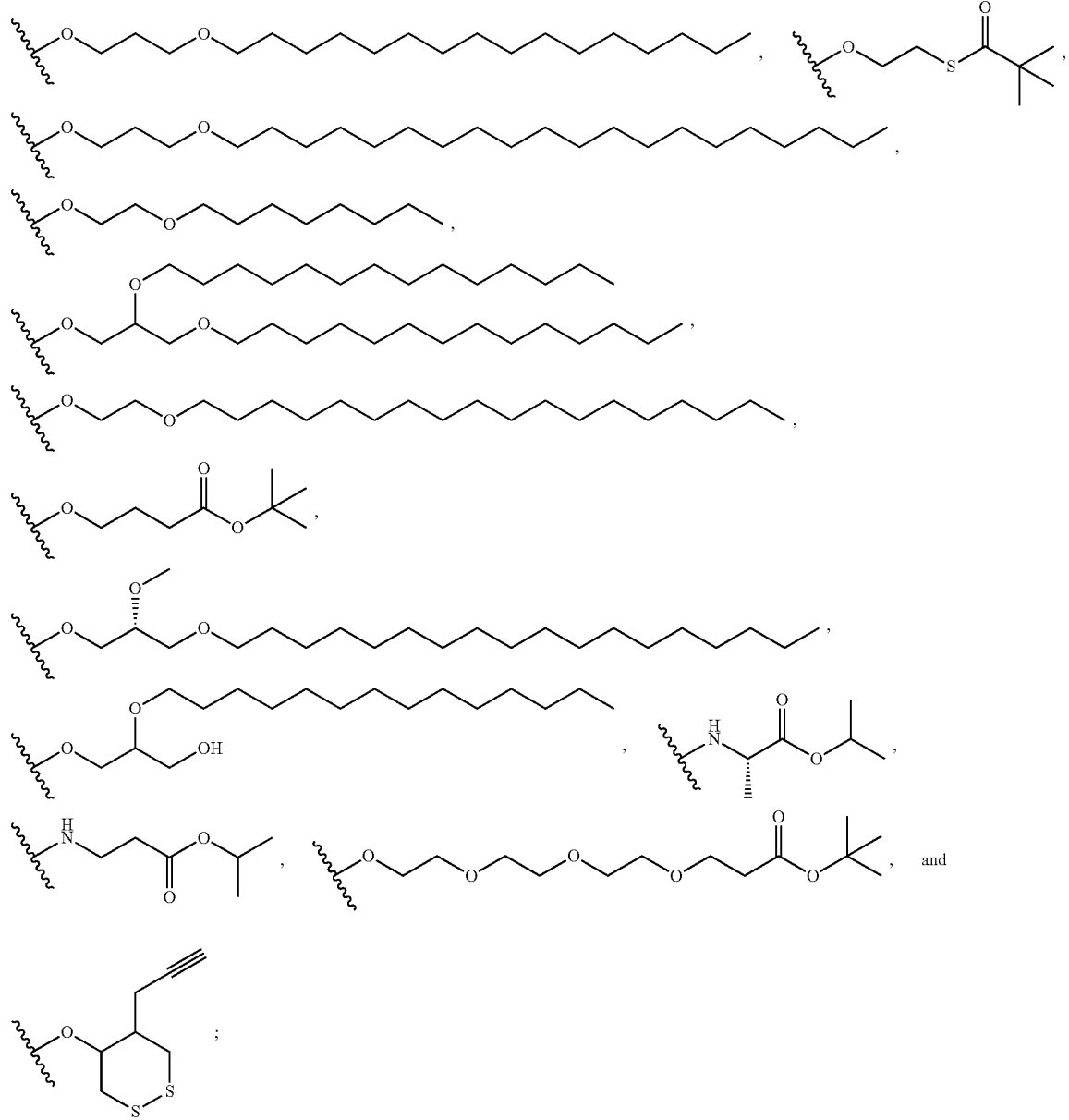

$X^d$ and $X^{d1}$ are each independently selected from the group consisting of O and S;

$R^1$ and $R^{1a}$ are each H;

$R^2$ and $R^{2a}$ are each independently selected from the group consisting of H, F, Cl, I, Br, OH, CN, $N_3$, $CF_3$, $CH_3$, $CH_2OH$, and $CH_2CH_3$;

$R^3$ is selected from the group consisting of H, F, Cl, I, Br, OH, CN, $N_3$, $CF_3$, $CH_3$, $CH_2OH$, and $CH_2CH_3$;

$R^4$ and $R^{4a}$ are each independently selected from the group consisting of H, F, Cl, I, Br, OH, CN, $N_3$, $CF_3$, $CH_3$, $CH_2OH$, and $CH_2CH_3$;

$R^5$ is selected from the group consisting of H, F, Cl, I, Br, OH, CN, $N_3$, $CF_3$, $CH_3$, $CH_2OH$, and $CH_2CH_3$;

$R^6$ and $R^{6a}$ are each independently selected from the group consisting of H, F, Cl, I, Br, OH, CN, $N_3$, $CF_3$, $CH_3$, $CH_2OH$, $CH_2CH_3$, —CH=$CH_2$, —C≡CH, and —C≡C—CH;

$R^7$ and $R^{7a}$ are each independently selected from the group consisting of H, $CF_3$, $CH_3$, and $CH_2CH_3$;

$R^8$ and $R^{8a}$ are each independently selected from the group consisting of H, $CF_3$, $CH_3$, and $CH_2CH_3$;

optionally $R^3$ and $R^{6a}$ are connected to $C_2$-$C_6$ alkylene, $C_2$-$C_6$ alkenylene, —O—$C_1$-$C_6$ alkylene, or —O—$C_2$-$C_6$ alkenylene, such that where $R^3$ and $R^{6a}$ are connected to form —O—$C_1$-$C_6$ alkylene or —O—$C_2$-$C_6$ alkenylene, said O is bound at the $R^3$ position; and optionally $R^5$ and $R^6$ are connected to form $C_1$-$C_6$ alkylene, $C_2$-$C_6$ alkenylene, —O—$C_1$-$C_6$ alkylene, or —O—$C_2$-$C_6$ alkenylene, such that where $R^5$ and $R^6$ are connected to form —O—$C_1$-$C_6$ alkylene or —O—$C_2$-$C_6$ alkenylene, said O is bound at the $R^5$ position.

4. The compound according to claim 1, or a pharmaceutically acceptable salt thereof, wherein Base$^1$ and Base$^2$ are each independently selected from the group consisting of

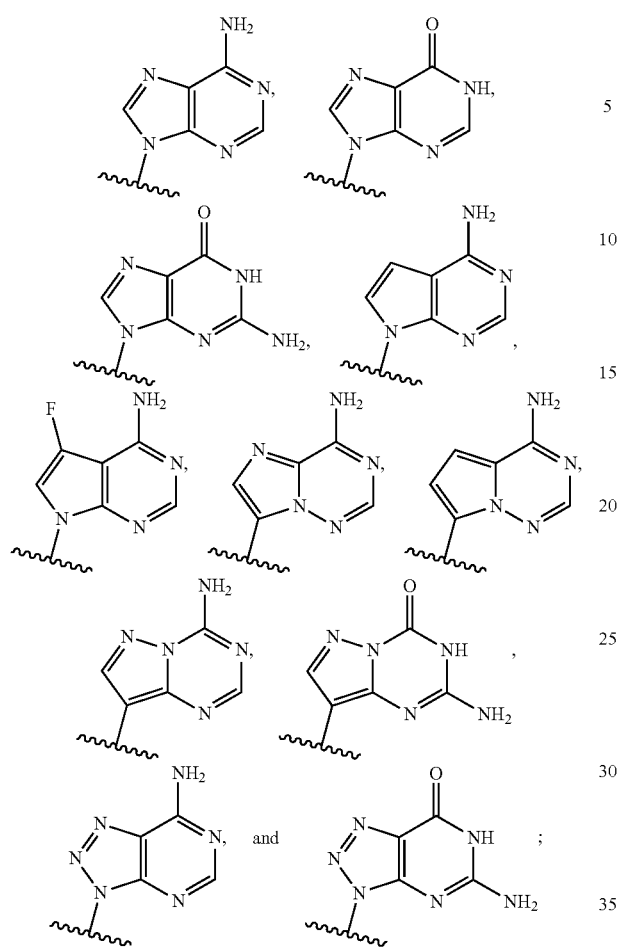

Y and Y$^a$ are each independently selected from the group consisting of —O— and —S—;
X$^a$ and X$^{a1}$ are each O;
X$^b$ and X$^{b1}$ are each O;
X$^c$ and X$^{c1}$ are each independently selected from the group consisting of —OH and —SH;
X$^d$ and X$^{d1}$ are each independently selected from the group consisting of O and S;
R$^1$ and R$^{1a}$ are each H;
R$^2$ and R$^{2a}$ are each independently selected from the group consisting of H, F, Cl, OH, CN, N$_3$, and CH$_3$;
R$^3$ is selected from the group consisting of H, F, Cl, OH, CN, N$_3$, and CH$_3$;
R$^4$ and R$^{4a}$ are each independently selected from the group consisting of H, F, Cl, OH, CN, N$_3$, and CH$_3$;
R$^5$ is selected from the group consisting of H, F, Cl, OH, CN, N$_3$, and CH$_3$;
R$^6$ and R$^{6a}$ are each independently selected from the group consisting of H, F, CN, N$_3$, CH$_3$, —CH=CH$_2$, and —C≡CH;
R$^7$ and R$^{7a}$ are each H;
R$^8$ and R$^{8a}$ are each H;
optionally R$^3$ and R$^{6a}$ are connected to form —O—C$_1$-C$_6$ alkylene or —O—C$_2$-C$_6$ alkenylene, such that O is bound at the R$^3$ position; and
optionally R$^5$ and R$^6$ are connected to form C$_1$-C$_6$ alkylene, C$_2$-C$_6$ alkenylene, —O—C$_1$-C$_6$ alkylene, or —O—C$_2$-C$_6$ alkenylene, such that where R$^5$ and R$^6$ are connected to form —O—C$_1$-C$_6$ alkylene or —O—C$_2$-C$_6$ alkenylene, said O is bound at the R$^5$ position.

5. The compound according to claim 1, or a pharmaceutically acceptable salt thereof, wherein
Base$^1$ and Base$^2$ are each independently selected from the group consisting of

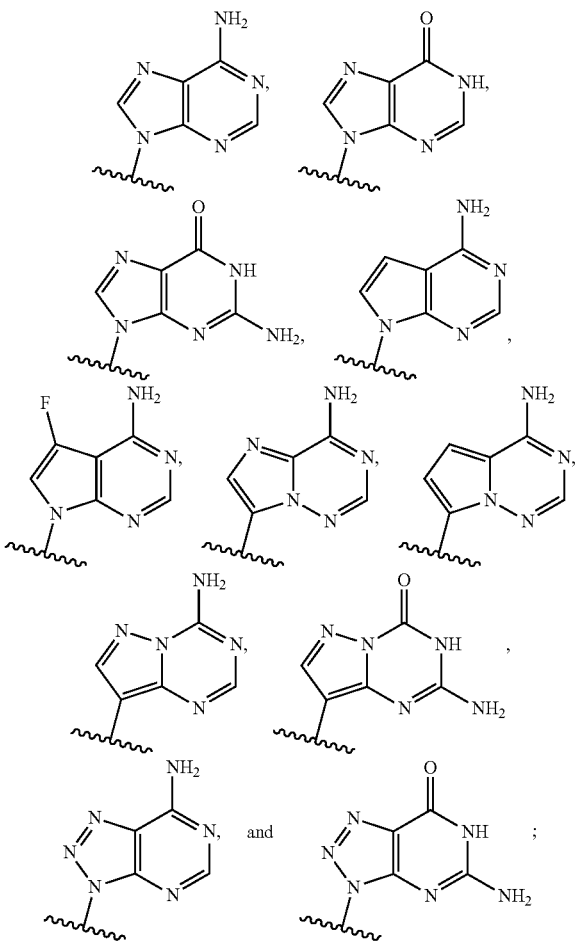

Y and Y$^a$ are each independently selected from the group consisting of —O— and —S—;
X$^a$ and X$^{a1}$ are each O;
X$^b$ and X$^{b1}$ are each O;
X$^c$ and X$^{c1}$ are each independently selected from the group consisting of —OH and —SH;
X$^d$ and X$^{d1}$ are each independently selected from the group consisting of O and S;
R$^1$ and R$^{1a}$ are each H;
R$^2$ and R$^{2a}$ a are each independently selected from the group consisting of H, F, Cl, OH, CN, N$_3$, and CH$_3$;
R$^3$ is selected from the group consisting of H, F, Cl, OH, CN, N$_3$, and CH$_3$;
R$^4$ and R$^{6a}$ are each independently selected from the group consisting of H, F, Cl, OH, CN, N$_3$, and CH$_3$;
R$^5$ is selected from the group consisting of H, F, Cl, OH, CN, N$_3$, and CH$_3$;
R$^6$ and R$^{6a}$ a are each independently selected from the group consisting of H, F, CN, N$_3$, CH$_3$, —CH=CH$_2$, and —C≡CH;
R$^7$ and R$^{7a}$ a are each H;
R$^8$ and R$^{8a}$ are each H;

optionally R³ and R⁶ᵃ are connected to form —O—$C_1$-$C_6$ alkylene or —O—$C_2$-$C_6$ alkenylene, such that where R³ and R⁶ᵃ are connected to form —O—$C_1$-$C_6$ alkylene or —O—$C_2$-$C_6$ alkenylene, said O is bound at the R³ position; and optionally R⁵ and R⁶ are connected to form $C_1$-$C_6$ alkylene, $C_2$-$C_6$ alkenylene, —O—$C_1$-$C_6$ alkylene, or —O—$C_2$-$C_6$ alkenylene, such that where R⁵ and R⁶ are connected to form —O—$C_1$-$C_6$ alkylene or —O—$C_2$-$C_6$ alkenylene, said O is bound at the R⁵ position.

6. The compound according to claim 1, or a pharmaceutically acceptable salt thereof, wherein
Base¹ and Base² are each independently selected from the group consisting of

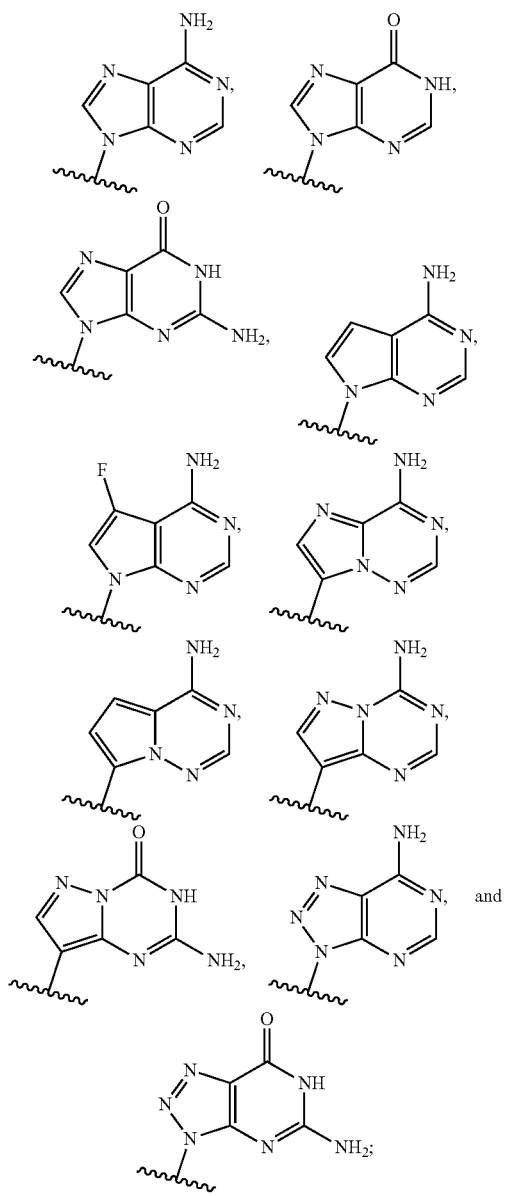

Y and $Y^a$ are each independently selected from the group consisting of —O— and —S—; $X^a$ and $X^{a1}$ are each O; $X^b$ and $X^{b1}$ are each O;

$X^c$ and $X^{c1}$ are each independently selected from the group consisting of SH and OH;

$X^d$ and $X^{d1}$ are each independently selected from the group consisting of O and S;

R¹ and $R^{1a}$ are each H;

R² and $R^{2a}$ are each independently selected from the group consisting of H, F, and OH;

R³ is selected from the group consisting of H, F, and OH;

R⁴ and $R^{4a}$ are each independently selected from the group consisting of H, F, and OH;

R⁵ is selected from the group consisting of H, F, and OH;

R⁶ and $R^{6a}$ are each H;

R⁷ and $R^{7a}$ are each H;

R⁸ and $R^{8a}$ are each H; and optionally R³ and R⁶ᵃ are connected to form —O—$C_1$-$C_6$ alkylene or —O—$C_2$-$C_6$ alkenylene, such that where R³ and R⁶ᵃ are connected to form —O—$C_1$-$C_6$ alkylene or —O—$C_2$-$C_6$ alkenylene, said O is bound at the R³ position.

7. The compound according to claim 1, or a pharmaceutically acceptable salt thereof, wherein
Base¹ and Base² are each independently selected from the group consisting of

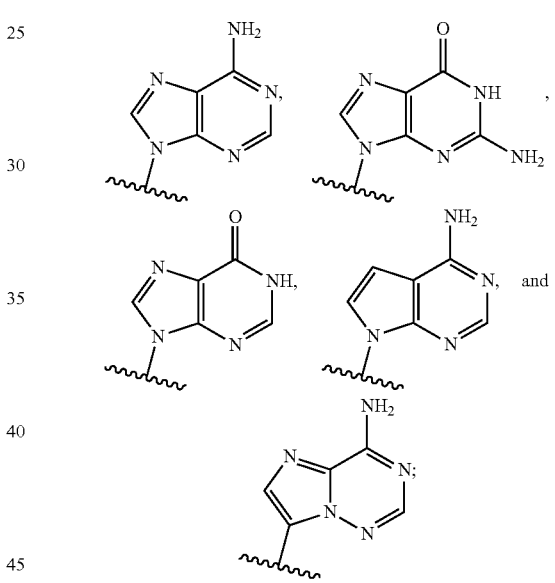

Y and $Y^a$ are each independently selected from the group consisting of —O— and —S—;

$X^a$ and $X^{a1}$ are each O;

$X^b$ and $X^{b1}$ are each O;

$X^c$ and $X^{c1}$ are each independently selected from the group consisting of —SH and —OH;

$X^d$ and $X^{d1}$ are each independently selected from the group consisting of O and S;

R¹ and $R^{1a}$ are each H;

R² is H;

$R^{2a}$ is selected from the group consisting of H, F, and OH;

R³ is selected from the group consisting of H, F, and OH;

R⁴ is selected from the group consisting of H, F, and OH;

$R^{4a}$ is H;

R⁵ is selected from the group consisting of H, F, and OH;

R⁶ and $R^{6a}$ are each H;

R⁷ and $R^{7a}$ are each H; and

R⁸ and $R^{8a}$ are each H.

8. A compound selected from the group consisting of:
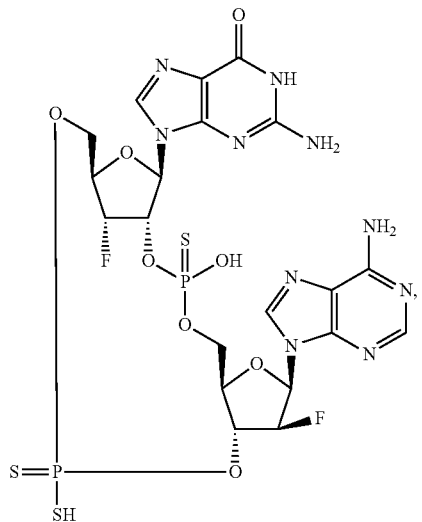
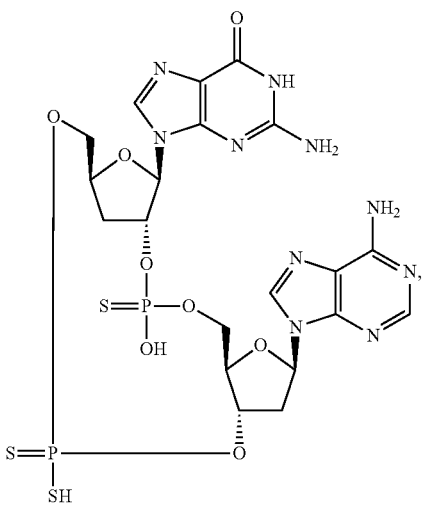
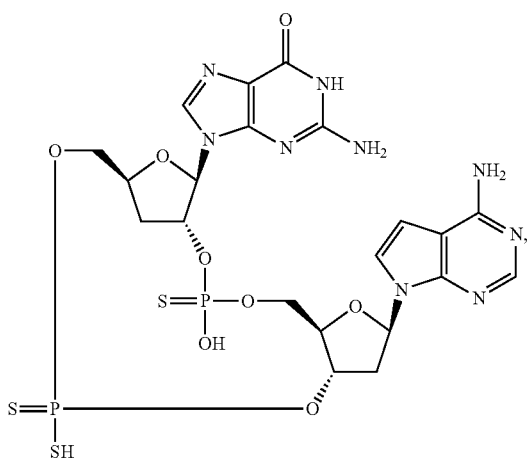
-continued
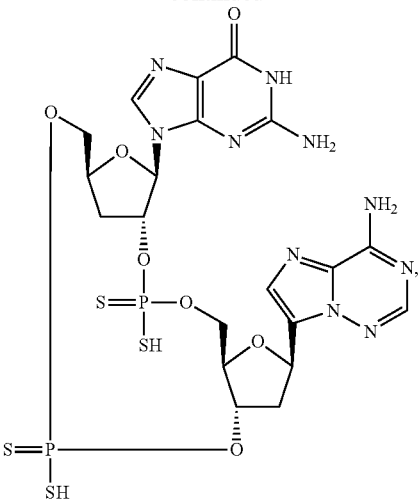
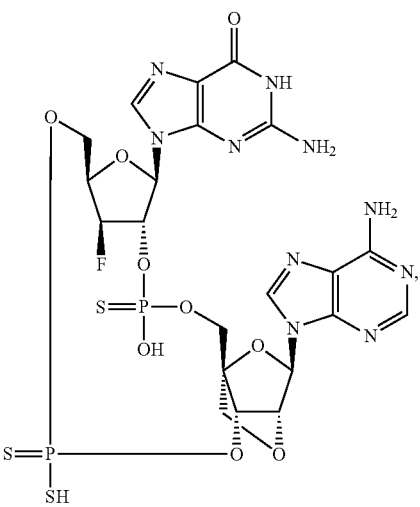
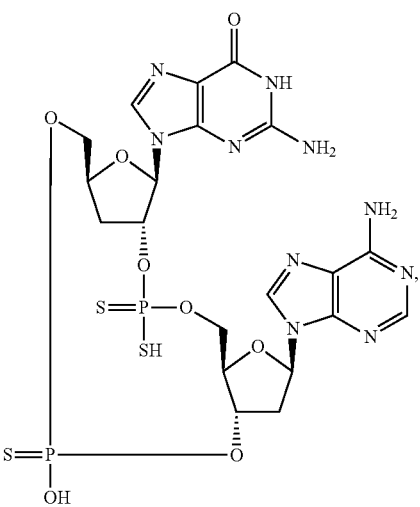

205
-continued
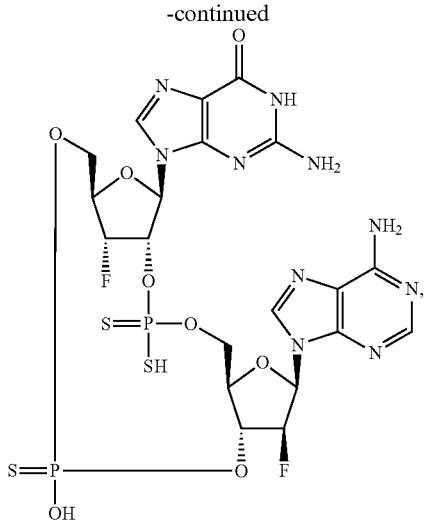
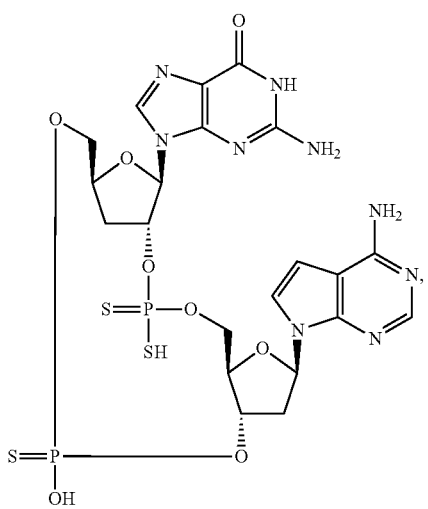
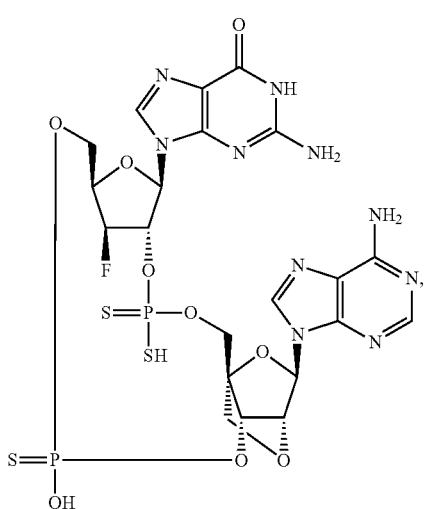
206
-continued
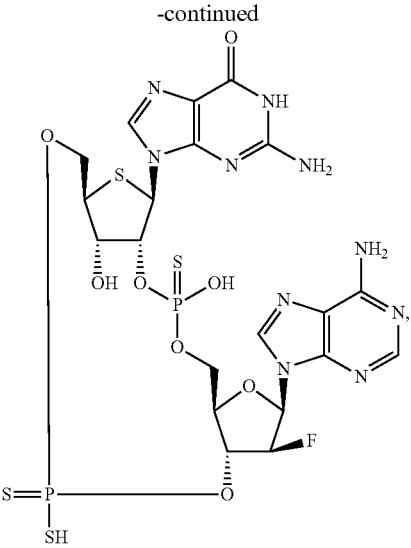
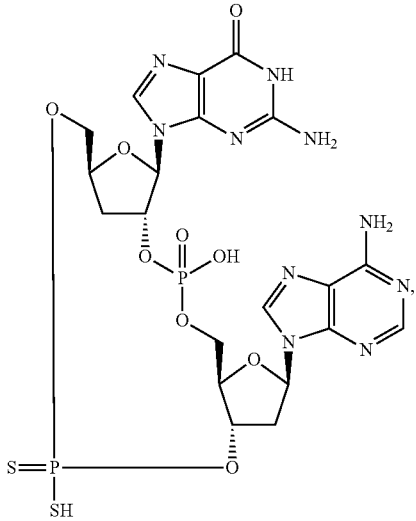

207
-continued
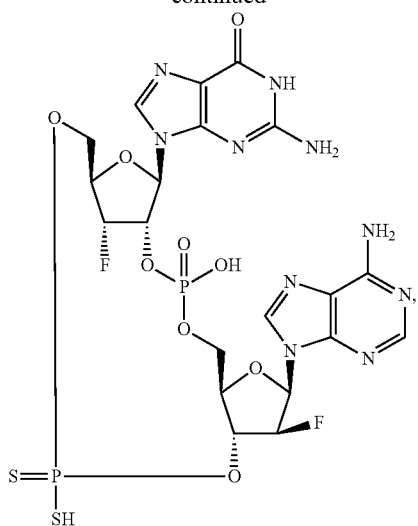
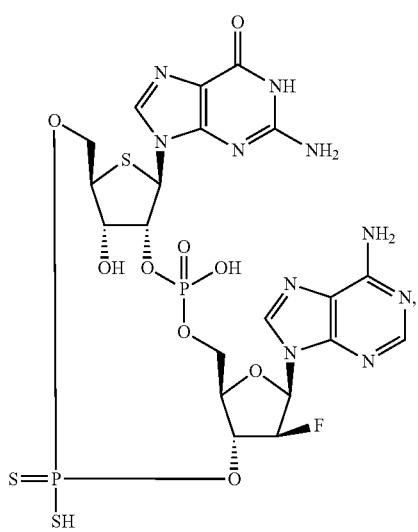
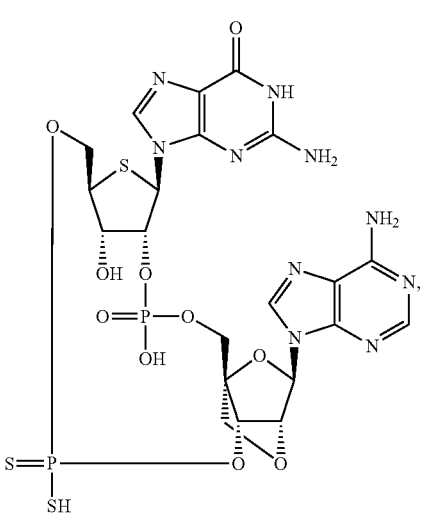
208
-continued
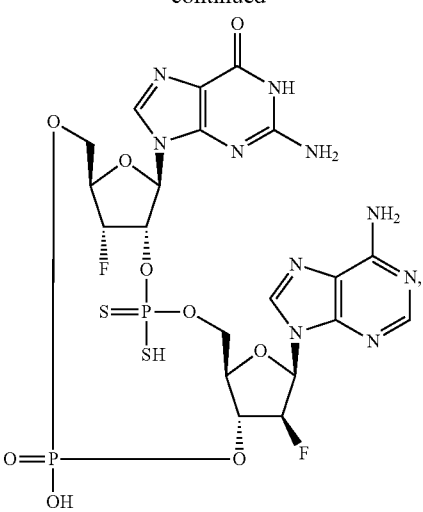

-continued

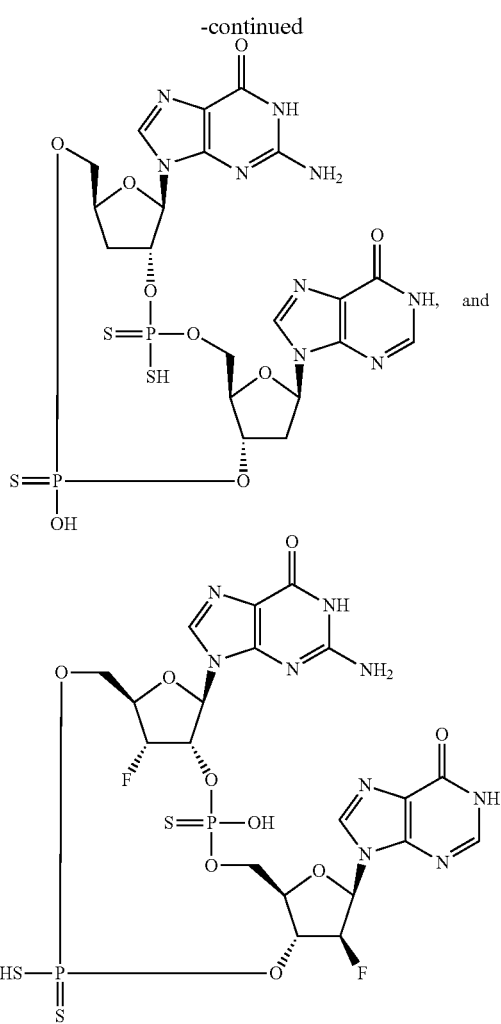

or a pharmaceutically acceptable salt thereof.

9. A pharmaceutical composition, said pharmaceutical composition comprising:
   (a) a compound according to claim 1 or a pharmaceutically acceptable salt thereof; and
   (b) a pharmaceutically acceptable carrier.

10. A method of inducing an immune response in a subject, said method comprising administering a therapeutically effective amount of a compound according to claim 1 to the subject.

11. A method of inducing an immune response in a subject, said method comprising administering a therapeutically effective amount of a pharmaceutical composition according to claim 9 to the subject.

12. A method of inducing a STING-dependent type I interferon production in a subject, said method comprising administering a therapeutically effective amount of a compound according to claim 1 to the subject.

13. A method of inducing a STING-dependent type I interferon production in a subject, said method comprising administering a therapeutically effective amount of a pharmaceutical composition according to claim 9 to the subject.

14. A method of treating a cell proliferation disorder in a subject, said method comprising administering a therapeutically effective amount of a compound according to claim 1 to the subject.

15. The method of claim 14, wherein the cell proliferation disorder is cancer.

16. A method of treating a cell proliferation disorder in a subject, said method comprising administering a therapeutically effective amount of a pharmaceutical composition according to claim 9 to the subject.

17. The method of claim 16, wherein the cell proliferation disorder is cancer.

* * * * *

SEQUENCE LISTING

```
<160> NUMBER OF SEQ ID NOS: 4

<210> SEQ ID NO 1
<211> LENGTH: 414
<212> TYPE: PRT
<213> ORGANISM: Homo sapiens

<400> SEQUENCE: 1

Met Pro His Ser Ser Leu His Pro Ser Ile Pro Cys Pro Arg Gly His
1               5                   10                  15

Gly Ala Gln Lys Ala Ala Leu Val Leu Leu Ser Ala Cys Leu Val Thr
            20                  25                  30

Leu Trp Gly Leu Gly Glu Pro Pro Glu His Thr Leu Arg Tyr Leu Val
        35                  40                  45

Leu His Leu Ala Ser Leu Gln Leu Gly Leu Leu Leu Asn Gly Val Cys
    50                  55                  60

Ser Leu Ala Glu Glu Leu His His Ile His Ser Arg Tyr Arg Gly Ser
65                  70                  75                  80

Tyr Trp Arg Thr Val Arg Ala Cys Leu Gly Cys Pro Leu Arg Arg Gly
                85                  90                  95

Ala Leu Leu Leu Leu Ser Ile Tyr Phe Tyr Tyr Ser Leu Pro Asn Ala
            100                 105                 110

Val Gly Pro Pro Phe Thr Trp Met Leu Ala Leu Leu Gly Leu Ser Gln
        115                 120                 125

Ala Leu Asn Ile Leu Leu Gly Leu Lys Gly Leu Ala Pro Ala Glu Ile
    130                 135                 140
```

```
Ser Ala Val Cys Glu Lys Gly Asn Phe Asn Val His Gly Leu Ala
145                 150                 155                 160

Trp Ser Tyr Tyr Ile Gly Tyr Leu Arg Leu Ile Leu Pro Glu Leu Gln
                165                 170                 175

Ala Arg Ile Arg Thr Tyr Asn Gln His Tyr Asn Asn Leu Leu Arg Gly
            180                 185                 190

Ala Val Ser Gln Arg Leu Tyr Ile Leu Leu Pro Leu Asp Cys Gly Val
        195                 200                 205

Pro Asp Asn Leu Ser Met Ala Asp Pro Asn Ile Arg Phe Leu Asp Lys
    210                 215                 220

Leu Pro Gln Gln Thr Ala Asp Arg Ala Gly Ile Lys Asp Arg Val Tyr
225                 230                 235                 240

Ser Asn Ser Ile Tyr Glu Leu Leu Glu Asn Gly Gln Arg Ala Gly Thr
                245                 250                 255

Cys Val Leu Glu Tyr Ala Thr Pro Leu Gln Thr Leu Phe Ala Met Ser
            260                 265                 270

Gln Tyr Ser Gln Ala Gly Phe Ser Arg Glu Asp Arg Leu Glu Gln Ala
        275                 280                 285

Lys Leu Phe Cys Gln Thr Leu Glu Asp Ile Leu Ala Asp Ala Pro Glu
290                 295                 300

Ser Gln Asn Asn Cys Arg Leu Ile Ala Tyr Gln Glu Pro Ala Asp Asp
305                 310                 315                 320

Ser Ser Phe Ser Leu Ser Gln Glu Val Leu Arg His Leu Arg Gln Glu
                325                 330                 335

Glu Lys Glu Glu Val Thr Val Gly Ser Leu Lys Thr Ser Ala Val Pro
            340                 345                 350

Ser Thr Ser Thr Met Ser Gln Glu Pro Glu Leu Leu Ile Ser Gly Met
        355                 360                 365

Glu Lys Pro Leu Pro Leu Arg Thr Asp Phe Ser Gly Gly Leu Asn
370                 375                 380

Asp Ile Phe Glu Ala Gln Lys Ile Glu Trp His Glu Gly Ser Leu Glu
385                 390                 395                 400

Val Leu Phe Gln Gly Pro His His His His His His
                405                 410
```

<210> SEQ ID NO 2
<211> LENGTH: 6482
<212> TYPE: DNA
<213> ORGANISM: Homo sapiens

<400> SEQUENCE: 2

```
ggaacggctc cgcccactat taatgaaatt aaaaattcca attttaaaaa acgcagcaag      60
agaaacattt gtatgaaaga atgcgtagaa ggaaagaaaa atgtcgtcga catgctgaac     120
aacaagatta atatgcctcc gtgtataaaa aaatattga acgatttgaa agaaaacaat     180
gtaccgcgcg gcggtatgta caggaagagg tttatactaa actgttacat tgcaaacgtg     240
gtttcgtgtg ccaagtgtga aaaccgatgt taatcaagg ctctgacgca tttctacaac     300
cacgactcca agtgtgtggg tgaagtcatg catcttttaa tcaaatccca agatgtgtat     360
aaaccaccaa actgccaaaa aatgaaaact gtcgacaagc tctgtccgtt tgctggcaac     420
tgcaagggtc tcaatcctat ttgtaattat tgaataataa aacaattata aatgctaaat     480
ttgttttttta ttaacgatac aaaccaaacg caacaagaac atttgtagta ttatctataa     540
ttgaaaacgc gtagttataa tcgctgaggt aatatttaaa atcattttca aatgattcac     600
```

| | |
|---|---|
| agttaatttg cgacaatata attttatttt cacataaact agacgccttg tcgtcttctt | 660 |
| cttcgtattc cttctctttt tcattttcct cttcataaaa attaacatag ttattatcgt | 720 |
| atccatatat gtatctatcg tatagagtaa attttttgtt gtcataaata tatatgtctt | 780 |
| ttttaatggg gtgtatagta ccgctgcgca tagttttcct gtaatttaca acagtgctat | 840 |
| tttctggtag ttcttcggag tgtgttgctt taattattaa atttatataa tcaatgaatt | 900 |
| tgggatcgtc ggttttgtac aatatgttgc cggcatagta cgcagcttct tctagttcaa | 960 |
| ttacaccatt ttttagcagc accggattaa cataactttc caaaatgttg tacgaaccgt | 1020 |
| taaacaaaaa cagttcacct ccctttctta tactattgtc tgcgagcagt tgtttgttgt | 1080 |
| taaaaataac agccattgta atgagacgca caaactaata tcacaaactg gaaatgtcta | 1140 |
| tcaatatata gttgctgatc agatctgatc atggagataa ttaaaatgat aaccatctcg | 1200 |
| caaataaata agtattttac tgttttcgta acagttttgt aataaaaaaa cctataaata | 1260 |
| taggatccat gccccactcc agcctgcatc catccatccc gtgtcccagg ggtcacgggg | 1320 |
| cccagaaggc agccttggtt ctgctgagtg cctgcctggt gacccctttgg ggctaggag | 1380 |
| agccaccaga gcacactctc cggtacctgg tgctccacct agcctccctg cagctgggac | 1440 |
| tgctgttaaa cggggtctgc agcctggctg aggagctgca ccacatccac tccaggtacc | 1500 |
| ggggcagcta ctggaggact gtgcgggcct gcctgggctg ccccctccgc cgtggggccc | 1560 |
| tgttgctgct gtccatctat ttctactact ccctcccaaa tgcggtcggc ccgcccttca | 1620 |
| cttggatgct tgccctcctg ggcctctcgc aggcactgaa catcctcctg ggcctcaagg | 1680 |
| gcctggcccc agctgagatc tctgcagtgt gtgaaaaagg gaatttcaac gtggcccatg | 1740 |
| ggctggcatg gtcatattac atcggatatc tgcggctgat cctgccagag ctccaggccc | 1800 |
| ggattcgaac ttcaatcag cattacaaca acctgctacg gggtgcagtg agccagcggc | 1860 |
| tgtatattct cctcccattg gactgtgggg tgcctgataa cctgagtatg gctgaccca | 1920 |
| acattcgctt cctggataaa ctgccccagc agaccgctga ccgtgctggc atcaaggatc | 1980 |
| gggtttacag caacagcatc tatgagcttc tggagaacgg gcagcgggcg gcacctgtg | 2040 |
| tcctggagta cgccaccccc ttgcagactt tgtttgccat gtcacaatac agtcaagctg | 2100 |
| gctttagccg ggaggatagg cttgagcagg ccaaactctt ctgccagaca cttgaggaca | 2160 |
| tcctggcaga tgccctgag tctcagaaca actgccgcct cattgcctac caggaacctg | 2220 |
| cagatgacag cagcttctcg ctgtcccagg aggttctccg gcacctgcgg caggaggaaa | 2280 |
| aggaagaggt tactgtgggc agcttgaaga cctcagcgt gcccagtacc tccacgatgt | 2340 |
| cccaagagcc tgagctcctc atcagtggaa tggaaaagcc cctccctctc cgcacggatt | 2400 |
| tctctggcgg tggcctgaac gacatcttcg aagcccagaa atcgaatgg catgaaggca | 2460 |
| gcctggaagt gctgttccag ggcccacacc accatcatca ccatcaccat taatgagcgg | 2520 |
| ccgcactcga gcaccaccac caccaccact aacctaggta gctgagcgca tgcaagctga | 2580 |
| tccgggttat tagtacattt attaagcgct agattctgtg cgttgttgat ttacagacaa | 2640 |
| ttgttgtacg tattttaata attcattaaa tttataatct ttagggtggt atgttagagc | 2700 |
| gaaaatcaaa tgattttcag cgtctttata tctgaattta aatattaaat cctcaataga | 2760 |
| tttgtaaaat aggtttcgat tagtttcaaa caagggttgt ttttccgaac cgatggctgg | 2820 |
| actatctaat ggattttcgc tcaacgccac aaaacttgcc aaatcttgta gcagcaatct | 2880 |
| agctttgtcg atattcgttt gtgttttgtt ttgtaataaa ggttcgacgt cgttcaaaat | 2940 |
| attatgcgct tttgtatttc tttcatcact gtcgttagtg tacaattgac tcgacgtaaa | 3000 |

```
cacgttaaat agagcttgga catatttaac atcgggcgtg ttagctttat taggccgatt    3060
atcgtcgtcg tcccaaccct cgtcgttaga agttgcttcc gaagacgatt ttgccatagc    3120
cacacgacgc ctattaattg tgtcggctaa cacgtccgcg atcaaatttg tagttgagct    3180
ttttggaatt atttctgatt gcgggcgttt ttgggcgggt ttcaatctaa ctgtgcccga    3240
ttttaattca gacaacacgt tagaaagcga tggtgcaggc ggtggtaaca tttcagacgg    3300
caaatctact aatggcggcg gtggtggagc tgatgataaa tctaccatcg gtggaggcgc    3360
aggcggggct ggcggcggag gcggaggcgg aggtggtggc ggtgatgcag acggcggttt    3420
aggctcaaat gtctctttag gcaacacagt cggcacctca actattgtac tggtttcggg    3480
cgccgttttt ggtttgaccg gtctgagacg agtgcgattt ttttcgtttc taatagcttc    3540
caacaattgt tgtctgtcgt ctaaaggtgc agcgggttga ggttccgtcg cattggtgg    3600 agcgggcggc aattcagaca tcgatggtgg tggtggtggt ggaggcgctg gaatgttagg    3660
cacgggagaa ggtggtggcg gcggtgccgc cggtataatt tgttctggtt tagtttgttc    3720
gcgcacgatt gtgggcaccg gcgcaggcgc cgctggctgc acaacggaag gtcgtctgct    3780
tcgaggcagc gcttggggtg gtggcaattc aatattataa ttggaataca atcgtaaaa    3840 atctgctata agcattgtaa tttcgctatc gtttaccgtg ccgatattta caaccgctc    3900 aatgtaagca attgtattgt aaagagattg tctcaagctc ggatcgatcc cgcacgccga    3960
taacaagcct tttcattttt actacagcat tgtagtggcg agacacttcg ctgtcgtcga    4020
ggtttaaacg cttcctcgct cactgactcg ctgcgctcgg tcgttcggct gcggcgagcg    4080
gtatcagctc actcaaaggc ggtaatacgg ttatccacag aatcagggga taacgcagga    4140
aagaacatgt gagcaaaagg ccagcaaaag gccaggaacc gtaaaaaggc cgcgttgctg    4200 gcgttttttcc ataggctccg ccccctgac gagcatcaca aaaatcgacg ctcaagtcag    4260
aggtggcgaa acccgacagg actataaaga taccaggcgt ttccccctgg aagctccctc    4320
gtgcgctctc ctgttccgac cctgccgctt accggatacc tgtccgcctt tctcccttcg    4380
ggaagcgtgg cgctttctca tagctcacgc tgtaggtatc tcagttcggt gtaggtcgtt    4440
cgctccaagc tgggctgtgt gcacgaaccc cccgttcagc ccgaccgctg cgccttatcc    4500
ggtaactatc gtcttgagtc aacccggta agacacgact tatcgccact ggcagcagcc    4560
actggtaaca ggattagcag agcgaggtat gtaggcggtg ctacagagtt cttgaagtgg    4620
tggcctaact acggctacac tagaaggaca gtatttggta tctgcgctct gctgaagcca    4680
gttaccttcg gaaaaagagt ggtagctct tgatccggca acaaaccac cgctggtagc    4740 ggtggttttt ttgtttgcaa gcagcagatt acgcgcagaa aaaaggatc tcaagaagat    4800 cctttgatct tttctacggg gtctgacgct cagtggaacg aaaactcacg ttaagggatt    4860
ttggtcatga gattatcaaa aaggatcttc acctagatcc ttttaaatta aaaatgaagt    4920
tttaaatcaa tctaaagtat atatgagtaa acttggtctg acagttacca atgcttaatc    4980
agtgaggcac ctatctcagc gatctgtcta tttcgttcat ccatagttgc ctgactcccc    5040
gtcgtgtaga taactacgat acgggagggc ttaccatctg gccccagtgc tgcaatgata    5100
ccgcgagacc cacgctcacc ggctccagat ttatcagcaa taaaccagcc agccggaagg    5160
gccgagcgca gaagtggtcc tgcaacttta tccgcctcca tccagtctat taattgttgc    5220
cgggaagcta gagtaagtag ttcgccagtt aatagtttgc gcaacgttgt tgccattgct    5280
acaggcatcg tggtgtcacg ctcgtcgttt ggtatggctt cattcagctc cggttcccaa    5340
```

```
cgatcaaggc gagttacatg atcccccatg ttgtgcaaaa aagcggttag ctccttcggt    5400
cctccgatcg ttgtcagaag taagttggcc gcagtgttat cactcatggt tatggcagca    5460
ctgcataatt ctcttactgt catgccatcc gtaagatgct tttctgtgac tggtgagtac    5520
tcaaccaagt cattctgaga atagtgtatg cggcgaccga gttgctcttg cccggcgtca    5580
atacgggata ataccgcgcc acatagcaga actttaaaag tgctcatcat tggaaaacgt    5640 tcttcgggc gaaaactctc aaggatctta ccgctgttga tccagttc gatgtaaccc      5700 actcgtgcac ccaactgatc ttcagcatct tttactttca ccagcgtttc tgggtgagca    5760
aaaacaggaa ggcaaaatgc cgcaaaaaag ggaataaggg cgacacggaa atgttgaata    5820
ctcatactct tcctttttca atattattga agcatttatc agggttattg tctcatgagc    5880
ggatacatat ttgaatgtat ttagaaaaat aaacaaatag gggttccgcg cacatttccc    5940
cgaaaagtgc cacctgacgc gccctgtagc ggcgcattaa gcgcggcggg tgtggtggtt    6000
acgcgcagcg tgaccgctac acttgccagc gccctagcgc ccgctccttt cgctttcttc    6060
ccttcctttc tcgccacgtt cgccggcttt ccccgtcaag ctctaaatcg ggggctccct    6120
ttagggttcc gatttagtgc tttacggcac ctcgacccca aaaaacttga ttagggtgat    6180
ggttcacgta gtgggccatc gccctgatag acggttttc gccctttgac gttggagtcc    6240
acgttcttta atagtggact cttgttccaa actggaacaa cactcaaccc tatctcggtc    6300
tattcttttg atttataagg gattttgccg atttcggcct attggttaaa aaatgagctg    6360
atttaacaaa aatttaacgc gaattttaac aaaatattaa cgtttacaat tcccattcg    6420 ccattcaggc tgcgcaactg ttgggaaggg cgatcggtgc gggcctcttc gctattacgc    6480
ca                                                                   6482
```

<210> SEQ ID NO 3
<211> LENGTH: 414
<212> TYPE: PRT
<213> ORGANISM: Homo sapiens

<400> SEQUENCE: 3

```
Met Pro His Ser Ser Leu His Pro Ser Ile Pro Cys Pro Arg Gly His
1               5                   10                  15

Gly Ala Gln Lys Ala Ala Leu Val Leu Leu Ser Ala Cys Leu Val Thr
            20                  25                  30

Leu Trp Gly Leu Gly Glu Pro Pro Glu His Thr Leu Arg Tyr Leu Val
        35                  40                  45

Leu His Leu Ala Ser Leu Gln Leu Gly Leu Leu Asn Gly Val Cys
    50                  55                  60

Ser Leu Ala Glu Glu Leu Arg His Ile His Ser Arg Tyr Arg Gly Ser
65                  70                  75                  80

Tyr Trp Arg Thr Val Arg Ala Cys Leu Gly Cys Pro Leu Arg Arg Gly
                85                  90                  95

Ala Leu Leu Leu Leu Ser Ile Tyr Phe Tyr Ser Leu Pro Asn Ala
            100                 105                 110

Val Gly Pro Pro Phe Thr Trp Met Leu Ala Leu Gly Leu Ser Gln
        115                 120                 125

Ala Leu Asn Ile Leu Leu Gly Leu Lys Gly Leu Pro Ala Glu Ile
    130                 135                 140

Ser Ala Val Cys Glu Lys Gly Asn Phe Asn Val Ala His Gly Leu Ala
145                 150                 155                 160

Trp Ser Tyr Tyr Ile Gly Tyr Leu Arg Leu Ile Leu Pro Glu Leu Gln
```

```
                    165                 170                 175
Ala Arg Ile Arg Thr Tyr Asn Gln His Tyr Asn Asn Leu Leu Arg Gly
            180                 185                 190

Ala Val Ser Gln Arg Leu Tyr Ile Leu Leu Pro Leu Asp Cys Gly Val
        195                 200                 205

Pro Asp Asn Leu Ser Met Ala Asp Pro Asn Ile Arg Phe Leu Asp Lys
    210                 215                 220

Leu Pro Gln Gln Thr Gly Asp Arg Ala Gly Ile Lys Asp Arg Val Tyr
225                 230                 235                 240

Ser Asn Ser Ile Tyr Glu Leu Leu Glu Asn Gly Gln Arg Ala Gly Thr
                245                 250                 255

Cys Val Leu Glu Tyr Ala Thr Pro Leu Gln Thr Leu Phe Ala Met Ser
            260                 265                 270

Gln Tyr Ser Gln Ala Gly Phe Ser Arg Glu Asp Arg Leu Glu Gln Ala
        275                 280                 285

Lys Leu Phe Cys Arg Thr Leu Glu Asp Ile Leu Ala Asp Ala Pro Glu
    290                 295                 300

Ser Gln Asn Asn Cys Arg Leu Ile Ala Tyr Gln Glu Pro Ala Asp Asp
305                 310                 315                 320

Ser Ser Phe Ser Leu Ser Gln Glu Val Leu Arg His Leu Arg Gln Glu
                325                 330                 335

Glu Lys Glu Glu Val Thr Val Gly Ser Leu Lys Thr Ser Ala Val Pro
            340                 345                 350

Ser Thr Ser Thr Met Ser Gln Glu Pro Glu Leu Leu Ile Ser Gly Met
        355                 360                 365

Glu Lys Pro Leu Pro Leu Arg Thr Asp Phe Ser Gly Gly Gly Leu Asn
    370                 375                 380

Asp Ile Phe Glu Ala Gln Lys Ile Glu Trp His Glu Gly Ser Leu Glu
385                 390                 395                 400

Val Leu Phe Gln Gly Pro His His His His His His
                405                 410
```

<210> SEQ ID NO 4
<211> LENGTH: 6482
<212> TYPE: DNA
<213> ORGANISM: HOMO SAPIENS

<400> SEQUENCE: 4

| | |
|---|---|
| ggaacggctc cgcccactat taatgaaatt aaaaattcca atttaaaaaa acgcagcaag | 60 |
| agaaacattt gtatgaaaga atgcgtagaa ggaaagaaaa atgtcgtcga catgctgaac | 120 |
| aacaagatta atatgcctcc gtgtataaaa aaatattga acgatttgaa agaaaacaat | 180 |
| gtaccgcgcg gcggtatgta caggaagagg tttatactaa actgttacat tgcaaacgtg | 240 |
| gtttcgtgtg ccaagtgtga aaaccgatgt ttaatcaagg ctctgacgca tttctacaac | 300 |
| cacgactcca agtgtgtggg tgaagtcatg catcttttaa tcaaatccca agatgtgtat | 360 |
| aaaccaccaa actgccaaaa aatgaaaact gtcgacaagc tctgtccgtt tgctggcaac | 420 |
| tgcaagggtc tcaatcctat ttgtaattat tgaataataa acaattata aatgtcaaat | 480 |
| ttgttttta ttaacgatac aaaccaaacg caacaagaac atttgtagta ttatctataa | 540 |
| ttgaaaacgc gtagttataa tcgctgaggt aatatttaaa atcattttca aatgattcac | 600 |
| agttaatttg cgacaatata atttatttt cacataaact agacgccttg tcgtcttctt | 660 |
| cttcgtattc cttctctttt tcattttct cttcataaaa attaacatag ttattatcgt | 720 |

| | | |
|---|---|---|
| atccatatat gtatctatcg tatagagtaa atttttgtt gtcataaata tatatgtctt | 780 |
| ttttaatggg gtgtatagta ccgctgcgca tagtttttct gtaatttaca acagtgctat | 840 |
| tttctggtag ttcttcggag tgtgttgctt taattattaa atttatataa tcaatgaatt | 900 |
| tgggatcgtc ggttttgtac aatatgttgc cggcatagta cgcagcttct tctagttcaa | 960 |
| ttacaccatt ttttagcagc accggattaa cataactttc caaaatgttg tacgaaccgt | 1020 |
| taaacaaaaa cagttcacct cccttttcta tactattgtc tgcgagcagt tgtttgttgt | 1080 |
| taaaaataac agccattgta atgagacgca caaactaata tcacaaactg gaaatgtcta | 1140 |
| tcaatatata gttgctgatc agatctgatc atggagataa ttaaaatgat aaccatctcg | 1200 |
| caaataaata agtattttac tgttttcgta acagttttgt aataaaaaaa cctataaata | 1260 |
| taggatccat gccccactcc agcctgcatc catccatccc gtgtcccagg gtcacggggg | 1320 |
| cccagaaggc agccttggtt ctgctgagtg cctgcctggt gacccctttgg gggctaggag | 1380 |
| agccaccaga gcacactctc cggtacctgg tgctccacct agcctccctg cagctgggac | 1440 |
| tgctgttaaa cggggtctgc agcctggctg aggagctgcg ccacatccac tccaggtacc | 1500 |
| ggggcagcta ctggaggact gtgcgggcct gcctgggctg cccctccgc cgtggggccc | 1560 |
| tgttgctgct gtccatctat ttctactact ccctcccaaa tgcggtcggc ccgcccttca | 1620 |
| cttggatgct tgccctcctg ggcctctcgc aggcactgaa catcctcctg ggcctcaagg | 1680 |
| gcctggcccc agctgagatc tctgcagtgt gtgaaaaagg gaatttcaac gtggcccatg | 1740 |
| ggctggcatg gtcatattac atcggatatc tgcggctgat cctgccagag ctccaggccc | 1800 |
| ggattcgaac ttacaatcag cattacaaca acctgctacg gggtgcagtg agccagcggc | 1860 |
| tgtatattct cctcccattg gactgtgggg tgcctgataa cctgagtatg gctgaccca | 1920 |
| acattcgctt cctggataaa ctgccccagc agaccggtga ccgtgctggc atcaaggatc | 1980 |
| gggtttacag caacagcatc tatgagcttc tggagaacgg gcagcgggcg ggcacctgtg | 2040 |
| tcctggagta cgccacccc ttgcagactt tgtttgccat gtcacaatac agtcaagctg | 2100 |
| gctttagccg ggaggatagg cttgagcagg ccaaactctt ctgccggaca cttgaggaca | 2160 |
| tcctggcaga tgcccctgag tctcagaaca actgccgcct cattgcctac caggaacctg | 2220 |
| cagatgacag cagcttctcg ctgtcccagg aggttctccg gcacctgcgg caggaggaaa | 2280 |
| aggaagaggt tactgtgggc agcttgaaga cctcagcgt gcccagtacc tccacgatgt | 2340 |
| cccaagagcc tgagctcctc atcagtggaa tggaaaagcc cctccctctc cgcacggatt | 2400 |
| tctctggcgg tggcctgaac gacatcttcg aagcccagaa atcgaatggg catgaaggca | 2460 |
| gcctggaagt gctgttccag ggcccacacc accatcatca ccatcaccat taatgagcgg | 2520 |
| ccgcactcga gcaccaccac caccaccact aacctaggta gctgagcgca tgcaagctga | 2580 |
| tccgggttat tagtacattt attaagcgct agattctgtg cgttgttgat ttacagacaa | 2640 |
| ttgttgtacg tattttaata attcattaaa tttataatct ttagggtggt atgttagagc | 2700 |
| gaaaatcaaa tgattttcag cgtctttata tctgaattta atattaaat cctcaataga | 2760 |
| tttgtaaaat aggtttcgat tagtttcaaa caagggttgt ttttccgaac cgatggctgg | 2820 |
| actatctaat ggattttcgc tcaacgccac aaaacttgcc aaatcttgta gcagcaatct | 2880 |
| agctttgtcg atattcgttt gtgttttgtt ttgtaataaa ggttcgacgt cgttcaaaat | 2940 |
| attatgcgct tttgtatttc tttcatcact gtcgttagtg tacaattgac tcgacgtaaa | 3000 |
| cacgttaaat agagcttgga catatttaac atcgggcgtg ttagctttat taggccgatt | 3060 |
| atcgtcgtcg tcccaaccct cgtcgttaga agttgcttcc gaagacgatt tgccatagc | 3120 |

```
cacacgacgc ctattaattg tgtcggctaa cacgtccgcg atcaaatttg tagtttgagct    3180 tttggaatt atttctgatt gcgggcgttt ttgggcgggt ttcaatctaa ctgtgcccga     3240
ttttaattca gacaacacgt tagaaagcga tggtgcaggc ggtggtaaca tttcagacgg    3300
caaatctact aatggcggcg gtggtggagc tgatgataaa tctaccatcg gtggaggcgc    3360
aggcggggct ggcggcggag gcggaggcgg aggtggtggc ggtgatgcag acggcggttt    3420
aggctcaaat gtctctttag gcaacacagt cggcacctca actattgtac tggtttcggg    3480
cgccgttttt ggtttgaccg gtctgagacg agtgcgattt ttttcgtttc taatagcttc    3540
caacaattgt tgtctgtcgt ctaaaggtgc agcgggttga ggttccgtcg gcattggtgg    3600
agcgggcggc aattcagaca tcgatggtgg tggtggtggt ggaggcgctg gaatgttagg    3660
cacgggagaa ggtggtggcg gcggtgccgc cggtataatt tgttctggtt tagtttgttc    3720
gcgcacgatt gtgggcaccg gcgcaggcgc cgctggctgc acaacggaag gtcgtctgct    3780
tcgaggcagc gcttggggtg gtggcaattc aatattataa ttggaataca aatcgtaaaa    3840
atctgctata agcattgtaa tttcgctatc gtttaccgtg ccgatattta caaccgctc    3900 aatgtaagca attgtattgt aaagagattg tctcaagctc ggatcgatcc cgcacgccga    3960
taacaagcct tttcattttt actacagcat tgtagtggcg agacacttcg ctgtcgtcga    4020
ggtttaaacg cttcctcgct cactgactcg ctgcgctcgg tcgttcggct gcggcgagcg    4080
gtatcagctc actcaaaggc ggtaatacgg ttatccacag aatcagggga taacgcagga    4140
aagaacatgt gagcaaaagg ccagcaaaag gccaggaacc gtaaaaaggc cgcgttgctg    4200 gcgttttttcc ataggctccg ccccctgac gagcatcaca aaaatcgacg ctcaagtcag    4260
aggtggcgaa acccgacagg actataaaga taccaggcgt ttccccctgg aagctccctc    4320
gtgcgctctc ctgttccgac cctgccgctt accggatacc tgtccgcctt tctcccttcg    4380
ggaagcgtgg cgctttctca tagctcacgc tgtaggtatc tcagttcggt gtaggtcgtt    4440
cgctccaagc tgggctgtgt gcacgaaccc cccgttcagc ccgaccgctg cgccttatcc    4500
ggtaactatc gtcttgagtc aacccggta agacacgact tatcgccact ggcagcagcc    4560
actggtaaca ggattagcag agcgaggtat gtaggcggtg ctacagagtt cttgaagtgg    4620
tggcctaact acggctacac tagaaggaca gtatttggta tctgcgctct gctgaagcca    4680
gttaccttcg gaaaaagagt tggtagctct tgatccggca acaaaccac cgctggtagc    4740 ggtggttttt ttgtttgcaa gcagcagatt acgcgcagaa aaaaaggatc tcaagaagat    4800
cctttgatct tttctacggg gtctgacgct cagtggaacg aaaactcacg ttaagggatt    4860
ttggtcatga gattatcaaa aaggatcttc acctagatcc tttaaatta aaaatgaagt    4920 tttaaatcaa tctaaagtat atatgagtaa acttggtctg acagttacca atgcttaatc    4980
agtgaggcac ctatctcagc gatctgtcta tttcgttcat ccatagttgc ctgactcccc    5040
gtcgtgtaga taactacgat acgggagggc ttaccatctg gccccagtgc tgcaatgata    5100
ccgcgagacc cacgctcacc ggctccagat ttatcagcaa taaccagcc agccggaagg    5160 gccgagcgca gaagtggtcc tgcaacttta tccgcctcca tccagtctat taattgttgc    5220
cgggaagcta gagtaagtag ttcgccagtt aatagtttgc gcaacgttgt tgccattgct    5280
acaggcatcg tggtgtcacg ctcgtcgttt ggtatggctt cattcagctc cggttcccaa    5340
cgatcaaggc gagttacatg atcccccatg ttgtgcaaaa aagcggttag ctccttcggt    5400
cctccgatcg ttgtcagaag taagttggcc gcagtgttat cactcatggt tatggcagca    5460
```

```
ctgcataatt ctcttactgt catgccatcc gtaagatgct tttctgtgac tggtgagtac    5520
tcaaccaagt cattctgaga atagtgtatg cggcgaccga gttgctcttg cccggcgtca    5580
atacgggata ataccgcgcc acatagcaga actttaaaag tgctcatcat tggaaaacgt    5640 tcttcgggc gaaaactctc aaggatctta ccgctgttga gatccagttc gatgtaaccc    5700
actcgtgcac ccaactgatc ttcagcatct tttactttca ccagcgtttc tgggtgagca    5760
aaaacaggaa ggcaaaatgc cgcaaaaaag ggaataaggg cgacacggaa atgttgaata    5820
ctcatactct ccttttttca atattattga agcatttatc agggttattg tctcatgagc    5880
ggatacatat ttgaatgtat ttagaaaaat aaacaaatag gggttccgcg cacatttccc    5940
cgaaaagtgc cacctgacgc gccctgtagc ggcgcattaa gcgcggcggg tgtggtggtt    6000
acgcgcagcg tgaccgctac acttgccagc gccctagcgc ccgctccttt cgctttcttc    6060
ccttcctttc tcgccacgtt cgccggcttt ccccgtcaag ctctaaatcg ggggctccct    6120
ttagggttcc gatttagtgc tttacggcac ctcgacccca aaaaacttga ttagggtgat    6180
ggttcacgta gtgggccatc gccctgatag acggttttc gccctttgac gttggagtcc    6240
acgttcttta atagtggact cttgttccaa actggaacaa cactcaaccc tatctcggtc    6300
tattcttttg atttataagg gattttgccg atttcggcct attggttaaa aaatgagctg    6360
atttaacaaa aatttaacgc gaattttaac aaaatattaa cgtttacaat ttcccattcg    6420
ccattcaggc tgcgcaactg ttgggaaggg cgatcggtgc gggcctcttc gctattacgc    6480
ca                                                                   6482
```